US009650602B2

(12) United States Patent
Su et al.

(10) Patent No.: US 9,650,602 B2
(45) Date of Patent: May 16, 2017

(54) REPROGRAMMING CELLS BY THREE-DIMENSIONAL CULTIVATION

(75) Inventors: Guannan Su, Beijing (CN); Yannan Zhao, Beijing (CN); Jianshu Wei, Beijing (CN); Bing Chen, Beijing (CN); Zhifeng Xiao, Beijing (CN); Jianwu Dai, Beijing (CN)

(73) Assignee: INSTITUTE OF GENETICS AND DEVELOPMENTAL BIOLOGY, CHINESE ACADEMY OF SCIENCES, Zhongguancun, Haidian District, Beijing (CN)

( * ) Notice: Subject to any disclaimer, the term of this patent is extended or adjusted under 35 U.S.C. 154(b) by 114 days.

(21) Appl. No.: 14/380,938

(22) PCT Filed: Mar. 13, 2012

(86) PCT No.: PCT/CN2012/072284
§ 371 (c)(1),
(2), (4) Date: Aug. 26, 2014

(87) PCT Pub. No.: WO2013/134931
PCT Pub. Date: Sep. 19, 2013

(65) Prior Publication Data
US 2015/0050733 A1 Feb. 19, 2015

(51) Int. Cl.
*C12N 5/07* (2010.01)
*C12N 5/00* (2006.01)
*C12N 5/0793* (2010.01)

(52) U.S. Cl.
CPC ......... *C12N 5/0062* (2013.01); *C12N 5/0619* (2013.01); *C12N 2500/30* (2013.01); *C12N 2506/00* (2013.01); *C12N 2533/76* (2013.01)

(58) Field of Classification Search
CPC . C12N 5/0062; C12N 2533/76; C12N 5/0607
See application file for complete search history.

(56) References Cited

FOREIGN PATENT DOCUMENTS

| CN | 101506350 A | 8/2009 |
|---|---|---|
| JP | 09-266789 A | 10/1997 |
| JP | 2001-231548 A | 8/2001 |
| JP | 2003-052361 A | 2/2003 |
| JP | 2003-219865 A | 8/2003 |
| JP | 2004-357694 A | 12/2004 |
| JP | 2009-213442 A | 9/2009 |
| WO | 2008/150001 A1 | 12/2008 |
| WO | 2009116951 A2 | 9/2009 |
| WO | 2011059112 A1 | 5/2011 |

OTHER PUBLICATIONS

Tolbert et al., Cell aggregate suspension culture for large-scale production of biomolecules. In Vitro, vol. 16, No. 6 (1980) pp. 486-490.*
R. Ian Freshney, "Suspension Cloning" in Culture of Animal Cells, (Hoboken, NJ, John Wiley & Sons, Inc., 2010), pp. 214-216. QH585.2.F74 2010.*
Thermo Scientific™ Nunc™ Dishes, Cell Culture/Petri. Datasheet. Fisher Scientific, 2014. pp. 267.*
Jiang, Chunyan, Research on related techniques of human induced pluripotent stem cell, Chinese Master's Theses Full-text Database (Medicine and Health Sciences), Nov. 15, 2011, No. 11, ISSN 1674-0246, See pp. 67-73.
Anokye-Danso, et al. (2011). Highly efficient miRNA-mediated reprogramming of mouse and human somatic cells to pluripotency. Cell Stem Cell 8, 376-388.
Birgersdotter, A., et al. (2005). Gene expression perturbation in vitro—a growing case for three-dimensional (3D) culture systems. Semin Cancer Biol 15, 405-412.
Cukierman, E., et al. (2001). Taking cell-matrix adhesions to the third dimension. Science 294, 1708-1712.
Eiraku, M., et al. (2011). Self-organizing optic-cup morphogenesis in three-dimensional culture. Nature 472, 51-56.
Eiraku, M., et al. (2008). Self-organized formation of polarized cortical tissues from ESCs and its active manipulation by extrinsic signals. Cell Stem Cell 3, 519-532.
Episkopou, V. (2005). SOX2 functions in adult neural stem cells. Trends Neurosci 28, 219-221.
Eshghi, S., and Schaffer, D.V. (2008). Engineering microenvironments to control stem cell fate and function.
Fischbach, C., et al. (2007). Engineering tumors with 3D scaffolds. Nat Methods 4, 855-860.
Golebiewska, A., et al. (2011). Critical appraisal of the side population assay in stem cell and cancer stem cell research. Cell Stem Cell 8, 136-147.
Griffith, L.G., and Swartz, M.A. (2006). Capturing complex 3D tissue physiology in vitro. Nat Rev Mol Cell Biol 7, 211-224.
Hendrix, M.J., et al. (2007). Reprogramming metastatic tumour cells with embryonic microenvironments. Nat Rev Cancer 7, 246-255.
Huangfu, D., et al. (2008). Induction of pluripotent stem cells by defined factors is greatly improved by small-molecule compounds. Nat Biotechnol 26, 795-797.
Ingber, D. (1991). Extracellular matrix and cell shape: potential control points for inhibition of angiogenesis. J Cell Biochem 47, 236-241.
Jensen, U.B., Lowell, S., and Watt, F.M. (1999). The spatial relationship between stem cells and their progeny in the basal layer of human epidermis: a new view based on whole-mount labelling and lineage analysis. Development 126, 2409-2418.
Jones, P.H., Harper, S., and Watt, F.M. (1995). Stem cell patterning and fate in human epidermis. Cell 80, 83-93.
Keung, A.J., Kumar, S., and Schaffer, D.V. (2010). Presentation counts: microenvironmental regulation of stem cells by biophysical and material cues. Annu Rev Cell Dev Biol 26, 533-556.
Kim, D., et al. (2009). Generation of human induced pluripotent stem cells by direct delivery of reprogramming proteins. Cell Stem Cell 4, 472-476.
Kim, J., et al. (2011). Direct reprogramming of mouse fibroblasts to neural progenitors. Proc Natl Acad Sci U S A 108, 7838-7843.
Li, R., et al. (2010). A mesenchymal-to-epithelial transition initiates and is required for the nuclear reprogramming of mouse fibroblasts. Cell Stem Cell 7, 51-63.

(Continued)

*Primary Examiner* — Kara Johnson
(74) *Attorney, Agent, or Firm* — Jun He Law Offices P.C.; Zhaohui Wang

(57) ABSTRACT

Methods for reprogramming cells by culturing the cells under a condition that allows formation of a three-dimensional cell aggregate are provided. The cells and cell aggregates obtained using the methods are also provided.

29 Claims, 56 Drawing Sheets

(56) References Cited

OTHER PUBLICATIONS

Liu, J., et al. (2007). Functional three-dimensional HepG2 aggregate cultures generated from an ultrasound trap: comparison with HepG2 spheroids. J Cell Biochem 102, 1180-1189.

Liu, Y., et al. (2009). Mouse fibroblasts lacking RB1 function form spheres and undergo reprogramming to a cancer stem cell phenotype. Cell Stem Cell 4, 336-347.

Manasek, F.J., Burnside, M.B., and Waterman, R.E. (1972). Myocardial cell shape change as a mechanism of embryonic heart looping. Dev Biol 29, 349-371.

Mani, S.A., et al. (2008). The epithelial-mesenchymal transition generates cells with properties of stem cells. Cell 133, 704-715.

McBeath, R., et al. (2004). Cell shape, cytoskeletal tension, and RhoA regulate stem cell lineage commitment. Dev Cell 6, 483-495.

Nelson, C.M., and Bissell, M.J. (2006). Of extracellular matrix, scaffolds, and signaling: tissue architecture regulates development, homeostasis, and cancer. Annu Rev Cell Dev Biol 22, 287-309.

Osafune, K., et al. (2006). Identification of multipotent progenitors in the embryonic mouse kidney by a novel colony-forming assay. Development 133, 151-161.

Pampaloni, F. Reynaud, E.G., and Stelzer, E.H. (2007). The third dimension bridges the gap between cell culture and live tissue. Nat Rev Mol Cell Biol 8, 839-845.

Shi, Y., Do, et al. (2008). A combined chemical and genetic approach for the generation of induced pluripotent stem cells. Cell Stem Cell 2, 525-528.

Takahashi, K., et al. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Vazin, T., and Schaffer, D.V. (2010). Engineering strategies to emulate the stem cell niche. Trends Biotechnol 28, 117-124.

Warren, L., Manos, P.D., et al. Highly efficient reprogramming to pluripotency and directed differentiation of human cells with synthetic modified mRNA. Cell Stem Cell 7, 618-630.

Yamada, K.M., and Cukierman, E. (2007). Modeling tissue morphogenesis and cancer in 3D. Cell 130, 601-610.

Yu, J., et al. (2007). Induced pluripotent stem cell lines derived from human somatic cells. Science 318, 1917-1920.

Zhou, H., et al. (2009). Generation of induced pluripotent stem cells using recombinant proteins. Cell Stem Cell 4, 381-384.

Zhu, S., et al. (2010). Reprogramming of human primary somatic cells by OCT4 and chemical compounds. Cell Stem Cell 7, 651-655.

Qunzhou Zhang et al.; "Three-Dimensional Spheroid Culture of Human Gingiva-Derived Mesenchymal Stem Cells Enhances Mitigation of Chemotherapy-Induced Oral Mucositis"; Stem Cells and Development; vol. 21, No. 6, 2012; p. 937 to 947.

Ruka Shimizu; "Acquisition of the ability to induce hair follicles of mouse skin fibroblasts by non-adherent culturing method"; Skin Surgery; vol. 20, No. 1, 2011; p. 53.

Wang Jun-sheng et al. "Self-organization and branching morphogenesis of primary salivary epithelial cells under three-dimensional culture", Journal of Clinical Rehabilitative Tissue Engineering Research Oct. 1, 2011 vol. 15, No. 40, p. 7549-7553.

\* cited by examiner

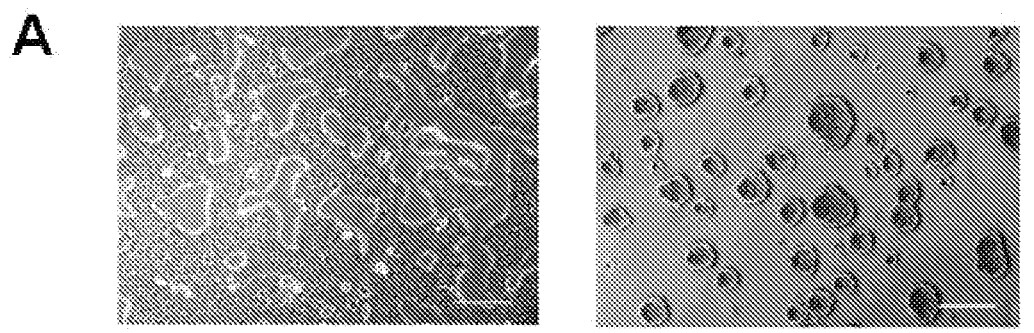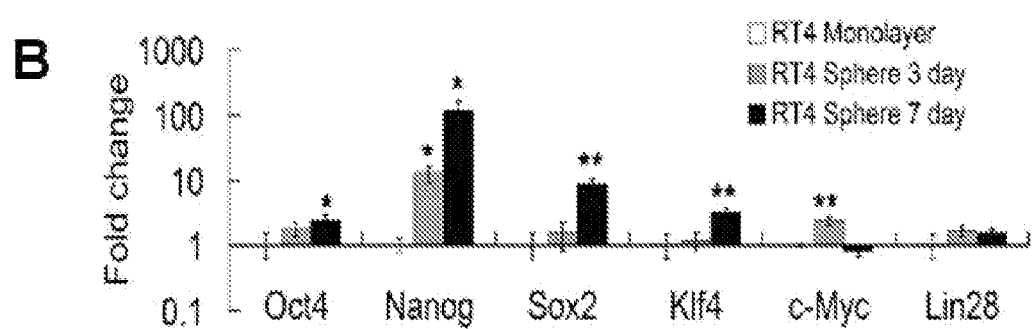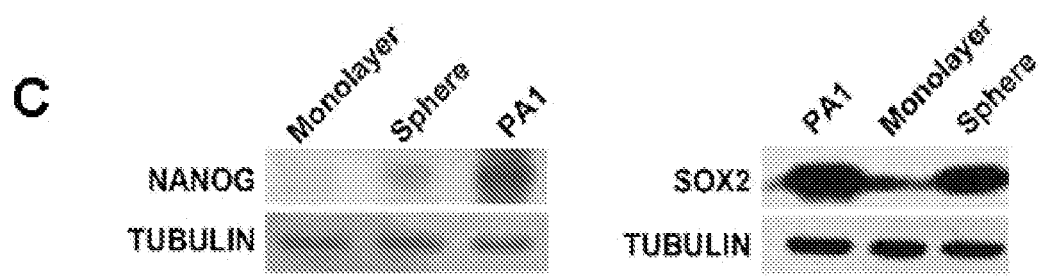
Figure 1

A
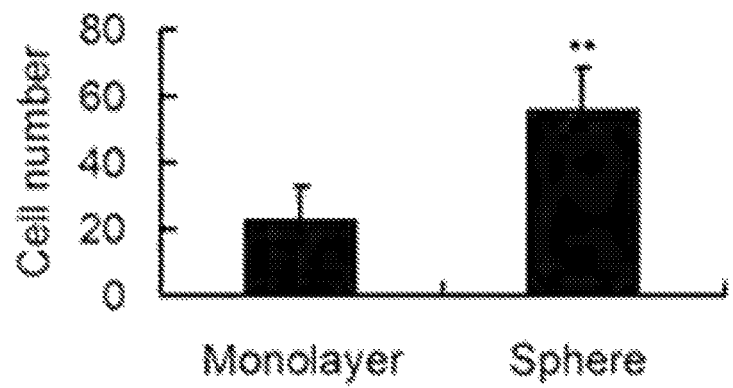
B
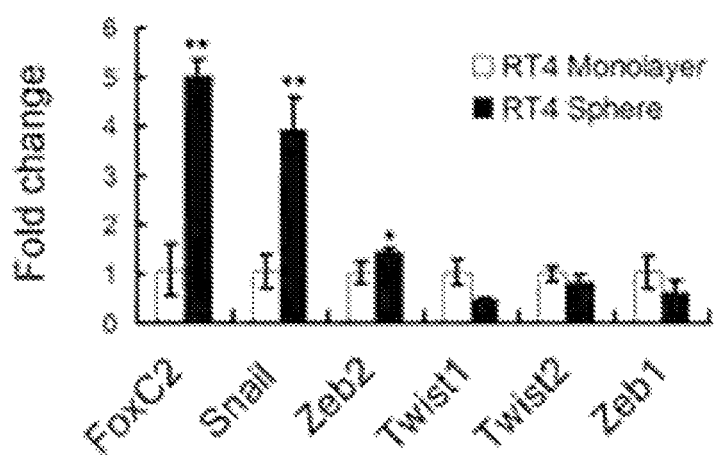
C
| Cell Number | 10^6 | 10^4 |
|---|---|---|
| Monolayer | 11/14 | 0/14 |
| Sphere | 14/14 | 4/14 |
Figure 2

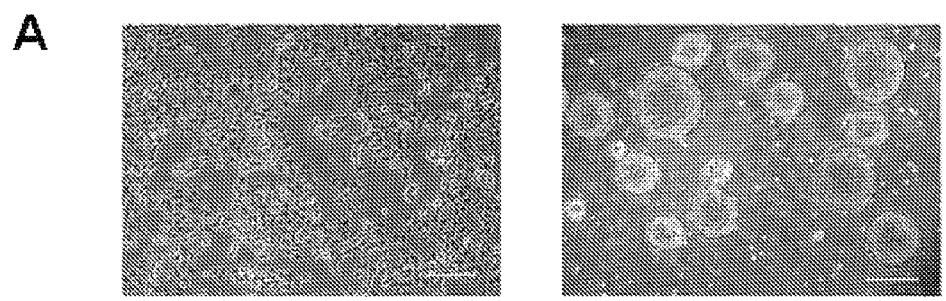
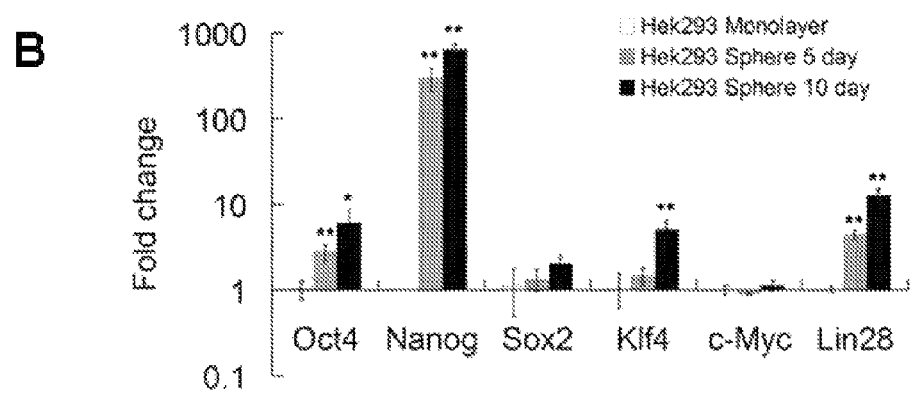
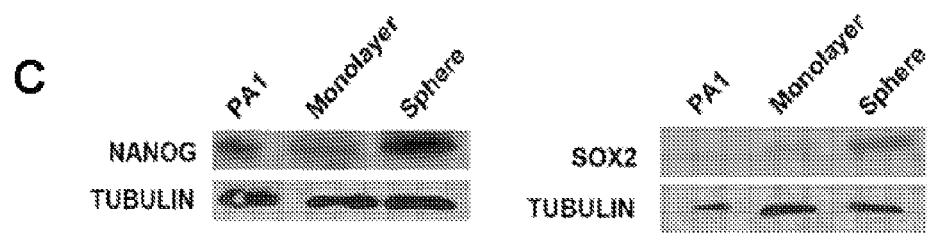
Figure 3 (A-C)

D
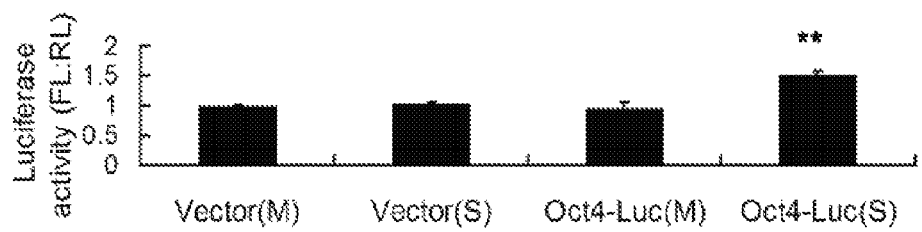
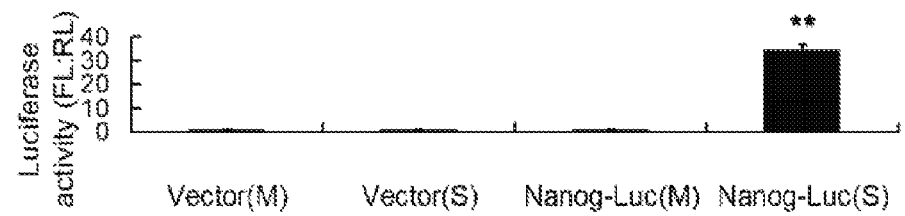
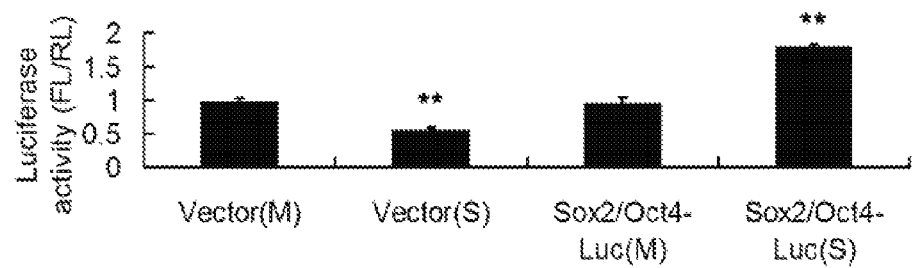
Figure 3 (D)

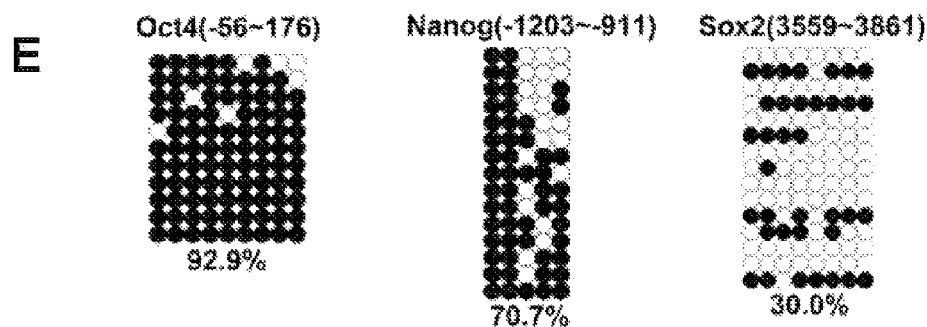
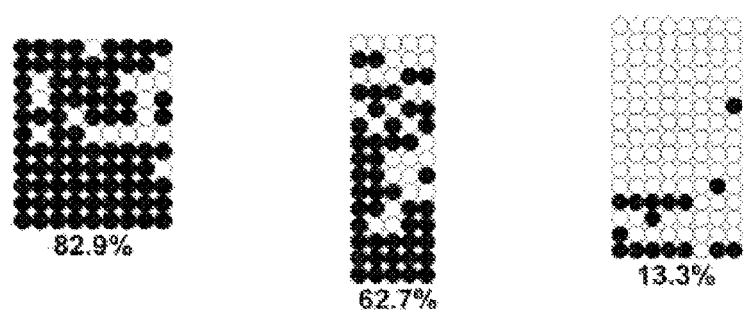
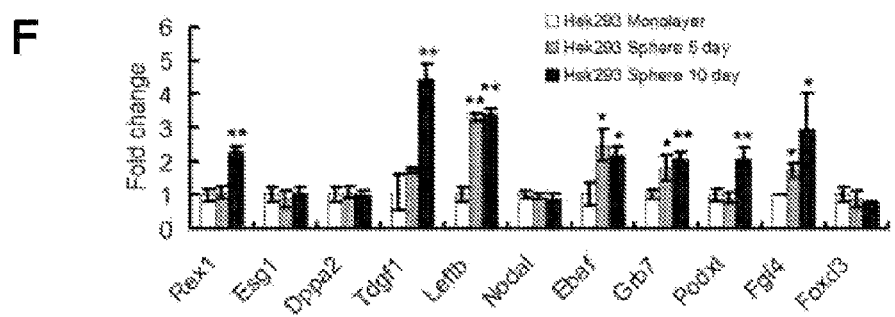
Figure 3 (E, F)

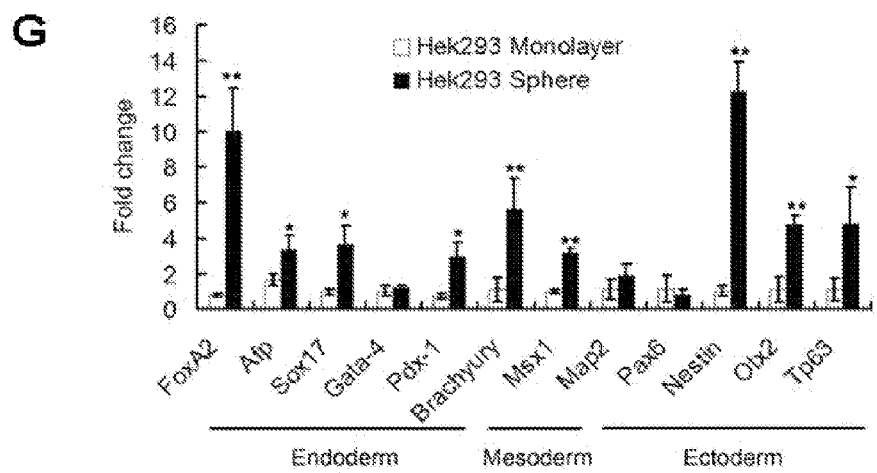
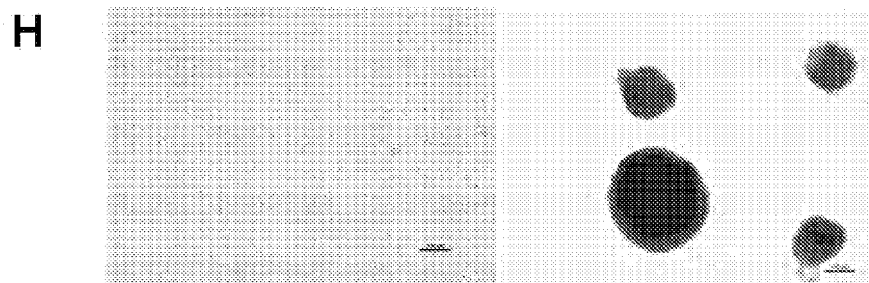
Figure 3 (G-I)

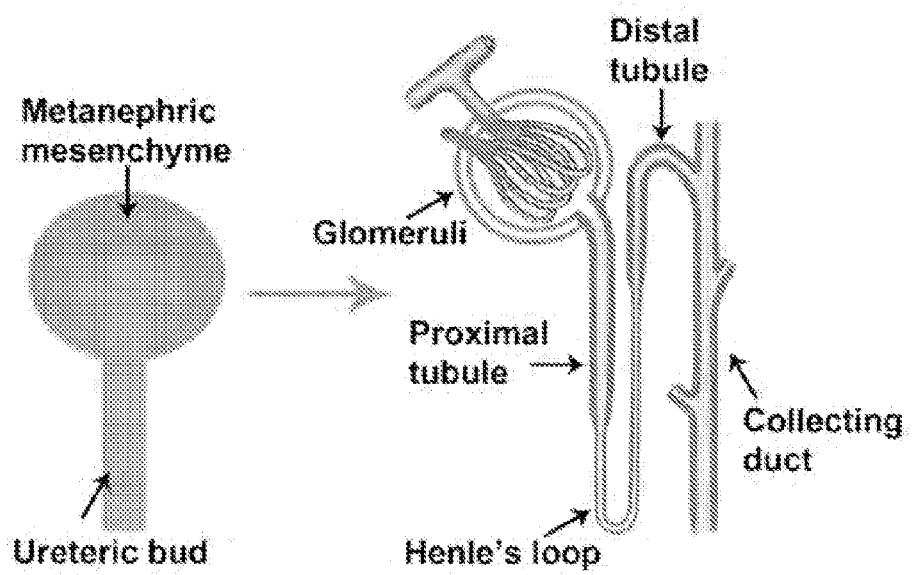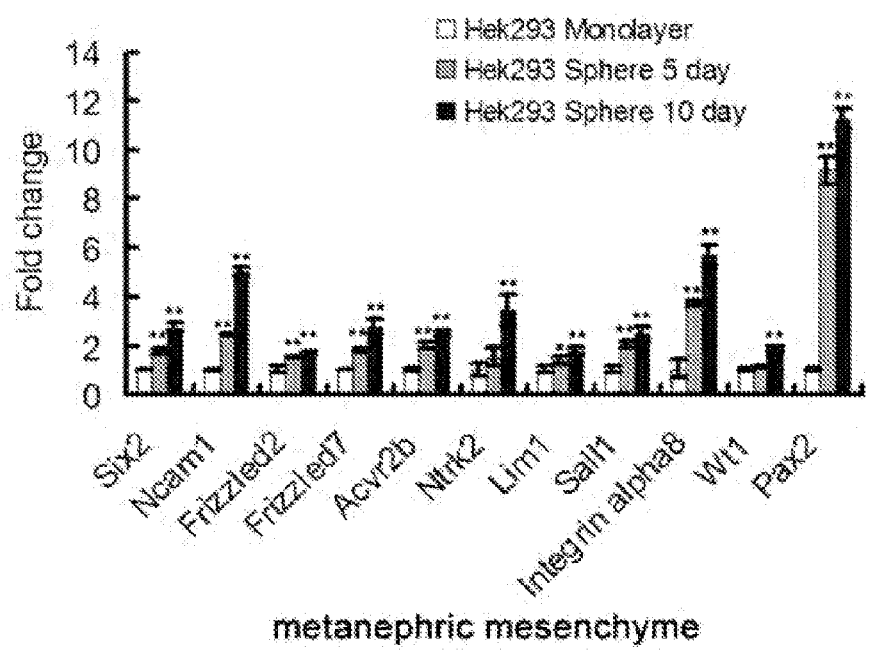
Figure 4 （A, B）

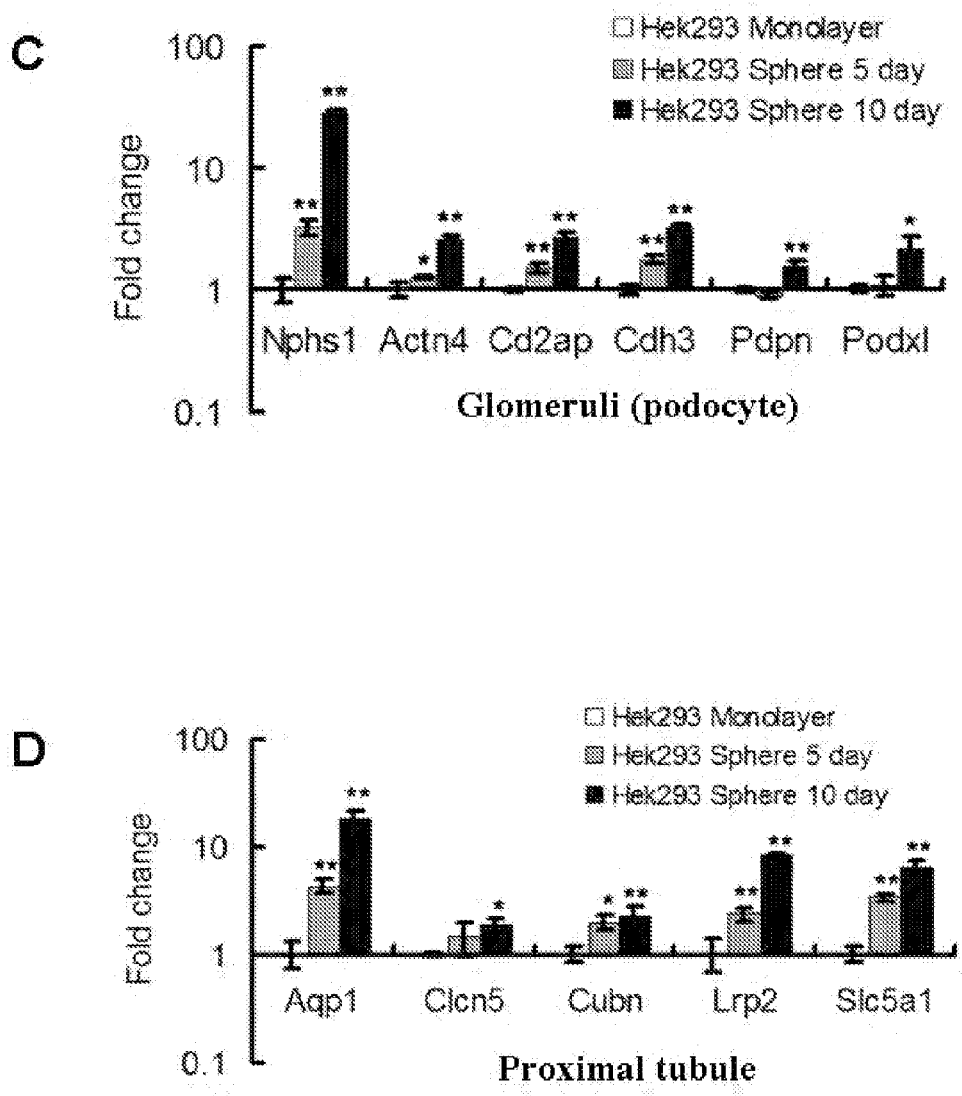
Figure 4 (C, D)

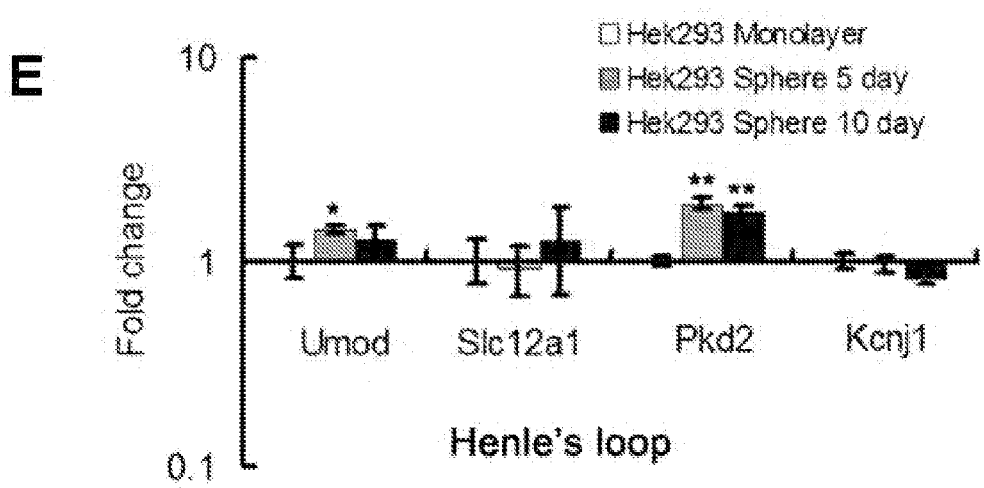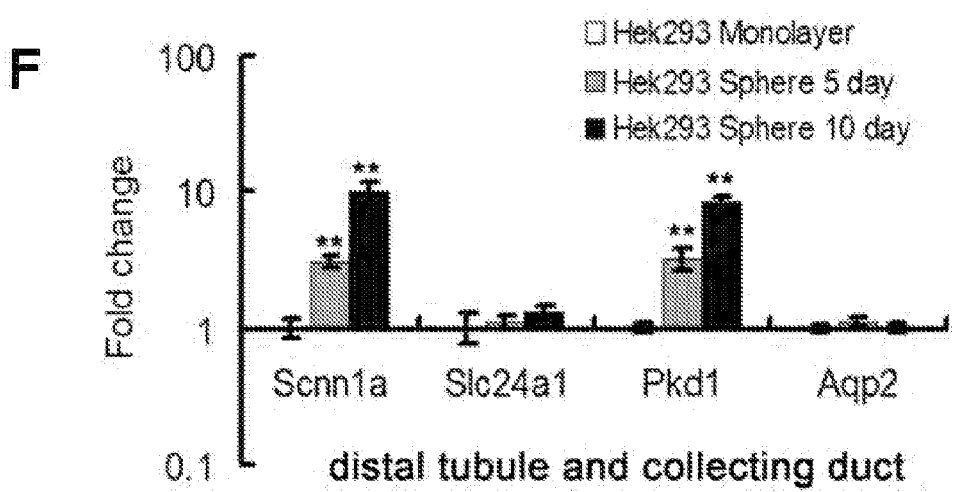
Figure 4 (E, F)

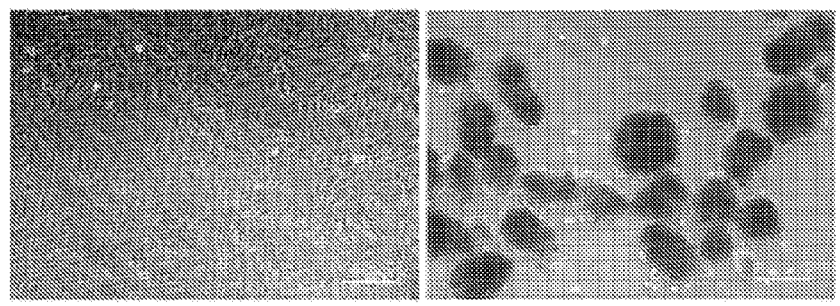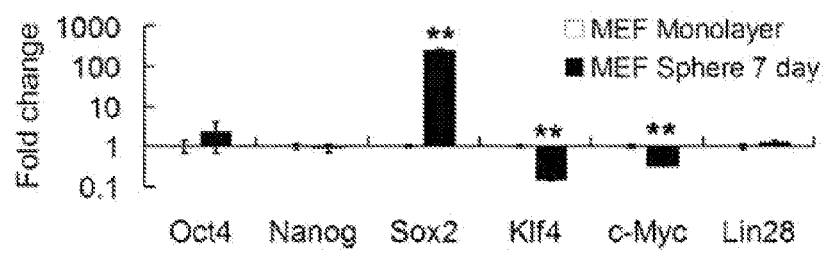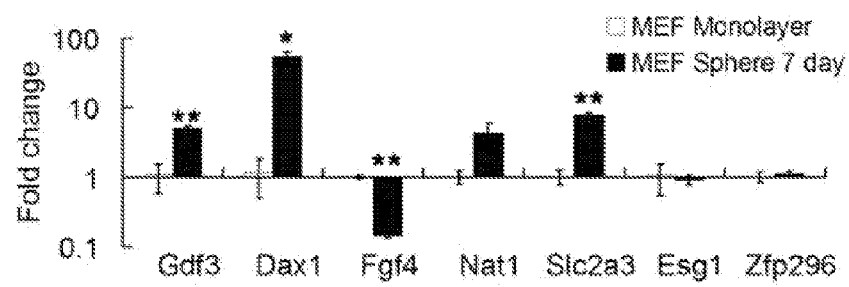
Figure 5 (A, B)

D
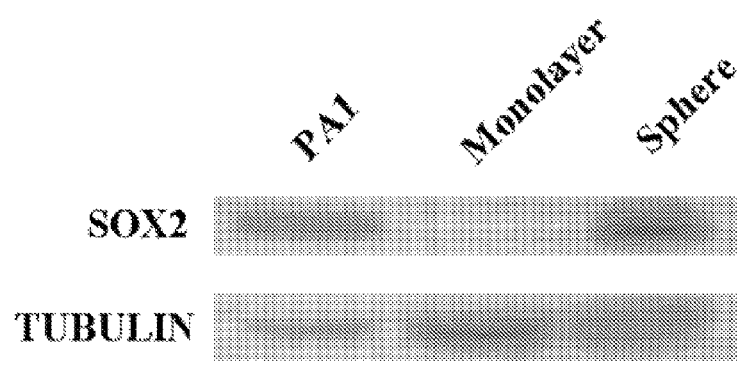
E
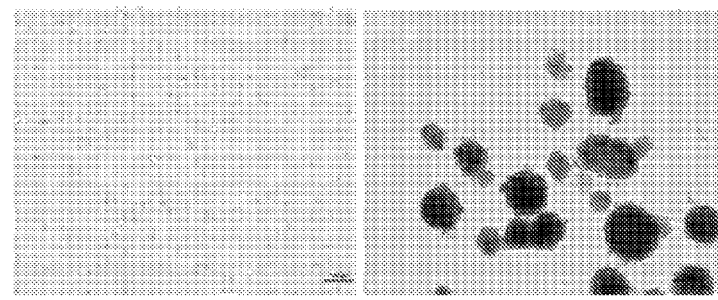
Figure 5 (D, E)

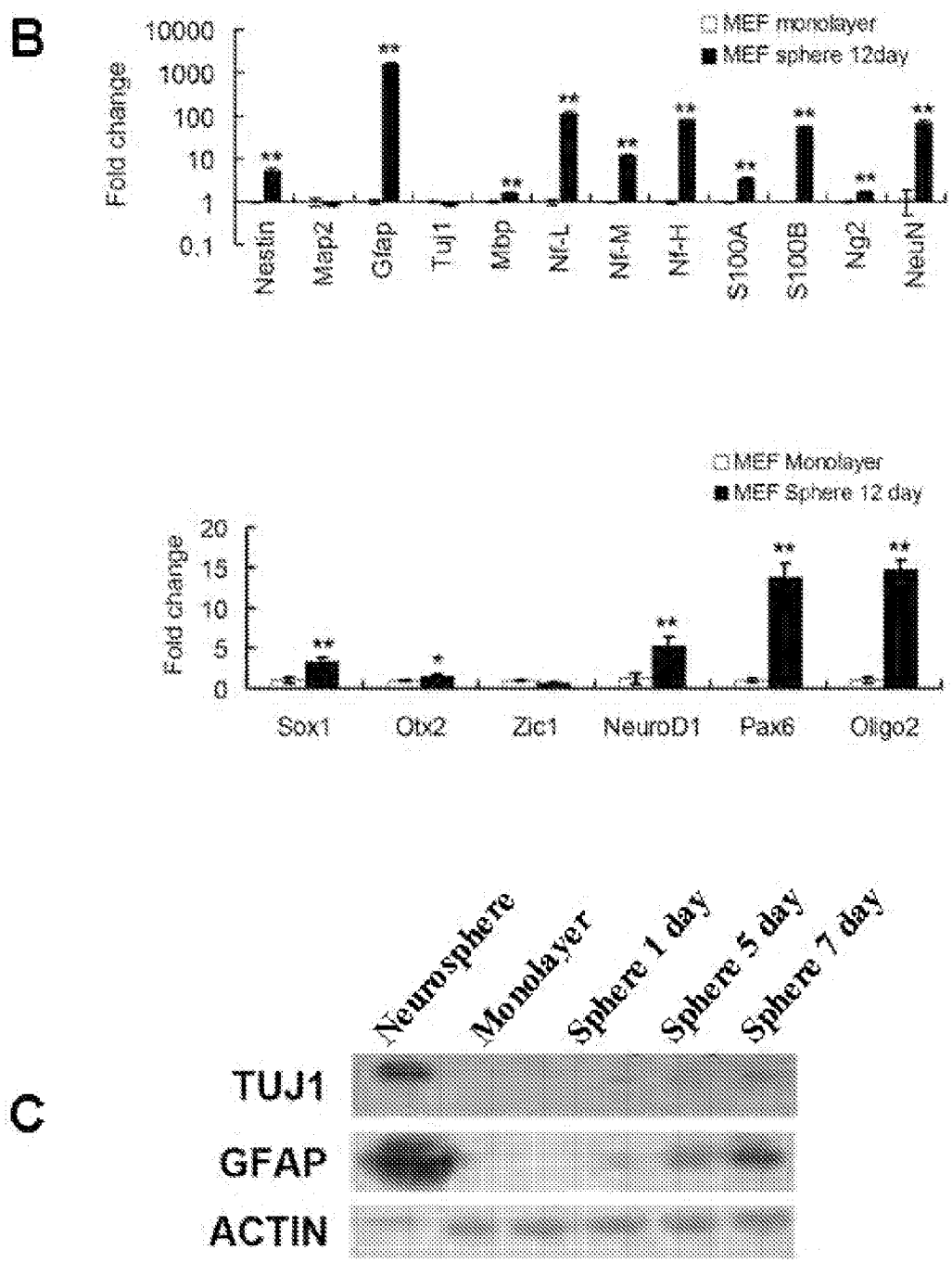
Figure 6 (B, C)

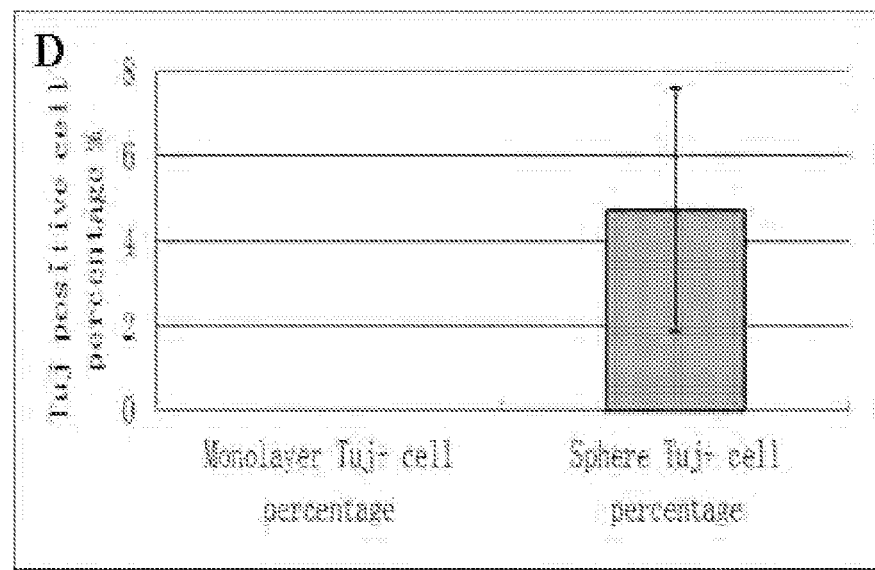
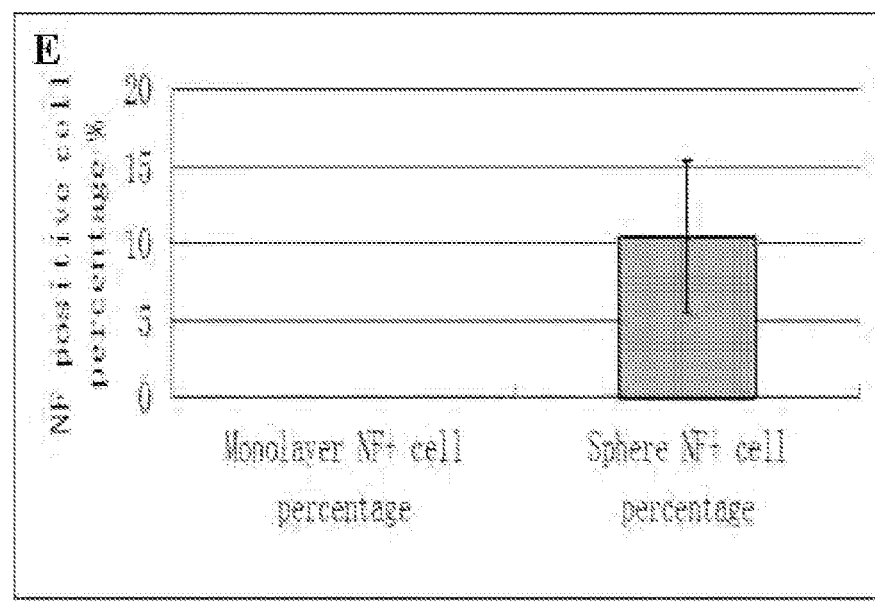
Figure 6 (D, E)

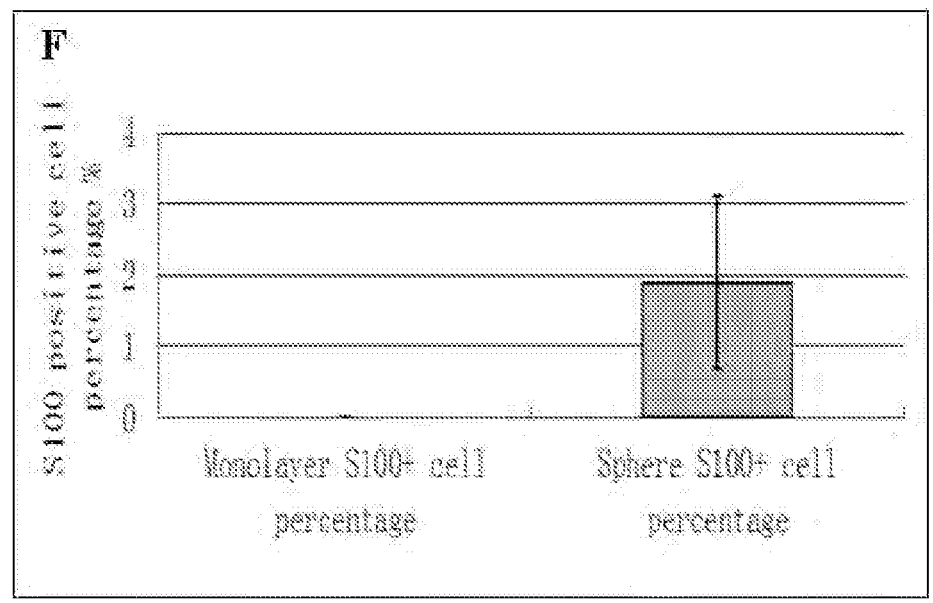
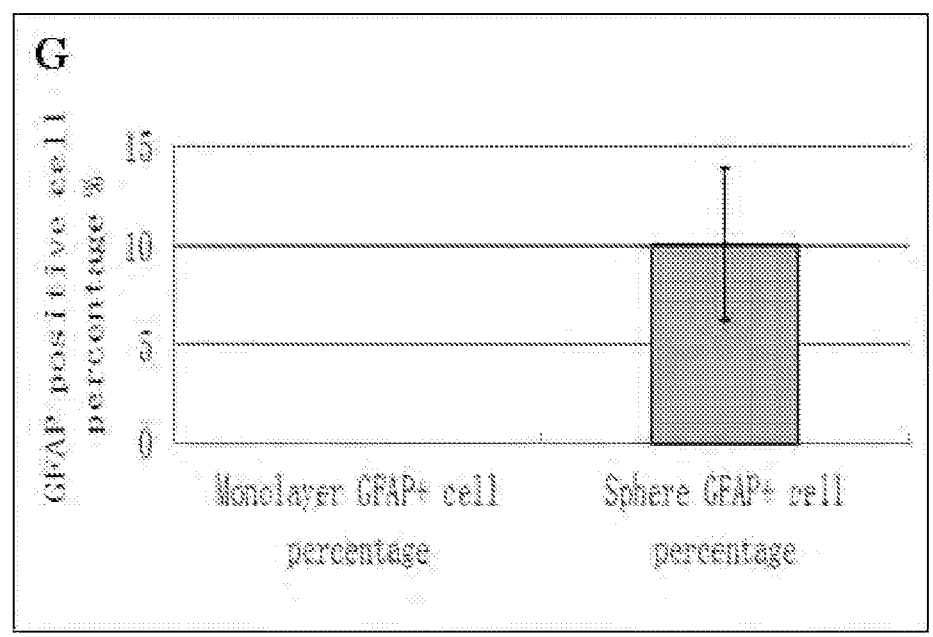
Figure 6 (F, G)

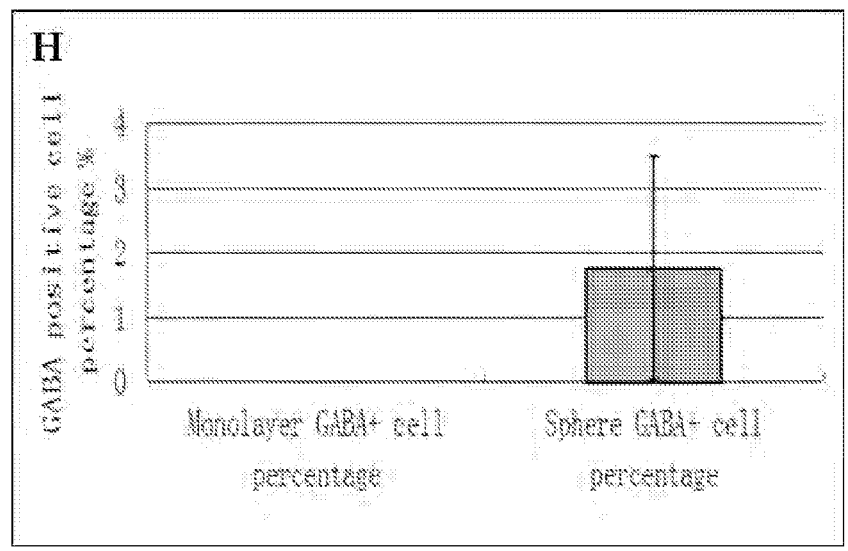
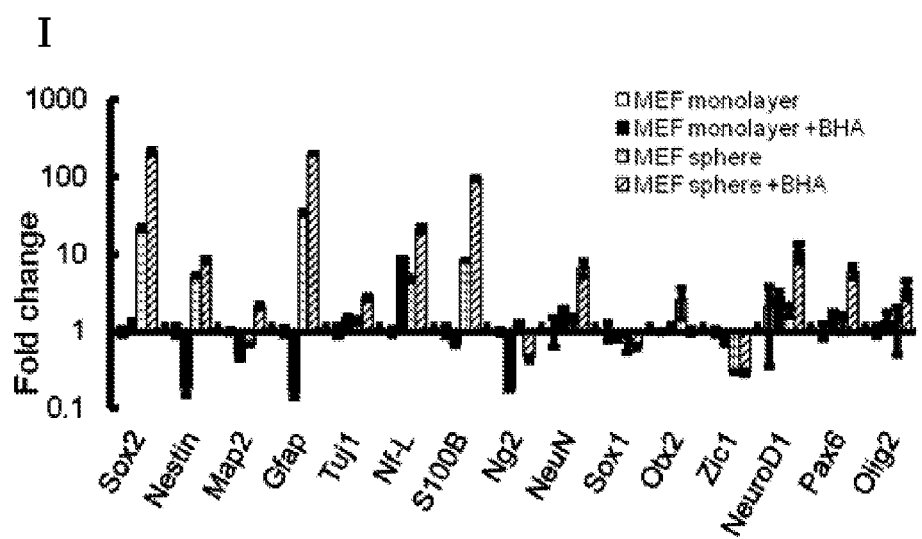
Figure 6 (H, I)

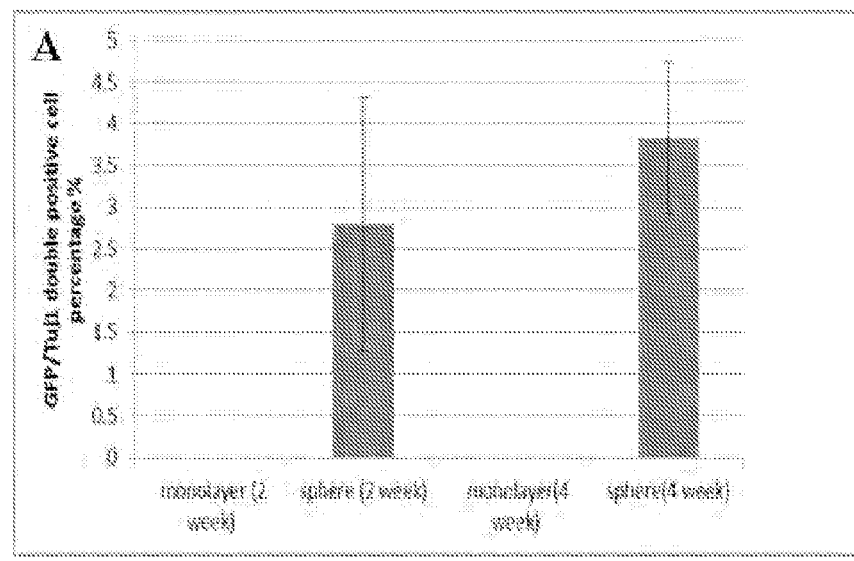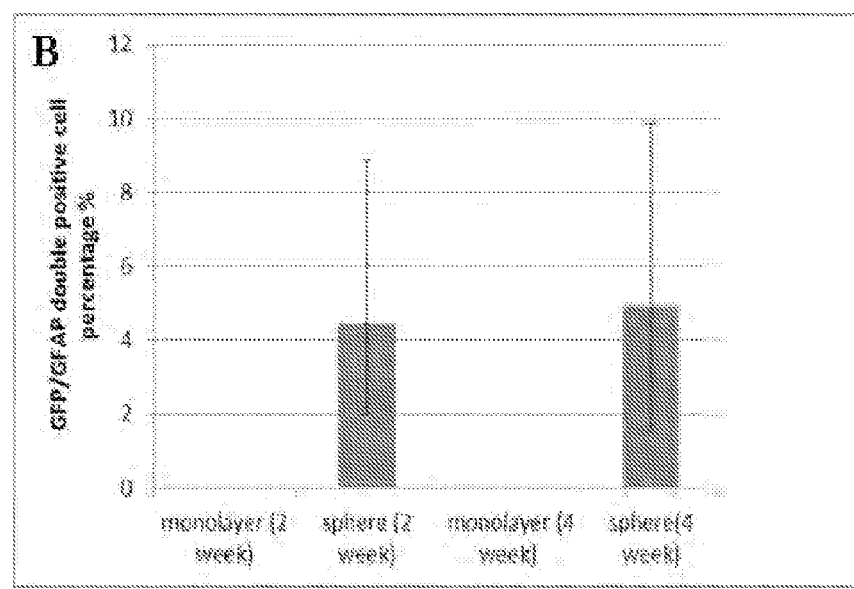
Figure 7 (A, B)

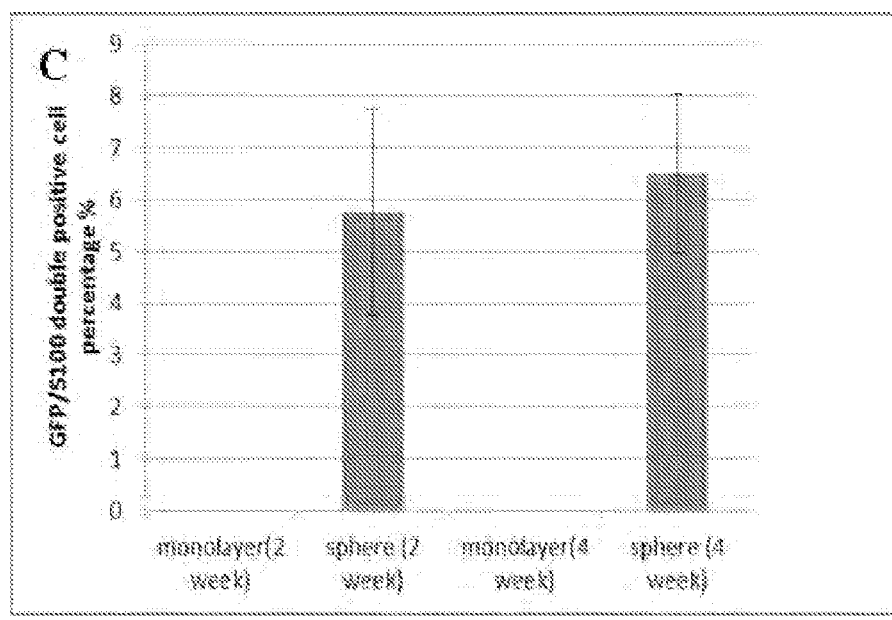
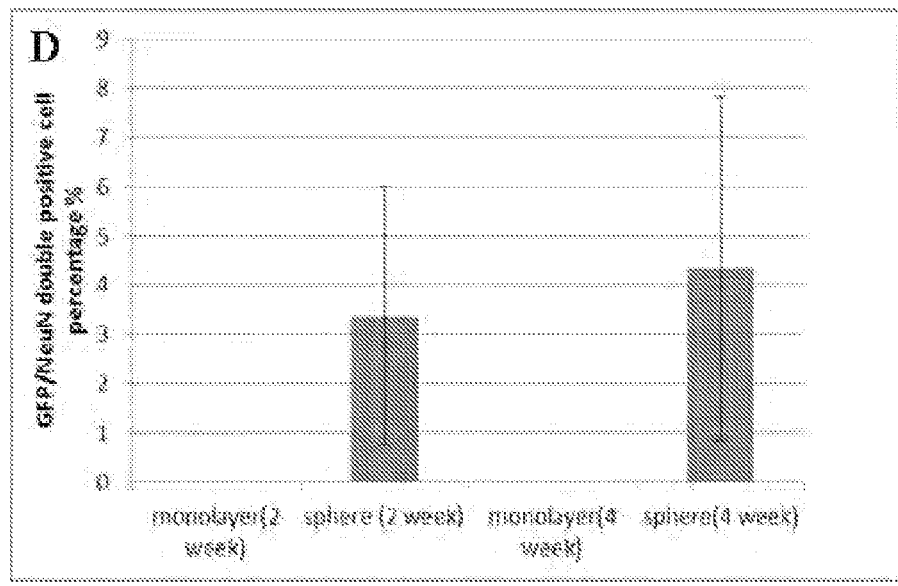
Figure 7 (C, D)

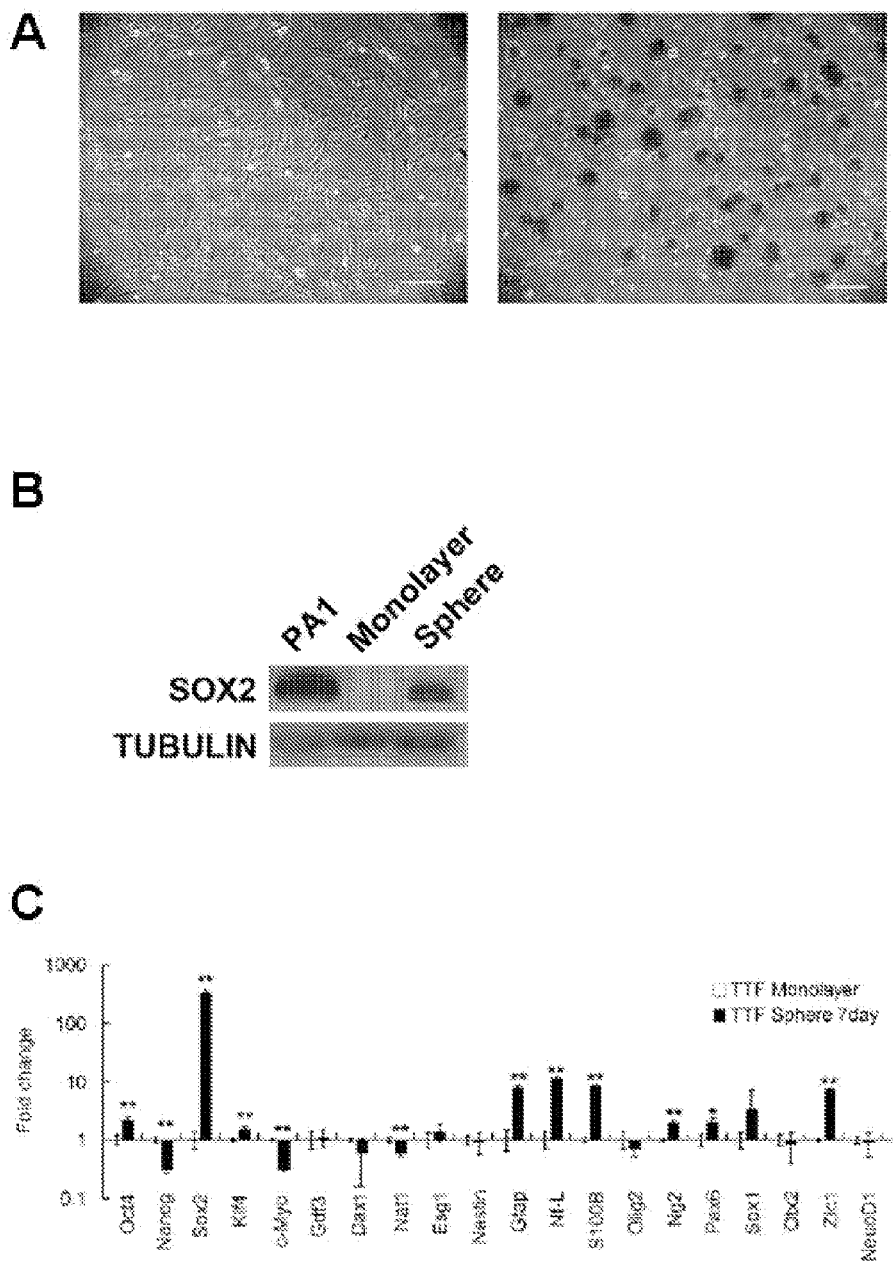
Figure 8 (A-C)

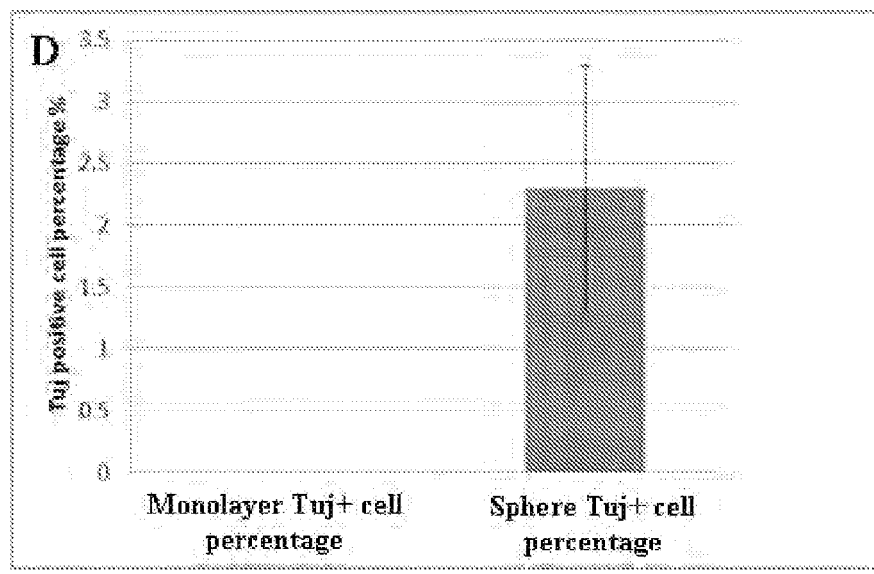
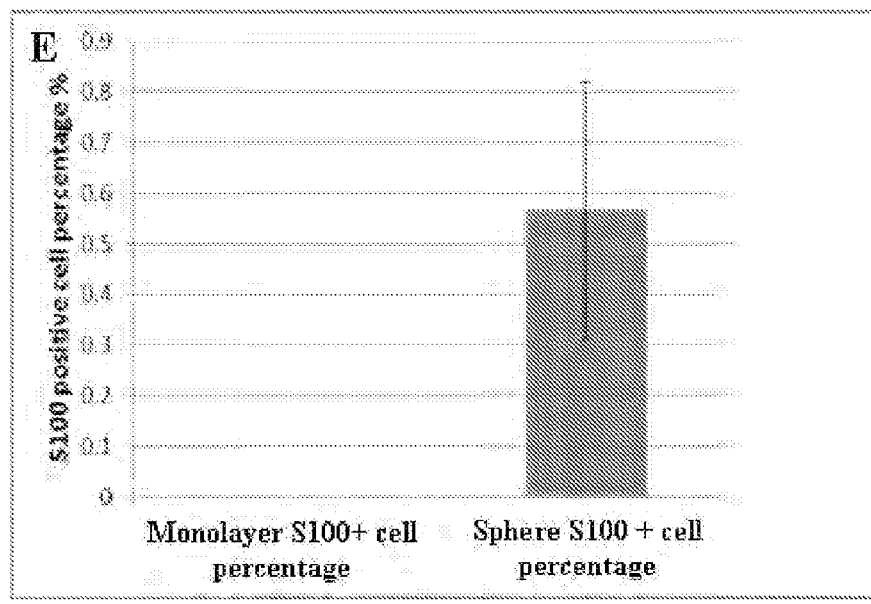
Figure 8 (D, E)

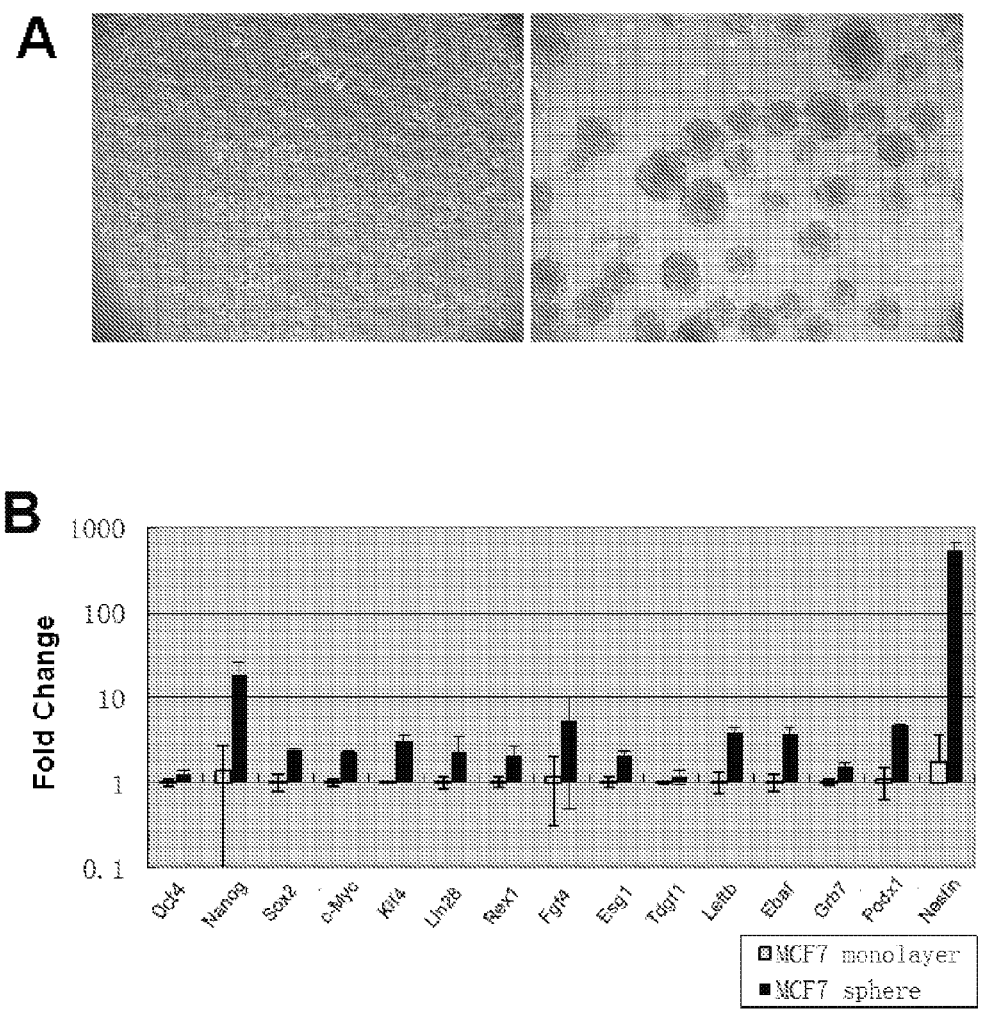
Figure 9 (A, B)

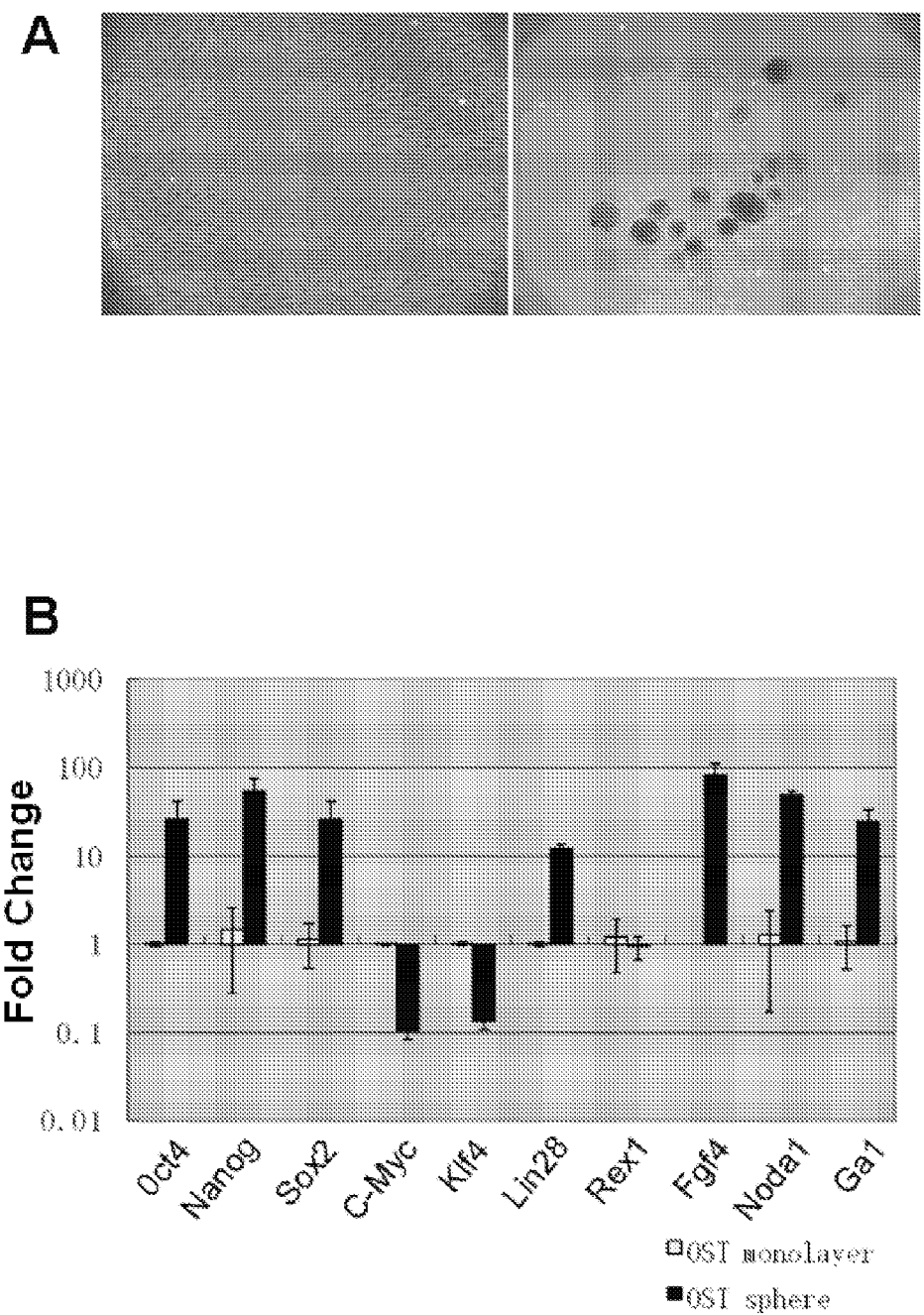
Figure 10 (A, B)

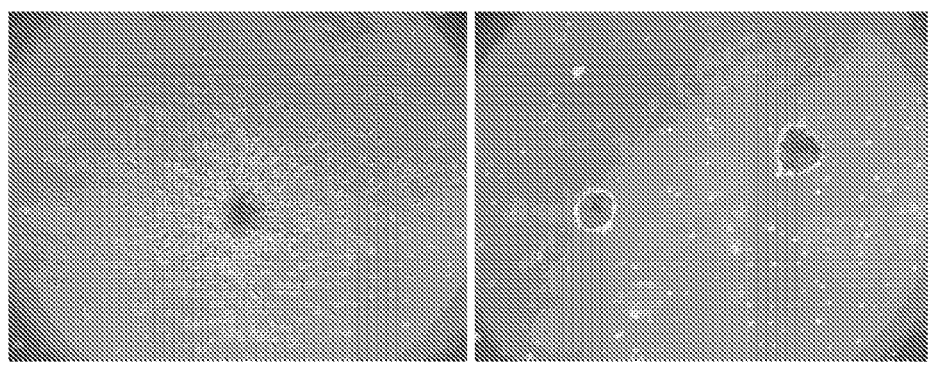
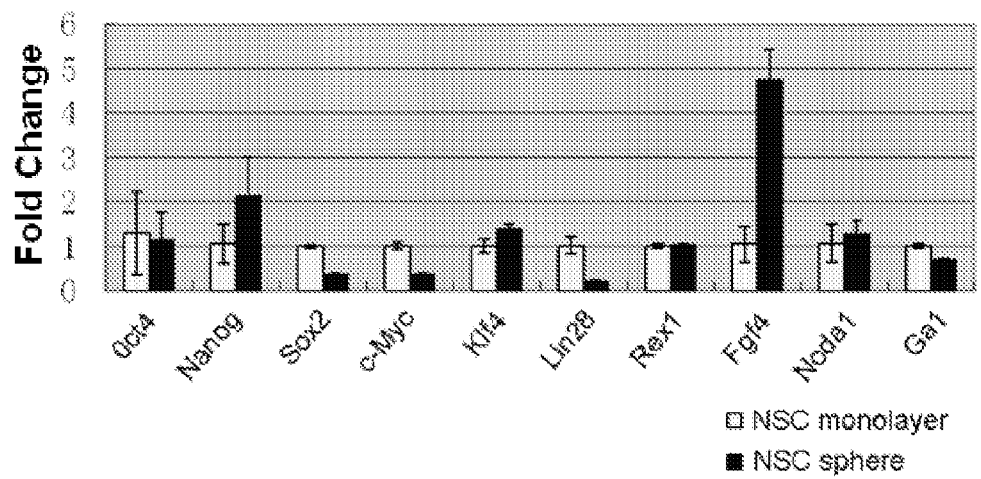
Figure 11 (A, B)

Acvr2b (NP_001097.2) (SEQ ID NO: 197)
MTAPWVALALLWGSLCAGSGRGEAETRECIYYNANWELERTNQSGLERCEGEQDKRLHC
YASWRNSSGTIELVKKGCWLDDFNCYDRQECVATEENPQVYFCCCEGNFCNERFTHLPEA
GGPEVTYEPPPTAPTLLTVLAYSLLPIGGLSLIVLLAFWMYRHRKPPYGHVDIHEDPGPPPP
SPLVGLKPLQLLEIKARGRFGCVWKAQLMNDFVAVKIFPLQDKQSWQSEREIFSTPGMKH
ENLLQFIAAEKRGSNLEVELWLITAFHDKGSLTDYLKGNIITWNELCHVAETMSRGLSYLH
EDVPWCRGEGHKPSIAHRDFKSKNVLLKSDLTAVLADFGLAVRFEPGKPPGDTHGQVGTR
RYMAPEVLEGAINFQRDAFLRIDMYAMGLVLWELVSRCKAADGPVDEYMLPFEEEIGQH
PSLEELQEVVVHKKMRPTIKDHWLKHPGLAQLCVTIEECWDHDAEARLSAGCVEERVSLI
RRSVNGTTSDCLVSLVTSVTNVDLPPKESSI c-Myc (NP_002458.2) (SEQ ID NO: 198)
MDFFRVVENQQPPATMPLNVSFTNRNYDLDYDSVQPYFYCDEEENFYQQQQQSELQPPAP
SEDIWKKFELLPTPPLSPSRRSGLCSPSYVAVTPFSLRGDNDGGGGSFSTADQLEMVTELLG
GDMVNQSFICDPDDETFIKNIIQDCMWSGFSAAAKLVSEKLASYQAARKDSGSPNPARGH
SVCSTSSLYLQDLSAAASECIDPSVVFPYPLNDSSSPKSCASQDSSAFSPSSDSLLSSTESSPQ
GSPEPLVLHEETPPTTSSDSEEEQEDEEEIDVVSVEKRQAPGKRSESGSPSAGGHSKPPHSPL
VLKRCHVSTHQHNYAAPPSTRKDYPAAKRVKLDSVRVLRQISNNRKCTSPRSSDTEENVK
RRTHNVLERQRRNELKRSFFALRDQIPELENNEKAPKVVILKKATAYILSVQAEEQKLISEE
DLLRKRREQLKHKLEQLRNSCA Dax1 (NP_031456.1) (SEQ ID NO: 199)
MAGEDHPWQGSILYNLLMSAKQKHASQEEREVRLGAQCWGCACGAQPVLGGERLSGG
QARSLLYRCCFCGENHPRQGGILYSMLTNARQPSVATQAPRARFGAPCWGCACGSAEPLV
GREGLPAGQAPSLLYRCCFCGEEHPRQGSILYSLLTSAQQTHVSREAPEAHRRGEWWQLS
YCTQSVGGPEGLQSTQAMAFLYRSYVCGEEQPQQISVASGTPVSADQTPATPQEQPRAPW
WDASPGVQRLITLKDPQVVCEAASAGLLKTLRFVKYLPCFQILPLDQQLVLVRSCWAPLL
MLELAQDHLHFEMMEIPETNTTQEMLTTRRQETEGPEPALPQATEQPQMVSAEAGHLLPA
AAVQAIKSFFFKCWSLNIDTKEYAYLKGTVLFNPDLPGLQCVKYIEGLQWRTQQILTEHIR
MMQREYQIRSAELNSALFLLRFINSDVVTELFFRPHGAVSMDDMMLEMLCAKL Ebaf (NP_001165896.1) (SEQ ID NO: 200)
MWPLWLCWALWVLPLAGPGAALTEEQLLGSLLRQLQLSEVPVLDRADMEKLVIPAHVRA
QYVVLLRRSHGDRSRGKRFSQSFREVAGRFLASEAALHRHGRLSPRSAQARVTVEWLRV
RDDGSNRTSLIDSRLVSVHESGWKAFDVTEAVNFWQQLSRPRQPLLLQVSVQREHLGPLA
SGAHKLVRFASQGAPAGLGEPQLELHTLDLRDYGAQGDCDPEAPMTEGTRCCRQEMYID
LQGMKWAKNWVLEPPGFLAYECVGTCQQPPEALAFNWPFLGPRQCIASETASLPMIVSIK
EGGRTRPQVVSLPNMRVQKCSCASDGALVPRRLQP

Figure 12 A

Esg1 (NP_001020461.1) (SEQ ID NO: 201)
MGTLPARRHIPPWVKVPEDLKDPEVFQVQTRLLKAIFGPDGSRIPYIEQVSKAMLELKALE
SSDLTEVVVYGSYLYKLRTKWMLQSMAEWHRQRQERGMLKLAEAMNALELGPWMK

Fgf4 (NP_001998.1) (SEQ ID NO: 202)
MSGPGTAAVALLPAVLLALLAPWAGRGGAAAPTAPNGTLEAELERRWESLVALSLARLPV
AAQPKEAAVQSGAGDYLLGIKRLRRLYCNVGIGFHLQALPDGRIGGAHADTRDSLLELSP
VERGVVSIFGVASRFFVAMSSKGKLYGSPFFTDECTFKEILLPNNYNAYESYKYPGMFIALS
KNGKTKKGNRVSPTMKVTHFLPRL

Frizzled 2 (NP_001457.1) (SEQ ID NO: 203)
MRPRSALPRLLLPLLLLPAAGPAQFHGEKGISIPDHGFCQPISIPLCTDIAYNQTIMPNLLGH
TNQEDAGLEVHQFYPLVKVQCSPELRFFLCSMYAPVCTVLEQAIPPCRSICERARQGCEAL
MNKFGFQWPERLRCEHFPRHGAEQICVGQNHSEDGAPALLTTAPPPGLQPGAGGTPGGPG
GGGAPPRYATLEHPFHCPRVLKVPSYLSYKFLGERDCAAPCEPARPDGSMFFSQEETRFAR
LWILTWSVLCCASTFFTVTTYLVDMQRFRYPERPIIFLSGCYTMVSVAYIAGFVLQERVVC
NERFSEDGYRTVVQGTKKEGCTILFMMLYFFSMASSIWWVILSLTWFLAAGMKWGHEAI
EANSQYFHILAAWAVPAVKTITILAMGQIDGDLLSGVCFVGLNSLDPLRGFVLAPLFVYLFI
GTSFLLAGFVSLFRIRTIMKHDGTKTEKLERLMVRIGVFSVLYTVPATIVIACYFYEQAFRE
HWERSWVSQHCKSLAIPCPAHYTPRMSPDFTVYMIKYLMTLIVGITSGFWIWSGKTLHSW
RKFYTRLTNSRHGETTV Frizzled 7 (NP_003498.1) (SEQ ID NO: 204)
MRDPGAAAPLSSLGLCALVLALLGALSAGAGAQPYHGEKGISVPDHGFCQPISIPLCTDIA
YNQTILPNLLGHTNQEDAGLEVHQFYPLVKVQCSPELRFFLCSMYAPVCTVLDQAIPPCRS
LCERARQGCEALMNKFGFQWPERLRCENFPVHGAGEICVGQNTSDGSGGPGGGPTAYPT
APYLPDLPFTALPPGASDGRGRPAFPFSCPRQLKVPPYLGYRFLGERDCGAPCEPGRANGL
MYFKEEERRFARLWVGVWSVLCCASTLFTVLTYLVDMRRFSYPERPIIFLSGCYFMVAVA
HVAGFLLEDRAVCVERFSDDGYRTVAQGTKKEGCTILFMVLYFTGMASSIWWVILSLTWF
LAAGMKWGHEAIEANSQYFHLAAWAVPAVKTITILAMGQVDGDLLSGVCYVGLSSVDAL
RGFVLAPLFVYLFIGTSFLLAGFVSLFRIRTIMKHDGTKTEKLEKLMVRIGVFSVLYTVPATI
VLACYFYEQAFREHWERTWLLQTCKSYAVPCPPGHFPPMSPDFTVFMIKYLMTMIVGITT
GFWIWSGKTLQSWRRFYHRLSHSSKGETAV Gdf3 (NP_032134.2) (SEQ ID NO: 205)
MQPYQRLLALGFLLLTLPWGQTSEFQDSDLLQFLGLEKAPSPHRFQPVPRVLRKHRARHA
AAASGASQDLCYVKELGVRGNLLQLLPDQGFFLNTQKPFQDGSCLQKVLYFNLSAIKEK
AKLTMAQLTDLGPRSYYNLRPELVVALSVVQDRGVWGRSHPKVGRLLFLRSVPGPQGQ
LQFNLQGALKDWSSNRLKNLDLHLEILVKEDRYSRVTVQPENPCDRLLRSLHASLLVVTL
NPKHCHPSSRKRRAAISVPKGFCRNFCHRHQLFINFQDLGWHKWVIAPKGFMANYCHGE
CPFSMTTYLNSSNYAFMQALMHMADPKVPKAVCVPTKLSPISMLYQDSDKNVILRHYED
MVVDECGCG

Figure 12 B

Grb7 (NP_001025173.1) (SEQ ID NO: 206)
MELDLSPPHLSSSPEDLCPAPGTPPGTPRPPDTPLPEEVKRSQPLLIPTTGRKLREEERRATS
LPSIPNPFPELCSPPSQSPILGGPSSARGLLPRDASRPHVVKVYSEDGACRSVEVAAGATAR
HVCEMLVQRAHALSDETWGLVECHPHLALERGLEDHESVVLVQAAWPVGGDSRFVFRK
NFAKYELFKSSPHSLFPEKMVSSCLDAHTGISHEDLIQNFLNAGSFPEIQGFLQLRGSGRKL
WKRFFCFLRRSGLYYSTKGTSKDPRHLQYVADVNESNVYVVTQGRKLYGMPTDFGFCVK
PNKLRNGHKGLRIFCSEDEQSRTCWLAAFRLFKYGVQLYKNYQQAQSRHLHPSCLGSPPL
RSASDNTLVAMDFSGHAGRVIENPREALSVALEEAQAWRKKTNHRLSLPMPASGTSLSAAI
HRTQLWFHGRISREESQRLIGQQGLVDGLFLVRESQRNPQGFVLSLCHLQKVKHYLILPSE
EEGRLYFSMDDGQTRFTDLLQLVEFHQLNRGILPCLLRHCCTRVAL

Integrin Alpha 8 (NP_003629.1) (SEQ ID NO: 207)
MSPGASRGPRGSQAPLIAPLCCAAAALGMLLWSPACQAFNLDVEKLTVYSGPKGSYFGYA
VDFHIPDARTASVLVGAPKANTSQPDIVEGGAVYYCPWPAEGSAQCRQIPFDTTNNRKIRV
NGTKEPIEFKSNQWFGATVKAHKGKVVACAPLYHWRTLKPTPEKDPVGTCYVAIQNFSAY
AEFSPCRNSNADPEGQGYCQAGFSLDFYKNGDLIVGGPGSFYWQGQVITASVADIIANYSF
KDILRKLAGEKQTEVAPASYDDSYLGYSVAAGEFTGDSQQELVAGIPRGAQNFGYVSIINS
TDMTFIQNFTGEQMASYFGYTVVVSDVNSDGLDDVLVGAPLFMEREFESNPREVGQIYLY
LQVSSLLFRDPQILTGTETFGREGSAMAHLGDLNQDGYNDIAIGVPFAGKDQRGKVLIYN
GNKDGLNTKPSQVLQGVWASHAVPSGFGFTLRGDSDIDKNDYPDLIVGAFGTGKVAVYR
ARPVVTVDAQLLLHPMIINLENKTCQVPDSMTSAACFSLRVCASVTGQSIANTIVLMAEV
QLDSLKQKGAIKRTLFLDNHQAHRVFPLVIKRQKSHQCQDFIVYLRDETEFRDKLSPINISL
NYSLDESTFKEGLEVKPILNYYRENIVSEQAHILVDCGEDNLCVPDLKLSARPDKHQVIIG
DENIILMLIINARNEGEGAYEAELFVMIPEEADYVGIERNNKGFRPLSCEYKMENVTRMV
VCDLGNPMVSGTNYSLGLRFAVPRLEKTNMSINFDLQIRSSNKDNPDSNFVSLQINITAVAQ
VEIRGVSHPPQIVLPIHNWEPEEEPHKEEEVGPLVEHIYELHNIGPSTISDTILEVGWPFSAR
DEFLLYIFHIQTLGPLQCQPNPNINPQDIKPAASPEDTPELSAFLRNSTIIPHLVRKRDVHVVE
FHRQSPAKILNCTNIECLQISCAVGRLEGGESAVLKVRSRLWAHTFLQRKNDPYALASLVSF
EVKKMPYTDQPAKLPEGSIAIKTSVIWATPNVSFSIPLWVIILAILLGLLVLAILTLALWKCGF
FDRARPPQEDMTDREQLTNDKTPEA Klf4 (NP_004226.3) (SEQ ID NO: 208)
MRQPPGESDMAVSDALLPSFSTFASGPAGREKTLRQAGAPNNRWREELSHMKRLPPVLPG
RPYDLAAATVATDLESGGAGAACGGSNLAPLPRRETEEFNDLLDLDFILSNSLTHPPESVAA
TVSSSASASSSSSPSSSGPASAPSTCSFTYPIRAGNDPGVAPGGTGGGLLYGRESAPPPTAPF
NLADINDVSPSGGFVAELLRPELDPVYIPPQQPQPPGGGLMGKFVLKASLSAPGSEYGSPS
VISVSKGSPDGSHPVVVAPYNGGPPRTCPKIKQEAVSSCTHLGAGPPLSNGHRPAAHDFPL
GRQLPSRTTPTLGLEEVLSSRDCHPALPLPPGFHPHPGPNYPSFLPDQMQPQVPPLHYQEL
MPPGSCMPEEPKPKRGRRSWPRKRTATHTCDYAGCGKTYTKSSHLKAHLRTHTGEKPYH
CDWDGCGWKFARSDELTRHYRKHTGHRPFQCQKCDRAFSRSDHLALHMKRHF

Figure 12 C

Leftb (NP_066277.1) (SEQ ID NO: 209)
MQPLWLCWALWVLPLASPGAALTGEQLLGSLLRQLQLKEVPTLDRADMEELVIPTIIVRA
QYVALLQRSHGDRSRGKRFSQSFREVAGRFLALEASTHLLVFGMEQRLPPNSELVQAVLRL
FQEPVPKAALHRHGRLSPRSARARVTVFWLRVRDDGSNRTSLIDSRLVSVHFSGWKAFDV
TLAVNFWQQLSRPRQPLLLQVSVQRLHLGPLASGAHKLVRFASQGAPAGLGEPQLLELHTL
DLGDYGAQGDCDPEAPMTEGTRCCRQEMYIDLQGMKWAENWVLEPPGFLAYECVGTCR
QPPEALAFKWPFLGPRQCIASETDSLPMIVSIKEGGRTRPQVVSLPNMRVQKCSCASDGAL
VPRRLQP Lim1 (NP_005559.2) (SEQ ID NO: 210)
MVHCAGCKRPILDRFLLNVLDRAWHVKCVQCCECKCNLTEKCFSREGKLYCKNDFFRCF
GTKCAGCAQGISPSDLVRRARSKVFIILNCFTCMMCNKQLSTGEELYIIDENKFVCKEDYL
SNSSVAKENSLHSATTGSDPSLSPDSQDPSQDDAKDSESANVSDKEAGSNENDDQNLGAK
RRGPRTTIKAKQLETLKAAFAATPKPTRHIREQLAQETGLNMRVIQVWFQNRRSKERRMK
QLSALGARRHAFFRSPRRMRPLVDRLEPGELIPNGPFSFYGDYQSEYYGPGGNYDITPQGP
PSSQAQTPVDLPFVPSSGPSGTPLGGLEHPLPGHHPSSEAQRFTDILAHPPGDSPSPEPSLPG
PLIISMSAEVFGPSPPFSSLSVNGGASYGNIILSHPPEMNEAAVW Lin28 (NP_078950.1) (SEQ ID NO: 211)
MGSVSNQQFAGGCAKAAEEAPEEAPEDAARAADEPQLLHGAGICKWFNVRMGFGFLSM
TARAGVALDPPVDVFVHQSKLHMEGFRSLKEGEAVEFTFKKSAKGLESIRVTGPGGVFCIG
SERRPKGKSMQKRRSKGDRCYNCGGLDHHAKECKLPPQPKKCHFCQSISHMVASCPLKA
QQGPSAQGKPTYFREEEEEIHSPTLLPEAQN Nanog (NP_079141.2) (SEQ ID NO: 212)
MSVDPACPQSLPCFEASDCKESSPMPVICGPEENYPSLQMSSAEMPHTETVSPLPSSMDLLI
QDSPDSSTSPKGKQPTSAEKSVAKKEDKVPVKKQKTRTVFSSTQLCVLNDRFQRQKYLSL
QQMQELSNILNLSYKQVKTWFQNRMKSKRWQKNNWPKNSNGVTQKASAPTYPSLYSS
YHQGCLVNPTGNLPMWSNQTWNNSTWSNQTQNIQSWSNHSWNTQTWCTQSWNNQAW
NSPFYNCGEESLQSCMQFQPNSPASDLEAALEAAGEGLNVIQQTTRYFSTPQTMDLFLNYS
MNMQPEDV Nat1 (NP_032699.1) (SEQ ID NO: 213)
MDIEAYFERIGYKNSVNKLDLATLTEVLQHQMRAVPFENLNMHCGEAMHLDLQDIFDHIV
RKKRGGWCLQVNIILLYWALTKMGFETTMLGGYVYITPVSKYSSEMVIILLVQVTISDRK
YIVDSAYGGSYQMWEPLELTSGKDQPQVPAIFLLTEENGTWYLDQIRREQYVPNEEFVNS
DLLEKNKYRKIYSFTLEPRVIEDFFYVNSYLQTSPASVFVSTSFCSLQTSEGVHCLVGSTFTS
RRFSYKDDVDLVEFKYVNEEEIEDVLKTAFGISLERKFVPKHGELVFTI

Figure 12 D

Ncam1 (NP_000606.3) (SEQ ID NO: 214)
MLQTKDLIWTLFFLGTAVSLQVDIVPSQGEISVGESKFFLCQVAGDAKDKDISWFSPNGEK
LTPNQQRISVVWNDDSSSTLTIYNANIDDAGIYKCVVTGEDGSESEATVNVKIFQKLMFKN
APTPQEFREGEDAVIVCDVVSSLPPTIIWKHKGRDVILKKDVRFIVLSNNYLQIRGIKKTDE
GTYRCEGRILARGEINFKDIQVIVNVPPTIQARQNIVNATANLGQSVTLVCDAEGFPEPTMS
WTKDGEQIEQEEDDEKYIFSDDSSQLTIKKVDKNDEAEYICIAENKAGEQDATIHLKVFAK
PKITYVENQTAMELEEQVTLTCEASGDPIPSITWRTSTRNISSEEKTLDGHMVVRSHARVSS
LTLKSIQYTDAGEYICTASNTIGQDSQSMYLEVQYAPKLQGPVAVYTWEGNQVNITCEVFA
YPSATISWFRDGQLLPSSNYSNIKIYNTPSASYLEVTPDSENDFGNYNCTAVNRIGQESLEFI
LVQADTPSSPSIDQVEPYSSTAQVQFDEPEATGGVPILKYKAEWRAVGEEVWHSKWYDAK
EASMEGIVTIVGLKPETTYAVRLAALNGKGLGEISAASEFKTQPVQGEPSAPKLEGQMGED
GNSIKVNLIKQDDGGSPIRIYLVRYRALSSEWKPEIRLPSGSDIIVMLKSLDWNAEYEVYV
VAENQQGKSKAAHFVFRTSAQPTAIPANGSPTSGLSTGAIVGILIVIFVLLLVVVDITCYFLN
KCGLFMCIAVNLCGKAGPGAKGKDMEEGKAAFSKDESKEPIVEVRTEEERTPNHDGGKH
TEPNETTPLTEPEKGPVEAKPECQETETKPAPAEVKTVPNDATQTKENESKA

Figure 12 E

Nestin (NP_006608.1) (SEQ ID NO: 215)
MEGCMGEESFQMWELNRRLEAYLARVKALEEQNELLSAELGGLRAQSADTSWRAHADD
ELAALRALVDQRWREKHAAEVARDNLAEELEGVAGRCQQLRLARERTTEEVARNRRAVE
AEKCARAWLSSQVAELERELEALRVAHEFERVGLNAQAACAPRCPAPPRGPPAPAPEVEEL
ARRLGEAWRGAVRGYQERVAHMETSLGQARERLGRAVQGAREGRLELQQLQAERGGLL
ERRAALEQRLEGRWQERLRATEKFQLAVEALEQEKQGLQSQIAQVLEGRQQLAIILKMSL
SLEVATYRTLLEAENSRLQTPGGGSKTSLSFQDPKLELQFPRTPEGRRLGSLLPVLSPTSLPS
PLPATLETPVPAFLKNQEFLQARTPTLASTPIPPTPQAPSPAVDAEIRAQDAPLSLLQTQGGR
KQAPEPLRAEARVAIPASVLPGPEEPGGQRQEASTGQSPEDHASLAPPLSPDHSSLEAKDGE
SGGSRVFSICRGEGEGQIWGLVEKETAIEGKVVSSLQQEIWEEEDLNRKEIQDSQVPLEKET
LKSLGEEIQESLKTLENQSHETLERENQECPRSLEEDLETLKSLEKENKELLKDVEVVRPLE
KEAVGQLKPTGKEDTQTLQSLQKENQELMKSLEGNLETELFPGTENQELVSSLQENLESLT
ALEKENQEPLRSPEVGDEEALRPLTKENQEPLRSLEDENKEAFRSLEKENQEPLKTLEEED
QSIVRPLETENIIKSLRSLEEQDQETLRTLEKETQQRRRSLGEQDQMTLRPPEKVDLEPLKS
LDQEIARPLENENQEFLKSLKEESVEAVKSLETEILESLKSAGQENLETLKSPETQAPLWTP
EEINQGAMNPLEKEIQEPLESVEVNQETFRLLEEENQESLRSLGAWNLENLRSPEEVDKES
QRNLEEEENLGKGEYQESLRSLEEEGQELPQSADVQRWEDTVEKDQELAQESPPGMAGV
ENEDEAELNLREQDGFTGKEEVVEQGELNATEEVWIPGEGHPESPEPKEQRGLVEGASVK
GGAEGLQDPEGQSQQVGAPGLQAPQGLPEAIEPLVEDDVAPGGDQASPEVMLGSEPAMG
ESAAGAEPGPGQGVGGLGDPGHLTREEVMEPPLEEESLEAKRVQGLEGPRKDLEEAGGL
GTEFSELPGKSRDPWEPPREGREESEAEAPRGAEEAFPAETLGHTGSDAPSPWPLGSEEAE
EDVPPVLVSPSPTYTPILEDAPGPQPQAEGSQEASWGVQGRAEALGKVESEQEELGSGEIP
EGPQEEGEESREESEEDELGETLPDSTPLGFYLRSPTSPRWDPTGEQRPPPQGETGKEGWD
PAVLASEGLEAPPSEKEEGEEGEEECGRDSDLSEEFEDLGTEAPFLPGVPGEVAEPLGQVPQ
LLLDPAAWDRDGESDGFADEEESGEEGEEDQEEGREPGAGRWGPGSSVGSLQALSSSQRG
EFLESDSVSVSVPWDDSLRGAVAGAPKTALETESQDSAEPSGSEEESDPVSLEREDKVPGP
LEIPSGMEDAGPGADIIGVNGQGPNLEGKSQHVNGGVMNGLEQSEEVGQGMPLVSEGDR
GSPFQEEEGSALKTSWAGAPVHLGQGQFLKFTQREGDRESWSSGED Nodal (NP_060525.3) (SEQ ID NO: 216)
MHAHCLPFLLHAWWALLQAGAATVATALLRTRGQPSSPSPLAYMLSLYRDPLPRADIIRSL
QAEDVAVDGQNWTFAFDFSFLSQQEDLAWAELRLQLSSPVDLPTEGSLAIEIFHQPKPDTE
QASDSCLERFQMDLFTVTLSQVTFSLGSMVLEVTRPLSKWLKHPGALEKQMSRVAGECW
PRPPTPPATNVLLMLYSNLSQEQRQLGGSTLLWEAESSWRAQEGQLSWEWGKRHRRHHL
PDRSQLCRKVKFQVDFNLIGWGSWIIYPKQYNAYRCEGECPNPVGEEFHPTNHAYIQSLL
KRYQPHRVPSTCCAPVKTKPLSMLYVDNGRVLLDHHKDMIVEECGCL

Figure 12 F

Ntrk2 (NP_001007098.1) (SEQ ID NO: 217)
MSSWIRWHGPAMARLWGFCWLVVGFWRAAFACPTSCKCSASRIWCSDPSPGIVAFPRLEP
NSVDPENITEIFIANQKRLEHNEDDVEAYVGLRNLTIVDSGLKFVAHKAFLKNSNLQHINFT
RNKLTSLSRKHFRHLDLSELILVGNPFTCSCDIMWIKTLQEAKSSPDTQDLYCLNESSKNIP
LANLQIPNCGLPSANLAAPNLTVEEGKSITLSCSVAGDPVPNMYWDVGNLVSKHMNETSH
TQGSLRITNISSDDSGKQISCVAENLVGEDQDSVNLTVHFAPTITFLESPTSDHHWCIPFTVK
GNPKPALQWFYNGAILNESKYICTKIHVTNHTEYHGCLQLDNPTHMNNGDYTLIAKNEY
GKDEKQISAHFMGWPGIDDGANPNYPDVIYEDYGTAANDIGDTTNRSNEIPSTDVTDKTG
REHLSVYAVVVIASVVGFCLLVMLFLLKLARHSKFGMKGFVLFHKIPLDG Oct4 (NP_001167002.1) (SEQ ID NO: 218)
MGVLFGKVFSQTTICRFEALQLSFKNMCKLRPLLQKWVEEADNNENLQEICKAETLVQA
RKRKRTSIENRVRGNLENLFLQCPKPTLQQISHIAQQLGLEKDVVRVWFCNRRQKGKRSS
SDYAQREDFEAAGSPFSGGPVSFPLAPGPHFGTPGYGSPHFTALYSSVPFPEGEAFPPVSVT
TLGSPMHSN Olig2 (NP_058663.2) (SEQ ID NO: 219)
MDSDASLVSSRPSSPEPDDLFLPARSKGGSSSGFTGGTVSSSTPSDCPPELSSELRGAMGAS
GAHPGDKLGGGGFKSSSSSTSSSTSSAATSSTKKDKKQMTEPELQQLRLKINSRERKRMH
DLNIAMDGLREVMPYAHGPSVRKLSKIATLLLARNYILMLTNSLEEMKRLVSEIYGGHHA
GFHPSACGGLAHSAPLPTATAHPAAAAHAAHHPAVHHPILPPAAAAAAAAAAAAVSSAS
LPGSGLSSVGSIRPPHGLLKSPSAAAAAPLGGGGGGSGGSGGFQHWGGMPCPCSMCQVP
PPHHHVSAMGAGTLPRLTSDAK Pax2 (NP_000269.2) (SEQ ID NO: 220)
MDMHCKADPFSAMHPGHGGVNQLGGVFVNGRPLPDVVRQRIVELAHQGVRPCDISRQL
RVSHGCVSKILGRYYETGSIKPGVIGGSKPKVATPKVVDKIAEYKRQNPTMFAWEIRDRLL
AEGICDNDTVPSVSSINRHRTKVQQPFHPTPDGAGTGVTAPGHTIVPSTASPPVSSASNDPV
GSYSINGILGIPRSNGEKRKRDEDVSEGSVPNGDSQSGVDSLRKHLRADTFTQQQLEALDR
VFERPSYPDVFQASEIIKSEQGNEYSLPALTPGLDEVKSSLSASTNPELGSNVSGTQTYPVV
TGRDMASTTLPGYPPHVPPTGQGSYPTSTLAGMVPGSEFSGNPYSHPQYTAYNEAWRFSN
PALLSSPYYYSAAPRSAPAAAAAAYDRH Pax6 (NP_001231127.1) (SEQ ID NO: 221)
MQNSHSGVNQLGGVFVNGRPLPDSTRQKIVELAHSGARPCDISRILQTHADAKVQVLDN
ENVSNGCVSKILGRYYETGSIRPRAIGGSKPRVATPEVVSKIAQYKRECPSIFAWEIRDRLLS
EGVCTNDNIPSVSSINRVLRNLASEKQQMGADGMYDKLRMLNGQTGSWGTRPGWYPGT
SVPGQPTQDGCQQQEGGGENTNSISSNGEDSDEAQMRLQLKRKLQRNRTSFTQEQIEALE
KEFERTHYPDVFARERLAAKIDLPEARIQVWFSNRRAKWRREEKLRNQRRQASNTPSHIPI
SSSFSTSVYQPIPQPTTPVSSFTSGSMLGRTDTALTNTYSALPPMPSFTMANNLPMQPPVPS
QTSSYSCMLPTSPSVNGRSYDTYTPPHMQTHMNSQPMGTSGTTSTGLISPGVSVPVQVPG
SEPDMSQYWPRLQ

Figure 12 G

Podxl (NP_001018121.1) (SEQ ID NO: 222)
MRCALALSALLLLLSTPPLLPSSPSPSPSPSQNATQTTTDSSNKTAPTPASSVTIMATDTAQQ
STVPTSKANEILASVKATTLGVSSDSPGTTTLAQQVSGPVNTTVARGGGSGNPTTTIESPKS
TKSADTTTVATSTATAKPNTTSSQNGAEDTTNSGGKSSHSVTTDLTSTKAEHLTTPHPTSPL
SPRQPTSTHPVATPTSSGHDHLMKISSSSSTVAIPGYTFTSPGMTTTLLETVFHHVSQAGLEL
LTSGDLPTLASQSAGITASSVISQRTQQTSSQMPASSTAPSSQETVQPTSPATALRTPTLPETM
SSSPTAASTTHRYPKTPSPTVAHESNWAKCEDLETQTQSEKQLVLNLTGNTLCAGGASDEK
LISLICRAVKATFNPAQDKCGIRLASVPGSQTVVVKEITIHTKLPAKDVYERLKDKWDELK
EAGVSDMKLGDQGPPEEAEDRFSMPLIITIVCMASFLLLVAALYGCCHQRLSQRKDQQRLT
EELQTVENGYHDNPTLEVMETSSEMQEKKVVSLNGELGDSWIVPLDNLTKDDLDEEEDT
HL Rex1 (NP_065746.3) (SEQ ID NO: 223)
MLRSTGFFRAIDCPYWSGAPGGPCRRPYCHFRHRGARGSGAPGDGGEAPPAAGLGYDPY
NPELPKPPAQRENGTLGLGEEPRPDVLELELVNQAIEAVRSEVELEQRRYRELLETTREHRS
AEAPALAPRGPNASPTVGPDEDAFPLAFDYSPGSHGLLSPDAGYQPTPLAAPAEPGSKYSL
ASLDRGQGRGGGGGGALEYVPKAVSQPRRHSRPVPSGKYVVDNSRPPTDLEYDPLSNYS
ARHLSRASSRDERAAKRPRGSRGSEPYTPAPKKLCDPFGSCDARFSDSEDEAATVPGNEPT
TASTPKARADPEIKATGQPPSKEGLEAEGGGLRETKETAVQCDVGDLQPPPAKPASPAQVQ
SSQDGGCPKEGKPKKKKTGAPPAPSCKDGAQGKDKTKDKGRGRPVEKPRADKKGPQAS
SPRRKAERPEGTKKKPSSATPVATSGKGRPDRPARRPSPTSGDSRPAAGRGPPRPLQLPDRK
STKAPSGKLVERKARSLDEGASQDAPKLKKRALSHADLFGDESEDEAAGPGVPSVWPSA
LPSLSSDSDSDSDSSLGFPEAQGPPKRLKASPPPSPAPSSSSSSSSSTSSAGADVDYSALEKE
VDFDSDPMEECLRIFNESTSVKTEDRGRLARQPPKEEKSEEKGLSGLTTLFPGQKRRISHLS
KQGQEVEPPRRGPAVPPARPPTAQEVCYLRAQQAQRASASLLQAPARLAEKSPSVHISAPG
EKRRIAHIPNPRLAAAPTGAKRTLAASGSQSSNGPEPGGQQLKTRTLSGMASKTTTTIIPKR
IAHSPSLQSLKKPIIPKEFGGKVPTVIRQRYLNLFIEECLKFCTSNQEAIEKALNEEKVAYDR
SPSKNIYLNVAVNTLKKLRGLAPSAVPGLSKTSGRRVVSHEVVLGGRLAAKTSFSLSRPSSP
RVEDLKGAALYSRLREYLLTQDQLKENGYPFPHPERPGGAIIFTAEEKRPKDSSCRTCCRC
GTEYLVSSSGRCIRDEECYYHWGRLRRNRVAGGWETQYMCCSAAAGSVGCQVAKQHVQ
DGRKERLEGFVKTFEKELSGDTHPGIYALDCEMSYTTYGLELTRVTVVDTDVHVVYDTFV
KPDNEIVDYNTRFSGVTEADLADTSVTLRDVQAVLLSMFSADTILIGHSLESDLLALKVIH
STVVDTSVLFPHRLGLPYKRSLRNLMADYLRQIIQDNVDGHSSSEDAGACMHLVIWKVR
EDAKTKR

Figure 12 H

Slc2a3 (NP_035531.3) (SEQ ID NO: 224)
MGTTKVTPSLVFAVTVATIGSFQFGYNTGVINAPETILKDFLNYTLEERLEDLPSEGLLTAL
WSLCVAIFSVGGMIGSFSVGLFVNRFGRRNSMLLVNLLAIIAGCLMGFAKIAESVEMLILG
RLLIGIFCGLCTGFVPMYIGEVSPTALRGAFGTLNQLGIVVGILVAQIFGLDFILGSEELWPG
LLGITIPAILQSAALPFCPESPRFLLINKKEEDQATEILQRLWGTSDVVQEIQEMKDESVRM
SQEKQVTVLELFRSPNYVQPLLISIVLQLSQQLSGINAVFYYSTGIFKDAGVQEPIYATIGAG
VVNTIFTVVSLFLVERAGRRTLHMIGLGGMAVCSVFMTISLLLKDDYEAMSFVCIVAILIYV
AFFEIGPGPIPWFIVAELFSQGPRPAAIAVAGCCNWTSNFLVGMLFPSAAAYLGAYVFIIFAA
FLIFFLIFTFFKVPETKGRTFEDIARAFEGQAIISGKGPAGVELNSMQPVKETPGNA

Sall1 (NP_001121364.1) (SEQ ID NO: 225)
MNDTVNKTDQVDCSDLSEHNGLDREESMEVEAPVANKSGSGTSSGSHSSTAPSSSSSSSSS
SGGGGSSSTGTSAITTSLPQLGDLTTLGNFSVINSNVIIENLQSTKVAVAQFSQEARCGGASG
GKLAVPALMEQLLALQQQQIHQLQLIEQIRHQILLLASQNADLPTSSSPSQGTLRTSANPLS
TLSSHLSQQLAAAAGLAQSLASQSASISGVKQLPPIQLPQSSSGNTIIPSNSGSSPNMNILAA
AVTTPSSEKVASSAGASIIVSNPAVSSSSSPAFAISSLLSPASNPLLPQQASANSVFPSPLPNIG
TTAEDLNSLSALAQQRKSKPPNVTAFEAKSTSDEAFFKHKCRFCAKVFGSDSALQIHLRSH
TGERPFKCNICGNRFSTKGNLKVHFQRHKEKYPHIQMNPYPVPEHLDNIPTSTGIPYGMSI
PPEKPVTSWLDTKPVLPTLTTSVGLPLPPTLPSLIPFIKTEEPAPIPISHSATSPPGSVKSDSGG
PESATRNLGGLPEEAEGSTLPPSGGKSEESGMVTNSVPTASSSVLSSPAADCGPAGSATTFT
NPLLPLMSEQFKAKFPFGGLLDSAQASETSKLQQLVENIDKKATDPNECIICHRVLSCQSAL
KMHYRTHTGERPFKCKICGRAFTTKGNLKTHYSVHRAMPPLRVQHSCPICQKKFTNAVVL
QQHIRMHMGGQIPNTPVPDSYSESMESDTGSFDEKNFDDLDNFSDENMEDCPEGSIPDTP
KSADASQDSLSSSPLPLEMSSIAALENQMKMINAGLAEQLQASLKSVENGSIEGDVLTNDS
SSVGGDMESQSAGSPAISESTSSMQALSPSNSTQEFHKSPSIEEKPQRAVPSEFANGLSPTPV
NGGALDLTSSHAEKIIKEDSLGILFPFRDRGKFKNTACDICGKTFACQSALDIHYRSHTKER
PFICTVCNRGFSTKGNLKQHMLTHQMRDLPSQLFEPSSNLGPNQNSAVIPANSLSSLIKTEV
NGFVHVSPQDSKDTPTSHVPSGPLSSSATSPVLLPALPRRTPKQHYCNTCGKTFSSSSALQI
HERTHTGEKPFACTICGRAFTTKGNLKVHMGTHMWNSTPARRGRRLSVDGPMTFLGGNP
VKFPEMFQKDLAARSGSGDPSSFWNQYAAALSNGLAMKANEISVIQNGGIPPIPGSLGSG
NSSPVSGLTGNLERLQNSEPNAPLAGLEKMASSENGTNFRFTRFVEDSKEIVTS Six2 (NP_058628.3) (SEQ ID NO: 226)
MSMLPTFGFTQEQVACVCEVLQQGGNIERLGRFLWSLPACEHLHKNESVLKAKAVVAFH
RGNFRELYKILESIIQFSPIINIIAKLQQLWLKAIIYIEAEKLRGRPLGAVGKYRVRRKFPLPR
SIWDGEETSYCFKEKSRSVLREWYAHNPYPSPREKRELAEATGLTTTQVSNWFKNRRQRD
RAAEAKERENNENSNSNSHNPLNGSGKSVLGSSEDEKTPSGTPDHSSSSPALLLSPPPPGLP
SLHSLGHPPGPSAVPVPVPGGGGADPLQHHHGLQDSILNPMSANLVDLGS

Figure 12 I

Sox1 (NP_033259.2) (SEQ ID NO: 227)
MYSMMMETDLHSPGGAQAPTNLSGPAGAGGGGGGGGGGGGGGGTKANQDRVKRPMN
AFMVWSRGQRRKMAQENPKMIINSEISKRLGAEWKVMSEAEKRPFIDEAKRLRALHMK
EHPDYKYRPRRKTKTLLKKDKYSLAGGLLAAGAGGGGAAVAMGVGVGVGAAAVGQRL
ESPGGAAGGGYAHVNGWANGAYPGSVAAAAAAAAMMQEAQLAYGQHPGAGGAHPHA
HPAHPHPHHPHAHPHNPQPMHRYDMGALQYSPISNSQGYMSASPSGYGGIPYGAAAAAA
AAAGGAHQNSAVAAAAAAAAAASSGALGALGSLVKSEPSGSPPAPAHSRAPCPGDLREMIS
MYLPAGEGGDPAAAAAAAAQSRLHSLPQHYQGAGAGVNGTVPLTHI
Sox2 (NP_003097.1) (SEQ ID NO: 228)
MYNMMETELKPPGPQQTSGGGGGNSTAAAAGGNQKNSPDRVKRPMNAFMVWSRGQRR
KMAQENPKMHNSEISKRLGAEWKLLSETEKRPFIDEAKRLRALHMKEHPDYKYRPRRKT
KTLMKKDKYTLPGGLLAPGGNSMASGVGVGAGLGAGVNQRMDSYAHMNGWSNGSYS
MMQDQLGYPQHPGLNAHGAAQMQPMHRYDVSALQYNSMTSSQTYMNGSPTYSMSYS
QQGTPGMALGSMGSVVKSEASSSPPVVTSSSHSRAPCQAGDLRDMISMYLPGAEVPEPAA
PSRLHMSQHYQSGPVPGTAINGTLPLSHM

Tdgf1 (NP_001167607.1) (SEQ ID NO: 229)
MAISKVFELGLVAGLGHQEFARPSRGYLAFRDDSIWPQEEPAIRPRSSQRVPPMGIQHSKEL
NRTCCLNGGTCMLGSFCACPPSFYGRNCEHDVRKENCGSVPHDTWLPKKCSLCKCWHG
QLRCFPQAFLPGCDGLVMDEHLVASRTPELPPSARTTTFMLVGICLSIQSYY Wt1 (NP_000369.3) (SEQ ID NO: 230)
MQDPASTCVPEPASQHTLRSGPGCLQQPEQQGVRDPGGIWAKLGAAEASAERLQGRRSR
GASGSEPQQMGSDVRDLNALLPAVPSLGGGGGCALPVSGAAQWAPVLDFAPPGASAYGS
LGGPAPPPAPPPPPPPPHSFIKQEPSWGGAEPHEEQCLSAFTVHFSGQFTGTAGACRYGPF
GPPPPSQASSGQARMFPNAPYLPSCLESQPAIRNQGYSTVTFDGTPSYGHTPSHHAAQFPN
HSFKHEDPMGQQGSLGEQQYSVPPPVYGCHTPTDSCTGSQALLLRTPYSSDNLYQMTSQL
ECMTWNQMNLGATLKGHSTGYESDNHTTPILCGAQYRIHTHGVFRGIQDVRRVPGVAPTL
VRSASETSEKRPFMCAYPGCNKRYFKLSHLQMHSRKHTGEKPYQCDFKDCERRFSRSDQ
LKRHQRRHTGVKPFQCKTCQRKFSRSDHLKTHTRTHTGEKPFSCRWPSCQKKFARSDELV
RHHNMHQRNMTKLQLAL

Figure 12 J

Actn4 (NP_004915.2) (SEQ ID NO: 231)
MVDYHAANQSYQYGPSSAGNGAGGGGSMGDYMAQEDDWDRDLLLDPAWEKQQRKTF
TAWCNSHLRKAGTQIENIDEDFRDGLKLMLLLEVISGERLPKPERGKMRVHKINNVNKAL
DFIASKGVKLVSIGAEEIVDGNAKMTLGMIWTIILRFAIQDISVEETSAKEGLLLWCQRKTA
PYKNVNVQNFHISWKDGLAFNALIIIRIIRPELIEYDKLRKDDPVTNLNNAFEVAEKYLDIP
KMLDAEDIVNTARPDEKAIMTYVSSFYHAFSGAQKAETAANRICKVLAVNQENEHLMED
YEKLASDLLEWIRRTIPWLEDRVPQKTIQEMQQKLEDFRDYRRVHKPPKVQEKCQLEINF
NTLQTKLRLSNRPAFMPSEGKMVSDINNGWQHLEQALKGYEEWLLNEIRRLERLDHLAE
KFRQKASIHEAWTDGKEAMLKHRDYETATLSDIKALIRKHEAFESDLAAHQDRVEQIAAI
AQELNELDYYDSIINVNTRCQKICDQWDALGSLTHSRREALEKTEKQLEAIDQLIILEYAK
RAAPFNNWMESAMEDLQDMFIVHTIEEIEGLISAHDQFKSTLPDADREREAILAIHKEAQR
IAESNHIKLSGSNPYTTVTPQIINSKWEKVQQLVPKRDHALLEEQSKQQSNEHLRRQFASQ
ANVVGPWIQTKMEEIGRISIIEMNGTLEDQLSHLKQYERSIVDYKPNLDLLEQQHQLIQEAL
IFDNKHTNYTMEHIRVGWEQLLTTIARTINEVENQILTRDAKGISQEQMQEFRASFNHFDK
DHGGALGPEEFKACLISLGYDVENDRQGEAEFNRIMSLVDPNIISGLVTFQAFIDFMSRETT
DTDTADQVIASFKVLAGDKNFITAEELRRELPPDQAEYCIARMAPYQGPDAVPGALDYKS
FSTALYGESDL Afp (NP_001125.1) (SEQ ID NO: 232)
MKWVESIFLIFLLNFTESRTLHRNEYGIASILDSYQCTAEISLADLATIFFAQFVQEATYKEV
SKMVKDALTAIEKPTGDEQSSGCLENQLPAFLEELCHEKEILEKYGHSDCCSQSEEGRHNC
FLAHKKPTPASIPLFQVPEPVTSCEAYEEDRETFMNKFIYEIARRHPFLYAPTILLWAARYDK
IIPSCCKAENAVECFQTKAATVTKELRESSLLNQHACAVMKNFGTRTFQAITVTKLSQKFT
KVNFTEIQKLVLDVAHVHEHCCRGDVLDCLQDGEKIMSYICSQQDTLSNKITECCKLTTLE
RGQCIIHAENDEKPEGLSPNLNRFLGDRDFNQFSSGEKNIFLASFVHEYSRRHPQLAVSVIL
RVAKGYQELLEKCFQTENPLECQDKGEEELQKYIQESQALAKRSCGLFQKLGEYYLQNAF
LVAYTKKAPQLTSSELMAITRKMAATAATCCQLSEDKLLACGEGAADIIIGHLCIRHEMTP
VNPGVGQCCTSSYANRRPCFSSLVVDETYVPPAFSDDKFIFHKDLCQAQGVALQTMKQEF
LINLVKQKPQITEEQLEAVIADFSGLLEKCCQGQEQEVCFAEEGQKLISKTRAALGV Aqp1 (NP_001171989.1) (SEQ ID NO: 233)
MPGARPLPLVLVPQNTLAWMQLDAKAPAHPRPLQLLGRVGPGSRQLADGVNSGQGLGIEI
IGTLQLVLCVLATTDRRRRDLGGSAPLAIGLSVALGHILLAIDYTGCGINPARSFGSAVITIIN
FSNHWIFWVGPFIGGALAVLIYDFILAPRSSDLTDRVKVWTSGQVEEYDLDADDINSRVEM
KPK

Figure 13 A

Branchyury (NP_003172.1) (SEQ ID NO: 234)
MSSPGTESAGKSLQYRVDHLLSAVENELQAGSEKGDPTERELRVGLEESELWLRFKELTNE
MIVTKNGRRMFPVLKVNVSGLDPNAMYSFLLDFVAADNHRWKYVNGEWVPGGKPEPQ
APSCVYIHPDSPNFGAHWMKAPVSFSKVKLTNKLNGGGQIMLNSLHKYEPRIHIVRVGGP
QRMITSHCFPETQFIAVTAYQNEEITALKIKYNPFAKAFLDAKERSDHKEMMEEPGDSQQP
GYSQWGWLLPGTSTLCPPANPHPQFGGALSLPSTHSCDRYPTLRSHRSSPYPSPYAHRNNS
PTYSDNSPACLSMLQSHDNWSSLGMPAHPSMLPVSHNASPPTSSSQYPSLWSVSNGAVTP
GSQAAAVSNGLGAQFFRGSPAIIYTPLTIIPVSAPSSSGSPLYEGAAAATDIVDSQYDAAAQ
GRLIASWTPVSPPSM Cd2ap (NP_036252.1) (SEQ ID NO: 235)
MVDYIVEYDYDAVHDDELTIRVGEIIRNVKKLQEEGWLEGELNGRRGMFPDNFVKEIKRE
TEFKDDSLPIKRERHGNVASLVQRISTYGLPAGGIQPHPQTKNIKKKTKKRQCKVLFEYIPQ
NEDELELKVGDIIDINEEVEEGWWSGTLNNKLGLFPSNFVKELEVTDDGETHEAQDDSET
VLAGPTSPIPSLGNVSETASGSVTQPKKIRGIGFGDIFKEGSVKLRTRTSSSETEEKKPEKPLI
LQSLGPKTQSVEITKTDTEGKIKAKEYCRTLFAYEGTNEDELTFKEGEIIHLISKETGEAGW
WRGELNGKEGVFPDNFAVQINELDKDFPKPKKPPPPAKAPAPKPELIAAEKKYFSLKPEEK
DEKSTLEQKPSKPAAPQVPPKKPTPPTKASNLLRSSGTVYPKRPEKPVPPPPPIAKINGEVSS
ISSKFETEPVSKLKLDSEQLPLRPKSVDFDSLTVRTSKETDVVNFDDIASSENLLHLTANRP
KMPGRRLPGRFNGGHSPTHSPEKILKLPKEEDSANLKPSELKKDTCYSPKPSVYLSTPSSA
SKANTTAFLTPLEIKAKVETDDVKKNSLDELRAQIIELLCIVEALKKDHGKELEKLRKDLE
EEKTMRSNLEMEIEKLKKAVLSS Cdh3 (NP_001784.2) (SEQ ID NO: 236)
MGLPRGPLASLLLLQVCWLQCAASEPCRAVFREAEVTLEAGGAEQEPGQALGKVFMGCP
GQEPALFSTDNDDFTVRNGETVQERRSLKERNPLKIFPSKRILRRIIKRDWVVAPISVPENG
KGPFPQRLNQLKSNKDRDTKIFYSITGPGADSPPEGVFAVEKETGWLLLNKPLDREEIAKY
ELFGHAVSENGASVEDPMNISIIVTDQNDIIKPKFTQDTFRGSVLEGVLPGTSVMQVTATDE
DDAIYTYNGVVAYSIHSQEPKDPHDLMFTIHRSTGTISVISSGLDREKVPEYTLTIQATDMD
GDGSTTTAVAVVEILDANDNAPMFDPQKYEAHVPENAVGHEVQRLTVTDLDAPNSPAWR
ATYLIMGGDDGDHFTITTHPESNQGILTTRKGLDFEAKNQHTLYVEVTNEAPFVLKLPTST
ATIVVHVEDVNEAPVFVPPSKVVEVQEGIPTGEPVCVYTAEDPDKENQKISYRILRDPAGW
LAMDPDSGQVTAVGTLDREDEQFVRNNIYEVMVLAMDNGSPPTTGTGTLLLTLIDVNDH
GPVPEPRQITICNQSPVRQVLNITDKDLSPHTSPFQAQLTDDSDIYWTAEVNEEGDTVVLSL
KKFLKQDTYDVHLSLSDHGNKEQLTVIRATVCDCHGHVETCPGPWKGGFILPVLGAVLAL
LFLLLVLLLLVRKKRKIKEPLLLPEDDTRDNVFYYGEEGGGEEDQDYDITQLHRGLEARPE
VVLRNDVAPTIPTPMYRPRPANPDEIGNFIIENLKAANTDPTAPPYDTLLVFDYEGSGSDA
ASLSSLTSSASDQDQDYDYLNEWGSRFKKLADMYGGGEDD

Figure 13 B

Clcn5 (NP_000075.1) (SEQ ID NO: 237)
MDFLEEPIPGVGTYDDFNTIDWVREKSRDRDRHREITNKSKESTWALIHSVSDAFSGWLL
MLLIGLLSGSLAGLIDISAHWMTDLKEGICTGGFWFNHEHCCWNSEHVTFEERDKCPEW
NSWSQLIISTDEGAFAYIVNYFMYVLWALLFAFLAVSLVKVFAPYACGSGIPEIKTILSGFIIR
GYLGKWTLVIKTITLVLAVSSGLSLGKEGPLVHVACCCGNILCHCFNKYRKNEAKRREVLS
AAAAAGVSVAFGAPIGGVLFSLEEVSYYFPLKTLWRSFFAALVAAFTLRSINPFGNSRLVLF
YVEFHTPWHLFELVPFILLGIFGGLWGALFIRTNIAWCRKRKTTQLGKYPVIEVLVVTAITAI
LAFPNEYTRMSTSELISELFNDCGLLDSSKLCDYENRFNTSKGGELPDRPAGVGVYSAMW
QLALTLILKIVITIFTFGMKIPSGLFIPSMAVGAIAGRLLGVGMEQLAYYHQEWTVFNSWCS
QGADCITPGLYAMVGAAACLGGVTRMTVSLVVIMFELTGGLEYIVPLMAAAMTSKWVAD
ALGREGIYDAIIRLNGYPFLEAKEEFAIIKTLAMDVMKPRRNDPLLTVLTQDSMTVEDVE
TIISETTYSGFPVVVSRESQRLVGFVLRRDLIISIENARKKQDGVVSTSIIYFTEHSPPLPPYTP
PTLKLRNILDLSPFTVTDLTPMEIVVDIFRKLGLRQCLVTHNGRLLGIITKKDVLKHIAQMA
NQDPDSILFN

Figure 13 C

Cubn (NP_001072.2) (SEQ ID NO: 238)
MMNMSLPFLWSLLTLLIFAEVNGEAGELELQRQKRSINIQQPRMATERGNLVFLTGSAQNI
EFRTGSLGKIKLNDEDLSECLHQIQKNKEDIIELKGSAIGLPQNISSQIYQLNSKLVDLERKF
QGLQQTVDKKVCSSNPCQNGGTCLNLHDSFFCICPPQWKGPLCSADVNECEIYSGTPLSC
QNGGTCVNTMGSYSCHCPPETYGPQCASKYDDCEGGSVARCVHGICEDLMREQAGEPK
YSCVCDAGWMFSPNSPACTLDRDECSFQPGPCSTLVQCFNTQGSFYCGACPTGWQGNGY
ICEDINECEINNGGCSVAPPVECVNTPGSSHCQACPPGYQGDGRVCTLTDICSVSNGGCHP
DASCSSTLGSLPLCTCLPGYTGNGYGPNGCVQLSNICLSHPCLNGQCIDTVSGYFCKCDSG
WTGVNCTENINECLSNPCLNGGTCVDGVDSFSCECTRLWTGALCQVPQQVCGESLSGING
SFSYRSPDVGYVHDVNCFWVIKTEMGKVLRITFTFFRLESMDNCPHEFLQVYDGDSSSAF
QLGRFCGSSLPHELLSSDNALYFHLYSEHLRNGRGFTVRWETQQPECGGILTGPYGSIKSPG
YPGNYPPGRDCVWIVVTSPDLLVTFTFGTLSLEHIIDDCNKDYLEIRDGPLYQDPLLGKFCT
TFSVPPLQTTGPFARIHFHSDSQISDQGFHITYLTSPSDLRCGGNYTDPEGELFLPELSGPFT
HTRQCVYMMKQPQGEQIQINFTHVELQCQSDSSQNYIEVRDGETLLGKVCGNGTISHIKSI
TNSVWIRFKIDASVEKASFRAVYQVACGDELTGEGVIRSPFFPNVYPGERTCRWTIHQPQS
QVILLNFTVFEIGSSAHCETDYVEIGSSSILGSPENKKYCGTDIPSFITSVYNFLYVTFVKSSS
TENHGFMAKFSAEDLACGEILTESTGTIQSPGHPNVYPHGINCTWIHILVQPNHLIHILMFETF
HLEFHYNCTNDYLEVYDTDSETSLGRYCGKSIPPSLTSSGNSLMLVFVTDSDLAYEGFLIN
YEAISAATACLQDYTDDLGTFTSPNFPNNYPNNWECIYRITVRTGQLIAVHFTNFSLEEAIG
NYYTDFLEIRDGGYEKSPLLGIFYGSNLPPTIISHSNKLWLKFKSDQIDTRSGFSAYWDGSS
TGCGGNLTTSSGTFISPNYPMPYYHSSECYWWLKSSHGSAFELEFKDFHLEHHPNCTLDY
LAVYDGPSSNSHLLTQLCGDEKPPLIRSSGDSMFIKLRTDEGQQGRGFKAEYRQTCENVVI
VNQTYGILESIGYPNPYSENQHCNWTIRATTGNTVNYTFLAFDLEHHINCSTDYLELYDGP
RQMGRYCGVDLPPPGSTTSSKLQVLLLTDGVGRREKGFQMQWFVYGCGGELSGATGSFS
SPGFPNRYPPNKECIWYIRTDPGSSIQLTIHDFDVEYHSRCNFDVLEIYGGPDFHSPRIAQLC
TQRSPENPMQVSSTGNELAIRFKTDLSINGRGFNASWQAVTGGCGGHFQAPSGEHSPNYP
SPYRSNTDCSWVIRVDRNHRVLLNFTDFDLEPQDSCIMAYDGLSSTMSRLARTCGREQLA
NPIVSSGNSLFLRFQSGPSRQNRGFRAQFRQACGGHILTSSFDTVSSPRFPANYPNNQNCSW
HQAQPPLNHITLSFTHFELERSTTCARDFVEILDGGHEDAPLRGRYCGTDMPHPITSFSSAL
TLRFVSDSSISAGGFHTTVTASVSACGGTFYMAEGIFNSPGYPDIYPPNVECVWNIVSSPGN
RLQLSFISFQLEDSQDCSRDFVEIREGNATGHLVGRYCGNSFPLNYSSIVGHTLWVRFISDG
SGSGTGFQATFMKIFGNDNIVGTHGKVASPFWPENYPHNSNYQWTVNVNASHVVHGRIL
EMDIEEIQNCYYDKLRIYDGPSIHARLIGAYCGTQTESFSSTGNSLTFHFYSDSSISGKGFLL
EWFAVDAPDGVLPTIAPGACGGFLRTGDAPVFLFSPGWPDSYSNRVDCTWLIQAPDSTVE
LNILSLDIESHRTCAYDSLVIRDGDNNLAQQLAVLCGREIPGPIRSTGEYMFIRFTSDSSVTR
AGFNASFHKSCGGYLHADRGHTSPKYPETYPSNLNCSWHVLVQSGLTIAVHFEQPFQIPNG
DSSCNQGDYLVLRNGPDICSPPLGPPGGNGHFCGSHASSTLFTSDNQMFVQFISDHSNEGQ
GFKIKYEAKSLACGGNVYIHDADSAGYVTSPNHPHNYPPHADCIWILAAPPETRIQLQFED
REDIEVTPNCTSNYLELRDGVDSDAPILSKFCGTSLPSSQWSSGEVMYLRFRSDNSPTHVG
FKAKYSIAQCGGRVPGQSGVVESIGHPTLPYRDNLFCEWHLQGLSGHYLTISFEDFNLQNS
SGCLEKDFVEIWDNHTSGNILGRYCGNTIPDSIDTSSNTAVVRFVTDGSVTASGFRLRFESSM
EECGGDLQGSIGTFTSPNYPNPNPHGRICEWRITAPEGRRITLMFNNLRLATHPSCNNEHVI

Figure 13 D

VFNGIRSNSPQLEKLCSSVNVSNEIKSSGNTMKVIFFTDGSRPYGGFTASYTSSEDAVCGGS
LPNTPEGNFTSPGYDGVRNYSRNLNCEWTLSNPNQGNSSISIHFEDFYLESHQDCQFDVLE
FRVGDADGPLMWRLCGPSKPTLPLVIPYSQVWIHFVTNERVEHIGFHAKYSFTDCGGIQIG
DSGVITSPNYPNAYDSLTHCSSLLEAPQGHTITLTFSDFDIEPHTTCAWDSVTVRNGGSPESP
IIGQYCGNSNPRTIQSGSNQLVVTFNSDHSLQGGGFYATWNTQTLGCGGIFHSDNGTIRSPH
WPQNFPENSRCSWTAITHKSKHLEISFDNNFLIPSGDGQCQNSFVKVWAGTEEVDKALLA
TGCGNVAPGPVITPSNTFTAVFQSQEAPAQGFSASFVSRCGSNFTGPSGYIISPNYPKQYDN
NMNCTYVIEANPLSVVLLTFVSFHLEARSAVTGSCVNDGVHIIRGYSVMSTPFATVCGDEM
PAPLTIAGPVLLNFYSNEQITDFGFKFSYRIISCGGVFNFSSGIITSPAYSYADYPNDMHCLYT
ITVSDDKVIELKFSDFDVVPSTSCSHDYLAIYDGANTSDPLLGKFCGSKRPPNVKSSNNSM
LLVFKTDSFQTAKGWKMSFRQTLGPQQGCGGYLTGSNNTFASPDSDSNGMYDKNLNCV
WIIAPVNKVIHLTFNTFALEAASTRQRCLYDYVKLYDGDSENANLAGTFCGSTVPAPFISS
GNFLTVQFISDLTLEREGFNATYTIMDMPCGGTYNATWTPQNISSPNSSDPDVPFSICTWVI
DSPPHQQVKITVWALQLTSQDCTQNYLQLQDSPQGHGNSRFQFCGRNASAVPVFYSSMST
AMVIFKSGVVNRNSRMSFTYQIADCNRDYHKAFGNLRSPGWPDNYDNDKDCTVTLTAP
QNHTISLFFHSLGIENSVECRNDFLEVRNGSNSNSPLLGKYCGTLLPNPVFSQNNELYLRFK
SDSVTSDRGYEIIWTSSPSGCGGTLYGDRGSFTSPGYPGTYPNNTYCEWVLVAPAGRLVTI
NFYHSIDDPGDCVQNYLTLYDGPNASSPSSGPYCGGDTSIAPFVASSNQVFIKFHADYARR
PSAFRLTWDS

Figure 13 D (Continued)

Foxa2 (NP_068556.2) (SEQ ID NO: 239)
MHSASSMLGAVKMEGHEPSDWSSYYAEPEGYSSVSNMNAGLGMNGMNTYMSMSAAA
MGSGSGNMSAGSMNMSSYVGAGMSPSLAGMSPGAGAMAGMGGSAGAAGVAGMGPHL
SPSLSPLGGQAAGAMGGLAPYANMNSMSPMYGQAGLSRARDPKTYRRSYTHAKPPYSYI
SLITMAIQQSPNKMLTLSEIYQWIMDLFPFYRQNQQRWQNSIRHSLSFNDCFLKVPRSPDK
PGKGSFWTLHPDSGNMFENGCYLRRQKRFKCEKQLALKEAAGAAGSGKKAAAGAQAS
QAQLGEAAGPASETPAGTESPHSSASPCQEHKRGGLGELKGTPAAALSPPEPAPSPGQQQQ
AAAHLLGPPHHPGLPPEAHLKPEHHYAFNHPFSINNLMSSEQQHHHSHHHHQPHKMDLK
AYEQVMHYPGYGSPMPGSLAMGPVTNKTGLDASPLAADTSYYQGVYSRPIMNSS Gfap (NP_001124492.1) (SEQ ID NO: 240)
MERRRITSARRSYASETVVRGLGPSRQLGTMPRFSLSRMTPPLPARVDFSLAGALNAGFKE
TRASERAEMMELNDRFASYIEKVRFLEQQNKALAAELNQLRAKEPTKLADVYQAELREL
RLRLDQLTANSARLEVERDNFAQDLGTLRQKLQDETNLRLEAENNLAAYRQEADEATLA
RVDLERKVESLEEEIQFLRKIYEEEVRELREQLAQQQVIIVEMDVAKPDLTAALREIRTQYE
AVATSNMQETEEWYRSKFADLTDAASRNAELLRQAKHEANDYRRQLQALTCDLESLRGT
NESLERQMREQEERHARESASYQEALARLEEEGQSLKEEMARHLQEYQDLLNVKLALDI
EIATYRKLLEGEENRITIPVQTFSNLQIRGGKSTKEGEGQKVTRPLKRLTIQVVPIQAHQIEN
GALPALP

Figure 13 E

Lrp2 (NP_004516.2) (SEQ ID NO: 241)

MDRGPAAVACTLLLALVACLAPASGQECDSAHFRCGSGHCIPADWRCDGTKDCSDDADEI
GCAVVTCQQGYFKCQSEGQCIPNSWVCDQDQDCDDGSDERQDCSQSTCSSHQITCSNGQ
CIPSEYRCDHVRDCPDGADENDCQYPTCEQLTCDNGACYNTSQKCDWKVDCRDSSDEIN
CTEICLHNEFSCGNGECIPRAYVCDHDNDCQDGSDEHACNYPTCGGYQFTCPSGRCIYQN
WVCDGEDDCKDNGDEDGCESGPHDVHKCSPREWSCPESGRCISIYKVCDGILDCPGRED
ENNTSTGKYCSMTLCSALNCQYQCHETPYGGACFCPPGYIINIINDSRTCVEFDDCQIWGI
CDQKCESRPGRHLCHCEEGYILERGQYCKANDSFGEASIIFSNGRDLLIGDIHGRSFRILVE
SQNRGVAVGVAFHYHLQRVFWTDTVQNKVFSVDINGLNIQEVLNVSVETPENLAVDWVN
NKIYLVETKVNRIDMVNLDGSYRVTLITENLGHPRGIAVDPTVGYLFFSDWESLSGEPKLE
RAFMDGSNRKDLVKTKLGWPAGVTLDMISKRVYWVDSRFDYIETVTYDGIQRKTVVHG
GSLIPHPFGVSLFEGQVFFTDWTKMAVLKANKFTETNPQVYYQASLRPYGVTVYHSLRQP
YATNPCKDNNGGCEQVCVLSHRTDNDGLGFRCKCTFGFQLDTDERHCIAVQNFLIFSSQV
AIRGIPFTLSTQEDVMVPVSGNPSFFVGIDFDAQDSTIFFSDMSKIIMIFKQKIDGTGREILA
ANRVENVESLAFDWISKNLYWTDSHYKSISVMRLADKTRRTVVQYLNNPRSVVVHPFAG
YLFFTDWFRPAKIMRAWSDGSHLLPVINTTLGWPNGLAIDWAASRLYWVDAYFDKIEHST
FDGLDRRRLGHIEQMTHPFGLAIFGEHLFFTDWRLGAIIRVRKADGGEMTVIRSGIAYILHL
KSYDVNIQTGSNACNQPTHPNGDCSHFCFPVPNFQRVCGCPYGMRLASNHLTCEGDPTNE
PPTEQCGLFSFPCKNGRCVPNYYLCDGVDDCHDNSDEQLCGTLNNTCSSSAFTCGHGECI
PAHWRCDKRNDCVDGSDEHNCPTHAPASCLDTQYTCDNHQCISKNWVCDTDNDCGDGS
DEKNCNSTETCQPSQFNCPNHRCIDLSFVCDGDKDCVDGSDEVGCVLNCTASQFKCASG
DKCIGVTNRCDGVFDCSDNSDEAGCPTRPPGMCHSDEFQCQEDGICIPNFWECDGHPDCL
YGSDEHNACVPKTCPSSYFHCDNGNCIHRAWLCDRDNDCGDMSDEKDCPTQPFRCPSW
QWQCLGHNICVNLSVVCDGIFDCPNGTDESPLCNGNSCSDFNGGCTHECVQEPFGAKCL
CPLGFLLANDSKTCEDIDECDILGSCSQHCYNMRGSFRCSCDTGYMLESDGRTCKVTASE
SLLLLVASQNKIIADSVTSQVHNIYSLVENGSYIVAVDFDSISGRIFWSDATQGKTWSAFQN
GTDRRVVFDSSIILTETIAIDWVGRNLYWTDYALETIEVSKIDGSIIRTVLISKNLTNPRGLAL
DPRMNEHLLFWSDWGHHPRIERASMDGSMRTVIVQDKIFWPCGLTIDYPNRLLYFMDSY
LDYMDFCDYNGHHRRQVIASDLIIRHPYALTLFEDSVYWTDRATRRVMRANKWHGGNQS
VVMYNIQWPLGIVAVHPSKQPNSVNPCAFSRCSHLCLLSSQGPHFYSCVCPSGWSLSPDLL
NCLRDDQPFLITVRQHIIFGISLNPEVKSNDAMVPIAGIQNGLDVEFDDAEQYIYWVENPG
EIHRVKTDGTNRTVFASISMVGPSMNLALDWISRNLYSTNPRTQSIEVLTLHGDIRYRKTLI
ANDGTALGVGFPIGITVDPARGKLYWSDQGTDSGVPAKIASANMDGTSVKTLFTGNLEHL
ECVTLDIEEQKLYWAVTGRGVIERGNVDGTDRMILVIIQLSHPWGIAVIIDSFLYYTDEQYE
VIERVDKATGANKIVLRDNVPNLRGLQVYHRRNAAESSNGCSNNMNACQQICLPVPGGL
FSCACATGFKLNPDNRSCSPYNSFIVVSMLSAIRGFSLELSDHSETMVPVAGQGRNALHVD
VDVSSGFIYWCDFSSSVASDNAIRRIKPDGSSLMNIVTHGIGENGVRGIAVDWVAGNLYFT
NAFVSETLIEVLRINTTYRRVLLKVTVDMPRHIVVDPKNRYLFWADYGQRPKIERSFLDCT
NRTVLVSEGIVTPRGLAVDRSDGYVYWVDDSLDIIARIRINGENSEVIRYGSRYPTPYGITV
FENSIIWVDRNLKKIFQASKEPENTEPPTVIRDNINWLRDVTIFDKQVQPRSPAEVNNNPCL
ENNGGCSIILCFALPGLIITPKCDCAFGTLQSDGKNCAISTENFLIFALSNSLRSLIILDPENIIS
PPFQTINVERTVMSLDYDSVSDRIYFTQNLASGVGQISYATLSSGIHTPTVIASGIGTADGIA

Figure 13 F

FDWITRRIYYSDYLNQMINSMAEDGSNRTVIARVPKPRAIVLDPCQGYLYWADWDTHAKI
ERATLGGNFRVPIVNSSLVMPSGLTLDYEEDLLYWVDASLQRIERSTLTGVDREVIVNAAV
HAFGLTLYGQYIYWTDLYTQRIYRANKYDGSGQIAMTTNLLSQPRGINTVVKNQKQQCN
NPCEQFNGGCSHICAPGPNGAECQCPHEGNWYLANNRKHCIVDNGERCGASSFTCSNGR
CISEEWKCDNDNDCGDGSDEMESVCALHTCSPTAFTCANGRCVQYSYRCDYYNDCGDG
SDEAGCLFRDCNATTEFMCNNRRCIPREFICNGVDNCHDNNTSDEKNCPDRTCQSGYTKC
HNSNICIPRVYLCDGDNDCGDNSDENPTYCTTHTCSSSEFQCASGRCIPQHWYCDQETDC
FDASDEPASCGHSERTCLADEFKCDGGRCIPSEWICDGDNDCGDMSDEDKRHQCQNQNC
SDSEFLCVNDRPPDRRCIPQSWVCDGDVDCTDGYDENQNCTRRTCSENEFTCGYGLCIPK
IFRCDRHNDCGDYSDERGCLYQTCQQNQFTCQNGRCISKTFVCDEDNDCGDGSDELMHL
CHTPEPTCPPHEFKCDNGRCIEMMKLCNHLDDCLDNSDEKGCGINECHDPSISGCDHNCT
DTLTSFYCSCRPGYKLMSDKRTCVDIDECTEMPFVCSQKCENVIGSYICKCAPGYLREPDG
KTCRQNSNIEPYLIFSNRYYLRNLTIDGYFYSLILEGLDNVVALDFDRVEKRLYWIDTQRQV
IERMFLNKTNKETIINHRLPAAESLAVDWVSRKLYWLDARLDGLFVSDLNGGHRRMLAQ
HCVDANNTFCFDNPRGLALHPQYGYLYWADWGHRAYIGRVGMDGTNKSVIISTKLEWP
NGITIDYTNDLLYWADAIILGYIEYSDLEGIIIRIITVYDGALPIIPFAITIFEDTIYWTDWNTR
TVEKGNKYDGSNRQTLVNTTHRPFDIHVYHPYRQPIVSNPCGTNNGGCSHLCLIKPGGKG
FTCECPDDFRTLQLSGSTYCMPMCSSTQFLCANNEKCIPIWWKCDGQKDCSDGSDELALC
PQRFCRLGQFQCSDGNCTSPQTLCNAHQNCPDGSDEDRLLCENHHCDSNEWQCANKRCI
PESWQCDTFNDCEDNSDEDSSHCASRTCRPGQFRCANGRCIPQAWKCDVDNDCGDHSDE
PIEECMSSAHLCDNFTEFSCKTNYRCIPKWAVCNGVDDCRDNSDFQGCEERTCHPVGDFR
CKNHHCIPLRWQCDGQNDCGDNSDEENCAPRECTESEFRCVNQQCIPSRWICDHYNDCG
DNSDERDCEMRTCHPEYFQCTSGHCVHSELKCDGSADCLDASDEADCPTRFPDGAYCQA
TMFECKNHVCIPPYWKCDGDDDCGDGSDEELHLCLDVPCNSPNRFRCDNNRCIYSHEVC
NGVDDCGDGTDETEEHCRKPTPKPCTEYEYKCGNGHCIPHDNVCDDADDCGDWSDELG
CNKGKERTCAENICEQNCTQLNEGGFICSCTAGFETNVFDRTSCLDINECEQFGTCPQHCR
NTKGSYECVCADGFTSMSDRPGKRCAAEGSSPLLLLPDNVRIRKYNLSSERFSEYLQDEE
YIQAVDYDWDPKDIGLSVVYYTVRGFGSRFGAIKRAYIPNFFSGRNNLVQFVDLKLKYV
MQPDGIAVDWVGRHIYWSDVKNKRIEVAKLDGRYRKWLISTDLDQPAAIAVNPKLGLMF
WTDWGKEPKIESAWMNGEDRNILVFEDLGWPTGLSIDYLNNDRIYWSDFKEDVIETIKYD
GTDRRVIAKEAMNPYSLDIFEDQLYWISKEKGEVWKQNKFGQGKKEKTLVVNPWLTQVR
IFHQLRYNKSVPNLCKQICSHLCLLRPGGYSCACPQGSSFEGSTTECDAAIELPINLPPPCR
CMHGGNCYFDETDLPKCKCPSGYTGKYCEMAFSKGISPGTTAVAVLLTILLIVVIGALAIA
GFTHYRRTGSLLPALPKLPSLSSLVKPSENGNGVTFRSGADLNMDIGVSGFGPETAIDRSM
AMSEDFVMEMGKQPIIFENPMYSARDSAVKVVQPIQVTVSENVDNKNYGSPINPSEIVPET
NPTSPAADGTQVTKWNLFKRKSKQTTNFENPIYAQMENEQKESVAATPPPSPSLPAKPKPP
SRRDPTPTYSATEDTFKDTANLVKEDSEV

Figure 13 F (Continued)

Map2 (NP_001035023.1) (SEQ ID NO: 242)
MADERKDEGKAPHWTSASLTEAAAHPHSPEMKDQGGAGEGLSRNANGFPYREEEEGAF
GEHRSQGTYSDTKENGINGELTSADRETAEEVSARIVQVVTAEAVAVLKGEQEKEAQHKD
QPAALPLAAEETANLPPSPPPSPASEQTATVEEAASGDLAQAPGAFKQAKDKVTDGISKSPE
KRSSLPRPSSILPPRRGVSGDREENSFSLNSSISSARRTTRSEPIRRAGKSGTSTPTTPGSTAIT
PGTPPSYSSRTPGTPGTPSYPRTPGTPKSGILVPSEKKVAIIRTPPKSPATPKQLRLINQPLPDL
KNVKSKIGSTDNIKYQPKGGQVRILNKKIDFSKVQSRCGSKDNIKHSAGGGNVQIVTKKID
LSHVTSKCGSLKNIRHRPGGGRVKIESVKLDFKEKAQAKVGSLDNAHHVPGGGNVKIDS
QKLNFREHAKARVDHGAEIITQSPSRSSVASPRRLSNVSSSGSINILESPQLATLAEDVTAA
LAKQGL

Mbp (NP_001020416.1) (SEQ ID NO: 243)
MGNIISGKRELSAEKASKDGEIIIRGEAGKKRSVGKLSQTASEDSDVFGEADAIQNNGTSA
EDTAVTDSKHTADPKNNWQGAHPADPGNRPHLIRLFSRDAPGREDNTFKDRPSESDELQTI
QEDPTAASGGLDVMASQKRPSQRSKYLATASTMDHARHGFLPRHRDTGILDSIGRFFSGD
RGAPKRGSGKVSSEP

Msx1 (NP_002439.2) (SEQ ID NO: 244)
MAPAADMTSLPLGVKVEDSAFGKPAGGGAGQAPSAAAATAAAMGADEEGAKPKVSPSL
LPFSVEALMADHRKPGAKESALAPSEGVQAAGGSAQPLGVPPGSLGAPDAPSSPRPLGHF
SVGGLLKLPEDALVKAESPEKPERTPWMQSPRFSPPPARRLSPPACTLRKHKTNRKPRTPFT
TAQLLALERKFRQKQYLSIAERAEFSSSLSLTETQVKIWFQNRRAKAKRLQEAELEKLKM
AAKPMLPPAAFGLSFPLGGPAAVAAAAGASLYGASGPFQRAALPVAPVGLYTAHVGYSMY
HLT

Figure 13 G

Nestin (NP_006608.1) (SEQ ID NO: 215)
MEGCMGEESFQMWELNRRLEAYLARVKALEEQNELLSAELGGLRAQSADTSWRAHADD
ELAALRALVDQRWREKHAAEVARDNLAEELEGVAGRCQQLRLARERTTEEVARNRRAVE
AEKCARAWLSSQVAELERELEALRVAHEEERVGLNAQAACAPRCPAPPRGPPAPAPEVEEL
ARRLGEAWRGAVRGYQERVAHMETSLGQARERLGRAVQGAREGRLELQQLQAERGGLL
ERRAALEQRLEGRWQERLRATEKFQLAVEALEQEKQGLQSQIAQVLEGRQQLAHLKMSL
SLEVATYRTLLEAENSRLQTPGGGSKTSLSFQDPKLELQFPRTPEGRRLGSLLPVLSPTSLPS
PLPATLETPVPAFLKNQEFLQARTPTLASTPIPPTPQAPSPAVDAEIRAQDAPLSLLQTQGGR
KQAPEPLRAEARVAIPASVLPGPEEPGGQRQEASTGQSPEDIIASLAPPLSPDIISSLEAKDGE
SGGSRVFSICRGEGEGQIWGLVEKETAIEGKVVSSLQQEIWEEEDLNRKEIQDSQVPLEKET
LKSLGEEIQESLKTLENQSHETLERENQECPRSLEEDLETLKSLEKENKELLKDVEVVRPLE
KEAVGQLKPTGKEDTQTLQSLQKENQELMKSLEGNLETFLFPGTENQELVSSLQENLESLT
ALEKENQEPLRSPEVGDEEALRPLTKENQEPLRSLEDENKEAFRSLEKENQEPLKTLEEED
QSIVRPLETENHKSLRSLEEQDQETLRTLEKETQQRRRSLGEQDQMTLRPPEKVDLEPLKS
LDQEIARPLENENQEFLKSLKEESVEAVKSLETEILESLKSAGQENLETLKSPETQAPLWTP
EEINQGAMNPLEKEIQEPLESVEVNQETFRLLEEENQESLRSLGAWNLENLRSPEEVDKES
QRNLEEEENLGKGEYQESLRSLEEEGQELPQSADVQRWEDTVEKDQELAQESPPGMAGV
ENEDEAELNLREQDGFTGKEEVVEQGELNATEEVWIPGEGIIPESPEPKEQRGLVEGASVK
GGAEGLQDPEGQSQQVGAPGLQAPGLPEAIEPLVEDDVAPGGDQASPEVMLGSEPAMG
ESAAGAEPGPGQGVGGLGDPGHLTREEVMEPPLEEESLEAKRVQGLEGPRKDLEEAGGL
GTEFSELPGKSRDPWEPPREGREESEAEAPRGAEEAFPAETLGHTGSDAPSPWPLGSEEAE
EDVPPVLVSPSPTYTPILEDAPGPQPQAEGSQEASWGVQGRAEALGKVESEQEELGSGEIP
EGPQEEGEESREESEEDELGETLPDSTPLGFYLRSPTSPRWDPTGEQRPPPQGETGKEGWD
PAVLASEGLEAPPSEKEEGEEGEEECGRDSDLSEEFEDLGTEAPFLPGVPGEVAEPLGQVPQ
LLLDPAAWDRDGESDGFADEEESGEEGEEDQEEGREPGAGRWGPGSSVGSLQALSSSQRG
EFLESDSVSVSVPWDDSLRGAVAGAPKTALETESQDSAEPSGSEEESDPVSLEREDKVPGP
LEIPSGMEDAGPGADIIGVNGQGPNLEGKSQIIVNGGVMNGLEQSEEVGQGMPLVSEGDR
GSPFQEEEGSALKTSWAGAPVHLGQGQFLKFTQREGDRESWSSGED NeuN (NP_001020102.2) (SEQ ID NO: 245)
MAQPYPPAQYPPPPQNGIPAEYAPPPPHPTQDYSGQTPVPPEHGMTLYTPAQTHPEQPGTE
ASTQPIAGTQTVPQADEAAQTDNQQLIIPSDPTEKQQPKRLIIVSNIPFRFRDPDLRQMFGQ
FGKILDVEIIFNERGSKGFGFVTFETSSDADRAREKLNGTIVEGRKIEVNNATARVMTNKKP
GNPYANGWKLNPVVGTVYGPEFYAVTSFPYPTTGTAVAYRGAHLRGRGRAVYNTFRAAPP
PPPIPTYGAVVYQDGFYGAEIYGGYAAYRYAQPAAATAAAYSDSYGRVYAAADPYHHTIG
PTATYSIGTM

Figure 13 H

NeuroD1 (NP_035024.1) (SEQ ID NO: 246)
MTKSYSESGLMGEPQPQGPPSWTDECLSSQDEEHEADKKEDELEAMNAEEDSLRNGGEE
EEEDEDLEEEEEEEEEEEDQKPKRRGPKKKKMTKARLERFKLRRMKANARERNRMHGL
NAALDNLRKVVPCYSKTQKLSKIETLRLAKNYIWALSEILRSGKSPDLVSFVQTLCKGLSQ
PTTNLVAGCLQLNPRTFLPEQNPDMPPHLPTASASFPVHPYSYQSPGLPSPPYGTMDSSHVF
HVKPPPHAYSAALEPFFESPLTDCTSPSFDGPLSPPLSINGNFSFKHEPSAEFEKNYAFTMHY
PAATLAGPQSHGSIFSSGAAAPRCEIPIDNIMSFDSHSHHERVMSAQLNAIFHD NF-H (NP_035034.2) (SEQ ID NO: 247)
MMSFGSADALLGAPFAPLHGGGSLHYSLSRKAGPGGTRSAAGSSSGFHSWARTSVSSVSA
SPSRFRGAASSTDSLDTLSNGPEGCVVAAVAARSEKEQLQALNDRFAGYIDKVRQLEAHN
RSLEGEAAALRQQQAGRAAMGELYEREVREMRGAVLRLGAARGQLRLEQEHLLEDIAH
VRQRLDEEARQREEAEAAARALARFAQEAEAARVELQKKAQALQEECGYLRRHHQEEV
GELLGQIQGCGAAQAQAQAEARDALKCDVTSALREIRAQLEGHAVQSTLQSEEWFRVRL
DRLSEAAKVNTDAMRSAQEEITEYRRQLQARTTELEALKSTKESLERQRSELEDRHQADI
ASYQDAIQQLDSELRNTKWEMAAQLREYQDLLNVKMALDIEIAAYRKLLEGEECRIGFGP
SPFSLTEGLPKIPSISTHIKVKSEEMIKVVEKSEKETVIVEGQTEEIRVTEGVTEEEDKEAQG
QEGEEAEEGEEKEEEEGAAATSPPAEEAASPEKETKSRVKEEAKSPGEAKSPGEAKSPAEA
KSPGEAKSPGEAKSPGEAKSPAEPKSPAEPKSPAEAKSPAEPKSPATVKSPGEAKSPSEAKSP
AEAKSPAEAKSPAEAKSPAEAKSPAEAKSPAEAKSPATVKSPGEAKSPSEAKSPAEAKSPAE
AKSPAEAKSPAEVKSPGEAKSPAEPKSPAEAKSPAEVKSPAEAKSPAEVKSPGEAKSPAAVK
SPAEAKSPAAVKSPGEAKSPGEAKSPAEAKSPAEAKSPIEVKSPEKAKTPVKEGAKSPAEAK
SPEKAKSPVKEDIKPPAEAKSPEKAKSPVKEGAKPPEKAKPLDVKSPEAQTPVQEEAKHPT
DIRPPEQVKSPAKEKAKSPEKEEAKTSEKVAPKKEEVKSPVKEEVKAKEPPKKVEEEKTLP
TPKTEAKESKKDEAPKEAPKPKVEEKKETPTEKPKDSTAEAKKEEAGEKKKAVASEEETP
AKLGVKEEAKPKEKTETTKTEAEDTKAKEPSKPTETEKPKKEEMPAAPEKKDTKEEKTTE
SRKPEEKPKMEAKVKEDDKSLSKEPSKPKTEKAEKSSSTDQKESQPPEKTTEDKATKGEK NF-L (NP_035040.1) (SEQ ID NO: 248)
MSSFGYDPYFSTSYKRRYVETPRVHSSVRSGYSTARSAYSSYSAPVSSSLSVRRSYSSSSGS
LMPSLENLDLSQVAAISNDLKSIRTQEKAQLQDLNDRFASFIERVHELEQQNKVLEAELLV
LRQKHSEPSRFRALYEQEIRDLRLAAEDATNEKQALQGEREGLEETLRNLQARYEEEVLSR
EDAEGRLMEARKGADEAALARAELEKRIDSLMDEIAFLKKVHEEEIAELQAQIQYAQISV
EMDVSSKPDLSAALKDIRAQYEKLAAKNMQNAEEWFKSRFTVLTESAAKNTDAVRAAK
DEVSESRRLLKAKTLEIEACRGMNEALEKQLQELEDKQNADISAMQDTINKLENELRSTK
SEMARYLKEYQDLLNVKMALDIEIAAYRKLLEGEETRLSFTSVGSITSGYSQSSQVFGRSA
YSGLQSSSYLMSARSFPAYYTSHVQEEQTEVEETIEATKAEEAKDEPPSEGEAEEEEKEKEE
GEEEEGAEEEEAAKDESEDTKEEEEGGEGEEEDTKESEEEEKKEESAGEEQVAKKKD

Figure 13 I

NF-M (NP_032717.2) (SEQ ID NO: 249)
MSYTLDSLGNPSAYRRVTETRSSFSRVSGSPSSGFRSQSWSRGSPSTVSSSYKRSALAPRLA
YSSAMLSSAESSLDFSQSSSLLNGGSGGDYKLSRSNEKEQLQGLNDRFAGYIEKVHYLEQ
QNKEIEAEIQALRQKQASHAQLGDAYDQEIRELRATLEMVNHEKAQVQLDSDHLEEDIHR
LKERFEEEARLRDDTEAAIRALRKDIEESSMVKVELDKKVQSLQDEVAFLRSNHEEEVAD
LLAQIQASHITVERKDYLKTDISTALKEIRSQLECHSDQNMHQAEEWFKCRYAKLTEAAEQ
NKEAIRSAKEEIAEYRRQLQSKSIELESVRGTKESLERQLSDIEERHNHDLSSYQDTIQQLE
NELRGTKWEMARHLREYQDLLNVKMALDIEIAAYRKLLEGEETRFSTFSGSITGPLYTHR
QPSVTISSKIQKTKVEAPKLKVQHKFVEEIEETKVEDEKSEMEETLTAIAEELAASAKEEK
EEAEEKEEEPEAEKSPVKSPEAKEEEEEGEKEEEEEGQEEEEEEDEGVKSDQAEEGGSEKE
GSSEKDEGEQEEEEGETEAEGEGEEAEAKEEKKIEGKVEEVAVKEEIKVEKPEKAKSPMPK
SPVEEVKPKPEAKAGKGEHKEEEKVEEEKKEVTKESPKEEKVEKKEEKPKDVADKKKAE
SPVKEKAVEEVITISKSVKVSLEKDTKEEKLQPQEKVKEKAEEEGGSEEEGSDRSPQESKK
EDIAINGEVEGKEEEEQETQEKGSGREEEKGVVTNGLDVSPAEEKKGEDSSDDKVVVTKK
VEKITSEGGDGATKYITKSVTVTQKVEEHEETFEEKLVSTKKVEKVTSHAIVKEVTQGD

Figure 13 J

Ng2 (NP_620570.2) (SEQ ID NO: 250)
MLLGPGHPLSAPALALALTLALLVRSTAPASFFGENHLEVPVPSALTRVDLLLQFSTSQPEA
LLLLAAGQDDHLLLQLHSGCLQVRLALGQKELKLQTPADTVLSDSAPHTVVLTVSDSWA
VLSVDGVLNTSAPIPRASHLKATYGLFVGSSGSLDLPYLKGISRPLRGCLHSAILNGRNLLR
PLTSDVHEGCAEEFSAGDEVGLGFSGPHSLAAFPAWSTREEGTLEFTLTTRSQQAPLAFQA
GDKRGNFIYVDIFEGHLRAVVEKGQGTMLLRNSVPVADGQPHEVSVHIDVHRLEISVDQY
PTRTFNRGVLSYLEPRGSLLLGGLDTEASRHLQEHRLGLAPGAANISLVGCIEDFSVNGRR
QGLRDAWLTRDMSAGCRPEEDEYEEVYGPYETFSTLAPEAWPAMELPEPCIPEPGLPAVF
ANFTQLLTISPLVVAEGGTAWLEWRHVQPTLDLTEAELRKSQVLFSVSQSARHGDLELDIL
GAQTRKMFTLLDVVNRKARFVHDGSEDTSDQLMLEVSVTARAPVPSCLRRGQIYILPIQV
NPVNDPPRIIFPHGSLMVILEHTQKPLGPEIFQAYDPDSACEGLTFQLLGVSSGVPVEHRDQ
PGEPATEFSCRELEVGDIVYVHRGGPAQDLTFRVSDGMQASAPATLKVVAVRPAIQILHNTG
LHLAQGSAAAILPANLSVETNAVGQDVSVLFRVTGTLQFGELQKQGAGGVEGTEWWDTL
AFHQRDVEQGRVRYLSTDPQHHTQDTVEDLILEVQVGQETLSNLSFPVTIQRATVWMLRL
EPLHTQNPHQETLTPAHLEASLEEEEEGSPQPHTFHYELVQAPRRGNLLLQGTRLSDGES
FSQSDLQAGRVTYRATMRTSEAADDSFRFRVTSPPHFSPLYTFPIHIGGDPNAPVLTNVLLM
VPEGGEGVLSADHLFVKSLNSASYLYEVMEQPHHGKLAWRDPKGKSTPVTSFTNEDLLH
GRLVYQHDDSETIEDDIPFVATRQGEGSGDMAWEEVRGVFRVAIQPVNDHAPVQTISRVFH
VARGGQRLLTTDDVAFSDADSGFSDAQLVLTRKDLLFGSIVAMEEPTRPIYRFTQEDLRKK
QVLFVHSGADHGWLQLQVSDGQHQATAMLEVQASEPYLHVANSSSLVVPQGGQGTIDTA
VLQLDTNLDIRSGNEVHYHVTAGPQWGQLLRDGQSVTSFSQRDLLDGAILYSHNGSLSPQ
DTLAFSVAAGPVHTNTFLQVTIALEGPLAPLQLVQHKKIYVFQGEAAEIRRDQLEVVQEAV
LPADIMFSLRSPPNAGYLVMVSHGASAEEPPSLDPVQSFSQEAVNSGRVLYLHSRPGAWSD
SFSLDVASGLGDPLEGISVELEVLPTVIPLDVQNFSVPEGGTRTLAPPLVQITGPYFPTLPGL
VLQVLEPPQHGALQKEDHSQDGSLSTFSWREVEEQLIRYVHDGSETQTDAFVLLANASE
MDRQSQPVAFTITILPVNDQPPVLTTNTGLQIWEGAIVPIPPEALRGTDNDSGPEDLVYTIEQ
PSNGRIALRVAPDTEVHRFTQAQLDSGLVLFSHRGALEGGFHFDLSDGAHTSPGHFFRVVA
QKQALLSLEGTRKLTVCPESVQPLSSQSLSASSSTGADPRHLLYRVVRGPQLGRLLHAQQG
SAEEVLVNFTQAEVNAGNILYEHEMSSEPFWEAHDTIGLLLSSPPARDLAATLAVMVSFDA
ACPQRPSRLWKNKGLWVPEGQRAKITVAALDAANLLASVPASQRSRHDVLFQVTQFPTR
GQLLVSEEPLHARRPYFLQSELAAGQLVYAHGGGGTQQDGFRFRAHLQGPTGTSVAGPQT
SEAFVITVRDVNERPPQPQASIPLRVTRGSRAPVSRAQLSVVDPDSAPGEIEYEVQRAPHN
GFLSLAGDNTGPVTHFTQADVDAGRLAFVANGSSVAGVFQLSMSDGASPPIPMSLAVDVL
PSTIEVQLRAPLEVPQALGRTSLSRQQLQVISDREEPDVAYRLTQGPLYGQLLVGGQPASAF
SQLQVDQGDVVFVFTNFSSSQDHFKVVALARGVNASATVNVTVQALLHVWAGGPWPQG
TTLRLDPTVLDASELANRTGSMPHFRLLAGPRYGRVVRVSQGRTESRSNQLVEHFTQRDL
EEGQLGLEVGKPEGRSTGPAGDRLTLELWAKGVPPAVALLDFATEPYHAAKSYSVALLSVP
EAVRTETEKPGRSVPTGQPGQAASSPVPTAAKGGFLGFLEANMFSIIIPVCLILLLLALILPL
LFYLRKRNKTGKHDVQVLTAKPRNGLAGDTETFRKVEPGQAIPLITVPGQGPPPGGQPDP
ELLQFCRTPNPALRNGQYWV

Figure 13 K

Nphs1 (NP_004637.1) (SEQ ID NO: 251)
MALGTTLRASLLLLGLLTEGLAQLAIPASVPRGFWALPENLTVVEGASVELRCGVSTPGSA
VQWAKDGLLLGPDPRIPGFPRYRLEGDPARGEFHLIHEACDLSDDAEYECQVGRSEMGPE
LVSPRVILSILVPPKLLLLTPEAGTMVTWVAGQEYVVNCVSGDAKPAPDITILLSGQTISDIS
ANVNEGSQQKLFTVEATARVTPRSSDNRQLLVCEASSPALEAPIKASFTVNVLFPPGPPVIE
WPGLDEGHVRAGQSLELPCVARGGNPLATLQWLKNGQPVSTAWGTEHTQAVARSVLVM
TVRPEDHGAQLSCEAHNSVSAGTQEHGITLQVTFPPSAIIILGSASQTENKNVTLSCVSKSS
RPRVLLRWWLGWRQLLPMEETVMDGLIIGGIIISMSNLTFLARREDNGLTLTCEAFSEAFT
KETFKKSLILNVKYPAQKLWIEGPPEGQKLRAGTRVRLVCLAIGGNPEPSLMWYKDSRTV
TESRLPQESRRVHLGSVEKSGSTFSRELVLVTGPSDNQAKFTCKAGQLSASTQLAVQFPPT
NVTILANASALRPGDALNLTCVSVSSNPPVNLSWDKEGERLEGVAAPPRRAPFKGSAAAR
SVLLQVSSRDHGQRVTCRAHSAELRETVSSFYRLNVLYRPEFLGEQVLVVTAVEQGEALLP
VSVSANPAPEAFNWTFRGYRLSPAGGPRIIRILSSGALIILWNVTRADDGLYQLIICQNSEGT
AEARLRLDVHYAPTIRALQDPTEVNVGGSVDIVCTVDANPILPGMFNWERLGEDEEDQSL
DDMEKISRGPTGRLRIHHAKLAQAGAYQCIVDNGVAPPARRLLRLVVRFAPQVEHPTPLTK
VAAAGDSTSSATLHCRARGVPNIVFTWTKNGVPLDLQDPRYTEHTYHQGGVHSSLLTIAN
VSAAQDYALFTCTATNALGSDQTNIQLVSISRPDPPSGLKVVSLTPHSVGLEWKPGFDGGL
PQRFCIRYEALGTPGFHYVDVVPPQATTFTLTGLQPSTRYRVWLLASNALGDSGLADKGT
QLPITTPGLHQPSGEPEDQLPTEPPSGPSGLPLLPVLFALGGLLLLSNASCVGGVLWQRRLR
RLAEGISEKTEAGSEEDRVRNEYEESQWTGERDTQSSTVSTTEAEPYYRSLRDFSPQLPPT
QEEVSYSRGFTGEDEDMAFPGHLYDEVERTYPPSGAWGPLYDEVQMGPWDLHWPEDTY
QDPRGIYDQVAGDLDTLEPDSLPFELRGHLV Olig2 (NP_058663.2) (SEQ ID NO: 219)
MDSDASLVSSRPSSPEPDDLFLPARSKGGSSSGFTGGTVSSSTPSDCPPELSSELRGAMGAS
GAHPGDKLGGGGFKSSSSSTSSSTSSAATSSTKKDKKQMTEPELQQLRLKINSRERKRMII
DLNIAMDGLREVMPYAHGPSVRKLSKIATLLLARNYILMLTNSLEEMKRLVSEIYGGHHA
GFHPSACGGLAHSAPLPTATAHPAAAAHAAHHPAVHHPILPPAAAAAAAAAAAAAVSSAS
LPGSGLSSVGSIRPPHGLLKSPSAAAAAPLGGGGGGSGGSGGFQHWGGMPCPCSMCQVP
PPHHHVSAMGAGTLPRLTSDAK

Figure 13 L

Otx2 (NP_068374.1) (SEQ ID NO: 252)
MMSYLKQPPYAVNGLSLTTSGMDLLHPSVGYPGPWASCPAATPRKQRRERTTFTRAQLDV
LEALFAKTRYPDIFMREEVALKINLPESRVQVWFKNRRAKCRQQQQQQQNGGQNKVRPA
KKKTSPAREVSSESGTSGQFTPPSSTSVPTIASSSAPVSIWSPASISPLSDPLSTSSSCMQRSY
PMTYTQASGYSQGYAGSTSYFGGMDCGSYLTPMHHQLPGPGATLSPMGTNAVTSHLNQS
PASLSTQGYGASSLGFNSTTDCLDYKDQTASWKLNFNADCLDYKDQTSSWKFQVL

Pax6 (NP_001231127.1) (SEQ ID NO: 221)
MQNSHSGVNQLGGVFVNGRPLPDSTRQKIVELAHSGARPCDISRILQTHADAKVQVLDN
ENVSNGCVSKILGRYYETGSIRPRAIGGSKPRVATPEVVSKIAQYKRECPSIFAWEIRDRLLS
EGVCTNDNIPSVSSINRVLRNLASEKQQMGADGMYDKLRMLNGQTGSWGTRPGWYPGT
SVPGQPTQDGCQQQEGGGENTNSISSNGEDSDEAQMRLQLKRKLQRNRTSFTQEQIEALE
KEFERTHYPDVFARERLAAKIDLPEARIQVWFSNRRAKWRREEKLRNQRRQASNTPSHIPI
SSSFSTSVYQPIPQPTTPVSSFTSGSMLGRTDTALTNTYSALPPMPSFTMANNLPMQPPVPS
QTSSYSCMLPTSPSVNGRSYDTYTPPHMQTHMNSQPMGTSGTTSTGLISPGVSVPVQVPG
SEPDMSQYWPRLQ

Pdpn (NP_001006625.1) (SEQ ID NO: 253)
MPGAEDDVVTPGTSEDRYKSGLTTLVATSVNSVTGIRIEDLPTSESTVHAQEQSPSATASNV
ATSHSTEKVDGDTQTTVEKDGLSTVTLVGIIVGVLLAIGFIGAIIVVVMRKMSGRYSP Pdx-1 (NP_000200.1) (SEQ ID NO: 254)
MNGEEQYYAATQLYKDPCAFQRGPAPEFSASPPACLYMGRQPPPPPHPFPGALGALEQGS
PPDISPYEVPPLADDPAVAHLHHHLPAQLALPHPPAGPFPEGAEPGVLEEPNRVQLPFPWM
KSTKAHAWKGQWAGGAYAAEPEENKRTRTAYTRAQLLELEKEFLFNKYISRPRRVELAVM
LNLTERHIKIWFQNRRMKWKKEEDKKRGGGTAVGGGGVAEPEQDCAVTSGEELLALPPPP
PPGGAVPPAAPVAAREGRLPPGLSASPQPSSVAPRRPQEPR

Figure 13 M

Pkd1 (NP_000287.3) (SEQ ID NO: 255)
MPPAAPARLALALGLGLWLGALAGGPGRGCGPCFPPCLCGPAPGAACRVNCSGRGLRTL
GPALRIPADATALDVSHNLLRALDVGLLANLSALAELDISNNKISTLEEGIFANLFNLSEINL
SGNPFECDCGLAWLPRWAEEQQVRVVQPEAATCAGPGSLAGQPLLGIPLLDSGCGEEYVA
CLPDNSSGTVAAVSFSAAHEGLLQPEACSAFCFSTGQGLAALSEQGWCLCGAAQPSSASF
ACLSLCSGPPPPPAPTCRGPTLLQIIVFPASPGATLVGPIIGPLASGQLAAFIIIAAPLPVTATR
WDFGDGSAEVDAAGPAASHRYVLPGRYHVTAVLALGAGSALLGTDVQVEAAPAALELV
CPSSVQSDESLDLSIQNRGGSGLEAAYSIVALGEEPARAVHPLCPSDTEIFPGNGHCYRLVV
EKAAWLQAQEQCQAWAGAALAMVDSPAVQRFLVSRVTRSLDVWIGFSTVQGVEVGPAP
QGEAFSLESCQNWLPGEPHPATAEHCVRLGPTGWCNTDLCSAPHSYVCELQPGGPVQDA
ENLLVGAPSGDLQGPLTPLAQQDGLSAPIIEPVEVMVFPGLRLSREAFLTTAEFGTQELRRP
AQLRLQVYRLLSTAGTPENGSEPESRSPDNRTQLAPACMPGGRWCPGANICLPLDASCHP
QACANGCTSGPGLPGAPYALWREFLFSVPAGPPAQYSVTLHGQDVLMLPGDLVGLQHDA
GPGALLHCSPAPGHPGPQAPYLSANASSWLPHLPAQLEGTWACPACALRLLAATEQLTVL
LGLRPNPGLRLPGRYEVRAEVGNGVSRHNLSCSFDVVSPVAGLRVIYPAPRDGRLYVPTN
GSALVLQVDSGANATATARWPGGSVSARFENVCPALVATFVPGCPWETNDTLFSVVALPW
LSEGEHVVDVVVENSASRANLSLRVTAEEPICGLRATPSPEARVLQGVLVRYSPVVEAGSD
MVFRWTINDKQSLTFQNVVFNVIYQSAAVFKLSLTASNHVSNVTVNYNVTVERMNRMQG
LQVSTVPAVLSPNATLALTAGVLVDSAVEVAFLWTFGDGEQALHQFQPPYNESFPVPDPSV
AQVLVEHNVMHTYAAPGEYLLTVLASNAFENLTQQVPVSVRASLPSVAVGVSDGVLVAG
RPVTFYPIIPLPSPGGVLYTWDFGDGSPVLTQSQPAANIITYASRGTYIIVRLEVNNTVSGAA
AQADVRVFEELRGLSVDMSLAVEQGAPVVVSAAVQTGDNITWTFDMGDGTVLSGPEATV
EHVYLRAQNCTVTVGAASPAGHLARSLHVLVFVLEVLRVEPAACIPTQPDARLTAYVTGN
PAHYLFDWTFGDGSSNTTVRGCPTVTHNFTRSGTFPLALVLSSRVNRAHYFTSICVEPEVG
NVTLQPERQFVQLGDEAWLVACAWPPFPYRYTWDFGTEEAAPTRARGPEVTFIYRDPGSY
LVTVTASNNISAANDSALVEVQEPVLVTSIKVNGSLGLELQQPYLFSAVGRGRPASYLWDL
GDGGWLEGPEVTHAYNSTGDFTVRVAGWNEVSRSEAWLNVTVKRRVRGLVVNASRTVV
PLNGSVSFSTSLEAGSDVRYSWVLCDRCTPIPGGPTISYTFRSVGTFNIIVTAENEVGSAQD
SIFVYVLQLIEGLQVVGGGRYFPTNHTVQLQAVVRDGTNVSYSWTAWRDRGPALAGSGK
GFSLTVLEAGTYHVQLRATNMLGSAWADCTMDFVEPVGWLMVAASPNPAAVNTSVTLSA
ELAGGSGVVYTWSLEEGLSWETSEPITTHSFPTPGLHLVTMTAGNPLGSANATVEVDVQV
PVSGLSIRASEPGGSFVAAGSSVPFWGQLATGTNVSWCWAVPGGSSKRGPIIVTMVFPDAG
TFSIRLNASNAVSWVSATYNLTAEEPIVGLVLWASSKVVAPGQLVHFQILLAAGSAVTFRLQ
VGGANPEVLPGPRFSHSFPRVGDHVVSVRGKNHVSWAQAQVRIVVLEAVSGLQVPNCCE
PGIATGTERNFTARVQRGSRVAYAWYFSLQKVQGDSLVILSGRDVTYTPVAAGLLEIQVRA
FNALGSENRTLVLEVQDAVQYVALQSGPCFTNRSAQFEAATSPSPRRVAYHWDFGDGSPG
QDTDEPRAEIISYLRPGDYRVQVNASNLVSFFVAQATVTVQVLACREPEVDVVLPLQVLM
RRSQRNYLEAHVDLRDCVTYQTEYRWEVYRTASCQRPGRPARVALPGVDVSRPRLVLPRL
ALPVGHYCFVFVVSFGDTPLTQSIQANVTVAPERLVPIIEGGSYRVWSDTRDLVLDGSESY
DPNLEDGDQTPLSFHWACVASTQREAGGCALNFGPRGSSTVTIPRERLAAGVEYTFSLTV
WKAGRKEEATNQTVLIRSGRVPIVSLECVSCKAQAVYEVSRSSYVYLEGRCLNCSSGSKR
GRWAARTFSNKTLVLDETTTSTGSAGMRLVLRRGVLRDGEGYTFTLTVLGRSGEEEGCAS

Figure 13 N

IRLSPNRPPLGGSCRLFPLGAVHALTTKVHFECTGWHDAEDAGAPLVYALLLRRCRQGHC
EEFCVYKGSLSSYGAVLPPGFRPHFEVGLAVVVQDQLGAAVVALNRSLAITLPEPNGSATG
LTVWLHGLTASVLPGLLRQADPQHVIEYSLALVTVLNEYERALDVAAEPKHERQHRAQIR
KNITETLVSLRVHTVDDIQQIAAALAQCMGPSRELVCRSCLKQTLHKLEAMMLILQAETTA
GTVTPTAIGDSILNITGDLIHLASSDVRAPQPSELGAESPSRMVASQAYNLTSALMRILMRS
RVLNEEPLTLAGEEIVAQGKRSDPRSLLCYGGAPGPGCHFSIPEAFSGALANLSDVVQLIFL
VDSNPFPFGYISNYTVSTKVASMAFQTQAGAQIPIERLASERAITVKVPNNSDWAARGIIRS
SANSANSVVVQPQASVGAVVTLDSSNPAAGLHLQLNYTLLDGHYLSEEPEPYLAVYLHSE
PRPNEHNCSASRRIRPESLQGADHRPYTFFISPGSRDPAGSYHLNLSSHFRWSALQVSVGLY
TSLCQYFSEEDMVWRTEGLLPLEETSPRQAVCLTRHLTAFGASLFVPPSHVRFVFPEPTADV
NYIVMLTCAVCLVTYMVMAAILHKLDQLDASRGRAIPFCGQRGRFKYEILVKTGWGRGS
GTTAHVGIMLYGVDSRSGHRHLDGDRAFHRNSLDIFRIATPHSLGSVWKIRVWHDNKGLS
PAWFLQIIVIVRDLQTARSAFFLVNDWLSVETEANGGLVEKEVLAASDAALLRFRRLLVAE
LQRGFFDKHIWLSIWDRPPRSRFTRIQRATCCVLLICLFLGANAVWYGAVGDSAYSTGHVS
RLSPLSVDTVAVGLVSSVVVYPVYLAILFLFRMSRSKVAGSPSPTPAGQQVLDIDSCLDSSV
LDSSFLTFSGLHAFAFVGQMKSDLFLDDSKSLVCWPSGFGTLSWPDLLSDPSIVGSNLRQL
ARGQAGHGLGPEEDGFSLASPYSPAKSFSASDEDLIQQVLAEGVSSPAPTQDTHMETDLLS
SLSSTPGEKTETLALQRLGELGPPSPGLNWEQPQAARLSRTGLVEGLRKRLLPAWCASLAH
GLSLLLVAVAVAVSGWVGASFPPGVSVAWLLSSSASFLASFLGWEPLKVLLEALYFSLVAKR
LHPDEDDTLVESPAVTPVSARVPRVRPPHGFALFLAKEEARKVKRLHGMLRSLLVYMLFLL
VTLLASYGDASCHGHAYRLQSAIKQELHSRAFLAITRSEELWPWMAHVLLPYVHGNQSSP
ELGPPRLRQVRLQEALYPDPPGPRVHTCSAAGGFSTSDYDVGWESPHNGSGTWAYSAPDL
LGAWSWGSCAVYDSGGYVQELGLSLEESRDRLRFLQLHNWLDNRSRAVFLELTRYSPAV
GLHAAVTLRLEFPAAGRALAALSVRPFALRRLSAGLSLPLLTSVCLLLFAVHFAVAEARTW
HREGRWRVLRLGAWARWLLVALTAATALVRLAQLGAADRQWTRFVRGRPRRFTSFDQVA
QLSSAARGLAASLLFLLLVKAAQQLRFVRQWSVFGKTLCRALPELLGVTLGLVVLGVAYA
QLAILLVSSCVDSLWSVAQALLVLCPGTGLSTLCPAESWHLSPLLCVGLWALRLWGALRL
GAVILRWRYHALRGELYRPAWEPQDYEMVELFLRRLRLWMGLSKVKEFRHKVRFEGMEP
LPSRSSRGSKVSPDVPPPSAGSDASHPSTSSSQLDGLSVSLGRLGTRCEPEPSRLQAVFEALL
TQFDRLNQATEDVYQLEQQLHSLQGRRSSRAPAGSSRGPSPGLRPALPSRLARASRGVDLA
TGPSRTPLRAKNKVHPSST

Figure 13 N (Continued)

Pkd2 (NP_000288.1) (SEQ ID NO: 256)
MVNSSRVQPQQPGDAKRPPAPRAPDPGRLMAGCAAVGASLAAPGGLCEQRGLEIEMQRI
RQAAARDPPAGAAASPSPPLSSCSRQAWSRDNPGFEAEEEEEEVEGEEGGMVVEMDVEW
RPGSRRSAASSAVSSVGARSRGLGGYHGAGHPSGRRRRREDQGPPCPSPVGGGDPLHRHL
PLEGQPPRVAWAERLVRGLRGLWGTRLMEESSTNREKYLKSVLRELVTYLLFLIVLCILTY
GMMSSNVYYYTRMMSQLFLDTPVSKTEKTNFKTLSSMEDFWKFTEGSLLDGLYWKMQP
SNQTEADNRSFIFYENLLLGVPRIRQLRVRNGSCSIPQDLRDEIKECYDVYSVSSEDRAPFG
PRNGTAWIYTSEKDLNGSSHWGIIATYSGAGYYLDLSRTREETAAQVASLKKNVWLDRGT
RATFIDFSVYNANINLFCVVRLLVEFPATGGVIPSWQFQPLKLIRYVTTFDFFLAACEIIFCFF
IFYYVVEEILEIRIHKLHYFRSFWNCLDVVIVVLSVVAIGINIYRTSNVEVLLQFLEDQNTFP
NFEILAYWQIQFNNIAAVTVFFVWIKLFKFINFNRTMSQLSTTMSRCAKDLFGFAIMFFIIF
LAYAQLAYLVFGTQVDDFSTFQECIFTQFRIILGDINFAEIEEANRVLGPIYFTTFVFFMFFIL
LNMFLAIINDTYSEVKSDLAQQKAEMELSDLIRKGYHKALVKLKLKKNTVDDISESLRQG
GGKLNFDELRQDLKGKGHTDAEIEAIFTKYDQDGDQELTEHEHQQMRDDLEKEREDLDL
DHSSLPRPMSSRSFPRSLDDSEEDDDEDSGHSSRRRGSISSGVSYEEFQVLVRRVDRMEHSI
GSIVSKIDAVIVKLEIMERAKLKRREVLGRLLDGVAEDERLGRDSEIIIREQMERLVREELE
RWESDDAASQISHGLGTPVGLNGQPRPRSSRPSSSQSTEGMEGAGGNGSSNVHV

Podxl (NP_001018121.1) (SEQ ID NO: 222)
MRCALALSALLLLLSTPPLLPSSPSPSPSPSQNATQTTTDSSNKTAPTPASSVTIMATDTAQQ
STVPTSKANEILASVKATTLGVSSDSPGTTTLAQQVSGPVNTTVARGGGSGNPTTTIESPKS
TKSADTTTVATSTATAKPNTTSSQNGAEDTTNSGGKSSHSVTTDLTSTKAEHLTTPHPTSPL
SPRQPTSTHPVATPTSSGHDHLMKISSSSSTVAIPGYTFTSPGMTTTLLETVFHHVSQAGLEL
LTSGDLPTLASQSAGITASSVISQRTQQTSSQMPASSTAPSSQETVQPTSPATALRTPTLPETM
SSSPTAASTTHRYPKTPSPTVAHESNWAKCEDLETQTQSEKQLVLNLTGNTLCAGGASDEK
LISLICRAVKATFNPAQDKCGIRLASVPGSQTVVVKEITIITKLPAKDVYERLKDKWDELK
EAGVSDMKLGDQGPPEEAEDRFSMPLIITIVCMASFLLLVAALYGCCHQRLSQRKDQQRLT
EELQTVENGYHDNPTLEVMETSSEMQEKKVVSLNGELGDSWIVPLDNLTKDDLDEEEDT
HL S100A (NP_035439.1) (SEQ ID NO: 257)
MGSELESAMETLINVFHAHSGKEGDKYKLSKKELKDLLQTELSGFLDVQKDADAVDKV
MKELDENGDGEVDFKEYVVLVAALTVACNNFFWETS S100B (NP_033141.1) (SEQ ID NO: 258)
MSELEKAMVALIDVFHQYSGREGDKHKLKKSELKELINNELSHFLEEIKEQEVVDKVMET
LDEDGDGECDFQEFMAFVAMVTTACHEFFEHE

Figure 13 O

Scnn1a (NP_001029.1) (SEQ ID NO: 259)
MEGNKLEEQDSSPPQSTPGLMKGNKREEQGLGPEPAAPQQPTAEEEALIEFHRSYRELFEF
FCNNTTIHGAIRLVCSQHNRMKTAFWAVLWLCTFGMMYWQFGLLFGEYFSYPVSLNINL
NSDKLVFPAVTICTLNPYRYPEIKEELEELDRITEQTLFDLYKYSSFTTLVAGSRSRRDLRGT
LPHPLQRLRVPPPHGARRARSVASSLRDNNPQVDWKDWKIGFQLCNQNKSDCFYQTYS
SGVDAVREWYRFHYINILSRLPETLPSLEEDTLGNFIFACRFNQVSCNQANYSHFHHPMYG
NCYTFNDKNNSNLWMSSMPGINNGLSLMLRAEQNDFIPLLSTVTGARVMVIIGQDEPAFM
DDGGFNLRPGVETSISMRKETLDRLGGDYGDCTKNGSDVPVENLYPSKYTQQVCIHSCFQ
ESMIKECGCAYIFYPRPQNVEYCDYRKHSSWGYCYYKLQVDFSSDHLGCFTKCRKPCSVT
SYQLSAGYSRWPSVTSQEWVFQMLSRQNNYTVNNKRNGVAKVNIFFKELNYKTNSESPS
VTMVTLLSNLGSQWSLWFGSSVLSVVEMAELVFDLLVIMFLMLLRRFRSRYWSPGRGGR
GAQEVASTLASSPPSHFCPHPMSLSLSQPGPAPSPALTAPPPAYATLGPRPSPGGSAGASSST
CPLGGP Slc5a1 (NP_000334.1) (SEQ ID NO: 260)
MDSSTWSPKTTAVTRPVETHELIRNAADISHVIYFVVVMAVGLWAMFSTNRGTVGGFFLA
GRSMVWWPIGASLFASNIGSGHFVGLAGTGAASGIAIGGFEWNALVLVVVLGWLFVPIYI
KAGVVTMPEYLRKRFGGQRIQVYLSLLSLLLYIFTKISADIFSGAIFINLALGLNLYLAIFLL
LAITALYTITGGLAAVIYTDTLQTVIMLVGSLILTGFAFHEVGGYDAFMEKYMKAIPTIVSD
GNTTFQEKCYTPRADSFHIFRDPLTGDLPWPGFIFGMSILTLWYWCTDQVIVQRCLSAKN
MSHVKGGCILCGYLKLMPMFIMVMPGMISRILYTEKIACVVPSECEKYCGTKVGCTNIAY
PTLVVELMPNGLRGLMLSVMLASLMSSLTSIFNSASTLFTMDIYAKVRKRASEKELMIAGR
LFILVLIGISIAWVPIVQSAQSGQLFDYIQSITSYLGPPIAAVFLLAIFWKRVNEPGAFWGLIL
GLLIGISRMITEFAYGTGSCMEPSNCPTIICGVHYLYFAIILFAISFITIVVISLLTKPIPDVHLYR
LCWSLRNSKEERIDLDAEEENIQEGPKETIEIETQVPEKKKGIFRRAYDLFCGLEQHGAPK
MTEEEEKAMKMKMTDSEKPLWRTVLNVNGIILVTVAVFCHAYFA Sox 1 (NP_033259.2) (SEQ ID NO: 227)
MYSMMMETDLHSPGGAQAPTNLSGPAGAGGGGGGGGGGGGGTKANQDRVKRPMN
AFMVWSRGQRRKMAQENPKMHNSEISKRLGAEWKVMSEAEKRPFIDEAKRLRALHMK
EHPDYKYRPRRKTKTLLKKDKYSLAGGLLAAGAGGGGAAVAMGVGVGVGAAAVGQRL
ESPGGAAGGGYAHVNGWANGAYPGSVAAAAAAAMMQEAQLAYGQHPGAGGAHPHA
HPAHPHPHHPHAHPHNPQPMHRYDMGALQYSPISNSQGYMSASPSGYGGIPYGAAAAAA
AAAGGAHQNSAVAAAAAAAASSGALGALGSLVKSEPSGSPPAPAHSRAPCPGDLREMIS
MYLPAGEGGDPAAAAAAAQSRLHSLPQHYQGAGAGVNGTVPLTHI

Figure 13 P

Sox17 (NP_071899.1) (SEQ ID NO: 261)
MSSPDAGYASDDQSQTQSALPAVMAGLGPCPWAESLSPIGDMKVKGEAPANSGAPAGAA
GRAKGESRIRRPMNAFMVWAKDERKRLAQQNPDLHNAELSKMLGKSWKALTLAEKRPF
VEEAERLRVQHMQDHPNYKYRPRRRKQVKRLKRVEGGFLHGLAEPQAAALGPEGGRVA
MDGLGLQFPEQGFPAGPPLLPPHMGGHYRDCQSLGAPPLDGYPLPTPDTSPLDGVDPDPA
FFAAPMPGDCPAAGTYSYAQVSDYAGPPEPPAGPMIIPRLGPEPAGPSIPGLLAPPSALIIVY
YGAMGSPGAGGGRGFQMQPQHQHQHQHQHHPPGPGQPSPPPEALPCRDGTDPSQPAELL
GEVDRTEFEQYLHFVCKPEMGLPYQGHDSGVNLPDSHGAISSVVSDASSAVYYCNYPDV

Tp63 (NP_001108450.1) (SEQ ID NO: 262)
MNFETSRCATLQYCPDPYIQRFVETPAHFSWKESYYRSTMSQSTQTNEFLSPEVFQHIWDF
LEQPICSVQPIDLNFVDEPSEDGATNKIEISMDCIRMQDSDLSDPMWPQYTNLGLLNSMDQ
QIQNGSSSTSPYNTDHAQNSVTAPSPYAQPSSTFDALSPSPAIPSNTDYPGPHSFDVSFQQSS
TAKSATWTYSTELKKLYCQIAKTCPIQIKVMTPPPQGAVIRAMPVYKKAEHVTEVVKRCP
NHELSREFNEGQIAPPSHLIRVEGNSHAQYVEDPITGRQSVLVPYEPPQVGTEFTTVLYNFM
CNSSCVGGMNRRPILIIVTLETRDGQVLGRRCFEARICACPGRDRKADEDSIRKQQVSDST
KNGDGTKRPFRQNTHGIQMTSIKKRRSPDDELLYLPVRGRETYEMLLKIKESLELMQYLP
QHTIETYRQQQQQQHQHLLQKQTSIQSPSSYGNSSPPLNKMNSMNKLPSVSQLINPQQRN
ALTPTTIPDGMGANIPMMGTHMPMAGDMNGLSPTQALPPPLSMPSTSHCTPPPPYPTDCSI
VRIWQV

Tuj1 (NP_075768.1) (SEQ ID NO: 263)
MRLIVHIQAGQCGNQIGAKFWEVISDEHGIDPSGNYVGDSDLQLERISVYYNEASSHKYV
PRAILVDLEPGTMDSVRSGAFGHLFRPDNFIFGQSGAGNNWAKGHYTEGAELVDSVLDVV
RKECENCDCLQGFQLTHSLGGGTGSGMGTLLISKVREEYPDRIMNTFSVVPSPKVSDTVV
EPYNATLSIHQLVENTDETYCIDNEALYDICFRTLKLATPTYGDLNHLVSATMSGVTTSLRF
PGQLNADLRKLAVNMVPFPRLHFFMPGFAPLTARGSQQYRALTVPELTQQMFDAKNMMA
ACDPRHGRYLTVATVFRGRMSMKEVDEQMLAIQSKNSSYFVEWIPNNVKVAVCDIPPRGL
KMSSTFIGNSTAIQELFKRISEQFTAMFRRKAFLHWYTGEGMDEMEFTEAESNMNDLVSE
YQQYQDATAEEEGEMYEDDDEESEAQGPK

Figure 13 Q

Umod (NP_001008390.1) (SEQ ID NO: 264)
MGQPSLTWMLMVVVASWFTTAATDTSEARWCSECHSNATCTEDEAVTTCTCQEGFTGD
GLTCVDLDECAIPGAHNCSANSSCVNTPGSFSCVCPEGFRLSPGLGCTDVDECAEPGLSHC
HALATCVNVVGSYLCVCPAGYRGDGWHCECSPGSCGPGLDCVPEGDALVCADPCQAHR
TLDEYWRSTEYGEGYACDTDLRGWYRFVGQGGARMAETCVPVLRCNTAAPMWLNGTH
PSSDEGIVSRKACAHWSGHCCLWDASVQVKACAGGYYVYNLTAPPECHLAYCTDPSSVE
GTCEECSIDEDCKSNNGRWHCQCKQDFNITDISLLEHRLECGANDMKVSLGKCQLKSLGF
DKVFMYLSDSRCSGFNDRDNRDWVSVVTPARDGPCGTVLTRNETHATYSNTLYLADEHI
RDLNIKINFACSYPLDMKVSLKTALQPMVSALNIRVGGTGMFTVRMALFQTPSYTQPYQG
SSVTLSTEAFLYVGTMLDGGDLSRFALLMTNCYATPSSNATDPLKYFIIQDRCPHTRDSTIQ
VVENGESSQGRFSVQMFRFAGNYDLVYLIICEVYLCDTMNEKCKPTCSGTRFRSGSVIDQ
SRVLNLGPITRKGVQATVSRAFSSLGLLKVWLPLLLSATLTLTFQ Zic1 (NP_033599.2) (SEQ ID NO: 265)
MLLDAGPQYPAIGVTTFGASRHHSAGDVAERDVGLGINPFADGMGAFKLNPSSHELASAG
QTAFTSQAPGYAAAAALGHHHHPGHVGSYSSAAFNSTRDFLFRNRGFGDAAAAASAQHS
LFAASAGGFGGPHGHTDAAGHLLFSGLHEQAAGHASPNVVNGQMRLGFSGDMYPRPEQ
YGQVTSPRSEHYAAPQLHGYGPMNVNMAAIHIGAGAFFRYMRQPIKQELICKWIEPEQLA
NPKKSCNKTFSTMHELVTHVTVEHVGGPEQSNHICFWEECPREGKPFKAKYKLVNHIRVH
TGEKPFPCPFPGCGKVFARSENLKIHKRTHTGEKPFKCEFEGCDRRFANSSDRKKHMHVH
TSDKPYLCKMCDKSYTHPSSLRKHMKVHESSSQGSQPSPAASSGYESSTPPTIVSPTTDNP
TTSSMSPSSSAVHHTAGHSALSSNFNEWYV

Figure 13R

SEQUENCE LISTING

```
<160> NUMBER OF SEQ ID NOS: 265

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gttagaggtt aaggttagtg ggtg                                            24

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
aaaccttaaa aacttaacca aatcc                                           25

<210> SEQ ID NO 3
<211> LENGTH: 30
<212> TYPE: DNA
<213> ORGANISM: Artificial Sequence
```

```
<220> FEATURE:
<223> OTHER INFORMATION: Primer

<400> SEQUENCE: 3
gagttaaaga gttttgtttt taaaaattat                                    30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
tcccaaatct aataatttat catatctttc                                    30

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
ttgttttagg aaaggtaaag aaaggt                                        26

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
aattccaact tctccaaaat tataaca                                       27

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
cccctggtgc cgtgaag                                                  17

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gcaaattgct cgagttcttt ctg                                           23

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
atggaaatcc catcaccatc tt                                            22
```

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
cgccccactt gattttgg                                                 18

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ccaaaggcaa acaacccact t                                             21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgggaccttg tcttcctttt t                                             21

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
cccctttatt ttccgtagtt gtattt                                        26

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gattctcggc agactgattc aa                                            22

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
catcttgtga gtggataatc aggaa                                         25

<210> SEQ ID NO 16
<211> LENGTH: 24
<212> TYPE: DNA
<213> ORGANISM: Artificial Sequence
<220> FEATURE:
<223> OTHER INFORMATION: Primer

```
<400> SEQUENCE: 16 gacccccatct gttctttgat tttt                                           24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cactttgcac tggaacttac aaca                                            24

<210> SEQ ID NO 18
<211> LENGTH: 16
<212> TYPE: DNA
<213> ORGANISM: Artificial Sequence
<220> FEATURE:
<223> OTHER INFORMATION: Primer

<400> SEQUENCE: 18
cccgcgtcgg gagagt                                                     16

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
agcccaagaa gtgccacttc t                                               21

<210> SEQ ID NO 20
<211> LENGTH: 17
<212> TYPE: DNA
<213> ORGANISM: Artificial Sequence
<220> FEATURE:
<223> OTHER INFORMATION: Primer

<400> SEQUENCE: 20
gggccttcag cggacat                                                    17

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cacgccgcct ctctatcg                                                   18

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
cgtcagtatt tcgtgcagtc gta                                             23

<210> SEQ ID NO 23
```

```
<211> LENGTH: 19
<212> TYPE: DNA
<213> ORGANISM: Artificial Sequence
<220> FEATURE:
<223> OTHER INFORMATION: Primer

<400> SEQUENCE: 23
tgtgaatggg cgaccaaga                                                 19

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
gtgggactgc ctggtgatg                                                 19

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
gcgctgcgga agatcatc                                                  18

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ggtctgaatc ttgctcagct tgt                                            23

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
gcccagtgga gcatgca                                                   17

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
ggtgggacac cgagatggt                                                 19

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
```
gtttcccggg caatttaaca                                                  20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cccgacaagt gacagccatt                                                  20

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gccgagtcca tgcgaact                                                    18

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
ccatgatcgg ctgcttcat                                                   19

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
tccaagacta ccaccaccat cat                                              23

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
ttctttaaac tctgtaagga tggactgt                                         28

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
ggctgttgaa cgtgccaaa                                                   19

<210> SEQ ID NO 36
<211> LENGTH: 18
<212> TYPE: DNA

```
<213> ORGANISM: Artificial Sequence
<220> FEATURE:
<223> OTHER INFORMATION: Primer

<400> SEQUENCE: 36
tgcccgatga tggcattc                                                  18

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
cctgggtgcc taccactca                                                 19

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
aaatgcaggc aggtaacaag aag                                            23

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
acgatgtgcg caaagagaac t                                              21

<210> SEQ ID NO 40
<211> LENGTH: 17
<212> TYPE: DNA
<213> ORGANISM: Artificial Sequence
<220> FEATURE:
<223> OTHER INFORMATION: Primer

<400> SEQUENCE: 40
tgggcagcca ggtgtca                                                   17

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gagctggcga tgactgaact g                                              21

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
gcaaattcag ggctcactag aga                                            23
```

```
<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
actggacgtt tgcttttgac ttc                                              23

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
cagcccatgc cagatcct                                                    18

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
cattttcagc tgggagtttc tgt                                              23

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
gggtattatt gttccagact cagtga                                           26

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
tctacgggat gcccactga                                                   19

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ggccatttcg aagcttgttg                                                  20

<210> SEQ ID NO 49
<211> LENGTH: 21
<212> TYPE: DNA
<213> ORGANISM: Artificial Sequence
<220> FEATURE:
```

<223> OTHER INFORMATION: Primer

<400> SEQUENCE: 49
cttttatggg ctcggcagtt a                                    21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tcaccatgcc cactgcttag                                      20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
agtaccccgg catgttcatc                                      20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
cggttcccct tcttggtctt                                      20

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53
cctcgcgcac acctaagc                                        18

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
ggttttacct gtatggaaag ctatcc                               26

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
ctgaagccgg aacaccacta c                                    21

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
cgaggacatg aggttgttga tg                                    22

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
ccaacaggag gccatgctt                                        19

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
gagaatgcag gagggacata tgt                                   23

<210> SEQ ID NO 59
<211> LENGTH: 17
<212> TYPE: DNA
<213> ORGANISM: Artificial Sequence
<220> FEATURE:
<223> OTHER INFORMATION: Primer

<400> SEQUENCE: 59
tggcgcagca gaatcca                                          17

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
cgacttgccc agcatcttg                                        19

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
cgtcagccag tctccacaga                                       20

<210> SEQ ID NO 62
<211> LENGTH: 21
<212> TYPE: DNA
<213> ORGANISM: Artificial Sequence
<220> FEATURE:
<223> OTHER INFORMATION: Primer

```
<400> SEQUENCE: 62
caagaccagg ctgttccaag a                                              21

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
tgcctttccc atggatgaa                                                 19

<210> SEQ ID NO 64
<211> LENGTH: 17
<212> TYPE: DNA
<213> ORGANISM: Artificial Sequence
<220> FEATURE:
<223> OTHER INFORMATION: Primer

<400> SEQUENCE: 64
tgcccactgg cctttcc                                                   17

<210> SEQ ID NO 65
<211> LENGTH: 17
<212> TYPE: DNA
<213> ORGANISM: Artificial Sequence
<220> FEATURE:
<223> OTHER INFORMATION: Primer

<400> SEQUENCE: 65
gctgtggctg cgcttca                                                   17

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
tcctcctgcc gttcttggt                                                 19

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ctcgctcagc ctcactgaga                                                20

<210> SEQ ID NO 68
<211> LENGTH: 18
<212> TYPE: DNA
<213> ORGANISM: Artificial Sequence
<220> FEATURE:
<223> OTHER INFORMATION: Primer

<400> SEQUENCE: 68
ggcggccatc ttcagctt                                                  18

<210> SEQ ID NO 69
<211> LENGTH: 22
```

```
<212> TYPE: DNA
<213> ORGANISM: Artificial Sequence
<220> FEATURE:
<223> OTHER INFORMATION: Primer

<400> SEQUENCE: 69
tcaatcaatt tgccgatgtc tt                                              22

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
ccccgaccaa agttaaatcc a                                               21

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
cagacacagc cctcacaaac ac                                              22

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
tggtgaagct gggcatagg                                                  19

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
agccctgacc actccagttt ag                                              22

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
ccctctatgg ctgtttcttt ctct                                            24

<210> SEQ ID NO 75
<211> LENGTH: 18
<212> TYPE: DNA
<213> ORGANISM: Artificial Sequence
<220> FEATURE:
<223> OTHER INFORMATION: Primer

<400> SEQUENCE: 75
```
tcgggcgcag ctagatgt                                      18

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
tgtctgggta ccgggtcttg                                    20

<210> SEQ ID NO 77
<211> LENGTH: 18
<212> TYPE: DNA
<213> ORGANISM: Artificial Sequence
<220> FEATURE:
<223> OTHER INFORMATION: Primer

<400> SEQUENCE: 77
tttcccaccc cgagatga                                      18

<210> SEQ ID NO 78
<211> LENGTH: 16
<212> TYPE: DNA
<213> ORGANISM: Artificial Sequence
<220> FEATURE:
<223> OTHER INFORMATION: Primer

<400> SEQUENCE: 78
tgcggcgagc atccat                                        16

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
ttccgcgagc tctacaagat c                                  21

<210> SEQ ID NO 80
<211> LENGTH: 18
<212> TYPE: DNA
<213> ORGANISM: Artificial Sequence
<220> FEATURE:
<223> OTHER INFORMATION: Primer

<400> SEQUENCE: 80
cagcttggcg tggttgtg                                      18

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
cgattcatag tcctgtccaa caac                               24

<210> SEQ ID NO 82
<211> LENGTH: 21
<212> TYPE: DNA
<213> ORGANISM: Artificial Sequence

```
<220> FEATURE:
<223> OTHER INFORMATION: Primer

<400> SEQUENCE: 82
agcgataagt gccctcatct g                                        21

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
aggaggacgc aggcctagag                                          20

<210> SEQ ID NO 84
<211> LENGTH: 19
<212> TYPE: DNA
<213> ORGANISM: Artificial Sequence
<220> FEATURE:
<223> OTHER INFORMATION: Primer

<400> SEQUENCE: 84
gcgagcactg caccttcac                                           19

<210> SEQ ID NO 85
<211> LENGTH: 19
<212> TYPE: DNA
<213> ORGANISM: Artificial Sequence
<220> FEATURE:
<223> OTHER INFORMATION: Primer

<400> SEQUENCE: 85
ccatgatcgt cggcatcac                                           19

<210> SEQ ID NO 86
<211> LENGTH: 19
<212> TYPE: DNA
<213> ORGANISM: Artificial Sequence
<220> FEATURE:
<223> OTHER INFORMATION: Primer

<400> SEQUENCE: 86
gccacgactg cagggtctt                                           19

<210> SEQ ID NO 87
<211> LENGTH: 28
<212> TYPE: DNA
<213> ORGANISM: Artificial Sequence
<220> FEATURE:
<223> OTHER INFORMATION: Primer

<400> SEQUENCE: 87
cagcatattg ctctactgta tcacaaac                                 28

<210> SEQ ID NO 88
<211> LENGTH: 18
<212> TYPE: DNA
<213> ORGANISM: Artificial Sequence
<220> FEATURE:
<223> OTHER INFORMATION: Primer

<400> SEQUENCE: 88
agcatggcgc tggttctg                                            18
```

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
ggtcttcgtc gattaatacc ttgtg                                          25

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
ctgctctacc tatcagggaa acg                                            23

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
ccgatcagcc tcgtttcct                                                 19

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
gccgtgcaag ccaaaact                                                  18

<210> SEQ ID NO 93
<211> LENGTH: 19
<212> TYPE: DNA
<213> ORGANISM: Artificial Sequence
<220> FEATURE:
<223> OTHER INFORMATION: Primer

<400> SEQUENCE: 93
ggtggcatcc ctccaattc                                                 19

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
gcccactaac aggtgagctg tt                                             22

<210> SEQ ID NO 95
<211> LENGTH: 20
<212> TYPE: DNA
<213> ORGANISM: Artificial Sequence
<220> FEATURE:
<223> OTHER INFORMATION: Primer -continued

<400> SEQUENCE: 95
agccagcaaa actcccagaa                                              20

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
acattcggag ttgcccaaat a                                            21

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
ccacacaacg cccatcct                                                18

<210> SEQ ID NO 98
<211> LENGTH: 22
<212> TYPE: DNA
<213> ORGANISM: Artificial Sequence
<220> FEATURE:
<223> OTHER INFORMATION: Primer

<400> SEQUENCE: 98
gaagacaccg tgcgtgtgta tt                                           22

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
cgtctcttcc atcaacagaa tcat                                         24

<210> SEQ ID NO 100
<211> LENGTH: 17
<212> TYPE: DNA
<213> ORGANISM: Artificial Sequence
<220> FEATURE:
<223> OTHER INFORMATION: Primer

<400> SEQUENCE: 100
ggcgttgggt ggaaagg                                                 17

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
cggattcacc atgccaaact                                              20

<210> SEQ ID NO 102

```
<211> LENGTH: 16
<212> TYPE: DNA
<213> ORGANISM: Artificial Sequence
<220> FEATURE:
<223> OTHER INFORMATION: Primer

<400> SEQUENCE: 102
ggcgccaccc cattgt                                                         16

<210> SEQ ID NO 103
<211> LENGTH: 18
<212> TYPE: DNA
<213> ORGANISM: Artificial Sequence
<220> FEATURE:
<223> OTHER INFORMATION: Primer

<400> SEQUENCE: 103
cgggctcaag ctcatgct                                                       18

<210> SEQ ID NO 104
<211> LENGTH: 19
<212> TYPE: DNA
<213> ORGANISM: Artificial Sequence
<220> FEATURE:
<223> OTHER INFORMATION: Primer

<400> SEQUENCE: 104
cgctccggct taggtaacc                                                      19

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
ttttggctgg gcctacttca                                                     20

<210> SEQ ID NO 106
<211> LENGTH: 23
<212> TYPE: DNA
<213> ORGANISM: Artificial Sequence
<220> FEATURE:
<223> OTHER INFORMATION: Primer

<400> SEQUENCE: 106
tgatccagat gcagtttcac tca                                                 23

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
agtggaggac cccatgaaca                                                     20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
```

-continued ttgggcttgt ggtcattctg                                            20

<210> SEQ ID NO 109
<211> LENGTH: 17
<212> TYPE: DNA
<213> ORGANISM: Artificial Sequence
<220> FEATURE:
<223> OTHER INFORMATION: Primer

<400> SEQUENCE: 109
ggccgcggtg cttttta                                               17

<210> SEQ ID NO 110
<211> LENGTH: 17
<212> TYPE: DNA
<213> ORGANISM: Artificial Sequence
<220> FEATURE:
<223> OTHER INFORMATION: Primer

<400> SEQUENCE: 110
gggccgagca gcaagat                                               17

<210> SEQ ID NO 111
<211> LENGTH: 19
<212> TYPE: DNA
<213> ORGANISM: Artificial Sequence
<220> FEATURE:
<223> OTHER INFORMATION: Primer

<400> SEQUENCE: 111
agctccctgc caaggatgt                                             19

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
cctcctttag ttcatcccat ttgt                                       24

<210> SEQ ID NO 113
<211> LENGTH: 19
<212> TYPE: DNA
<213> ORGANISM: Artificial Sequence
<220> FEATURE:
<223> OTHER INFORMATION: Primer

<400> SEQUENCE: 113
aaccctgctc ggtcctttg                                             19

<210> SEQ ID NO 114
<211> LENGTH: 22
<212> TYPE: DNA
<213> ORGANISM: Artificial Sequence
<220> FEATURE:
<223> OTHER INFORMATION: Primer

<400> SEQUENCE: 114
ccagtggttg ctgaagttgt gt                                         22

<210> SEQ ID NO 115
<211> LENGTH: 24
<212> TYPE: DNA

```
<213> ORGANISM: Artificial Sequence
<220> FEATURE:
<223> OTHER INFORMATION: Primer

<400> SEQUENCE: 115
cccttcactg tgactgacct taca                                          24

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
cagtcccagc tttcggaaaa                                               20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
cactgcccac ctgagacgta                                               20

<210> SEQ ID NO 118
<211> LENGTH: 22
<212> TYPE: DNA
<213> ORGANISM: Artificial Sequence
<220> FEATURE:
<223> OTHER INFORMATION: Primer

<400> SEQUENCE: 118
acccccttca cagtcgtcat at                                            22

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119
tgaaactctg caaccaccta gatg                                          24

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
aggacgacag gaacaataga aactg                                         25

<210> SEQ ID NO 121
<211> LENGTH: 18
<212> TYPE: DNA
<213> ORGANISM: Artificial Sequence
<220> FEATURE:
<223> OTHER INFORMATION: Primer

<400> SEQUENCE: 121
gccaaggtcc gcaagaga                                                 18
```

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
aaacaacctt ccggcaatca                                               20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
gtcccatcac acggaaaggt                                               20

<210> SEQ ID NO 124
<211> LENGTH: 19
<212> TYPE: DNA
<213> ORGANISM: Artificial Sequence
<220> FEATURE:
<223> OTHER INFORMATION: Primer

<400> SEQUENCE: 124
gccccaagct gctaaaagc                                                19

<210> SEQ ID NO 125
<211> LENGTH: 18
<212> TYPE: DNA
<213> ORGANISM: Artificial Sequence
<220> FEATURE:
<223> OTHER INFORMATION: Primer

<400> SEQUENCE: 125
aaccgaccca gcctgctt                                                 18

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
gggtgactgc cacattcttt g                                             21

<210> SEQ ID NO 127
<211> LENGTH: 23
<212> TYPE: DNA
<213> ORGANISM: Artificial Sequence
<220> FEATURE:
<223> OTHER INFORMATION: Primer

<400> SEQUENCE: 127
tctgaggagg atgacgatga aga                                           23

<210> SEQ ID NO 128
<211> LENGTH: 23
<212> TYPE: DNA
<213> ORGANISM: Artificial Sequence
<220> FEATURE:

<223> OTHER INFORMATION: Primer

<400> SEQUENCE: 128
ctagaaatgc ttcccctcct tct                                    23

<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
tccccattga caatttacca tgt                                    23

<210> SEQ ID NO 130
<211> LENGTH: 17
<212> TYPE: DNA
<213> ORGANISM: Artificial Sequence
<220> FEATURE:
<223> OTHER INFORMATION: Primer

<400> SEQUENCE: 130
tccgctgcca tgtggaa                                           17

<210> SEQ ID NO 131
<211> LENGTH: 23
<212> TYPE: DNA
<213> ORGANISM: Artificial Sequence
<220> FEATURE:
<223> OTHER INFORMATION: Primer

<400> SEQUENCE: 131
ctccaggttg acttctcctc aga                                    23

<210> SEQ ID NO 132
<211> LENGTH: 18
<212> TYPE: DNA
<213> ORGANISM: Artificial Sequence
<220> FEATURE:
<223> OTHER INFORMATION: Primer

<400> SEQUENCE: 132
catggcttcc ggcacttg                                          18

<210> SEQ ID NO 133
<211> LENGTH: 18
<212> TYPE: DNA
<213> ORGANISM: Artificial Sequence
<220> FEATURE:
<223> OTHER INFORMATION: Primer

<400> SEQUENCE: 133
gccattgcgg tggatgag                                          18

<210> SEQ ID NO 134
<211> LENGTH: 19
<212> TYPE: DNA
<213> ORGANISM: Artificial Sequence
<220> FEATURE:
<223> OTHER INFORMATION: Primer

<400> SEQUENCE: 134
tcagcaagga cgggagctt                                         19

```
<210> SEQ ID NO 135
<211> LENGTH: 18
<212> TYPE: DNA
<213> ORGANISM: Artificial Sequence
<220> FEATURE:
<223> OTHER INFORMATION: Primer

<400> SEQUENCE: 135
gcttggcatc cccttgct                                                 18

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
acggtgcctg agctgttgtc                                               20

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
gactgtggag ctcttcctga ca                                            22

<210> SEQ ID NO 138
<211> LENGTH: 18
<212> TYPE: DNA
<213> ORGANISM: Artificial Sequence
<220> FEATURE:
<223> OTHER INFORMATION: Primer

<400> SEQUENCE: 138
tcggtggagg cgaagatg                                                 18

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
catggccttc cgtgttccta                                               20

<210> SEQ ID NO 140
<211> LENGTH: 17
<212> TYPE: DNA
<213> ORGANISM: Artificial Sequence
<220> FEATURE:
<223> OTHER INFORMATION: Primer

<400> SEQUENCE: 140
gcggcacgtc agatcca                                                  17

<210> SEQ ID NO 141
<211> LENGTH: 15
<212> TYPE: DNA
<213> ORGANISM: Artificial Sequence
<220> FEATURE:
<223> OTHER INFORMATION: Primer
```

```
<400> SEQUENCE: 141
cgaccgcccc aatgc                                              15

<210> SEQ ID NO 142
<211> LENGTH: 19
<212> TYPE: DNA
<213> ORGANISM: Artificial Sequence
<220> FEATURE:
<223> OTHER INFORMATION: Primer

<400> SEQUENCE: 142
tgggactcct cgggagttg                                          19

<210> SEQ ID NO 143
<211> LENGTH: 18
<212> TYPE: DNA
<213> ORGANISM: Artificial Sequence
<220> FEATURE:
<223> OTHER INFORMATION: Primer

<400> SEQUENCE: 143
aggcctggac cgctcagt                                           18

<210> SEQ ID NO 144
<211> LENGTH: 21
<212> TYPE: DNA
<213> ORGANISM: Artificial Sequence
<220> FEATURE:
<223> OTHER INFORMATION: Primer

<400> SEQUENCE: 144
agttatggag cggagcagca t                                       21

<210> SEQ ID NO 145
<211> LENGTH: 19
<212> TYPE: DNA
<213> ORGANISM: Artificial Sequence
<220> FEATURE:
<223> OTHER INFORMATION: Primer

<400> SEQUENCE: 145
aggcacacct gcgaactca                                          19

<210> SEQ ID NO 146
<211> LENGTH: 19
<212> TYPE: DNA
<213> ORGANISM: Artificial Sequence
<220> FEATURE:
<223> OTHER INFORMATION: Primer

<400> SEQUENCE: 146
cagccgtccc agtcacagt                                          19

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
ctggactgcg aactggagaa g                                       21

<210> SEQ ID NO 148
<211> LENGTH: 19
```

<212> TYPE: DNA
<213> ORGANISM: Artificial Sequence
<220> FEATURE:
<223> OTHER INFORMATION: Primer

<400> SEQUENCE: 148
tttgcacccc tcccaattc                                            19

<210> SEQ ID NO 149
<211> LENGTH: 22
<212> TYPE: DNA
<213> ORGANISM: Artificial Sequence
<220> FEATURE:
<223> OTHER INFORMATION: Primer

<400> SEQUENCE: 149
aaggtcagct ccagttcaac ct                                        22

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
agtcggttgc tgctccaatc                                           20

<210> SEQ ID NO 151
<211> LENGTH: 21
<212> TYPE: DNA
<213> ORGANISM: Artificial Sequence
<220> FEATURE:
<223> OTHER INFORMATION: Primer

<400> SEQUENCE: 151
ccaagatcac ctgcacttcg a                                         21

<210> SEQ ID NO 152
<211> LENGTH: 19
<212> TYPE: DNA
<213> ORGANISM: Artificial Sequence
<220> FEATURE:
<223> OTHER INFORMATION: Primer

<400> SEQUENCE: 152
tttcctgcgt cgtgttggt                                            19

<210> SEQ ID NO 153
<211> LENGTH: 23
<212> TYPE: DNA
<213> ORGANISM: Artificial Sequence
<220> FEATURE:
<223> OTHER INFORMATION: Primer

<400> SEQUENCE: 153
gagcaacctc ccgaattaac ttt                                       23

<210> SEQ ID NO 154
<211> LENGTH: 23
<212> TYPE: DNA
<213> ORGANISM: Artificial Sequence
<220> FEATURE:
<223> OTHER INFORMATION: Primer

<400> SEQUENCE: 154
tgccaatgag attttccagt ctt                                                    23

<210> SEQ ID NO 155
<211> LENGTH: 19
<212> TYPE: DNA
<213> ORGANISM: Artificial Sequence
<220> FEATURE:
<223> OTHER INFORMATION: Primer

<400> SEQUENCE: 155
caggcgcact ctggaaaag                                                         19

<210> SEQ ID NO 156
<211> LENGTH: 17
<212> TYPE: DNA
<213> ORGANISM: Artificial Sequence
<220> FEATURE:
<223> OTHER INFORMATION: Primer

<400> SEQUENCE: 156
ttgaccggct gcatgct                                                           17

<210> SEQ ID NO 157
<211> LENGTH: 16
<212> TYPE: DNA
<213> ORGANISM: Artificial Sequence
<220> FEATURE:
<223> OTHER INFORMATION: Primer

<400> SEQUENCE: 157
gccgtgcgtg gtggat                                                            16

<210> SEQ ID NO 158
<211> LENGTH: 21
<212> TYPE: DNA
<213> ORGANISM: Artificial Sequence
<220> FEATURE:
<223> OTHER INFORMATION: Primer

<400> SEQUENCE: 158
tgccaaggaa ccagacttca g                                                      21

<210> SEQ ID NO 159
<211> LENGTH: 19
<212> TYPE: DNA
<213> ORGANISM: Artificial Sequence
<220> FEATURE:
<223> OTHER INFORMATION: Primer

<400> SEQUENCE: 159
ccgcgtagat cccgatacc                                                         19

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
ccggctttac atccatgaca                                                        20

<210> SEQ ID NO 161
<211> LENGTH: 21
<212> TYPE: DNA
<213> ORGANISM: Artificial Sequence
<220> FEATURE:
<223> OTHER INFORMATION: Primer

<400> SEQUENCE: 161 tcttcccccct tgcctaatac c                                    21

<210> SEQ ID NO 162
<211> LENGTH: 25
<212> TYPE: DNA
<213> ORGANISM: Artificial Sequence
<220> FEATURE:
<223> OTHER INFORMATION: Primer

<400> SEQUENCE: 162
ttaggatagg gagcctcaga catag                                 25

<210> SEQ ID NO 163
<211> LENGTH: 22
<212> TYPE: DNA
<213> ORGANISM: Artificial Sequence
<220> FEATURE:
<223> OTHER INFORMATION: Primer

<400> SEQUENCE: 163
cctgagagag attcgcactc aa                                    22

<210> SEQ ID NO 164
<211> LENGTH: 25
<212> TYPE: DNA
<213> ORGANISM: Artificial Sequence
<220> FEATURE:
<223> OTHER INFORMATION: Primer

<400> SEQUENCE: 164
ctcctctgtc tcttgcatgt tactg                                 25

<210> SEQ ID NO 165
<211> LENGTH: 20
<212> TYPE: DNA
<213> ORGANISM: Artificial Sequence
<220> FEATURE:
<223> OTHER INFORMATION: Primer

<400> SEQUENCE: 165
tcacgcagca gatgttcgat                                       20

<210> SEQ ID NO 166
<211> LENGTH: 15
<212> TYPE: DNA
<213> ORGANISM: Artificial Sequence
<220> FEATURE:
<223> OTHER INFORMATION: Primer

<400> SEQUENCE: 166
gtggcgcggg tcaca                                            15

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
acagagacac gggcatcctt                                       20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168 caccctgtc accgctaaag                                              20

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
tcctccaaag tccccagcta                                             20

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
ccggcagtgg ttggttaata a                                           21

<210> SEQ ID NO 171
<211> LENGTH: 27
<212> TYPE: DNA
<213> ORGANISM: Artificial Sequence
<220> FEATURE:
<223> OTHER INFORMATION: Primer

<400> SEQUENCE: 171
aaccctatct tcacgtagcc aatagtt                                     27

<210> SEQ ID NO 172
<211> LENGTH: 22
<212> TYPE: DNA
<213> ORGANISM: Artificial Sequence
<220> FEATURE:
<223> OTHER INFORMATION: Primer

<400> SEQUENCE: 172
gaccagcggt tacatggtag tg                                          22

<210> SEQ ID NO 173
<211> LENGTH: 21
<212> TYPE: DNA
<213> ORGANISM: Artificial Sequence
<220> FEATURE:
<223> OTHER INFORMATION: Primer

<400> SEQUENCE: 173
ctcctcaccc cacctgtacc t                                           21

<210> SEQ ID NO 174
<211> LENGTH: 20
<212> TYPE: DNA
<213> ORGANISM: Artificial Sequence
<220> FEATURE:
<223> OTHER INFORMATION: Primer

<400> SEQUENCE: 174
ccttggtgca cgtcgagact                                             20

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
ggatgtccga gctggagaag                                             20

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
cccggagtac tggtggaaga                                             20

<210> SEQ ID NO 177
<211> LENGTH: 18
<212> TYPE: DNA
<213> ORGANISM: Artificial Sequence
<220> FEATURE:
<223> OTHER INFORMATION: Primer

<400> SEQUENCE: 177
catgcagaac gccgaaga                                               18

<210> SEQ ID NO 178
<211> LENGTH: 17
<212> TYPE: DNA
<213> ORGANISM: Artificial Sequence
<220> FEATURE:
<223> OTHER INFORMATION: Primer

<400> SEQUENCE: 178
cggcgctctc ggttagc                                                17

<210> SEQ ID NO 179
<211> LENGTH: 24
<212> TYPE: DNA
<213> ORGANISM: Artificial Sequence
<220> FEATURE:
<223> OTHER INFORMATION: Primer

<400> SEQUENCE: 179
ggctccagac attgtatttt cctt                                        24

<210> SEQ ID NO 180
<211> LENGTH: 18
<212> TYPE: DNA
<213> ORGANISM: Artificial Sequence
<220> FEATURE:
<223> OTHER INFORMATION: Primer

<400> SEQUENCE: 180
ggcaccctga gcttgcat                                               18

<210> SEQ ID NO 181

```
<211> LENGTH: 22
<212> TYPE: DNA
<213> ORGANISM: Artificial Sequence
<220> FEATURE:
<223> OTHER INFORMATION: Primer

<400> SEQUENCE: 181
gactcccaaa aattccctcc at                                            22

<210> SEQ ID NO 182
<211> LENGTH: 25
<212> TYPE: DNA
<213> ORGANISM: Artificial Sequence
<220> FEATURE:
<223> OTHER INFORMATION: Primer

<400> SEQUENCE: 182
acctttatca tctcttcgct tttga                                         25

<210> SEQ ID NO 183
<211> LENGTH: 24
<212> TYPE: DNA
<213> ORGANISM: Artificial Sequence
<220> FEATURE:
<223> OTHER INFORMATION: Primer

<400> SEQUENCE: 183
agcagcctac agtgacagtt atgg                                          24

<210> SEQ ID NO 184
<211> LENGTH: 19
<212> TYPE: DNA
<213> ORGANISM: Artificial Sequence
<220> FEATURE:
<223> OTHER INFORMATION: Primer

<400> SEQUENCE: 184
ggccgatggt gtgatggta                                                19

<210> SEQ ID NO 185
<211> LENGTH: 22
<212> TYPE: DNA
<213> ORGANISM: Artificial Sequence
<220> FEATURE:
<223> OTHER INFORMATION: Primer

<400> SEQUENCE: 185
aaaaccccaa gatgcacaac tc                                            22

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186
cctcggacat gaccttcca                                                19

<210> SEQ ID NO 187
<211> LENGTH: 23
<212> TYPE: DNA
<213> ORGANISM: Artificial Sequence
<220> FEATURE:
<223> OTHER INFORMATION: Primer

<400> SEQUENCE: 187
```

-continued acctgtctcc tccttcacat cag    23

<210> SEQ ID NO 188
<211> LENGTH: 18
<212> TYPE: DNA
<213> ORGANISM: Artificial Sequence
<220> FEATURE:
<223> OTHER INFORMATION: Primer

<400> SEQUENCE: 188
ttggtgaggg cggtgtct    18

<210> SEQ ID NO 189
<211> LENGTH: 20
<212> TYPE: DNA
<213> ORGANISM: Artificial Sequence
<220> FEATURE:
<223> OTHER INFORMATION: Primer

<400> SEQUENCE: 189
gggcatggac tgtggatctt    20

<210> SEQ ID NO 190
<211> LENGTH: 18
<212> TYPE: DNA
<213> ORGANISM: Artificial Sequence
<220> FEATURE:
<223> OTHER INFORMATION: Primer

<400> SEQUENCE: 190
cccctggtcc aggaagct    18

<210> SEQ ID NO 191
<211> LENGTH: 18
<212> TYPE: DNA
<213> ORGANISM: Artificial Sequence
<220> FEATURE:
<223> OTHER INFORMATION: Primer

<400> SEQUENCE: 191
aaggttttcg cgcgttca    18

<210> SEQ ID NO 192
<211> LENGTH: 21
<212> TYPE: DNA
<213> ORGANISM: Artificial Sequence
<220> FEATURE:
<223> OTHER INFORMATION: Primer

<400> SEQUENCE: 192
tctcccctgt gtgtgtcctt t    21

<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193
ctggcgcgaa actacatcct    20

<210> SEQ ID NO 194
<211> LENGTH: 21
<212> TYPE: DNA

<213> ORGANISM: Artificial Sequence
<220> FEATURE:
<223> OTHER INFORMATION: Primer

<400> SEQUENCE: 194
gctcaccagt cgcttcatct c                                    21

<210> SEQ ID NO 195
<211> LENGTH: 23
<212> TYPE: DNA
<213> ORGANISM: Artificial Sequence
<220> FEATURE:
<223> OTHER INFORMATION: Primer

<400> SEQUENCE: 195
cccaaaaaga aaagatgac caa                                   23

<210> SEQ ID NO 196
<211> LENGTH: 18
<212> TYPE: DNA
<213> ORGANISM: Artificial Sequence
<220> FEATURE:
<223> OTHER INFORMATION: Primer

<400> SEQUENCE: 196
ggccttcatg cgccttaa                                        18

<210> SEQ ID NO 197
<211> LENGTH: 512
<212> TYPE: PRT
<213> ORGANISM: Homo sapiens

<400> SEQUENCE: 197

```
Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
             20                  25                  30

Asn Ala Asn Trp Glu Leu Glu Arg Thr Asn Gln Ser Gly Leu Glu Arg
         35                  40                  45

Cys Glu Gly Glu Gln Asp Lys Arg Leu His Cys Tyr Ala Ser Trp Arg
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205
```

```
Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 198
<211> LENGTH: 454
<212> TYPE: PRT
<213> ORGANISM: Homo sapiens

<400> SEQUENCE: 198

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80
```

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 199
<211> LENGTH: 472
<212> TYPE: PRT
<213> ORGANISM: Mus musculus

<400> SEQUENCE: 199

```
Met Ala Gly Glu Asp His Pro Trp Gln Gly Ser Ile Leu Tyr Asn Leu
1               5                   10                  15

Leu Met Ser Ala Lys Gln Lys His Ala Ser Gln Glu Glu Arg Glu Val
            20                  25                  30

Arg Leu Gly Ala Gln Cys Trp Gly Cys Ala Cys Gly Ala Gln Pro Val
        35                  40                  45

Leu Gly Gly Glu Arg Leu Ser Gly Gly Gln Ala Arg Ser Leu Leu Tyr
    50                  55                  60

Arg Cys Cys Phe Cys Gly Glu Asn His Pro Arg Gln Gly Gly Ile Leu
65                  70                  75                  80

Tyr Ser Met Leu Thr Asn Ala Arg Gln Pro Ser Val Ala Thr Gln Ala
                85                  90                  95

Pro Arg Ala Arg Phe Gly Ala Pro Cys Trp Gly Cys Ala Cys Gly Ser
            100                 105                 110

Ala Glu Pro Leu Val Gly Arg Glu Gly Leu Pro Ala Gly Gln Ala Pro
        115                 120                 125

Ser Leu Leu Tyr Arg Cys Cys Phe Cys Gly Glu Glu His Pro Arg Gln
    130                 135                 140

Gly Ser Ile Leu Tyr Ser Leu Leu Thr Ser Ala Gln Gln Thr His Val
145                 150                 155                 160

Ser Arg Glu Ala Pro Glu Ala His Arg Arg Gly Glu Trp Trp Gln Leu
                165                 170                 175

Ser Tyr Cys Thr Gln Ser Val Gly Gly Pro Glu Gly Leu Gln Ser Thr
            180                 185                 190

Gln Ala Met Ala Phe Leu Tyr Arg Ser Tyr Val Cys Gly Glu Glu Gln
        195                 200                 205

Pro Gln Gln Ile Ser Val Ala Ser Gly Thr Pro Val Ser Ala Asp Gln
    210                 215                 220

Thr Pro Ala Thr Pro Gln Glu Gln Pro Arg Ala Pro Trp Trp Asp Ala
225                 230                 235                 240

Ser Pro Gly Val Gln Arg Leu Ile Thr Leu Lys Asp Pro Gln Val Val
                245                 250                 255

Cys Glu Ala Ala Ser Ala Gly Leu Leu Lys Thr Leu Arg Phe Val Lys
            260                 265                 270

Tyr Leu Pro Cys Phe Gln Ile Leu Pro Leu Asp Gln Gln Leu Val Leu
        275                 280                 285

Val Arg Ser Cys Trp Ala Pro Leu Leu Met Leu Glu Leu Ala Gln Asp
    290                 295                 300

His Leu His Phe Glu Met Met Glu Ile Pro Glu Thr Asn Thr Thr Gln
305                 310                 315                 320

Glu Met Leu Thr Thr Arg Arg Gln Glu Thr Gly Pro Glu Pro Ala
                325                 330                 335

Glu Pro Gln Ala Thr Glu Gln Pro Gln Met Val Ser Ala Glu Ala Gly
        340                 345                 350

His Leu Leu Pro Ala Ala Ala Val Gln Ala Ile Lys Ser Phe Phe Phe
    355                 360                 365

Lys Cys Trp Ser Leu Asn Ile Asp Thr Lys Glu Tyr Ala Tyr Leu Lys
370                 375                 380

Gly Thr Val Leu Phe Asn Pro Asp Leu Pro Gly Leu Gln Cys Val Lys
                385                 390                 395                 400

Tyr Ile Glu Gly Leu Gln Trp Arg Thr Gln Gln Ile Leu Thr Glu His
            405                 410                 415
```

```
Ile Arg Met Met Gln Arg Glu Tyr Gln Ile Arg Ser Ala Glu Leu Asn
            420                 425                 430

Ser Ala Leu Phe Leu Arg Phe Ile Asn Ser Asp Val Val Thr Glu
        435                 440                 445

Leu Phe Phe Arg Pro Ile Ile Gly Ala Val Ser Met Asp Asp Met Met
450                 455                 460

Leu Glu Met Leu Cys Ala Lys Leu
465                 470

<210> SEQ ID NO 200
<211> LENGTH: 332
<212> TYPE: PRT
<213> ORGANISM: Homo sapiens

<400> SEQUENCE: 200

Met Trp Pro Leu Trp Leu Cys Trp Ala Leu Trp Val Leu Pro Leu Ala
1               5                   10                  15

Gly Pro Gly Ala Ala Leu Thr Glu Glu Gln Leu Leu Gly Ser Leu Leu
            20                  25                  30

Arg Gln Leu Gln Leu Ser Glu Val Pro Val Leu Asp Arg Ala Asp Met
        35                  40                  45

Glu Lys Leu Val Ile Pro Ala His Val Arg Ala Gln Tyr Val Val Leu
50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ala Leu
                85                  90                  95

His Arg His Gly Arg Leu Ser Pro Arg Ser Ala Gln Ala Arg Val Thr
            100                 105                 110

Val Glu Trp Leu Arg Val Arg Asp Asp Gly Ser Asn Arg Thr Ser Leu
        115                 120                 125

Ile Asp Ser Arg Leu Val Ser Val His Glu Ser Gly Trp Lys Ala Phe
130                 135                 140

Asp Val Thr Glu Ala Val Asn Phe Trp Gln Gln Leu Ser Arg Pro Arg
145                 150                 155                 160

Gln Pro Leu Leu Leu Gln Val Ser Val Gln Arg Glu His Leu Gly Pro
                165                 170                 175

Leu Ala Ser Gly Ala His Lys Leu Val Arg Phe Ala Ser Gln Gly Ala
            180                 185                 190

Pro Ala Gly Leu Gly Glu Pro Gln Leu Glu Leu His Thr Leu Asp Leu
        195                 200                 205

Arg Asp Tyr Gly Ala Gln Gly Asp Cys Asp Pro Glu Ala Pro Met Thr
210                 215                 220

Glu Gly Thr Arg Cys Cys Arg Gln Glu Met Tyr Ile Asp Leu Gln Gly
225                 230                 235                 240

Met Lys Trp Ala Lys Asn Trp Val Leu Glu Pro Gly Phe Leu Ala
                245                 250                 255

Tyr Glu Cys Val Gly Thr Cys Gln Gln Pro Pro Glu Ala Leu Ala Phe
            260                 265                 270

Asn Trp Pro Phe Leu Gly Pro Arg Gln Cys Ile Ala Ser Glu Thr Ala
        275                 280                 285

Ser Leu Pro Met Ile Val Ser Ile Lys Glu Gly Gly Arg Thr Arg Pro
290                 295                 300

Gln Val Val Ser Leu Pro Asn Met Arg Val Gln Lys Cys Ser Cys Ala
```

```
              305                 310                 315                 320
Ser Asp Gly Ala Leu Val Pro Arg Arg Leu Gln Pro
                325                 330

<210> SEQ ID NO 201
<211> LENGTH: 116
<212> TYPE: PRT
<213> ORGANISM: Homo sapiens

<400> SEQUENCE: 201

Met Gly Thr Leu Pro Ala Arg Arg His Ile Pro Pro Trp Val Lys Val
1               5                   10                  15

Pro Glu Asp Leu Lys Asp Pro Glu Val Phe Gln Val Gln Thr Arg Leu
            20                  25                  30

Leu Lys Ala Ile Phe Gly Pro Asp Gly Ser Arg Ile Pro Tyr Ile Glu
        35                  40                  45

Gln Val Ser Lys Ala Met Leu Glu Leu Lys Ala Leu Glu Ser Ser Asp
    50                  55                  60

Leu Thr Glu Val Val Val Tyr Gly Ser Tyr Leu Tyr Lys Leu Arg Thr
65                  70                  75                  80

Lys Trp Met Leu Gln Ser Met Ala Glu Trp His Arg Gln Arg Gln Glu
                85                  90                  95

Arg Gly Met Leu Lys Leu Ala Glu Ala Met Asn Ala Leu Glu Leu Gly
            100                 105                 110

Pro Trp Met Lys
        115

<210> SEQ ID NO 202
<211> LENGTH: 206
<212> TYPE: PRT
<213> ORGANISM: Homo sapiens

<400> SEQUENCE: 202

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
```

```
                180                 185                 190
Val Ser Pro Thr Met Lys Val Thr His Phe Leu Pro Arg Leu
            195                 200                 205

<210> SEQ ID NO 203
<211> LENGTH: 565
<212> TYPE: PRT
<213> ORGANISM: Homo sapiens

<400> SEQUENCE: 203

Met Arg Pro Arg Ser Ala Leu Pro Arg Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
            35                  40                  45

Asp Ile Ala Tyr Asn Gln Thr Ile Met Pro Asn Leu Leu Gly His Thr
        50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
            195                 200                 205

Ser Tyr Leu Ser Tyr Lys Phe Leu Gly Glu Arg Asp Cys Ala Ala Pro
        210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr Trp Ser Val Leu Cys Cys
                245                 250                 255

Ala Ser Thr Phe Phe Thr Val Thr Thr Tyr Leu Val Asp Met Gln Arg
            260                 265                 270

Phe Arg Tyr Pro Glu Arg Pro Ile Ile Phe Leu Ser Gly Cys Tyr Thr
        275                 280                 285

Met Val Ser Val Ala Tyr Ile Ala Gly Phe Val Leu Gln Glu Arg Val
290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
                325                 330                 335

Phe Ser Met Ala Ser Ser Ile Trp Trp Val Ile Leu Ser Leu Thr Trp
            340                 345                 350
```

```
Phe Leu Ala Ala Gly Met Lys Trp Gly His Glu Ala Ile Glu Ala Asn
            355                 360                 365

Ser Gln Tyr Phe His Leu Ala Ala Trp Ala Val Pro Ala Val Lys Thr
    370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
            420                 425                 430

Ala Gly Phe Val Ser Leu Phe Arg Ile Arg Thr Ile Met Lys His Asp
        435                 440                 445

Gly Thr Lys Thr Glu Lys Leu Glu Arg Leu Met Val Arg Ile Gly Val
450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
                485                 490                 495

Gln His Cys Lys Ser Leu Ala Ile Pro Cys Pro Ala His Tyr Thr Pro
            500                 505                 510

Arg Met Ser Pro Asp Phe Thr Val Tyr Met Ile Lys Tyr Leu Met Thr
        515                 520                 525

Leu Ile Val Gly Ile Thr Ser Gly Phe Trp Ile Trp Ser Gly Lys Thr
530                 535                 540

Leu His Ser Trp Arg Lys Phe Tyr Thr Arg Leu Thr Asn Ser Arg His
545                 550                 555                 560

Gly Glu Thr Thr Val
                565

<210> SEQ ID NO 204
<211> LENGTH: 574
<212> TYPE: PRT
<213> ORGANISM: Homo sapiens

<400> SEQUENCE: 204

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160
```

```
Val Gly Gln Asn Thr Ser Asp Gly Ser Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
                195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
                245                 250                 255

Val Gly Val Trp Ser Val Leu Cys Cys Ala Ser Thr Leu Phe Thr Val
                260                 265                 270

Leu Thr Tyr Leu Val Asp Met Arg Arg Phe Ser Tyr Pro Glu Arg Pro
            275                 280                 285

Ile Ile Phe Leu Ser Gly Cys Tyr Phe Met Val Ala Val Ala His Val
            290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys
            355                 360                 365

Trp Gly His Glu Ala Ile Glu Ala Asn Ser Gln Tyr Phe His Leu Ala
            370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
                405                 410                 415

Ser Val Asp Ala Leu Arg Gly Phe Val Leu Ala Pro Leu Phe Val Tyr
            420                 425                 430

Leu Phe Ile Gly Thr Ser Phe Leu Leu Ala Gly Phe Val Ser Leu Phe
            435                 440                 445

Arg Ile Arg Thr Ile Met Lys His Asp Gly Thr Lys Thr Glu Lys Leu
450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
            515                 520                 525

Val Phe Met Ile Lys Tyr Leu Met Thr Met Ile Val Gly Ile Thr Thr
            530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
            565                 570
```

```
<210> SEQ ID NO 205
<211> LENGTH: 366
<212> TYPE: PRT
<213> ORGANISM: Mus musculus

<400> SEQUENCE: 205

Met Gln Pro Tyr Gln Arg Leu Leu Ala Leu Gly Phe Leu Leu Leu Thr
1               5                   10                  15

Leu Pro Trp Gly Gln Thr Ser Glu Phe Gln Asp Ser Asp Leu Leu Gln
            20                  25                  30

Phe Leu Gly Leu Glu Lys Ala Pro Ser Pro His Arg Phe Gln Pro Val
        35                  40                  45

Pro Arg Val Leu Arg Lys Ile Ile Arg Ala Arg Glu Ala Ala Ala Ala
    50                  55                  60

Ser Gly Ala Ser Gln Asp Leu Cys Tyr Val Lys Glu Leu Gly Val Arg
65                  70                  75                  80

Gly Asn Leu Leu Gln Leu Pro Asp Gln Gly Phe Phe Leu Asn Thr
                85                  90                  95

Gln Lys Pro Phe Gln Asp Gly Ser Cys Leu Gln Lys Val Leu Tyr Phe
            100                 105                 110

Asn Leu Ser Ala Ile Lys Glu Lys Ala Lys Leu Thr Met Ala Gln Leu
        115                 120                 125

Thr Leu Asp Leu Gly Pro Arg Ser Tyr Tyr Asn Leu Arg Pro Glu Leu
130                 135                 140

Val Val Ala Leu Ser Val Val Gln Asp Arg Gly Val Trp Gly Arg Ser
145                 150                 155                 160

His Pro Lys Val Gly Arg Leu Leu Phe Leu Arg Ser Val Pro Gly Pro
                165                 170                 175

Gln Gly Gln Leu Gln Phe Asn Leu Gln Gly Ala Leu Lys Asp Trp Ser
            180                 185                 190

Ser Asn Arg Leu Lys Asn Leu Asp Leu His Leu Glu Ile Leu Val Lys
        195                 200                 205

Glu Asp Arg Tyr Ser Arg Val Thr Val Gln Pro Glu Asn Pro Cys Asp
210                 215                 220

Arg Leu Leu Arg Ser Leu His Ala Ser Leu Leu Val Val Thr Leu Asn
225                 230                 235                 240

Pro Lys His Cys His Pro Ser Ser Arg Lys Arg Arg Ala Ala Ile Ser
                245                 250                 255

Val Pro Lys Gly Phe Cys Arg Asn Phe Cys His Arg His Gln Leu Phe
            260                 265                 270

Ile Asn Phe Gln Asp Leu Gly Trp His Lys Trp Val Ile Ala Pro Lys
        275                 280                 285

Gly Phe Met Ala Asn Tyr Cys His Gly Glu Cys Pro Phe Ser Met Thr
290                 295                 300

Thr Tyr Leu Asn Ser Ser Asn Tyr Ala Phe Met Gln Ala Leu Met His
305                 310                 315                 320

Met Ala Asp Pro Lys Val Pro Lys Ala Val Cys Val Pro Thr Lys Leu
                325                 330                 335

Ser Pro Ile Ser Met Leu Tyr Gln Asp Ser Asp Lys Asn Val Ile Leu
            340                 345                 350

Arg His Tyr Glu Asp Met Val Val Asp Glu Cys Gly Cys Gly
        355                 360                 365

<210> SEQ ID NO 206
```

<211> LENGTH: 532
<212> TYPE: PRT
<213> ORGANISM: Homo sapiens

<400> SEQUENCE: 206

```
Met Glu Leu Asp Leu Ser Pro Pro His Leu Ser Ser Pro Glu Asp
1               5                   10                  15

Leu Cys Pro Ala Pro Gly Thr Pro Pro Gly Thr Pro Arg Pro Pro Asp
                20                  25                  30

Thr Pro Leu Pro Glu Glu Val Lys Arg Ser Gln Pro Leu Leu Ile Pro
            35                  40                  45

Thr Thr Gly Arg Lys Leu Arg Glu Glu Arg Arg Ala Thr Ser Leu
50                  55                  60

Pro Ser Ile Pro Asn Pro Phe Pro Glu Leu Cys Ser Pro Pro Ser Gln
65                  70                  75                  80

Ser Pro Ile Leu Gly Gly Pro Ser Ser Ala Arg Gly Leu Leu Pro Arg
                85                  90                  95

Asp Ala Ser Arg Pro His Val Val Lys Val Tyr Ser Glu Asp Gly Ala
                100                 105                 110

Cys Arg Ser Val Glu Val Ala Ala Gly Ala Thr Ala Arg His Val Cys
            115                 120                 125

Glu Met Leu Val Gln Arg Ala His Ala Leu Ser Asp Glu Thr Trp Gly
        130                 135                 140

Leu Val Glu Cys His Pro His Leu Ala Leu Glu Arg Gly Leu Glu Asp
145                 150                 155                 160

His Glu Ser Val Val Glu Val Gln Ala Ala Trp Pro Val Gly Gly Asp
                165                 170                 175

Ser Arg Phe Val Phe Arg Lys Asn Phe Ala Lys Tyr Glu Leu Phe Lys
                180                 185                 190

Ser Ser Pro His Ser Leu Phe Pro Glu Lys Met Val Ser Ser Cys Leu
            195                 200                 205

Asp Ala His Thr Gly Ile Ser His Glu Asp Leu Ile Gln Asn Phe Leu
        210                 215                 220

Asn Ala Gly Ser Phe Pro Glu Ile Gln Gly Phe Leu Gln Leu Arg Gly
225                 230                 235                 240

Ser Gly Arg Lys Leu Trp Lys Arg Phe Phe Cys Phe Leu Arg Arg Ser
                245                 250                 255

Gly Leu Tyr Tyr Ser Thr Lys Gly Thr Ser Lys Asp Pro Arg His Leu
                260                 265                 270

Gln Tyr Val Ala Asp Val Asn Glu Ser Asn Val Tyr Val Val Thr Gln
            275                 280                 285

Gly Arg Lys Leu Tyr Gly Met Pro Thr Asp Phe Gly Phe Cys Val Lys
        290                 295                 300

Pro Asn Lys Leu Arg Asn Gly His Lys Gly Leu Arg Ile Phe Cys Ser
305                 310                 315                 320

Glu Asp Glu Gln Ser Arg Thr Cys Trp Leu Ala Ala Phe Arg Leu Phe
                325                 330                 335

Lys Tyr Gly Val Gln Leu Tyr Lys Asn Tyr Gln Gln Ala Gln Ser Arg
                340                 345                 350

His Leu His Pro Ser Cys Leu Gly Ser Pro Pro Leu Arg Ser Ala Ser
            355                 360                 365

Asp Asn Thr Leu Val Ala Met Asp Phe Ser Gly His Ala Gly Arg Val
        370                 375                 380

Ile Glu Asn Pro Arg Glu Ala Leu Ser Val Ala Leu Glu Glu Ala Gln
```

```
385                 390                 395                 400
Ala Trp Arg Lys Lys Thr Asn His Arg Leu Ser Leu Pro Met Pro Ala
                405                 410                 415

Ser Gly Thr Ser Leu Ser Ala Ala Ile His Arg Thr Gln Leu Trp Phe
                420                 425                 430

His Gly Arg Ile Ser Arg Glu Glu Ser Gln Arg Leu Ile Gly Gln Gln
                435                 440                 445

Gly Leu Val Asp Gly Leu Phe Leu Val Arg Glu Ser Gln Arg Asn Pro
450                 455                 460

Gln Gly Phe Val Leu Ser Leu Cys His Leu Gln Lys Val Lys His Tyr
465                 470                 475                 480

Leu Ile Leu Pro Ser Glu Glu Gly Arg Leu Tyr Phe Ser Met Asp
                485                 490                 495

Asp Gly Gln Thr Arg Phe Thr Asp Leu Leu Gln Leu Val Glu Phe His
                500                 505                 510

Gln Leu Asn Arg Gly Ile Leu Pro Cys Leu Leu Arg His Cys Cys Thr
                515                 520                 525

Arg Val Ala Leu
                530

<210> SEQ ID NO 207
<211> LENGTH: 1063
<212> TYPE: PRT
<213> ORGANISM: Homo sapiens

<400> SEQUENCE: 207

Met Ser Pro Gly Ala Ser Arg Gly Pro Arg Gly Ser Gln Ala Pro Leu
1               5                   10                  15

Ile Ala Pro Leu Cys Cys Ala Ala Ala Leu Gly Met Leu Leu Trp
            20                  25                  30

Ser Pro Ala Cys Gln Ala Phe Asn Leu Asp Val Glu Lys Leu Thr Val
                35                  40                  45

Tyr Ser Gly Pro Lys Gly Ser Tyr Phe Gly Tyr Ala Val Asp Phe His
            50                  55                  60

Ile Pro Asp Ala Arg Thr Ala Ser Val Leu Val Gly Ala Pro Lys Ala
65                  70                  75                  80

Asn Thr Ser Gln Pro Asp Ile Val Glu Gly Gly Ala Val Tyr Tyr Cys
                85                  90                  95

Pro Trp Pro Ala Glu Gly Ser Ala Gln Cys Arg Gln Ile Pro Phe Asp
            100                 105                 110

Thr Thr Asn Asn Arg Lys Ile Arg Val Asn Gly Thr Lys Glu Pro Ile
                115                 120                 125

Glu Phe Lys Ser Asn Gln Trp Phe Gly Ala Thr Val Lys Ala His Lys
130                 135                 140

Gly Lys Val Val Ala Cys Ala Pro Leu Tyr His Trp Arg Thr Leu Lys
145                 150                 155                 160

Pro Thr Pro Glu Lys Asp Pro Val Gly Thr Cys Tyr Val Ala Ile Gln
                165                 170                 175

Asn Phe Ser Ala Tyr Ala Glu Phe Ser Pro Cys Arg Asn Ser Asn Ala
            180                 185                 190

Asp Pro Glu Gly Gln Gly Tyr Cys Gln Ala Gly Phe Ser Leu Asp Phe
        195                 200                 205

Tyr Lys Asn Gly Asp Leu Ile Val Gly Gly Pro Gly Ser Phe Tyr Trp
    210                 215                 220
```

-continued

```
Gln Gly Gln Val Ile Thr Ala Ser Val Ala Asp Ile Ile Ala Asn Tyr
225                 230                 235                 240

Ser Phe Lys Asp Ile Leu Arg Lys Leu Ala Gly Glu Lys Gln Thr Glu
            245                 250                 255

Val Ala Pro Ala Ser Tyr Asp Asp Ser Tyr Leu Gly Tyr Ser Val Ala
        260                 265                 270

Ala Gly Glu Phe Thr Gly Asp Ser Gln Gln Glu Leu Val Ala Gly Ile
    275                 280                 285

Pro Arg Gly Ala Gln Asn Phe Gly Tyr Val Ser Ile Ile Asn Ser Thr
290                 295                 300

Asp Met Thr Phe Ile Gln Asn Phe Thr Gly Glu Gln Met Ala Ser Tyr
305                 310                 315                 320

Phe Gly Tyr Thr Val Val Ser Asp Val Asn Ser Asp Gly Leu Asp
                325                 330                 335

Asp Val Leu Val Gly Ala Pro Leu Phe Met Glu Arg Glu Phe Glu Ser
                340                 345                 350

Asn Pro Arg Glu Val Gly Gln Ile Tyr Leu Tyr Leu Gln Val Ser Ser
            355                 360                 365

Leu Leu Phe Arg Asp Pro Gln Ile Leu Thr Gly Thr Glu Thr Phe Gly
370                 375                 380

Arg Phe Gly Ser Ala Met Ala His Leu Gly Asp Leu Asn Gln Asp Gly
385                 390                 395                 400

Tyr Asn Asp Ile Ala Ile Gly Val Pro Phe Ala Gly Lys Asp Gln Arg
                405                 410                 415

Gly Lys Val Leu Ile Tyr Asn Gly Asn Lys Asp Gly Leu Asn Thr Lys
            420                 425                 430

Pro Ser Gln Val Leu Gln Gly Val Trp Ala Ser His Ala Val Pro Ser
            435                 440                 445

Gly Phe Gly Phe Thr Leu Arg Gly Asp Ser Asp Ile Asp Lys Asn Asp
        450                 455                 460

Tyr Pro Asp Leu Ile Val Gly Ala Phe Gly Thr Gly Lys Val Ala Val
465                 470                 475                 480

Tyr Arg Ala Arg Pro Val Val Thr Val Asp Ala Gln Leu Leu Leu His
                485                 490                 495

Pro Met Ile Ile Asn Leu Glu Asn Lys Thr Cys Gln Val Pro Asp Ser
            500                 505                 510

Met Thr Ser Ala Ala Cys Phe Ser Leu Arg Val Cys Ala Ser Val Thr
        515                 520                 525

Gly Gln Ser Ile Ala Asn Thr Ile Val Leu Met Ala Glu Val Gln Leu
    530                 535                 540

Asp Ser Leu Lys Gln Lys Gly Ala Ile Lys Arg Thr Leu Phe Leu Asp
545                 550                 555                 560

Asn His Gln Ala His Arg Val Phe Pro Leu Val Ile Lys Arg Gln Lys
                565                 570                 575

Ser His Gln Cys Gln Asp Phe Ile Val Tyr Leu Arg Asp Glu Thr Glu
            580                 585                 590

Phe Arg Asp Lys Leu Ser Pro Ile Asn Ile Ser Leu Asn Tyr Ser Leu
        595                 600                 605

Asp Glu Ser Thr Phe Lys Glu Gly Leu Glu Val Lys Pro Ile Leu Asn
    610                 615                 620

Tyr Tyr Arg Glu Asn Ile Val Ser Glu Gln Ala His Ile Leu Val Asp
625                 630                 635                 640

Cys Gly Glu Asp Asn Leu Cys Val Pro Asp Leu Lys Leu Ser Ala Arg
```

```
            645                 650                 655
Pro Asp Lys His Gln Val Ile Ile Gly Asp Glu Asn His Leu Met Leu
            660                 665                 670
Ile Ile Asn Ala Arg Asn Glu Gly Glu Gly Ala Tyr Glu Ala Glu Leu
            675                 680                 685
Phe Val Met Ile Pro Glu Glu Ala Asp Tyr Val Gly Ile Glu Arg Asn
            690                 695                 700
Asn Lys Gly Phe Arg Pro Leu Ser Cys Glu Tyr Lys Met Glu Asn Val
705                 710                 715                 720
Thr Arg Met Val Val Cys Asp Leu Gly Asn Pro Met Val Ser Gly Thr
                    725                 730                 735
Asn Tyr Ser Leu Gly Leu Arg Phe Ala Val Pro Arg Leu Glu Lys Thr
                    740                 745                 750
Asn Met Ser Ile Asn Phe Asp Leu Gln Ile Arg Ser Ser Asn Lys Asp
                    755                 760                 765
Asn Pro Asp Ser Asn Phe Val Ser Leu Gln Ile Asn Ile Thr Ala Val
            770                 775                 780
Ala Gln Val Glu Ile Arg Gly Val Ser His Pro Gln Ile Val Leu
785                 790                 795                 800
Pro Ile His Asn Trp Glu Pro Glu Glu Glu Pro His Lys Glu Glu Glu
                    805                 810                 815
Val Gly Pro Leu Val Glu His Ile Tyr Glu Leu His Asn Ile Gly Pro
            820                 825                 830
Ser Thr Ile Ser Asp Thr Ile Leu Glu Val Gly Trp Pro Phe Ser Ala
            835                 840                 845
Arg Asp Glu Phe Leu Leu Tyr Ile Phe His Ile Gln Thr Leu Gly Pro
            850                 855                 860
Leu Gln Cys Gln Pro Asn Pro Asn Ile Asn Pro Gln Asp Ile Lys Pro
865                 870                 875                 880
Ala Ala Ser Pro Glu Asp Thr Pro Glu Leu Ser Ala Phe Leu Arg Asn
                    885                 890                 895
Ser Thr Ile Pro His Leu Val Arg Lys Arg Asp Val His Val Val Glu
                    900                 905                 910
Phe His Arg Gln Ser Pro Ala Lys Ile Leu Asn Cys Thr Asn Ile Glu
            915                 920                 925
Cys Leu Gln Ile Ser Cys Ala Val Gly Arg Leu Glu Gly Gly Glu Ser
            930                 935                 940
Ala Val Leu Lys Val Arg Ser Arg Leu Trp Ala His Thr Phe Leu Gln
945                 950                 955                 960
Arg Lys Asn Asp Pro Tyr Ala Leu Ala Ser Leu Val Ser Phe Glu Val
                    965                 970                 975
Lys Lys Met Pro Tyr Thr Asp Gln Pro Ala Lys Leu Pro Glu Gly Ser
                    980                 985                 990
Ile Ala Ile Lys Thr Ser Val Ile Trp Ala Thr Pro Asn Val Ser Phe
            995                 1000                1005
Ser Ile Pro Leu Trp Val Ile Ile Leu Ala Ile Leu Leu Gly Leu
            1010                1015                1020
Leu Val Leu Ala Ile Leu Thr Leu Ala Leu Trp Lys Cys Gly Phe
            1025                1030                1035
Phe Asp Arg Ala Arg Pro Pro Gln Glu Asp Met Thr Asp Arg Glu
            1040                1045                1050
Gln Leu Thr Asn Asp Lys Thr Pro Glu Ala
            1055                1060
```

<210> SEQ ID NO 208
<211> LENGTH: 479
<212> TYPE: PRT
<213> ORGANISM: Homo sapiens

<400> SEQUENCE: 208

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
```

```
                370                 375                 380
Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
                420                 425                 430

Cys Gly Trp Lys Phe Ala Arg Ser Asp Glu Leu Thr Arg His Tyr Arg
                435                 440                 445

Lys His Thr Gly His Arg Pro Phe Gln Cys Gln Lys Cys Asp Arg Ala
                450                 455                 460

Phe Ser Arg Ser Asp His Leu Ala Leu His Met Lys Arg His Phe
465                 470                 475

<210> SEQ ID NO 209
<211> LENGTH: 366
<212> TYPE: PRT
<213> ORGANISM: Homo sapiens

<400> SEQUENCE: 209

Met Gln Pro Leu Trp Leu Cys Trp Ala Leu Trp Val Leu Pro Leu Ala
1               5                   10                  15

Ser Pro Gly Ala Ala Leu Thr Gly Glu Gln Leu Leu Gly Ser Leu Leu
                20                  25                  30

Arg Gln Leu Gln Leu Lys Glu Val Pro Thr Leu Asp Arg Ala Asp Met
                35                  40                  45

Glu Glu Leu Val Ile Pro Thr His Val Arg Ala Gln Tyr Val Ala Leu
                50                  55                  60

Leu Gln Arg Ser His Gly Asp Arg Ser Arg Gly Lys Arg Phe Ser Gln
65              70                  75                  80

Ser Phe Arg Glu Val Ala Gly Arg Phe Leu Ala Leu Glu Ala Ser Thr
                85                  90                  95

His Leu Leu Val Phe Gly Met Glu Gln Arg Leu Pro Pro Asn Ser Glu
                100                 105                 110

Leu Val Gln Ala Val Leu Arg Leu Phe Gln Glu Pro Val Pro Lys Ala
                115                 120                 125

Ala Leu His Arg His Gly Arg Leu Ser Pro Arg Ser Ala Arg Ala Arg
                130                 135                 140

Val Thr Val Glu Trp Leu Arg Val Arg Asp Asp Gly Ser Asn Arg Thr
145             150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
                180                 185                 190

Pro Arg Gln Pro Leu Leu Leu Gln Val Ser Val Gln Arg Glu His Leu
                195                 200                 205

Gly Pro Leu Ala Ser Gly Ala His Lys Leu Val Arg Phe Ala Ser Gln
                210                 215                 220

Gly Ala Pro Ala Gly Leu Gly Glu Pro Gln Leu Glu Leu His Thr Leu
225             230                 235                 240

Asp Leu Gly Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
                260                 265                 270
```

-continued

```
Gln Gly Met Lys Trp Ala Glu Asn Trp Val Leu Glu Pro Gly Phe
            275                 280                 285

Leu Ala Tyr Glu Cys Val Gly Thr Cys Arg Gln Pro Pro Glu Ala Leu
290                 295                 300

Ala Phe Lys Trp Pro Phe Leu Gly Pro Arg Gln Cys Ile Ala Ser Glu
305                 310                 315                 320

Thr Asp Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
                340                 345                 350

Cys Ala Ser Asp Gly Ala Leu Val Pro Arg Arg Leu Gln Pro
            355                 360                 365

<210> SEQ ID NO 210
<211> LENGTH: 406
<212> TYPE: PRT
<213> ORGANISM: Homo sapiens

<400> SEQUENCE: 210

Met Val His Cys Ala Gly Cys Lys Arg Pro Ile Leu Asp Arg Phe Leu
1               5                   10                  15

Leu Asn Val Leu Asp Arg Ala Trp His Val Lys Cys Val Gln Cys Cys
                20                  25                  30

Glu Cys Lys Cys Asn Leu Thr Glu Lys Cys Phe Ser Arg Glu Gly Lys
            35                  40                  45

Leu Tyr Cys Lys Asn Asp Phe Phe Arg Cys Phe Gly Thr Lys Cys Ala
        50                  55                  60

Gly Cys Ala Gln Gly Ile Ser Pro Ser Asp Leu Val Arg Arg Ala Arg
65                  70                  75                  80

Ser Lys Val Phe His Leu Asn Cys Phe Thr Cys Met Met Cys Asn Lys
                85                  90                  95

Gln Leu Ser Thr Gly Glu Glu Leu Tyr Ile Ile Asp Glu Asn Lys Phe
            100                 105                 110

Val Cys Lys Glu Asp Tyr Leu Ser Asn Ser Val Ala Lys Glu Asn
        115                 120                 125

Ser Leu His Ser Ala Thr Thr Gly Ser Asp Pro Ser Leu Ser Pro Asp
130                 135                 140

Ser Gln Asp Pro Ser Gln Asp Ala Lys Ser Glu Ser Ala Asn
145                 150                 155                 160

Val Ser Asp Lys Glu Ala Gly Ser Asn Glu Asn Asp Gln Asn Leu
                165                 170                 175

Gly Ala Lys Arg Arg Gly Pro Arg Thr Thr Ile Lys Ala Lys Gln Leu
            180                 185                 190

Glu Thr Leu Lys Ala Ala Phe Ala Thr Pro Lys Pro Thr Arg His
        195                 200                 205

Ile Arg Glu Gln Leu Ala Gln Glu Thr Gly Leu Asn Met Arg Val Ile
210                 215                 220

Gln Val Trp Phe Gln Asn Arg Arg Ser Lys Glu Arg Arg Met Lys Gln
225                 230                 235                 240

Leu Ser Ala Leu Gly Ala Arg Arg His Ala Phe Phe Arg Ser Pro Arg
                245                 250                 255

Arg Met Arg Pro Leu Val Asp Arg Leu Glu Pro Gly Glu Leu Ile Pro
            260                 265                 270

Asn Gly Pro Phe Ser Phe Tyr Gly Asp Tyr Gln Ser Glu Tyr Tyr Gly
        275                 280                 285
```

```
Pro Gly Gly Asn Tyr Asp Phe Phe Pro Gln Gly Pro Ser Ser Gln
    290                 295                 300

Ala Gln Thr Pro Val Asp Leu Pro Phe Val Pro Ser Ser Gly Pro Ser
305                 310                 315                 320

Gly Thr Pro Leu Gly Gly Leu Glu His Pro Leu Pro Gly His His Pro
                325                 330                 335

Ser Ser Glu Ala Gln Arg Phe Thr Asp Ile Leu Ala His Pro Pro Gly
            340                 345                 350

Asp Ser Pro Ser Pro Glu Pro Ser Leu Pro Gly Pro Leu His Ser Met
        355                 360                 365

Ser Ala Glu Val Phe Gly Pro Ser Pro Pro Phe Ser Ser Leu Ser Val
    370                 375                 380

Asn Gly Gly Ala Ser Tyr Gly Asn His Leu Ser His Pro Pro Glu Met
385                 390                 395                 400

Asn Glu Ala Ala Val Trp
                405

<210> SEQ ID NO 211
<211> LENGTH: 209
<212> TYPE: PRT
<213> ORGANISM: Homo sapiens

<400> SEQUENCE: 211

Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn

<210> SEQ ID NO 212
<211> LENGTH: 305
<212> TYPE: PRT
<213> ORGANISM: Homo sapiens
```

<400> SEQUENCE: 212

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305
```

<210> SEQ ID NO 213
<211> LENGTH: 290
<212> TYPE: PRT
<213> ORGANISM: Mus musculus

<400> SEQUENCE: 213

```
Met Asp Ile Glu Ala Tyr Phe Glu Arg Ile Gly Tyr Lys Asn Ser Val
1               5                   10                  15

Asn Lys Leu Asp Leu Ala Thr Leu Thr Glu Val Leu Gln His Gln Met
            20                  25                  30

Arg Ala Val Pro Phe Glu Asn Leu Asn Met His Cys Gly Glu Ala Met
        35                  40                  45
```

```
His Leu Asp Leu Gln Asp Ile Phe Asp His Ile Val Arg Lys Arg
    50                  55                  60
Gly Gly Trp Cys Leu Gln Val Asn His Leu Leu Tyr Trp Ala Leu Thr
65                  70                  75                  80
Lys Met Gly Phe Glu Thr Thr Met Leu Gly Gly Tyr Val Tyr Ile Thr
                85                  90                  95
Pro Val Ser Lys Tyr Ser Ser Glu Met Val His Leu Leu Val Gln Val
                100                 105                 110
Thr Ile Ser Asp Arg Lys Tyr Ile Val Asp Ser Ala Tyr Gly Gly Ser
            115                 120                 125
Tyr Gln Met Trp Glu Pro Leu Glu Leu Thr Ser Gly Lys Asp Gln Pro
        130                 135                 140
Gln Val Pro Ala Ile Phe Leu Leu Thr Glu Glu Asn Gly Thr Trp Tyr
145                 150                 155                 160
Leu Asp Gln Ile Arg Arg Glu Gln Tyr Val Pro Asn Glu Glu Phe Val
                165                 170                 175
Asn Ser Asp Leu Leu Glu Lys Asn Lys Tyr Arg Lys Ile Tyr Ser Phe
            180                 185                 190
Thr Leu Glu Pro Arg Val Ile Glu Asp Phe Gly Tyr Val Asn Ser Tyr
        195                 200                 205
Leu Gln Thr Ser Pro Ala Ser Val Phe Val Ser Thr Ser Phe Cys Ser
210                 215                 220
Leu Gln Thr Ser Glu Gly Val His Cys Leu Val Gly Ser Thr Phe Thr
225                 230                 235                 240
Ser Arg Arg Phe Ser Tyr Lys Asp Asp Asp Leu Val Glu Phe Lys
                245                 250                 255
Tyr Val Asn Glu Glu Glu Ile Glu Asp Val Leu Lys Thr Ala Phe Gly
                260                 265                 270
Ile Ser Leu Glu Arg Lys Phe Val Pro Lys His Gly Glu Leu Val Phe
            275                 280                 285
Thr Ile
    290

<210> SEQ ID NO 214
<211> LENGTH: 848
<212> TYPE: PRT
<213> ORGANISM: Homo sapiens

<400> SEQUENCE: 214

Met Leu Gln Thr Lys Asp Leu Ile Trp Thr Leu Phe Phe Leu Gly Thr
1               5                   10                  15
Ala Val Ser Leu Gln Val Asp Ile Val Pro Ser Gln Gly Glu Ile Ser
                20                  25                  30
Val Gly Glu Ser Lys Phe Phe Leu Cys Gln Val Ala Gly Asp Ala Lys
            35                  40                  45
Asp Lys Asp Ile Ser Trp Phe Ser Pro Asn Gly Glu Lys Leu Thr Pro
        50                  55                  60
Asn Gln Gln Arg Ile Ser Val Val Trp Asn Asp Asp Ser Ser Ser Thr
65                  70                  75                  80
Leu Thr Ile Tyr Asn Ala Asn Ile Asp Asp Ala Gly Ile Tyr Lys Cys
                85                  90                  95
Val Val Thr Gly Glu Asp Gly Ser Glu Ser Glu Ala Thr Val Asn Val
                100                 105                 110
Lys Ile Phe Gln Lys Leu Met Phe Lys Asn Ala Pro Thr Pro Gln Glu
```

-continued

```
            115                 120                 125
Phe Arg Glu Gly Glu Asp Ala Val Ile Val Cys Asp Val Ser Ser
130                 135                 140
Leu Pro Pro Thr Ile Ile Trp Lys His Lys Gly Arg Asp Val Ile Leu
145                 150                 155                 160
Lys Lys Asp Val Arg Phe Ile Val Leu Ser Asn Asn Tyr Leu Gln Ile
                165                 170                 175
Arg Gly Ile Lys Lys Thr Asp Glu Gly Thr Tyr Arg Cys Glu Gly Arg
            180                 185                 190
Ile Leu Ala Arg Gly Glu Ile Asn Phe Lys Asp Ile Gln Val Ile Val
        195                 200                 205
Asn Val Pro Pro Thr Ile Gln Ala Arg Gln Asn Ile Val Asn Ala Thr
    210                 215                 220
Ala Asn Leu Gly Gln Ser Val Thr Leu Val Cys Asp Ala Glu Gly Phe
225                 230                 235                 240
Pro Glu Pro Thr Met Ser Trp Thr Lys Asp Gly Glu Gln Ile Glu Gln
                245                 250                 255
Glu Glu Asp Asp Glu Lys Tyr Ile Phe Ser Asp Asp Ser Ser Gln Leu
            260                 265                 270
Thr Ile Lys Lys Val Asp Lys Asn Asp Glu Ala Glu Tyr Ile Cys Ile
        275                 280                 285
Ala Glu Asn Lys Ala Gly Glu Gln Asp Ala Thr Ile His Leu Lys Val
    290                 295                 300
Phe Ala Lys Pro Lys Ile Thr Tyr Val Glu Asn Gln Thr Ala Met Glu
305                 310                 315                 320
Leu Glu Glu Gln Val Thr Leu Thr Cys Glu Ala Ser Gly Asp Pro Ile
                325                 330                 335
Pro Ser Ile Thr Trp Arg Thr Ser Thr Arg Asn Ile Ser Ser Glu Glu
            340                 345                 350
Lys Thr Leu Asp Gly His Met Val Val Arg Ser His Ala Arg Val Ser
        355                 360                 365
Ser Leu Thr Leu Lys Ser Ile Gln Tyr Thr Asp Ala Gly Glu Tyr Ile
    370                 375                 380
Cys Thr Ala Ser Asn Thr Ile Gly Gln Asp Ser Gln Ser Met Tyr Leu
385                 390                 395                 400
Glu Val Gln Tyr Ala Pro Lys Leu Gln Gly Pro Val Ala Val Tyr Thr
                405                 410                 415
Trp Glu Gly Asn Gln Val Asn Ile Thr Cys Glu Val Phe Ala Tyr Pro
            420                 425                 430
Ser Ala Thr Ile Ser Trp Phe Arg Asp Gly Gln Leu Leu Pro Ser Ser
        435                 440                 445
Asn Tyr Ser Asn Ile Lys Ile Tyr Asn Thr Pro Ser Ala Ser Tyr Leu
    450                 455                 460
Glu Val Thr Pro Asp Ser Glu Asn Asp Phe Gly Asn Tyr Asn Cys Thr
465                 470                 475                 480
Ala Val Asn Arg Ile Gly Gln Glu Ser Leu Glu Phe Ile Leu Val Gln
                485                 490                 495
Ala Asp Thr Pro Ser Ser Pro Ser Ile Asp Gln Val Glu Pro Tyr Ser
            500                 505                 510
Ser Thr Ala Gln Val Gln Phe Asp Glu Pro Glu Ala Thr Gly Gly Val
        515                 520                 525
Pro Ile Leu Lys Tyr Lys Ala Glu Trp Arg Ala Val Gly Glu Glu Val
    530                 535                 540
```

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
            610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
            690                 695                 700

Pro Thr Ser Gly Leu Ser Thr Gly Ala Ile Val Gly Ile Leu Ile Val
705                 710                 715                 720

Ile Phe Val Leu Leu Leu Val Val Asp Ile Thr Cys Tyr Phe Leu
                725                 730                 735

Asn Lys Cys Gly Leu Phe Met Cys Ile Ala Val Asn Leu Cys Gly Lys
                740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
            805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
            835                 840                 845

<210> SEQ ID NO 215
<211> LENGTH: 1621
<212> TYPE: PRT
<213> ORGANISM: Homo sapiens

<400> SEQUENCE: 215

Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
            20                  25                  30

Asn Glu Leu Leu Ser Ala Glu Leu Gly Gly Leu Arg Ala Gln Ser Ala
        35                  40                  45

Asp Thr Ser Trp Arg Ala His Ala Asp Glu Leu Ala Ala Leu Arg
    50                  55                  60

Ala Leu Val Asp Gln Arg Trp Arg Glu Lys His Ala Ala Glu Val Ala

```
                65                  70                  75                  80
Arg Asp Asn Leu Ala Glu Glu Leu Gly Val Ala Gly Arg Cys Gln
                    85                  90                  95

Gln Leu Arg Leu Ala Arg Glu Arg Thr Thr Glu Glu Val Ala Arg Asn
                    100                 105                 110

Arg Arg Ala Val Glu Ala Glu Lys Cys Arg Ala Trp Leu Ser Ser
                115                 120                 125

Gln Val Ala Glu Leu Glu Arg Glu Leu Glu Ala Leu Arg Val Ala His
        130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Ala Pro Glu Val Glu
                165                 170                 175

Glu Leu Ala Arg Arg Leu Gly Glu Ala Trp Arg Gly Ala Val Arg Gly
                180                 185                 190

Tyr Gln Glu Arg Val Ala His Met Glu Thr Ser Leu Gly Gln Ala Arg
            195                 200                 205

Glu Arg Leu Gly Arg Ala Val Gln Gly Ala Arg Glu Gly Arg Leu Glu
        210                 215                 220

Leu Gln Gln Leu Gln Ala Glu Arg Gly Gly Leu Leu Glu Arg Arg Ala
225                 230                 235                 240

Ala Leu Glu Gln Arg Leu Glu Gly Arg Trp Gln Glu Arg Leu Arg Ala
                245                 250                 255

Thr Glu Lys Phe Gln Leu Ala Val Glu Ala Leu Glu Gln Glu Lys Gln
                260                 265                 270

Gly Leu Gln Ser Gln Ile Ala Gln Val Leu Glu Gly Arg Gln Gln Leu
            275                 280                 285

Ala His Leu Lys Met Ser Leu Ser Leu Glu Val Ala Thr Tyr Arg Thr
        290                 295                 300

Leu Leu Glu Ala Glu Asn Ser Arg Leu Gln Thr Pro Gly Gly Gly Ser
305                 310                 315                 320

Lys Thr Ser Leu Ser Phe Gln Asp Pro Lys Leu Glu Leu Gln Phe Pro
                325                 330                 335

Arg Thr Pro Glu Gly Arg Arg Leu Gly Ser Leu Leu Pro Val Leu Ser
                340                 345                 350

Pro Thr Ser Leu Pro Ser Pro Leu Pro Ala Thr Leu Glu Thr Pro Val
            355                 360                 365

Pro Ala Phe Leu Lys Asn Gln Glu Phe Leu Gln Ala Arg Thr Pro Thr
        370                 375                 380

Leu Ala Ser Thr Pro Ile Pro Pro Thr Pro Gln Ala Pro Ser Pro Ala
385                 390                 395                 400

Val Asp Ala Glu Ile Arg Ala Gln Asp Ala Pro Leu Ser Leu Leu Gln
                405                 410                 415

Thr Gln Gly Gly Arg Lys Gln Ala Pro Glu Pro Leu Arg Ala Glu Ala
                420                 425                 430

Arg Val Ala Ile Pro Ala Ser Val Leu Pro Gly Pro Glu Glu Pro Gly
            435                 440                 445

Gly Gln Arg Gln Glu Ala Ser Thr Gly Gln Ser Pro Glu Asp His Ala
        450                 455                 460

Ser Leu Ala Pro Pro Leu Ser Pro Asp His Ser Ser Leu Glu Ala Lys
465                 470                 475                 480

Asp Gly Glu Ser Gly Gly Ser Arg Val Phe Ser Ile Cys Arg Gly Glu
                485                 490                 495
```

```
Gly Glu Gly Gln Ile Trp Gly Leu Val Glu Lys Glu Thr Ala Ile Glu
            500                 505                 510

Gly Lys Val Val Ser Ser Leu Gln Gln Glu Ile Trp Glu Glu Glu Asp
            515                 520                 525

Leu Asn Arg Lys Glu Ile Gln Asp Ser Gln Val Pro Leu Glu Lys Glu
            530                 535                 540

Thr Leu Lys Ser Leu Gly Glu Glu Ile Gln Glu Ser Leu Lys Thr Leu
545                 550                 555                 560

Glu Asn Gln Ser His Glu Thr Leu Glu Arg Glu Asn Gln Cys Pro
                565                 570                 575

Arg Ser Leu Glu Glu Asp Leu Glu Thr Leu Lys Ser Leu Glu Lys Glu
            580                 585                 590

Asn Lys Glu Leu Leu Lys Asp Val Glu Val Arg Pro Leu Glu Lys
            595                 600                 605

Glu Ala Val Gly Gln Leu Lys Pro Thr Gly Lys Glu Asp Thr Gln Thr
            610                 615                 620

Leu Gln Ser Leu Gln Lys Glu Asn Gln Glu Leu Met Lys Ser Leu Glu
625                 630                 635                 640

Gly Asn Leu Glu Thr Phe Leu Phe Pro Gly Thr Glu Asn Gln Glu Leu
                645                 650                 655

Val Ser Ser Leu Gln Glu Asn Leu Glu Ser Leu Thr Ala Leu Glu Lys
            660                 665                 670

Glu Asn Gln Glu Pro Leu Arg Ser Pro Glu Val Gly Asp Glu Glu Ala
            675                 680                 685

Leu Arg Pro Leu Thr Lys Glu Asn Gln Glu Pro Leu Arg Ser Leu Glu
            690                 695                 700

Asp Glu Asn Lys Glu Ala Phe Arg Ser Leu Glu Lys Glu Asn Gln Glu
705                 710                 715                 720

Pro Leu Lys Thr Leu Glu Glu Asp Gln Ser Ile Val Arg Pro Leu
            725                 730                 735

Glu Thr Glu Asn His Lys Ser Leu Arg Ser Leu Glu Glu Gln Asp Gln
            740                 745                 750

Glu Thr Leu Arg Thr Leu Glu Lys Glu Thr Gln Arg Arg Ser
            755                 760                 765

Leu Gly Glu Gln Asp Gln Met Thr Leu Arg Pro Pro Glu Lys Val Asp
770                 775                 780

Leu Glu Pro Leu Lys Ser Leu Asp Gln Glu Ile Ala Arg Pro Leu Glu
785                 790                 795                 800

Asn Glu Asn Gln Glu Phe Leu Lys Ser Leu Lys Glu Glu Ser Val Glu
                805                 810                 815

Ala Val Lys Ser Leu Glu Thr Glu Ile Leu Glu Ser Leu Lys Ser Ala
            820                 825                 830

Gly Gln Glu Asn Leu Glu Thr Leu Lys Ser Pro Glu Thr Gln Ala Pro
            835                 840                 845

Leu Trp Thr Pro Glu Glu Ile Asn Gln Gly Ala Met Asn Pro Leu Glu
850                 855                 860

Lys Glu Ile Gln Glu Pro Leu Glu Ser Val Glu Val Asn Gln Glu Thr
865                 870                 875                 880

Phe Arg Leu Leu Glu Glu Asn Gln Glu Ser Leu Arg Ser Leu Gly
                885                 890                 895

Ala Trp Asn Leu Glu Asn Leu Arg Ser Pro Glu Glu Val Asp Lys Glu
            900                 905                 910
```

-continued

```
Ser Gln Arg Asn Leu Glu Glu Glu Asn Leu Gly Lys Gly Glu Tyr
        915                 920                 925

Gln Glu Ser Leu Arg Ser Leu Glu Glu Gly Gln Glu Leu Pro Gln
    930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Glu Asp
                965                 970                 975

Glu Ala Glu Leu Asn Leu Arg Glu Gln Asp Gly Phe Thr Gly Lys Glu
            980                 985                 990

Glu Val Val Glu Gln Gly Glu Leu Asn Ala Thr Glu Glu Val Trp Ile
        995                 1000                1005

Pro Gly Glu Gly His Pro Glu Ser Pro Glu Pro Lys Glu Gln Arg
    1010                1015                1020

Gly Leu Val Glu Gly Ala Ser Val Lys Gly Gly Ala Glu Gly Leu
    1025                1030                1035

Gln Asp Pro Glu Gly Gln Ser Gln Gln Val Gly Ala Pro Gly Leu
    1040                1045                1050

Gln Ala Pro Gln Gly Leu Pro Glu Ala Ile Glu Pro Leu Val Glu
    1055                1060                1065

Asp Asp Val Ala Pro Gly Gly Asp Gln Ala Ser Pro Glu Val Met
    1070                1075                1080

Leu Gly Ser Glu Pro Ala Met Gly Glu Ser Ala Ala Gly Ala Glu
    1085                1090                1095

Pro Gly Pro Gly Gln Gly Val Gly Gly Leu Gly Asp Pro Gly His
    1100                1105                1110

Leu Thr Arg Glu Glu Val Met Glu Pro Pro Leu Glu Glu Glu Ser
    1115                1120                1125

Leu Glu Ala Lys Arg Val Gln Gly Leu Glu Gly Pro Arg Lys Asp
    1130                1135                1140

Leu Glu Glu Ala Gly Gly Leu Gly Thr Glu Phe Ser Glu Leu Pro
    1145                1150                1155

Gly Lys Ser Arg Asp Pro Trp Glu Pro Pro Arg Glu Gly Arg Glu
    1160                1165                1170

Glu Ser Glu Ala Glu Ala Pro Arg Gly Ala Glu Glu Ala Phe Pro
    1175                1180                1185

Ala Glu Thr Leu Gly His Thr Gly Ser Asp Ala Pro Ser Pro Trp
    1190                1195                1200

Pro Leu Gly Ser Glu Glu Ala Glu Glu Asp Val Pro Pro Val Leu
    1205                1210                1215

Val Ser Pro Ser Pro Thr Tyr Thr Pro Ile Leu Glu Asp Ala Pro
    1220                1225                1230

Gly Pro Gln Pro Gln Ala Glu Gly Ser Gln Glu Ala Ser Trp Gly
    1235                1240                1245

Val Gln Gly Arg Ala Glu Ala Leu Gly Lys Val Glu Ser Glu Gln
    1250                1255                1260

Glu Glu Leu Gly Ser Gly Glu Ile Pro Glu Gly Pro Gln Glu Glu
    1265                1270                1275

Gly Glu Glu Ser Arg Glu Glu Ser Glu Glu Asp Glu Leu Gly Glu
    1280                1285                1290

Thr Leu Pro Asp Ser Thr Pro Leu Gly Phe Tyr Leu Arg Ser Pro
    1295                1300                1305

Thr Ser Pro Arg Trp Asp Pro Thr Gly Glu Gln Arg Pro Pro Pro
```

```
Gln Gly Glu Thr Gly Lys Glu Gly Trp Asp Pro Ala Val Leu Ala
    1325            1330                1335

Ser Glu Gly Leu Glu Ala Pro Pro Ser Lys Glu Glu Gly Glu
    1340            1345                1350

Glu Gly Glu Glu Glu Cys Gly Arg Asp Ser Asp Leu Ser Glu Glu
    1355            1360                1365

Phe Glu Asp Leu Gly Thr Glu Ala Pro Phe Leu Pro Gly Val Pro
    1370            1375                1380

Gly Glu Val Ala Glu Pro Leu Gly Gln Val Pro Gln Leu Leu Leu
    1385            1390                1395

Asp Pro Ala Ala Trp Asp Arg Asp Gly Glu Ser Asp Gly Phe Ala
    1400            1405                1410

Asp Glu Glu Glu Ser Gly Glu Glu Gly Glu Glu Asp Gln Glu Glu
    1415            1420                1425

Gly Arg Glu Pro Gly Ala Gly Arg Trp Gly Pro Gly Ser Ser Val
    1430            1435                1440

Gly Ser Leu Gln Ala Leu Ser Ser Ser Gln Arg Gly Glu Phe Leu
    1445            1450                1455

Glu Ser Asp Ser Val Ser Val Ser Val Pro Trp Asp Asp Ser Leu
    1460            1465                1470

Arg Gly Ala Val Ala Gly Ala Pro Lys Thr Ala Leu Glu Thr Glu
    1475            1480                1485

Ser Gln Asp Ser Ala Glu Pro Ser Gly Ser Glu Glu Glu Ser Asp
    1490            1495                1500

Pro Val Ser Leu Glu Arg Glu Asp Lys Val Pro Gly Pro Leu Glu
    1505            1510                1515

Ile Pro Ser Gly Met Glu Asp Ala Gly Pro Gly Ala Asp Ile Ile
    1520            1525                1530

Gly Val Asn Gly Gln Gly Pro Asn Leu Glu Gly Lys Ser Gln His
    1535            1540                1545

Val Asn Gly Gly Val Met Asn Gly Leu Glu Gln Ser Glu Glu Val
    1550            1555                1560

Gly Gln Gly Met Pro Leu Val Ser Glu Gly Asp Arg Gly Ser Pro
    1565            1570                1575

Phe Gln Glu Glu Glu Gly Ser Ala Leu Lys Thr Ser Trp Ala Gly
    1580            1585                1590

Ala Pro Val His Leu Gly Gly Gln Phe Leu Lys Phe Thr Gln
    1595            1600                1605

Arg Glu Gly Asp Arg Glu Ser Trp Ser Ser Gly Glu Asp
    1610            1615                1620
```

<210> SEQ ID NO 216
<211> LENGTH: 347
<212> TYPE: PRT
<213> ORGANISM: Homo sapiens

<400> SEQUENCE: 216

```
Met His Ala His Cys Leu Pro Phe Leu Leu His Ala Trp Trp Ala Leu
1               5                   10                  15

Leu Gln Ala Gly Ala Ala Thr Val Ala Thr Ala Leu Leu Arg Thr Arg
            20                  25                  30

Gly Gln Pro Ser Ser Pro Ser Pro Leu Ala Tyr Met Leu Ser Leu Tyr
        35                  40                  45
```

Arg Asp Pro Leu Pro Arg Ala Asp Ile Ile Arg Ser Leu Gln Ala Glu
    50                  55                  60

Asp Val Ala Val Asp Gly Gln Asn Trp Thr Phe Ala Phe Asp Phe Ser
65                  70                  75                  80

Phe Leu Ser Gln Gln Glu Asp Leu Ala Trp Ala Glu Leu Arg Leu Gln
                85                  90                  95

Leu Ser Ser Pro Val Asp Leu Pro Thr Glu Gly Ser Leu Ala Ile Glu
            100                 105                 110

Ile Phe His Gln Pro Lys Pro Asp Thr Glu Gln Ala Ser Asp Ser Cys
        115                 120                 125

Leu Glu Arg Phe Gln Met Asp Leu Phe Thr Val Thr Leu Ser Gln Val
    130                 135                 140

Thr Phe Ser Leu Gly Ser Met Val Leu Glu Val Thr Arg Pro Leu Ser
145                 150                 155                 160

Lys Trp Leu Lys His Pro Gly Ala Leu Glu Lys Gln Met Ser Arg Val
                165                 170                 175

Ala Gly Glu Cys Trp Pro Arg Pro Thr Pro Pro Ala Thr Asn Val
            180                 185                 190

Leu Leu Met Leu Tyr Ser Asn Leu Ser Gln Glu Gln Arg Gln Leu Gly
        195                 200                 205

Gly Ser Thr Leu Leu Trp Glu Ala Glu Ser Ser Trp Arg Ala Gln Glu
    210                 215                 220

Gly Gln Leu Ser Trp Glu Trp Gly Lys Arg His Arg His His Leu
225                 230                 235                 240

Pro Asp Arg Ser Gln Leu Cys Arg Lys Val Lys Phe Gln Val Asp Phe
                245                 250                 255

Asn Leu Ile Gly Trp Gly Ser Trp Ile Ile Tyr Pro Lys Gln Tyr Asn
            260                 265                 270

Ala Tyr Arg Cys Glu Gly Glu Cys Pro Asn Pro Val Gly Glu Glu Phe
        275                 280                 285

His Pro Thr Asn His Ala Tyr Ile Gln Ser Leu Leu Lys Arg Tyr Gln
    290                 295                 300

Pro His Arg Val Pro Ser Thr Cys Cys Ala Pro Val Lys Thr Lys Pro
305                 310                 315                 320

Leu Ser Met Leu Tyr Val Asp Asn Gly Arg Val Leu Leu Asp His His
                325                 330                 335

Lys Asp Met Ile Val Glu Glu Cys Gly Cys Leu
            340                 345

<210> SEQ ID NO 217
<211> LENGTH: 477
<212> TYPE: PRT
<213> ORGANISM: Homo sapiens

<400> SEQUENCE: 217

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

-continued

```
Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Phe Val Leu Phe His Lys Ile Pro Leu Asp Gly
465                 470                 475

<210> SEQ ID NO 218
<211> LENGTH: 190
```

```
<212> TYPE: PRT
<213> ORGANISM: Homo sapiens

<400> SEQUENCE: 218

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
            20                  25                  30

Leu Leu Gln Lys Trp Val Glu Glu Ala Asp Asn Asn Glu Asn Leu Gln
        35                  40                  45

Glu Ile Cys Lys Ala Glu Thr Leu Val Gln Ala Arg Lys Arg Lys Arg
    50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
            100                 105                 110

Gln Lys Gly Lys Arg Ser Ser Asp Tyr Ala Gln Arg Glu Asp Phe
        115                 120                 125

Glu Ala Ala Gly Ser Pro Phe Ser Gly Pro Val Ser Phe Pro Leu
    130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
            180                 185                 190

<210> SEQ ID NO 219
<211> LENGTH: 323
<212> TYPE: PRT
<213> ORGANISM: Mus musculus

<400> SEQUENCE: 219

Met Asp Ser Asp Ala Ser Leu Val Ser Ser Arg Pro Ser Ser Pro Glu
1               5                   10                  15

Pro Asp Asp Leu Phe Leu Pro Ala Arg Ser Lys Gly Gly Ser Ser Ser
            20                  25                  30

Gly Phe Thr Gly Gly Thr Val Ser Ser Thr Pro Ser Asp Cys Pro
        35                  40                  45

Pro Glu Leu Ser Ser Glu Leu Arg Gly Ala Met Gly Ala Ser Gly Ala
    50                  55                  60

His Pro Gly Asp Lys Leu Gly Gly Gly Phe Lys Ser Ser Ser Ser
65                  70                  75                  80

Ser Thr Ser Ser Thr Ser Ser Ala Ala Thr Ser Ser Thr Lys Lys
                85                  90                  95

Asp Lys Lys Gln Met Thr Glu Pro Glu Leu Gln Gln Leu Arg Leu Lys
            100                 105                 110

Ile Asn Ser Arg Glu Arg Lys Arg Met His Asp Leu Asn Ile Ala Met
        115                 120                 125

Asp Gly Leu Arg Glu Val Met Pro Tyr Ala His Gly Pro Ser Val Arg
    130                 135                 140

Lys Leu Ser Lys Ile Ala Thr Leu Leu Leu Ala Arg Asn Tyr Ile Leu
145                 150                 155                 160
```

```
Met Leu Thr Asn Ser Leu Glu Glu Met Lys Arg Leu Val Ser Glu Ile
                165                 170                 175
Tyr Gly Gly His His Ala Gly Phe His Pro Ser Ala Cys Gly Gly Leu
            180                 185                 190
Ala His Ser Ala Pro Leu Pro Thr Ala Thr Ala His Pro Ala Ala Ala
        195                 200                 205
Ala His Ala Ala His His Pro Ala Val His His Pro Ile Leu Pro Pro
    210                 215                 220
Ala Ala Ala Ala Ala Ala Ala Ala Ala Ala Ala Ala Ala Val Ser Ser
225                 230                 235                 240
Ala Ser Leu Pro Gly Ser Gly Leu Ser Ser Val Gly Ser Ile Arg Pro
                245                 250                 255
Pro His Gly Leu Leu Lys Ser Pro Ser Ala Ala Ala Ala Ala Pro Leu
            260                 265                 270
Gly Gly Gly Gly Gly Gly Ser Gly Gly Ser Gly Gly Phe Gln His Trp
        275                 280                 285
Gly Gly Met Pro Cys Pro Cys Ser Met Cys Gln Val Pro Pro Pro His
    290                 295                 300
His His Val Ser Ala Met Gly Ala Gly Thr Leu Pro Arg Leu Thr Ser
305                 310                 315                 320
Asp Ala Lys

<210> SEQ ID NO 220
<211> LENGTH: 393
<212> TYPE: PRT
<213> ORGANISM: Homo sapiens

<400> SEQUENCE: 220

Met Asp Met His Cys Lys Ala Asp Pro Phe Ser Ala Met His Pro Gly
1               5                   10                  15
His Gly Gly Val Asn Gln Leu Gly Gly Val Phe Val Asn Gly Arg Pro
            20                  25                  30
Leu Pro Asp Val Val Arg Gln Arg Ile Val Glu Leu Ala His Gln Gly
        35                  40                  45
Val Arg Pro Cys Asp Ile Ser Arg Gln Leu Arg Val Ser His Gly Cys
    50                  55                  60
Val Ser Lys Ile Leu Gly Arg Tyr Tyr Glu Thr Gly Ser Ile Lys Pro
65              70                  75                  80
Gly Val Ile Gly Gly Ser Lys Pro Lys Val Ala Thr Pro Lys Val Val
            85                  90                  95
Asp Lys Ile Ala Glu Tyr Lys Arg Gln Asn Pro Thr Met Phe Ala Trp
        100                 105                 110
Glu Ile Arg Asp Arg Leu Leu Ala Glu Gly Ile Cys Asp Asn Asp Thr
    115                 120                 125
Val Pro Ser Val Ser Ser Ile Asn Arg Ile Ile Arg Thr Lys Val Gln
130                 135                 140
Gln Pro Phe His Pro Thr Pro Asp Gly Ala Gly Thr Gly Val Thr Ala
145                 150                 155                 160
Pro Gly His Thr Ile Val Pro Ser Thr Ala Ser Pro Pro Val Ser Ser
                165                 170                 175
Ala Ser Asn Asp Pro Val Gly Ser Tyr Ser Ile Asn Gly Ile Leu Gly
            180                 185                 190
Ile Pro Arg Ser Asn Gly Glu Lys Arg Lys Arg Asp Glu Asp Val Ser
        195                 200                 205
```

-continued

```
Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Leu Glu Ala
225                 230                 235                 240

Leu Asp Arg Val Phe Glu Arg Pro Ser Tyr Pro Asp Val Phe Gln Ala
            245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
            275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
            355                 360                 365

Leu Ser Ser Pro Tyr Tyr Tyr Ser Ala Ala Pro Arg Ser Ala Pro Ala
370                 375                 380

Ala Ala Ala Ala Tyr Asp Arg His
385                 390

<210> SEQ ID NO 221
<211> LENGTH: 436
<212> TYPE: PRT
<213> ORGANISM: Mus musculus

<400> SEQUENCE: 221

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Glu Asn Val Ser Asn
    50                  55                  60

Gly Cys Val Ser Lys Ile Leu Gly Arg Tyr Tyr Glu Thr Gly Ser Ile
65                  70                  75                  80

Arg Pro Arg Ala Ile Gly Gly Ser Lys Pro Arg Val Ala Thr Pro Glu
                85                  90                  95

Val Val Ser Lys Ile Ala Gln Tyr Lys Arg Glu Cys Pro Ser Ile Phe
            100                 105                 110

Ala Trp Glu Ile Arg Asp Arg Leu Leu Ser Glu Gly Val Cys Thr Asn
        115                 120                 125

Asp Asn Ile Pro Ser Val Ser Ser Ile Asn Arg Val Leu Arg Asn Leu
    130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
                165                 170                 175

Tyr Pro Gly Thr Ser Val Pro Gly Gln Pro Thr Gln Asp Gly Cys Gln
            180                 185                 190
```

Gln Gln Glu Gly Gly Glu Asn Thr Asn Ser Ile Ser Ser Asn Gly
            195                 200                 205

Glu Asp Ser Asp Glu Ala Gln Met Arg Leu Gln Leu Lys Arg Lys Leu
        210                 215                 220

Gln Arg Asn Arg Thr Ser Phe Thr Gln Glu Gln Ile Glu Ala Leu Glu
225                 230                 235                 240

Lys Glu Phe Glu Arg Thr His Tyr Pro Asp Val Phe Ala Arg Glu Arg
                245                 250                 255

Leu Ala Ala Lys Ile Asp Leu Pro Glu Ala Arg Ile Gln Val Trp Phe
            260                 265                 270

Ser Asn Arg Arg Ala Lys Trp Arg Arg Glu Glu Lys Leu Arg Asn Gln
        275                 280                 285

Arg Arg Gln Ala Ser Asn Thr Pro Ser His Ile Pro Ile Ser Ser Ser
290                 295                 300

Phe Ser Thr Ser Val Tyr Gln Pro Ile Pro Gln Pro Thr Thr Pro Val
305                 310                 315                 320

Ser Ser Phe Thr Ser Gly Ser Met Leu Gly Arg Thr Asp Thr Ala Leu
                325                 330                 335

Thr Asn Thr Tyr Ser Ala Leu Pro Pro Met Pro Ser Phe Thr Met Ala
            340                 345                 350

Asn Asn Leu Pro Met Gln Pro Pro Val Pro Ser Gln Thr Ser Ser Tyr
        355                 360                 365

Ser Cys Met Leu Pro Thr Ser Pro Ser Val Asn Gly Arg Ser Tyr Asp
370                 375                 380

Thr Tyr Thr Pro Pro His Met Gln Thr His Met Asn Ser Gln Pro Met
385                 390                 395                 400

Gly Thr Ser Gly Thr Thr Ser Thr Gly Leu Ile Ser Pro Gly Val Ser
                405                 410                 415

Val Pro Val Gln Val Pro Gly Ser Glu Pro Asp Met Ser Gln Tyr Trp
            420                 425                 430

Pro Arg Leu Gln
        435

<210> SEQ ID NO 222
<211> LENGTH: 558
<212> TYPE: PRT
<213> ORGANISM: Mus musculus

<400> SEQUENCE: 222

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Gln
            20                  25                  30

Asn Ala Thr Gln Thr Thr Thr Asp Ser Ser Asn Lys Thr Ala Pro Thr
        35                  40                  45

Pro Ala Ser Ser Val Thr Ile Met Ala Thr Asp Thr Ala Gln Gln Ser
    50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Thr Leu Ala
                85                  90                  95

Gln Gln Val Ser Gly Pro Val Asn Thr Thr Val Ala Arg Gly Gly Gly
            100                 105                 110

Ser Gly Asn Pro Thr Thr Thr Ile Glu Ser Pro Lys Ser Thr Lys Ser

```
                115                 120                 125
Ala Asp Thr Thr Thr Val Ala Thr Ser Thr Ala Thr Ala Lys Pro Asn
    130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
                180                 185                 190

Thr Ser Thr His Pro Val Ala Thr Pro Thr Ser Ser Gly His Asp His
                195                 200                 205

Leu Met Lys Ile Ser Ser Ser Ser Thr Val Ala Ile Pro Gly Tyr
    210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
                245                 250                 255

Pro Thr Leu Ala Ser Gln Ser Ala Gly Ile Thr Ala Ser Ser Val Ile
                260                 265                 270

Ser Gln Arg Thr Gln Gln Thr Ser Ser Gln Met Pro Ala Ser Ser Thr
        275                 280                 285

Ala Pro Ser Ser Gln Glu Thr Val Gln Pro Thr Ser Pro Ala Thr Ala
    290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
                340                 345                 350

Ser Glu Lys Gln Leu Val Leu Asn Leu Thr Gly Asn Thr Leu Cys Ala
        355                 360                 365

Gly Gly Ala Ser Asp Glu Lys Leu Ile Ser Leu Ile Cys Arg Ala Val
    370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
                405                 410                 415

Thr Lys Leu Pro Ala Lys Asp Val Tyr Glu Arg Leu Lys Asp Lys Trp
                420                 425                 430

Asp Glu Leu Lys Glu Ala Gly Val Ser Asp Met Lys Leu Gly Asp Gln
        435                 440                 445

Gly Pro Pro Glu Glu Ala Glu Asp Arg Phe Ser Met Pro Leu Ile Ile
    450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
                485                 490                 495

Thr Glu Glu Leu Gln Thr Val Glu Asn Gly Tyr His Asp Asn Pro Thr
        500                 505                 510

Leu Glu Val Met Glu Thr Ser Ser Glu Met Gln Glu Lys Lys Val Val
        515                 520                 525

Ser Leu Asn Gly Glu Leu Gly Asp Ser Trp Ile Val Pro Leu Asp Asn
        530                 535                 540
```

```
Leu Thr Lys Asp Asp Leu Asp Glu Glu Glu Asp Thr His Leu
545                 550                 555

<210> SEQ ID NO 223
<211> LENGTH: 1221
<212> TYPE: PRT
<213> ORGANISM: Homo sapiens

<400> SEQUENCE: 223

Met Leu Arg Ser Thr Gly Phe Phe Arg Ala Ile Asp Cys Pro Tyr Trp
1               5                   10                  15

Ser Gly Ala Pro Gly Gly Pro Cys Arg Arg Pro Tyr Cys His Phe Arg
                20                  25                  30

His Arg Gly Ala Arg Gly Ser Gly Ala Pro Gly Asp Gly Gly Glu Ala
            35                  40                  45

Pro Pro Ala Ala Gly Leu Gly Tyr Asp Pro Tyr Asn Pro Glu Leu Pro
        50                  55                  60

Lys Pro Pro Ala Gln Arg Glu Asn Gly Thr Leu Gly Leu Gly Glu Glu
65                  70                  75                  80

Pro Arg Pro Asp Val Leu Glu Leu Glu Leu Val Asn Gln Ala Ile Glu
                85                  90                  95

Ala Val Arg Ser Glu Val Glu Leu Glu Gln Arg Arg Tyr Arg Glu Leu
                100                 105                 110

Leu Glu Thr Thr Arg Glu His Arg Ser Ala Glu Ala Pro Ala Leu Ala
            115                 120                 125

Pro Arg Gly Pro Asn Ala Ser Pro Thr Val Gly Pro Asp Glu Asp Ala
        130                 135                 140

Phe Pro Leu Ala Phe Asp Tyr Ser Pro Gly Ser His Gly Leu Leu Ser
145                 150                 155                 160

Pro Asp Ala Gly Tyr Gln Pro Thr Pro Leu Ala Ala Pro Ala Glu Pro
                165                 170                 175

Gly Ser Lys Tyr Ser Leu Ala Ser Leu Asp Arg Gly Gln Gly Arg Gly
                180                 185                 190

Gly Gly Gly Gly Gly Ala Leu Glu Tyr Val Pro Lys Ala Val Ser Gln
            195                 200                 205

Pro Arg Arg His Ser Arg Pro Val Pro Ser Gly Lys Tyr Val Val Asp
        210                 215                 220

Asn Ser Arg Pro Pro Thr Asp Leu Glu Tyr Asp Pro Leu Ser Asn Tyr
225                 230                 235                 240

Ser Ala Arg His Leu Ser Arg Ala Ser Ser Arg Asp Glu Arg Ala Ala
                245                 250                 255

Lys Arg Pro Arg Gly Ser Arg Gly Ser Glu Pro Tyr Thr Pro Ala Pro
            260                 265                 270

Lys Lys Leu Cys Asp Pro Phe Gly Ser Cys Asp Ala Arg Phe Ser Asp
        275                 280                 285

Ser Glu Asp Glu Ala Ala Thr Val Pro Gly Asn Glu Pro Thr Thr Ala
    290                 295                 300

Ser Thr Pro Lys Ala Arg Ala Asp Pro Glu Ile Lys Ala Thr Gly Gln
305                 310                 315                 320

Pro Pro Ser Lys Glu Gly Leu Glu Ala Glu Gly Gly Leu Arg Glu
                325                 330                 335

Thr Lys Glu Thr Ala Val Gln Cys Asp Val Gly Asp Leu Gln Pro Pro
            340                 345                 350

Pro Ala Lys Pro Ala Ser Pro Ala Gln Val Gln Ser Ser Gln Asp Gly
```

```
                355                 360                 365
Gly Cys Pro Lys Glu Gly Lys Pro Lys Lys Lys Thr Gly Ala Pro
            370                 375                 380
Pro Ala Pro Ser Cys Lys Asp Gly Ala Gln Gly Lys Asp Lys Thr Lys
385                 390                 395                 400
Asp Lys Gly Arg Gly Arg Pro Val Glu Lys Pro Arg Ala Asp Lys Lys
                405                 410                 415
Gly Pro Gln Ala Ser Ser Pro Arg Arg Lys Ala Glu Arg Pro Glu Gly
            420                 425                 430
Thr Lys Lys Lys Pro Ser Ser Ala Thr Pro Val Ala Thr Ser Gly Lys
            435                 440                 445
Gly Arg Pro Asp Arg Pro Ala Arg Arg Pro Ser Pro Thr Ser Gly Asp
        450                 455                 460
Ser Arg Pro Ala Ala Gly Arg Gly Pro Arg Pro Leu Gln Leu Pro
465                 470                 475                 480
Asp Arg Lys Ser Thr Lys Ala Pro Ser Gly Lys Leu Val Glu Arg Lys
                485                 490                 495
Ala Arg Ser Leu Asp Glu Gly Ala Ser Gln Asp Ala Pro Lys Leu Lys
            500                 505                 510
Lys Arg Ala Leu Ser His Ala Asp Leu Phe Gly Asp Glu Ser Glu Asp
            515                 520                 525
Glu Ala Ala Gly Pro Gly Val Pro Ser Val Trp Pro Ser Ala Leu Pro
        530                 535                 540
Ser Leu Ser Ser Asp Ser Asp Ser Asp Ser Ser Leu Gly Phe
545                 550                 555                 560
Pro Glu Ala Gln Gly Pro Pro Lys Arg Leu Lys Ala Ser Pro Pro Pro
                565                 570                 575
Ser Pro Ala Pro Ser Ser Ser Ser Ser Ser Ser Thr Ser Ser
            580                 585                 590
Ala Gly Ala Asp Val Asp Tyr Ser Ala Leu Glu Lys Glu Val Asp Phe
            595                 600                 605
Asp Ser Asp Pro Met Glu Glu Cys Leu Arg Ile Phe Asn Glu Ser Thr
        610                 615                 620
Ser Val Lys Thr Glu Asp Arg Gly Arg Leu Ala Arg Gln Pro Pro Lys
625                 630                 635                 640
Glu Glu Lys Ser Glu Glu Lys Gly Leu Ser Gly Leu Thr Thr Leu Phe
                645                 650                 655
Pro Gly Gln Lys Arg Arg Ile Ser His Leu Ser Lys Gln Gly Gln Glu
            660                 665                 670
Val Glu Pro Pro Arg Arg Gly Pro Ala Val Pro Pro Ala Arg Pro Pro
        675                 680                 685
Thr Ala Gln Glu Val Cys Tyr Leu Arg Ala Gln Ala Gln Arg Ala
        690                 695                 700
Ser Ala Ser Leu Leu Gln Ala Pro Ala Arg Leu Ala Glu Lys Ser Pro
705                 710                 715                 720
Ser Val His Ile Ser Ala Pro Gly Glu Lys Arg Arg Ile Ala His Ile
                725                 730                 735
Pro Asn Pro Arg Leu Ala Ala Ala Pro Thr Gly Ala Lys Arg Thr Leu
            740                 745                 750
Ala Ala Ser Gly Ser Gln Ser Ser Asn Gly Pro Glu Pro Gly Gly Gln
            755                 760                 765
Gln Leu Lys Thr Arg Thr Leu Ser Gly Met Ala Ser Lys Thr Thr Thr
            770                 775                 780
```

```
Thr Ile Ile Pro Lys Arg Ile Ala His Ser Pro Ser Leu Gln Ser Leu
785                 790                 795                 800

Lys Lys Pro Ile Ile Pro Lys Glu Phe Gly Gly Lys Val Pro Thr Val
            805                 810                 815

Ile Arg Gln Arg Tyr Leu Asn Leu Phe Ile Glu Glu Cys Leu Lys Phe
        820                 825                 830

Cys Thr Ser Asn Gln Glu Ala Ile Glu Lys Ala Leu Asn Glu Glu Lys
    835                 840                 845

Val Ala Tyr Asp Arg Ser Pro Ser Lys Asn Ile Tyr Leu Asn Val Ala
850                 855                 860

Val Asn Thr Leu Lys Lys Leu Arg Gly Leu Ala Pro Ser Ala Val Pro
865                 870                 875                 880

Gly Leu Ser Lys Thr Ser Gly Arg Arg Val Val Ser His Glu Val Val
                885                 890                 895

Leu Gly Gly Arg Leu Ala Ala Lys Thr Ser Phe Ser Leu Ser Arg Pro
            900                 905                 910

Ser Ser Pro Arg Val Glu Asp Leu Lys Gly Ala Ala Leu Tyr Ser Arg
        915                 920                 925

Leu Arg Glu Tyr Leu Leu Thr Gln Asp Gln Leu Lys Glu Asn Gly Tyr
    930                 935                 940

Pro Phe Pro His Pro Glu Arg Pro Gly Gly Ala Ile Ile Phe Thr Ala
945                 950                 955                 960

Glu Glu Lys Arg Pro Lys Asp Ser Ser Cys Arg Thr Cys Cys Arg Cys
                965                 970                 975

Gly Thr Glu Tyr Leu Val Ser Ser Ser Gly Arg Cys Ile Arg Asp Glu
            980                 985                 990

Glu Cys Tyr Tyr His Trp Gly Arg Leu Arg Arg Asn Arg Val Ala Gly
        995                 1000                1005

Gly Trp Glu Thr Gln Tyr Met Cys Cys Ser Ala Ala Ala Gly Ser
    1010                1015                1020

Val Gly Cys Gln Val Ala Lys Gln His Val Gln Asp Gly Arg Lys
    1025                1030                1035

Glu Arg Leu Glu Gly Phe Val Lys Thr Phe Glu Lys Glu Leu Ser
    1040                1045                1050

Gly Asp Thr His Pro Gly Ile Tyr Ala Leu Asp Cys Glu Met Ser
    1055                1060                1065

Tyr Thr Thr Tyr Gly Leu Glu Leu Thr Arg Val Thr Val Val Asp
    1070                1075                1080

Thr Asp Val His Val Val Tyr Asp Thr Phe Val Lys Pro Asp Asn
    1085                1090                1095

Glu Ile Val Asp Tyr Asn Thr Arg Phe Ser Gly Val Thr Glu Ala
    1100                1105                1110

Asp Leu Ala Asp Thr Ser Val Thr Leu Arg Asp Val Gln Ala Val
    1115                1120                1125

Leu Leu Ser Met Phe Ser Ala Asp Thr Ile Leu Ile Gly His Ser
    1130                1135                1140

Leu Glu Ser Asp Leu Leu Ala Leu Lys Val Ile His Ser Thr Val
    1145                1150                1155

Val Asp Thr Ser Val Leu Phe Pro His Arg Leu Gly Leu Pro Tyr
    1160                1165                1170

Lys Arg Ser Leu Arg Asn Leu Met Ala Asp Tyr Leu Arg Gln Ile
    1175                1180                1185
```

-continued

```
Ile Gln Asp Asn Val Asp Gly His Ser Ser Glu Asp Ala Gly
    1190                1195                1200

Ala Cys Met His Leu Val Ile Trp Lys Val Arg Glu Asp Ala Lys
    1205                1210                1215

Thr Lys Arg
    1220

<210> SEQ ID NO 224
<211> LENGTH: 493
<212> TYPE: PRT
<213> ORGANISM: Mus musculus

<400> SEQUENCE: 224

Met Gly Thr Thr Lys Val Thr Pro Ser Leu Val Phe Ala Val Thr Val
1               5                   10                  15

Ala Thr Ile Gly Ser Phe Gln Phe Gly Tyr Asn Thr Gly Val Ile Asn
            20                  25                  30

Ala Pro Glu Thr Ile Leu Lys Asp Phe Leu Asn Tyr Thr Leu Glu Glu
        35                  40                  45

Arg Leu Glu Asp Leu Pro Ser Glu Gly Leu Leu Thr Ala Leu Trp Ser
    50                  55                  60

Leu Cys Val Ala Ile Phe Ser Val Gly Gly Met Ile Gly Ser Phe Ser
65                  70                  75                  80

Val Gly Leu Phe Val Asn Arg Phe Gly Arg Arg Asn Ser Met Leu Leu
                85                  90                  95

Val Asn Leu Leu Ala Ile Ile Ala Gly Cys Leu Met Gly Phe Ala Lys
            100                 105                 110

Ile Ala Glu Ser Val Glu Met Leu Ile Leu Gly Arg Leu Leu Ile Gly
        115                 120                 125

Ile Phe Cys Gly Leu Cys Thr Gly Phe Val Pro Met Tyr Ile Gly Glu
    130                 135                 140

Val Ser Pro Thr Ala Leu Arg Gly Ala Phe Gly Thr Leu Asn Gln Leu
145                 150                 155                 160

Gly Ile Val Val Gly Ile Leu Val Ala Gln Ile Phe Gly Leu Asp Phe
                165                 170                 175

Ile Leu Gly Ser Glu Glu Leu Trp Pro Gly Leu Leu Gly Leu Thr Ile
            180                 185                 190

Ile Pro Ala Ile Leu Gln Ser Ala Ala Leu Pro Phe Cys Pro Glu Ser
        195                 200                 205

Pro Arg Phe Leu Leu Ile Asn Lys Lys Glu Glu Asp Gln Ala Thr Glu
    210                 215                 220

Ile Leu Gln Arg Leu Trp Gly Thr Ser Asp Val Val Gln Glu Ile Gln
225                 230                 235                 240

Glu Met Lys Asp Glu Ser Val Arg Met Ser Gln Glu Lys Gln Val Thr
                245                 250                 255

Val Leu Glu Leu Phe Arg Ser Pro Asn Tyr Val Gln Pro Leu Leu Ile
            260                 265                 270

Ser Ile Val Leu Gln Leu Ser Gln Gln Leu Ser Gly Ile Asn Ala Val
        275                 280                 285

Phe Tyr Tyr Ser Thr Gly Ile Phe Lys Asp Ala Gly Val Gln Glu Pro
    290                 295                 300

Ile Tyr Ala Thr Ile Gly Ala Gly Val Val Asn Thr Ile Phe Thr Val
305                 310                 315                 320

Val Ser Leu Phe Leu Val Glu Arg Ala Gly Arg Arg Thr Leu His Met
                325                 330                 335
```

```
Ile Gly Leu Gly Gly Met Ala Val Cys Ser Val Phe Met Thr Ile Ser
                340                 345                 350

Leu Leu Leu Lys Asp Asp Tyr Glu Ala Met Ser Phe Cys Ile Val
            355                 360                 365

Ala Ile Leu Ile Tyr Val Ala Phe Phe Glu Ile Gly Pro Gly Pro Ile
        370                 375                 380

Pro Trp Phe Ile Val Ala Glu Leu Phe Ser Gln Gly Pro Arg Pro Ala
385                 390                 395                 400

Ala Ile Ala Val Ala Gly Cys Cys Asn Trp Thr Ser Asn Phe Leu Val
                405                 410                 415

Gly Met Leu Phe Pro Ser Ala Ala Tyr Leu Gly Ala Tyr Val Phe
            420                 425                 430

Ile Ile Phe Ala Ala Phe Leu Ile Phe Phe Leu Ile Phe Thr Phe Phe
                435                 440                 445

Lys Val Pro Glu Thr Lys Gly Arg Thr Phe Glu Asp Ile Ala Arg Ala
            450                 455                 460

Phe Glu Gly Gln Ala His Ser Gly Lys Gly Pro Ala Gly Val Glu Leu
465                 470                 475                 480

Asn Ser Met Gln Pro Val Lys Glu Thr Pro Gly Asn Ala
                485                 490

<210> SEQ ID NO 225
<211> LENGTH: 1227
<212> TYPE: PRT
<213> ORGANISM: Homo sapiens

<400> SEQUENCE: 225

Met Asn Asp Thr Val Asn Lys Thr Asp Gln Val Asp Cys Ser Asp Leu
1               5                   10                  15

Ser Glu His Asn Gly Leu Asp Arg Glu Glu Ser Met Glu Val Glu Ala
                20                  25                  30

Pro Val Ala Asn Lys Ser Gly Ser Gly Thr Ser Ser Gly Ser His Ser
            35                  40                  45

Ser Thr Ala Pro Ser Ser Ser Ser Ser Ser Ser Ser Ser Gly Gly
        50                  55                  60

Gly Gly Ser Ser Ser Thr Gly Thr Ser Ala Ile Thr Thr Ser Leu Pro
65                  70                  75                  80

Gln Leu Gly Asp Leu Thr Thr Leu Gly Asn Phe Ser Val Ile Asn Ser
                85                  90                  95

Asn Val Ile Ile Glu Asn Leu Gln Ser Thr Lys Val Ala Val Ala Gln
                100                 105                 110

Phe Ser Gln Glu Ala Arg Cys Gly Gly Ala Ser Gly Gly Lys Leu Ala
            115                 120                 125

Val Pro Ala Leu Met Glu Gln Leu Leu Ala Leu Gln Gln Gln Gln Ile
        130                 135                 140

His Gln Leu Gln Leu Ile Glu Gln Ile Arg His Gln Ile Leu Leu Leu
145                 150                 155                 160

Ala Ser Gln Asn Ala Asp Leu Pro Thr Ser Ser Ser Pro Ser Gln Gly
                165                 170                 175

Thr Leu Arg Thr Ser Ala Asn Pro Leu Ser Thr Leu Ser His Leu
                180                 185                 190

Ser Gln Gln Leu Ala Ala Ala Gly Leu Ala Gln Ser Leu Ala Ser
        195                 200                 205

Gln Ser Ala Ser Ile Ser Gly Val Lys Gln Leu Pro Pro Ile Gln Leu
```

-continued

```
                210                 215                 220
Pro Gln Ser Ser Ser Gly Asn Thr Ile Ile Pro Ser Asn Ser Gly Ser
225                 230                 235                 240

Ser Pro Asn Met Asn Ile Leu Ala Ala Ala Val Thr Thr Pro Ser Ser
                245                 250                 255

Glu Lys Val Ala Ser Ser Ala Gly Ala Ser His Val Ser Asn Pro Ala
            260                 265                 270

Val Ser Ser Ser Ser Pro Ala Phe Ala Ile Ser Ser Leu Leu Ser
        275                 280                 285

Pro Ala Ser Asn Pro Leu Leu Pro Gln Gln Ala Ser Ala Asn Ser Val
        290                 295                 300

Phe Pro Ser Pro Leu Pro Asn Ile Gly Thr Thr Ala Glu Asp Leu Asn
305                 310                 315                 320

Ser Leu Ser Ala Leu Ala Gln Gln Arg Lys Ser Lys Pro Pro Asn Val
                325                 330                 335

Thr Ala Phe Glu Ala Lys Ser Thr Ser Asp Glu Ala Phe Phe Lys His
            340                 345                 350

Lys Cys Arg Phe Cys Ala Lys Val Phe Gly Ser Asp Ser Ala Leu Gln
        355                 360                 365

Ile His Leu Arg Ser His Thr Gly Glu Arg Pro Phe Lys Cys Asn Ile
        370                 375                 380

Cys Gly Asn Arg Phe Ser Thr Lys Gly Asn Leu Lys Val His Phe Gln
385                 390                 395                 400

Arg His Lys Glu Lys Tyr Pro His Ile Gln Met Asn Pro Tyr Pro Val
                405                 410                 415

Pro Glu His Leu Asp Asn Ile Pro Thr Ser Thr Gly Ile Pro Tyr Gly
            420                 425                 430

Met Ser Ile Pro Pro Glu Lys Pro Val Thr Ser Trp Leu Asp Thr Lys
        435                 440                 445

Pro Val Leu Pro Thr Leu Thr Thr Ser Val Gly Leu Pro Leu Pro Pro
        450                 455                 460

Thr Leu Pro Ser Leu Ile Pro Phe Ile Lys Thr Glu Glu Pro Ala Pro
465                 470                 475                 480

Ile Pro Ile Ser His Ser Ala Thr Ser Pro Pro Gly Ser Val Lys Ser
                485                 490                 495

Asp Ser Gly Gly Pro Glu Ser Ala Thr Arg Asn Leu Gly Gly Leu Pro
            500                 505                 510

Glu Glu Ala Glu Gly Ser Thr Leu Pro Pro Ser Gly Gly Lys Ser Glu
        515                 520                 525

Glu Ser Gly Met Val Thr Asn Ser Val Pro Thr Ala Ser Ser Ser Val
        530                 535                 540

Leu Ser Ser Pro Ala Ala Asp Cys Gly Pro Ala Gly Ser Ala Thr Thr
545                 550                 555                 560

Phe Thr Asn Pro Leu Leu Pro Leu Met Ser Glu Gln Phe Lys Ala Lys
                565                 570                 575

Phe Pro Phe Gly Gly Leu Leu Asp Ser Ala Gln Ala Ser Glu Thr Ser
            580                 585                 590

Lys Leu Gln Gln Leu Val Glu Asn Ile Asp Lys Lys Ala Thr Asp Pro
        595                 600                 605

Asn Glu Cys Ile Ile Cys His Arg Val Leu Ser Cys Gln Ser Ala Leu
        610                 615                 620

Lys Met His Tyr Arg Thr His Thr Gly Glu Arg Pro Phe Lys Cys Lys
625                 630                 635                 640
```

```
Ile Cys Gly Arg Ala Phe Thr Thr Lys Gly Asn Leu Lys Thr His Tyr
            645                 650                 655

Ser Val His Arg Ala Met Pro Pro Leu Arg Val Gln His Ser Cys Pro
        660                 665                 670

Ile Cys Gln Lys Lys Phe Thr Asn Ala Val Val Leu Gln Gln His Ile
            675                 680                 685

Arg Met His Met Gly Gly Gln Ile Pro Asn Thr Pro Val Pro Asp Ser
        690                 695                 700

Tyr Ser Glu Ser Met Glu Ser Asp Thr Gly Ser Phe Asp Glu Lys Asn
705                 710                 715                 720

Phe Asp Asp Leu Asp Asn Phe Ser Asp Glu Asn Met Glu Asp Cys Pro
            725                 730                 735

Glu Gly Ser Ile Pro Asp Thr Pro Lys Ser Ala Asp Ala Ser Gln Asp
        740                 745                 750

Ser Leu Ser Ser Ser Pro Leu Pro Leu Glu Met Ser Ser Ile Ala Ala
        755                 760                 765

Leu Glu Asn Gln Met Lys Met Ile Asn Ala Gly Leu Ala Glu Gln Leu
    770                 775                 780

Gln Ala Ser Leu Lys Ser Val Glu Asn Gly Ser Ile Glu Gly Asp Val
785                 790                 795                 800

Leu Thr Asn Asp Ser Ser Ser Val Gly Gly Asp Met Glu Ser Gln Ser
            805                 810                 815

Ala Gly Ser Pro Ala Ile Ser Glu Ser Thr Ser Ser Met Gln Ala Leu
        820                 825                 830

Ser Pro Ser Asn Ser Thr Gln Glu Phe His Lys Ser Pro Ser Ile Glu
        835                 840                 845

Glu Lys Pro Gln Arg Ala Val Pro Ser Glu Phe Ala Asn Gly Leu Ser
    850                 855                 860

Pro Thr Pro Val Asn Gly Gly Ala Leu Asp Leu Thr Ser Ser His Ala
865                 870                 875                 880

Glu Lys Ile Ile Lys Glu Asp Ser Leu Gly Ile Leu Phe Pro Phe Arg
            885                 890                 895

Asp Arg Gly Lys Phe Lys Asn Thr Ala Cys Asp Ile Cys Gly Lys Thr
        900                 905                 910

Phe Ala Cys Gln Ser Ala Leu Asp Ile His Tyr Arg Ser His Thr Lys
        915                 920                 925

Glu Arg Pro Phe Ile Cys Thr Val Cys Asn Arg Gly Phe Ser Thr Lys
    930                 935                 940

Gly Asn Leu Lys Gln His Met Leu Thr His Gln Met Arg Asp Leu Pro
945                 950                 955                 960

Ser Gln Leu Phe Glu Pro Ser Ser Asn Leu Gly Pro Asn Gln Asn Ser
            965                 970                 975

Ala Val Ile Pro Ala Asn Ser Leu Ser Ser Leu Ile Lys Thr Glu Val
        980                 985                 990

Asn Gly Phe Val His Val Ser Pro Gln Asp Ser Lys Asp Thr Pro Thr
        995                 1000                1005

Ser His Val Pro Ser Gly Pro Leu Ser Ser Ser Ala Thr Ser Pro
    1010                1015                1020

Val Leu Leu Pro Ala Leu Pro Arg Arg Thr Pro Lys Gln His Tyr
    1025                1030                1035

Cys Asn Thr Cys Gly Lys Thr Phe Ser Ser Ser Ser Ala Leu Gln
    1040                1045                1050
```

```
Ile His Glu Arg Thr His Thr Gly Glu Lys Pro Phe Ala Cys Thr
    1055                1060                1065
Ile Cys Gly Arg Ala Phe Thr Thr Lys Gly Asn Leu Lys Val His
    1070                1075                1080
Met Gly Thr His Met Trp Asn Ser Thr Pro Ala Arg Arg Gly Arg
    1085                1090                1095
Arg Leu Ser Val Asp Gly Pro Met Thr Phe Leu Gly Gly Asn Pro
    1100                1105                1110
Val Lys Phe Pro Glu Met Phe Gln Lys Asp Leu Ala Ala Arg Ser
    1115                1120                1125
Gly Ser Gly Asp Pro Ser Ser Phe Trp Asn Gln Tyr Ala Ala Ala
    1130                1135                1140
Leu Ser Asn Gly Leu Ala Met Lys Ala Asn Glu Ile Ser Val Ile
    1145                1150                1155
Gln Asn Gly Gly Ile Pro Pro Ile Pro Gly Ser Leu Gly Ser Gly
    1160                1165                1170
Asn Ser Ser Pro Val Ser Gly Leu Thr Gly Asn Leu Glu Arg Leu
    1175                1180                1185
Gln Asn Ser Glu Pro Asn Ala Pro Leu Ala Gly Leu Glu Lys Met
    1190                1195                1200
Ala Ser Ser Glu Asn Gly Thr Asn Phe Arg Phe Thr Arg Phe Val
    1205                1210                1215
Glu Asp Ser Lys Glu Ile Val Thr Ser
    1220                1225
```

<210> SEQ ID NO 226
<211> LENGTH: 291
<212> TYPE: PRT
<213> ORGANISM: Homo sapiens

<400> SEQUENCE: 226

```
Met Ser Met Leu Pro Thr Phe Gly Phe Thr Gln Glu Gln Val Ala Cys
1               5                   10                  15
Val Cys Glu Val Leu Gln Gln Gly Gly Asn Ile Glu Arg Leu Gly Arg
                20                  25                  30
Phe Leu Trp Ser Leu Pro Ala Cys Glu His Leu His Lys Asn Glu Ser
            35                  40                  45
Val Leu Lys Ala Lys Ala Val Val Ala Phe His Arg Gly Asn Phe Arg
        50                  55                  60
Glu Leu Tyr Lys Ile Leu Glu Ser His Gln Phe Ser Pro His Asn His
65                  70                  75                  80
Ala Lys Leu Gln Gln Leu Trp Leu Lys Ala His Tyr Ile Glu Ala Glu
                85                  90                  95
Lys Leu Arg Gly Arg Pro Leu Gly Ala Val Gly Lys Tyr Arg Val Arg
                100                 105                 110
Arg Lys Phe Pro Leu Pro Arg Ser Ile Trp Asp Gly Glu Glu Thr Ser
            115                 120                 125
Tyr Cys Phe Lys Glu Lys Ser Arg Ser Val Leu Arg Glu Trp Tyr Ala
        130                 135                 140
His Asn Pro Tyr Pro Ser Pro Arg Glu Lys Arg Glu Leu Ala Glu Ala
145                 150                 155                 160
Thr Gly Leu Thr Thr Thr Gln Val Ser Asn Trp Phe Lys Asn Arg Arg
                165                 170                 175
Gln Arg Asp Arg Ala Ala Glu Ala Lys Glu Arg Glu Asn Asn Glu Asn
                180                 185                 190
```

```
Ser Asn Ser Asn Ser His Asn Pro Leu Asn Gly Ser Gly Lys Ser Val
            195                 200                 205

Leu Gly Ser Ser Glu Asp Glu Lys Thr Pro Ser Gly Thr Pro Asp His
        210                 215                 220

Ser Ser Ser Ser Pro Ala Leu Leu Ser Pro Pro Pro Gly Leu
225                 230                 235                 240

Pro Ser Leu His Ser Leu Gly His Pro Pro Gly Pro Ser Ala Val Pro
                245                 250                 255

Val Pro Val Pro Gly Gly Gly Ala Asp Pro Leu Gln His His His
            260                 265                 270

Gly Leu Gln Asp Ser Ile Leu Asn Pro Met Ser Ala Asn Leu Val Asp
            275                 280                 285

Leu Gly Ser
    290

<210> SEQ ID NO 227
<211> LENGTH: 391
<212> TYPE: PRT
<213> ORGANISM: Mus musculus

<400> SEQUENCE: 227

Met Tyr Ser Met Met Met Glu Thr Asp Leu His Ser Pro Gly Gly Ala
1               5                   10                  15

Gln Ala Pro Thr Asn Leu Ser Gly Pro Ala Gly Ala Gly Gly Gly Gly
            20                  25                  30

Gly Gly Gly Gly Gly Gly Gly Gly Gly Gly Thr Lys Ala Asn Gln
        35                  40                  45

Asp Arg Val Lys Arg Pro Met Asn Ala Phe Met Val Trp Ser Arg Gly
50                  55                  60

Gln Arg Arg Lys Met Ala Gln Glu Asn Pro Lys Met His Asn Ser Glu
65                  70                  75                  80

Ile Ser Lys Arg Leu Gly Ala Glu Trp Lys Val Met Ser Glu Ala Glu
                85                  90                  95

Lys Arg Pro Phe Ile Asp Glu Ala Lys Arg Leu Arg Ala Leu His Met
            100                 105                 110

Lys Glu His Pro Asp Tyr Lys Tyr Arg Pro Arg Arg Lys Thr Lys Thr
        115                 120                 125

Leu Leu Lys Lys Asp Lys Tyr Ser Leu Ala Gly Gly Leu Leu Ala Ala
    130                 135                 140

Gly Ala Gly Gly Gly Ala Ala Val Ala Met Gly Val Gly Val Gly
145                 150                 155                 160

Val Gly Ala Ala Ala Val Gly Gln Arg Leu Glu Ser Pro Gly Gly Ala
                165                 170                 175

Ala Gly Gly Gly Tyr Ala His Val Asn Gly Trp Ala Asn Gly Ala Tyr
            180                 185                 190

Pro Gly Ser Val Ala Ala Ala Ala Ala Ala Met Met Gln Glu
        195                 200                 205

Ala Gln Leu Ala Tyr Gly Gln His Pro Gly Ala Gly Gly Ala His Pro
    210                 215                 220

His Ala His Pro Ala His Pro His Pro His Pro His Ala His Pro
225                 230                 235                 240

His Asn Pro Gln Pro Met His Arg Tyr Asp Met Gly Ala Leu Gln Tyr
                245                 250                 255

Ser Pro Ile Ser Asn Ser Gln Gly Tyr Met Ser Ala Ser Pro Ser Gly
```

```
                    260                 265                 270
Tyr Gly Gly Ile Pro Tyr Gly Ala Ala Ala Ala Ala Ala Ala
                275                 280                 285
Gly Gly Ala His Gln Asn Ser Ala Val Ala Ala Ala Ala Ala
                290                 295                 300
Ala Ala Ser Ser Gly Ala Leu Gly Ala Leu Gly Ser Leu Val Lys Ser
305                 310                 315                 320
Glu Pro Ser Gly Ser Pro Ala Pro Ala His Ser Arg Ala Pro Cys
                325                 330                 335
Pro Gly Asp Leu Arg Glu Met Ile Ser Met Tyr Leu Pro Ala Gly Glu
                340                 345                 350
Gly Gly Asp Pro Ala Ala Ala Ala Ala Ala Gln Ser Arg Leu
                355                 360                 365
His Ser Leu Pro Gln His Tyr Gln Gly Ala Gly Ala Gly Val Asn Gly
                370                 375                 380
Thr Val Pro Leu Thr His Ile
385                 390

<210> SEQ ID NO 228
<211> LENGTH: 317
<212> TYPE: PRT
<213> ORGANISM: Homo sapiens

<400> SEQUENCE: 228

Met Tyr Asn Met Met Glu Thr Glu Leu Lys Pro Pro Gly Pro Gln Gln
1                   5                  10                  15
Thr Ser Gly Gly Gly Gly Asn Ser Thr Ala Ala Ala Ala Gly Gly
                20                  25                  30
Asn Gln Lys Asn Ser Pro Asp Arg Val Lys Arg Pro Met Asn Ala Phe
                35                  40                  45
Met Val Trp Ser Arg Gly Gln Arg Arg Lys Met Ala Gln Glu Asn Pro
    50                  55                  60
Lys Met His Asn Ser Glu Ile Ser Lys Arg Leu Gly Ala Glu Trp Lys
65                  70                  75                  80
Leu Leu Ser Glu Thr Glu Lys Arg Pro Phe Ile Asp Glu Ala Lys Arg
                85                  90                  95
Leu Arg Ala Leu His Met Lys Glu His Pro Asp Tyr Lys Tyr Arg Pro
                100                 105                 110
Arg Arg Lys Thr Lys Thr Leu Met Lys Lys Asp Lys Tyr Thr Leu Pro
                115                 120                 125
Gly Gly Leu Leu Ala Pro Gly Gly Asn Ser Met Ala Ser Gly Val Gly
                130                 135                 140
Val Gly Ala Gly Leu Gly Ala Gly Val Asn Gln Arg Met Asp Ser Tyr
145                 150                 155                 160
Ala His Met Asn Gly Trp Ser Asn Gly Ser Tyr Ser Met Met Gln Asp
                165                 170                 175
Gln Leu Gly Tyr Pro Gln His Pro Gly Leu Asn Ala His Gly Ala Ala
                180                 185                 190
Gln Met Gln Pro Met His Arg Tyr Asp Val Ser Ala Leu Gln Tyr Asn
                195                 200                 205
Ser Met Thr Ser Ser Gln Thr Tyr Met Asn Gly Ser Pro Thr Tyr Ser
                210                 215                 220
Met Ser Tyr Ser Gln Gln Gly Thr Pro Gly Met Ala Leu Gly Ser Met
225                 230                 235                 240
```

```
Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 229
<211> LENGTH: 172
<212> TYPE: PRT
<213> ORGANISM: Homo sapiens

<400> SEQUENCE: 229

Met Ala Ile Ser Lys Val Phe Glu Leu Gly Leu Val Ala Gly Leu Gly
1               5                   10                  15

His Gln Glu Phe Ala Arg Pro Ser Arg Gly Tyr Leu Ala Phe Arg Asp
            20                  25                  30

Asp Ser Ile Trp Pro Gln Glu Pro Ala Ile Arg Pro Arg Ser Ser
        35                  40                  45

Gln Arg Val Pro Pro Met Gly Ile Gln His Ser Lys Glu Leu Asn Arg
    50                  55                  60

Thr Cys Cys Leu Asn Gly Gly Thr Cys Met Leu Gly Ser Phe Cys Ala
65                  70                  75                  80

Cys Pro Pro Ser Phe Tyr Gly Arg Asn Cys Glu His Asp Val Arg Lys
                85                  90                  95

Glu Asn Cys Gly Ser Val Pro His Asp Thr Trp Leu Pro Lys Lys Cys
            100                 105                 110

Ser Leu Cys Lys Cys Trp His Gly Gln Leu Arg Cys Phe Pro Gln Ala
        115                 120                 125

Phe Leu Pro Gly Cys Asp Gly Leu Val Met Asp Glu His Leu Val Ala
    130                 135                 140

Ser Arg Thr Pro Glu Leu Pro Pro Ser Ala Arg Thr Thr Thr Phe Met
145                 150                 155                 160

Leu Val Gly Ile Cys Leu Ser Ile Gln Ser Tyr Tyr
                165                 170

<210> SEQ ID NO 230
<211> LENGTH: 497
<212> TYPE: PRT
<213> ORGANISM: Homo sapiens

<400> SEQUENCE: 230

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80
```

-continued

```
Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Ala Pro
            115                 120                 125

Pro Pro Pro Pro Pro Pro Pro His Ser Phe Ile Lys Gln Glu Pro
130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
            195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
            275                 280                 285

Tyr Ser Ser Asp Asn Leu Tyr Gln Met Thr Ser Gln Leu Glu Cys Met
290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
            325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
            355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
            405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
            435                 440                 445

Leu Lys Thr His Thr Arg Thr His Thr Gly Glu Lys Pro Phe Ser Cys
    450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu
```

```
<210> SEQ ID NO 231
<211> LENGTH: 911
<212> TYPE: PRT
<213> ORGANISM: Homo sapiens

<400> SEQUENCE: 231

Met Val Asp Tyr His Ala Ala Asn Gln Ser Tyr Gln Tyr Gly Pro Ser
1               5                   10                  15

Ser Ala Gly Asn Gly Ala Gly Gly Gly Ser Met Gly Asp Tyr Met
            20                  25                  30

Ala Gln Glu Asp Asp Trp Asp Arg Asp Leu Leu Leu Asp Pro Ala Trp
        35                  40                  45

Glu Lys Gln Gln Arg Lys Thr Phe Thr Ala Trp Cys Asn Ser His Leu
50                  55                  60

Arg Lys Ala Gly Thr Gln Ile Glu Asn Ile Asp Glu Asp Phe Arg Asp
65                  70                  75                  80

Gly Leu Lys Leu Met Leu Leu Leu Glu Val Ile Ser Gly Glu Arg Leu
                85                  90                  95

Pro Lys Pro Glu Arg Gly Lys Met Arg Val His Lys Ile Asn Asn Val
            100                 105                 110

Asn Lys Ala Leu Asp Phe Ile Ala Ser Lys Gly Val Lys Leu Val Ser
        115                 120                 125

Ile Gly Ala Glu Glu Ile Val Asp Gly Asn Ala Lys Met Thr Leu Gly
130                 135                 140

Met Ile Trp Thr Ile Ile Leu Arg Phe Ala Ile Gln Asp Ile Ser Val
145                 150                 155                 160

Glu Glu Thr Ser Ala Lys Glu Gly Leu Leu Leu Trp Cys Gln Arg Lys
                165                 170                 175

Thr Ala Pro Tyr Lys Asn Val Asn Val Gln Asn Phe His Ile Ser Trp
            180                 185                 190

Lys Asp Gly Leu Ala Phe Asn Ala Leu Ile His Arg His Arg Pro Glu
        195                 200                 205

Leu Ile Glu Tyr Asp Lys Leu Arg Lys Asp Asp Pro Val Thr Asn Leu
210                 215                 220

Asn Asn Ala Phe Glu Val Ala Glu Lys Tyr Leu Asp Ile Pro Lys Met
225                 230                 235                 240

Leu Asp Ala Glu Asp Ile Val Asn Thr Ala Arg Pro Asp Glu Lys Ala
                245                 250                 255

Ile Met Thr Tyr Val Ser Ser Phe Tyr His Ala Phe Ser Gly Ala Gln
            260                 265                 270

Lys Ala Glu Thr Ala Ala Asn Arg Ile Cys Lys Val Leu Ala Val Asn
        275                 280                 285

Gln Glu Asn Glu His Leu Met Glu Asp Tyr Glu Lys Leu Ala Ser Asp
290                 295                 300

Leu Leu Glu Trp Ile Arg Arg Thr Ile Pro Trp Leu Glu Asp Arg Val
305                 310                 315                 320

Pro Gln Lys Thr Ile Gln Glu Met Gln Gln Lys Leu Glu Asp Phe Arg
                325                 330                 335

Asp Tyr Arg Arg Val His Lys Pro Pro Lys Val Gln Glu Lys Cys Gln
            340                 345                 350

Leu Glu Ile Asn Phe Asn Thr Leu Gln Thr Lys Leu Arg Leu Ser Asn
        355                 360                 365

Arg Pro Ala Phe Met Pro Ser Glu Gly Lys Met Val Ser Asp Ile Asn
```

```
              370                 375                 380
Asn Gly Trp Gln His Leu Glu Gln Ala Glu Lys Gly Tyr Glu Glu Trp
385                 390                 395                 400

Leu Leu Asn Glu Ile Arg Arg Leu Glu Arg Leu Asp His Leu Ala Glu
                405                 410                 415

Lys Phe Arg Gln Lys Ala Ser Ile His Glu Ala Trp Thr Asp Gly Lys
                420                 425                 430

Glu Ala Met Leu Lys His Arg Asp Tyr Glu Thr Ala Thr Leu Ser Asp
                435                 440                 445

Ile Lys Ala Leu Ile Arg Lys His Glu Ala Phe Glu Ser Asp Leu Ala
                450                 455                 460

Ala His Gln Asp Arg Val Glu Gln Ile Ala Ala Ile Ala Gln Glu Leu
465                 470                 475                 480

Asn Glu Leu Asp Tyr Tyr Asp Ser His Asn Val Asn Thr Arg Cys Gln
                485                 490                 495

Lys Ile Cys Asp Gln Trp Asp Ala Leu Gly Ser Leu Thr His Ser Arg
                500                 505                 510

Arg Glu Ala Leu Glu Lys Thr Glu Lys Gln Leu Glu Ala Ile Asp Gln
                515                 520                 525

Leu His Leu Glu Tyr Ala Lys Arg Ala Ala Pro Phe Asn Asn Trp Met
                530                 535                 540

Glu Ser Ala Met Glu Asp Leu Gln Asp Met Phe Ile Val His Thr Ile
545                 550                 555                 560

Glu Glu Ile Glu Gly Leu Ile Ser Ala His Asp Gln Phe Lys Ser Thr
                565                 570                 575

Leu Pro Asp Ala Asp Arg Glu Arg Glu Ala Ile Leu Ala Ile His Lys
                580                 585                 590

Glu Ala Gln Arg Ile Ala Glu Ser Asn His Ile Lys Leu Ser Gly Ser
                595                 600                 605

Asn Pro Tyr Thr Thr Val Thr Pro Gln Ile Ile Asn Ser Lys Trp Glu
                610                 615                 620

Lys Val Gln Gln Leu Val Pro Lys Arg Asp His Ala Leu Leu Glu Glu
625                 630                 635                 640

Gln Ser Lys Gln Gln Ser Asn Glu His Leu Arg Arg Gln Phe Ala Ser
                645                 650                 655

Gln Ala Asn Val Val Gly Pro Trp Ile Gln Thr Lys Met Glu Glu Ile
                660                 665                 670

Gly Arg Ile Ser Ile Glu Met Asn Gly Thr Leu Glu Asp Gln Leu Ser
                675                 680                 685

His Leu Lys Gln Tyr Glu Arg Ser Ile Val Asp Tyr Lys Pro Asn Leu
                690                 695                 700

Asp Leu Leu Glu Gln Gln His Gln Leu Ile Gln Glu Ala Leu Ile Phe
705                 710                 715                 720

Asp Asn Lys His Thr Asn Tyr Thr Met Glu His Ile Arg Val Gly Trp
                725                 730                 735

Glu Gln Leu Leu Thr Thr Ile Ala Arg Thr Ile Asn Glu Val Glu Asn
                740                 745                 750

Gln Ile Leu Thr Arg Asp Ala Lys Gly Ile Ser Gln Glu Gln Met Gln
                755                 760                 765

Glu Phe Arg Ala Ser Phe Asn His Phe Asp Lys Asp His Gly Gly Ala
                770                 775                 780

Leu Gly Pro Glu Glu Phe Lys Ala Cys Leu Ile Ser Leu Gly Tyr Asp
785                 790                 795                 800
```

Val Glu Asn Asp Arg Gln Gly Glu Ala Glu Phe Asn Arg Ile Met Ser
            805                 810                 815

Leu Val Asp Pro Asn His Ser Gly Leu Val Thr Phe Gln Ala Phe Ile
            820                 825                 830

Asp Phe Met Ser Arg Glu Thr Thr Asp Thr Asp Thr Ala Asp Gln Val
            835                 840                 845

Ile Ala Ser Phe Lys Val Leu Ala Gly Asp Lys Asn Phe Ile Thr Ala
            850                 855                 860

Glu Glu Leu Arg Arg Glu Leu Pro Pro Asp Gln Ala Glu Tyr Cys Ile
865                 870                 875                 880

Ala Arg Met Ala Pro Tyr Gln Gly Pro Asp Ala Val Pro Gly Ala Leu
                885                 890                 895

Asp Tyr Lys Ser Phe Ser Thr Ala Leu Tyr Gly Glu Ser Asp Leu
                900                 905                 910

<210> SEQ ID NO 232
<211> LENGTH: 609
<212> TYPE: PRT
<213> ORGANISM: Homo sapiens

<400> SEQUENCE: 232

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly

```
                260                 265                 270
Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
            370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
            530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
            595                 600                 605

Val

<210> SEQ ID NO 233
<211> LENGTH: 186
<212> TYPE: PRT
<213> ORGANISM: Homo sapiens

<400> SEQUENCE: 233

Met Pro Gly Ala Arg Pro Leu Pro Leu Val Leu Val Pro Gln Asn Thr
1               5                   10                  15

Leu Ala Trp Met Gln Leu Asp Ala Lys Ala Pro Ala His Pro Arg Pro
```

```
                20                  25                  30
Leu Gln Leu Leu Gly Arg Val Gly Pro Gly Ser Arg Gln Leu Ala Asp
            35                  40                  45
Gly Val Asn Ser Gly Gln Gly Leu Gly Ile Glu Ile Ile Gly Thr Leu
        50                  55                  60
Gln Leu Val Leu Cys Val Leu Ala Thr Thr Asp Arg Arg Arg Arg Asp
65                  70                  75                  80
Leu Gly Gly Ser Ala Pro Leu Ala Ile Gly Leu Ser Val Ala Leu Gly
                85                  90                  95
His Leu Leu Ala Ile Asp Tyr Thr Gly Cys Gly Ile Asn Pro Ala Arg
            100                 105                 110
Ser Phe Gly Ser Ala Val Ile Thr His Asn Phe Ser Asn His Trp Ile
        115                 120                 125
Phe Trp Val Gly Pro Phe Ile Gly Gly Ala Leu Ala Val Leu Ile Tyr
        130                 135                 140
Asp Phe Ile Leu Ala Pro Arg Ser Ser Asp Leu Thr Asp Arg Val Lys
145                 150                 155                 160
Val Trp Thr Ser Gly Gln Val Glu Glu Tyr Asp Leu Asp Ala Asp Asp
                165                 170                 175
Ile Asn Ser Arg Val Glu Met Lys Pro Lys
            180                 185

<210> SEQ ID NO 234
<211> LENGTH: 435
<212> TYPE: PRT
<213> ORGANISM: Homo sapiens

<400> SEQUENCE: 234

Met Ser Ser Pro Gly Thr Glu Ser Ala Gly Lys Ser Leu Gln Tyr Arg
1               5                   10                  15
Val Asp His Leu Leu Ser Ala Val Glu Asn Glu Leu Gln Ala Gly Ser
            20                  25                  30
Glu Lys Gly Asp Pro Thr Glu Arg Glu Leu Arg Val Gly Leu Glu Glu
        35                  40                  45
Ser Glu Leu Trp Leu Arg Phe Lys Glu Leu Thr Asn Glu Met Ile Val
    50                  55                  60
Thr Lys Asn Gly Arg Arg Met Phe Pro Val Leu Lys Val Asn Val Ser
65                  70                  75                  80
Gly Leu Asp Pro Asn Ala Met Tyr Ser Phe Leu Leu Asp Phe Val Ala
                85                  90                  95
Ala Asp Asn His Arg Trp Lys Tyr Val Asn Gly Glu Trp Val Pro Gly
            100                 105                 110
Gly Lys Pro Glu Pro Gln Ala Pro Ser Cys Val Tyr Ile His Pro Asp
        115                 120                 125
Ser Pro Asn Phe Gly Ala His Trp Met Lys Ala Pro Val Ser Phe Ser
    130                 135                 140
Lys Val Lys Leu Thr Asn Lys Leu Asn Gly Gly Gln Ile Met Leu
145                 150                 155                 160
Asn Ser Leu His Lys Tyr Glu Pro Arg Ile His Ile Val Arg Val Gly
                165                 170                 175
Gly Pro Gln Arg Met Ile Thr Ser His Cys Phe Pro Glu Thr Gln Phe
            180                 185                 190
Ile Ala Val Thr Ala Tyr Gln Asn Glu Glu Ile Thr Ala Leu Lys Ile
        195                 200                 205
```

```
Lys Tyr Asn Pro Phe Ala Lys Ala Phe Leu Asp Ala Lys Glu Arg Ser
    210                 215                 220

Asp His Lys Glu Met Met Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
                260                 265                 270

Thr His Ser Cys Asp Arg Tyr Pro Thr Leu Arg Ser His Arg Ser Ser
            275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Gln Tyr Pro Ser Leu Trp Ser
                340                 345                 350

Val Ser Asn Gly Ala Val Thr Pro Gly Ser Gln Ala Ala Val Ser
    355                 360                 365

Asn Gly Leu Gly Ala Gln Phe Phe Arg Gly Ser Pro Ala His Tyr Thr
370                 375                 380

Pro Leu Thr His Pro Val Ser Ala Pro Ser Ser Ser Gly Ser Pro Leu
385                 390                 395                 400

Tyr Glu Gly Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
                420                 425                 430

Pro Ser Met
    435

<210> SEQ ID NO 235
<211> LENGTH: 639
<212> TYPE: PRT
<213> ORGANISM: Homo sapiens

<400> SEQUENCE: 235

Met Val Asp Tyr Ile Val Glu Tyr Asp Tyr Asp Ala Val His Asp Asp
1               5                   10                  15

Glu Leu Thr Ile Arg Val Gly Glu Ile Ile Arg Asn Val Lys Lys Leu
                20                  25                  30

Gln Glu Glu Gly Trp Leu Glu Gly Glu Leu Asn Gly Arg Arg Gly Met
            35                  40                  45

Phe Pro Asp Asn Phe Val Lys Glu Ile Lys Arg Glu Thr Glu Phe Lys
        50                  55                  60

Asp Asp Ser Leu Pro Ile Lys Arg Glu Arg His Gly Asn Val Ala Ser
65                  70                  75                  80

Leu Val Gln Arg Ile Ser Thr Tyr Gly Leu Pro Ala Gly Gly Ile Gln
                85                  90                  95

Pro His Pro Gln Thr Lys Asn Ile Lys Lys Thr Lys Lys Arg Gln
            100                 105                 110

Cys Lys Val Leu Phe Glu Tyr Ile Pro Gln Asn Glu Asp Glu Leu Glu
        115                 120                 125

Leu Lys Val Gly Asp Ile Ile Asp Ile Asn Glu Glu Val Glu Glu Gly
    130                 135                 140
```

```
Trp Trp Ser Gly Thr Leu Asn Asn Lys Leu Gly Leu Phe Pro Ser Asn
145                 150                 155                 160

Phe Val Lys Glu Leu Glu Val Thr Asp Asp Gly Glu Thr His Glu Ala
            165                 170                 175

Gln Asp Asp Ser Glu Thr Val Leu Ala Gly Pro Thr Ser Pro Ile Pro
                180                 185                 190

Ser Leu Gly Asn Val Ser Glu Thr Ala Ser Gly Ser Val Thr Gln Pro
            195                 200                 205

Lys Lys Ile Arg Gly Ile Gly Phe Gly Asp Ile Phe Lys Glu Gly Ser
        210                 215                 220

Val Lys Leu Arg Thr Arg Thr Ser Ser Ser Glu Thr Glu Glu Lys Lys
225                 230                 235                 240

Pro Glu Lys Pro Leu Ile Leu Gln Ser Leu Gly Pro Lys Thr Gln Ser
                245                 250                 255

Val Glu Ile Thr Lys Thr Asp Thr Glu Gly Lys Ile Lys Ala Lys Glu
            260                 265                 270

Tyr Cys Arg Thr Leu Phe Ala Tyr Glu Gly Thr Asn Glu Asp Glu Leu
        275                 280                 285

Thr Phe Lys Glu Gly Glu Ile Ile His Leu Ile Ser Lys Glu Thr Gly
290                 295                 300

Glu Ala Gly Trp Trp Arg Gly Glu Leu Asn Gly Lys Glu Gly Val Phe
305                 310                 315                 320

Pro Asp Asn Phe Ala Val Gln Ile Asn Glu Leu Asp Lys Asp Phe Pro
                325                 330                 335

Lys Pro Lys Lys Pro Pro Pro Ala Lys Ala Pro Ala Pro Lys Pro Pro
            340                 345                 350

Glu Leu Ile Ala Ala Glu Lys Lys Tyr Phe Ser Leu Lys Pro Glu Glu
        355                 360                 365

Lys Asp Glu Lys Ser Thr Leu Glu Gln Lys Pro Ser Lys Pro Ala Ala
        370                 375                 380

Pro Gln Val Pro Pro Lys Lys Pro Thr Pro Thr Lys Ala Ser Asn
385                 390                 395                 400

Leu Leu Arg Ser Ser Gly Thr Val Tyr Pro Lys Arg Pro Glu Lys Pro
                405                 410                 415

Val Pro Pro Pro Pro Ile Ala Lys Ile Asn Gly Glu Val Ser Ser
                420                 425                 430

Ile Ser Ser Lys Phe Glu Thr Glu Pro Val Ser Lys Leu Lys Leu Asp
        435                 440                 445

Ser Glu Gln Leu Pro Leu Arg Pro Lys Ser Val Asp Phe Asp Ser Leu
    450                 455                 460

Thr Val Arg Thr Ser Lys Glu Thr Asp Val Val Asn Phe Asp Asp Ile
465                 470                 475                 480

Ala Ser Ser Glu Asn Leu Leu His Leu Thr Ala Asn Arg Pro Lys Met
            485                 490                 495

Pro Gly Arg Arg Leu Pro Gly Arg Phe Asn Gly His Ser Pro Thr
                500                 505                 510

His Ser Pro Glu Lys Ile Leu Lys Leu Pro Lys Glu Glu Asp Ser Ala
    515                 520                 525

Asn Leu Lys Pro Ser Glu Leu Lys Lys Asp Thr Cys Tyr Ser Pro Lys
        530                 535                 540

Pro Ser Val Tyr Leu Ser Thr Pro Ser Ser Ala Ser Lys Ala Asn Thr
545                 550                 555                 560
```

```
Thr Ala Phe Leu Thr Pro Leu Glu Ile Lys Ala Lys Val Glu Thr Asp
                565                 570                 575
Asp Val Lys Lys Asn Ser Leu Asp Glu Leu Arg Ala Gln Ile Ile Glu
            580                 585                 590
Leu Leu Cys Ile Val Glu Ala Leu Lys Lys Asp His Gly Lys Glu Leu
        595                 600                 605
Glu Lys Leu Arg Lys Asp Leu Glu Glu Glu Lys Thr Met Arg Ser Asn
    610                 615                 620
Leu Glu Met Glu Ile Glu Lys Leu Lys Lys Ala Val Leu Ser Ser
625                 630                 635

<210> SEQ ID NO 236
<211> LENGTH: 829
<212> TYPE: PRT
<213> ORGANISM: Homo sapiens

<400> SEQUENCE: 236

Met Gly Leu Pro Arg Gly Pro Leu Ala Ser Leu Leu Leu Leu Gln Val
1               5                   10                  15
Cys Trp Leu Gln Cys Ala Ala Ser Glu Pro Cys Arg Ala Val Phe Arg
            20                  25                  30
Glu Ala Glu Val Thr Leu Glu Ala Gly Gly Ala Glu Gln Glu Pro Gly
        35                  40                  45
Gln Ala Leu Gly Lys Val Phe Met Gly Cys Pro Gly Gln Glu Pro Ala
    50                  55                  60
Leu Phe Ser Thr Asp Asn Asp Asp Phe Thr Val Arg Asn Gly Glu Thr
65                  70                  75                  80
Val Gln Glu Arg Arg Ser Leu Lys Glu Arg Asn Pro Leu Lys Ile Phe
                85                  90                  95
Pro Ser Lys Arg Ile Leu Arg Arg His Lys Arg Asp Trp Val Val Ala
            100                 105                 110
Pro Ile Ser Val Pro Glu Asn Gly Lys Gly Pro Phe Pro Gln Arg Leu
        115                 120                 125
Asn Gln Leu Lys Ser Asn Lys Asp Arg Asp Thr Lys Ile Phe Tyr Ser
    130                 135                 140
Ile Thr Gly Pro Gly Ala Asp Ser Pro Pro Glu Gly Val Phe Ala Val
145                 150                 155                 160
Glu Lys Glu Thr Gly Trp Leu Leu Leu Asn Lys Pro Leu Asp Arg Glu
                165                 170                 175
Glu Ile Ala Lys Tyr Glu Leu Phe Gly His Ala Val Ser Glu Asn Gly
            180                 185                 190
Ala Ser Val Glu Asp Pro Met Asn Ile Ser Ile Ile Val Thr Asp Gln
        195                 200                 205
Asn Asp His Lys Pro Lys Phe Thr Gln Asp Thr Phe Arg Gly Ser Val
    210                 215                 220
Leu Glu Gly Val Leu Pro Gly Thr Ser Val Met Gln Val Thr Ala Thr
225                 230                 235                 240
Asp Glu Asp Asp Ala Ile Tyr Thr Tyr Asn Gly Val Val Ala Tyr Ser
                245                 250                 255
Ile His Ser Gln Glu Pro Lys Asp Pro His Asp Leu Met Phe Thr Ile
            260                 265                 270
His Arg Ser Thr Gly Thr Ile Ser Val Ile Ser Ser Gly Leu Asp Arg
        275                 280                 285
Glu Lys Val Pro Glu Tyr Thr Leu Thr Ile Gln Ala Thr Asp Met Asp
    290                 295                 300
```

```
Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
            325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
            405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
            435                 440                 445

Val Gln Glu Gly Ile Pro Thr Gly Glu Pro Val Cys Val Tyr Thr Ala
450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
            485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
            565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
            645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
            690                 695                 700

Gly Gly Gly Glu Glu Asp Gln Asp Tyr Asp Ile Thr Gln Leu His Arg
705                 710                 715                 720
```

```
Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
                820                 825

<210> SEQ ID NO 237
<211> LENGTH: 746
<212> TYPE: PRT
<213> ORGANISM: Homo sapiens

<400> SEQUENCE: 237

Met Asp Phe Leu Glu Glu Pro Ile Pro Gly Val Gly Thr Tyr Asp Asp
1               5                   10                  15

Phe Asn Thr Ile Asp Trp Val Arg Glu Lys Ser Arg Asp Arg Asp Arg
            20                  25                  30

His Arg Glu Ile Thr Asn Lys Ser Lys Glu Ser Thr Trp Ala Leu Ile
        35                  40                  45

His Ser Val Ser Asp Ala Phe Ser Gly Trp Leu Leu Met Leu Leu Ile
    50                  55                  60

Gly Leu Leu Ser Gly Ser Leu Ala Gly Leu Ile Asp Ile Ser Ala His
65                  70                  75                  80

Trp Met Thr Asp Leu Lys Glu Gly Ile Cys Thr Gly Gly Phe Trp Phe
                85                  90                  95

Asn His Glu His Cys Cys Trp Asn Ser Glu His Val Thr Phe Glu Glu
            100                 105                 110

Arg Asp Lys Cys Pro Glu Trp Asn Ser Trp Ser Gln Leu Ile Ile Ser
        115                 120                 125

Thr Asp Glu Gly Ala Phe Ala Tyr Ile Val Asn Tyr Phe Met Tyr Val
    130                 135                 140

Leu Trp Ala Leu Leu Phe Ala Phe Leu Ala Val Ser Leu Val Lys Val
145                 150                 155                 160

Phe Ala Pro Tyr Ala Cys Gly Ser Gly Ile Pro Glu Ile Lys Thr Ile
                165                 170                 175

Leu Ser Gly Phe Ile Ile Arg Gly Tyr Leu Gly Lys Trp Thr Leu Val
            180                 185                 190

Ile Lys Thr Ile Thr Leu Val Leu Ala Val Ser Ser Gly Leu Ser Leu
        195                 200                 205

Gly Lys Glu Gly Pro Leu Val His Val Ala Cys Cys Cys Gly Asn Ile
    210                 215                 220

Leu Cys His Cys Phe Asn Lys Tyr Arg Lys Asn Glu Ala Lys Arg Arg
225                 230                 235                 240

Glu Val Leu Ser Ala Ala Ala Ala Gly Val Ser Val Ala Phe Gly
                245                 250                 255

Ala Pro Ile Gly Gly Val Leu Phe Ser Leu Glu Glu Val Ser Tyr Tyr
            260                 265                 270
```

```
Phe Pro Leu Lys Thr Leu Trp Arg Ser Phe Ala Ala Leu Val Ala
        275                 280                 285

Ala Phe Thr Leu Arg Ser Ile Asn Pro Phe Gly Asn Ser Arg Leu Val
290                 295                 300

Leu Phe Tyr Val Glu Phe His Thr Pro Trp His Leu Phe Glu Leu Val
305                 310                 315                 320

Pro Phe Ile Leu Leu Gly Ile Phe Gly Gly Leu Trp Gly Ala Leu Phe
                325                 330                 335

Ile Arg Thr Asn Ile Ala Trp Cys Arg Lys Arg Lys Thr Thr Gln Leu
                340                 345                 350

Gly Lys Tyr Pro Val Ile Glu Val Leu Val Thr Ala Ile Thr Ala
            355                 360                 365

Ile Leu Ala Phe Pro Asn Glu Tyr Thr Arg Met Ser Thr Ser Glu Leu
370                 375                 380

Ile Ser Glu Leu Phe Asn Asp Cys Gly Leu Leu Asp Ser Ser Lys Leu
385                 390                 395                 400

Cys Asp Tyr Glu Asn Arg Phe Asn Thr Ser Lys Gly Gly Glu Leu Pro
                405                 410                 415

Asp Arg Pro Ala Gly Val Gly Val Tyr Ser Ala Met Trp Gln Leu Ala
                420                 425                 430

Leu Thr Leu Ile Leu Lys Ile Val Ile Thr Ile Phe Thr Phe Gly Met
                435                 440                 445

Lys Ile Pro Ser Gly Leu Phe Ile Pro Ser Met Ala Val Gly Ala Ile
            450                 455                 460

Ala Gly Arg Leu Leu Gly Val Gly Met Glu Gln Leu Ala Tyr Tyr His
465                 470                 475                 480

Gln Glu Trp Thr Val Phe Asn Ser Trp Cys Ser Gln Gly Ala Asp Cys
                485                 490                 495

Ile Thr Pro Gly Leu Tyr Ala Met Val Gly Ala Ala Ala Cys Leu Gly
                500                 505                 510

Gly Val Thr Arg Met Thr Val Ser Leu Val Val Ile Met Phe Glu Leu
            515                 520                 525

Thr Gly Gly Leu Glu Tyr Ile Val Pro Leu Met Ala Ala Ala Met Thr
            530                 535                 540

Ser Lys Trp Val Ala Asp Ala Leu Gly Arg Glu Gly Ile Tyr Asp Ala
545                 550                 555                 560

His Ile Arg Leu Asn Gly Tyr Pro Phe Leu Glu Ala Lys Glu Glu Phe
                565                 570                 575

Ala His Lys Thr Leu Ala Met Asp Val Met Lys Pro Arg Arg Asn Asp
                580                 585                 590

Pro Leu Leu Thr Val Leu Thr Gln Asp Ser Met Thr Val Glu Asp Val
                595                 600                 605

Glu Thr Ile Ile Ser Glu Thr Thr Tyr Ser Gly Phe Pro Val Val Val
            610                 615                 620

Ser Arg Glu Ser Gln Arg Leu Val Gly Phe Val Leu Arg Arg Asp Leu
625                 630                 635                 640

Ile Ile Ser Ile Glu Asn Ala Arg Lys Lys Gln Asp Gly Val Val Ser
                645                 650                 655

Thr Ser Ile Ile Tyr Phe Thr Glu His Ser Pro Pro Leu Pro Pro Tyr
                660                 665                 670

Thr Pro Pro Thr Leu Lys Leu Arg Asn Ile Leu Asp Leu Ser Pro Phe
            675                 680                 685
```

-continued

```
Thr Val Thr Asp Leu Thr Pro Met Glu Ile Val Val Asp Ile Phe Arg
    690                 695                 700

Lys Leu Gly Leu Arg Gln Cys Leu Val Thr His Asn Gly Arg Leu Leu
705                 710                 715                 720

Gly Ile Ile Thr Lys Lys Asp Val Leu Lys His Ile Ala Gln Met Ala
                725                 730                 735

Asn Gln Asp Pro Asp Ser Ile Leu Phe Asn
                740                 745

<210> SEQ ID NO 238
<211> LENGTH: 3623
<212> TYPE: PRT
<213> ORGANISM: Homo sapiens

<400> SEQUENCE: 238

Met Met Asn Met Ser Leu Pro Phe Leu Trp Ser Leu Leu Thr Leu Leu
1               5                   10                  15

Ile Phe Ala Glu Val Asn Gly Glu Ala Gly Glu Leu Glu Leu Gln Arg
                20                  25                  30

Gln Lys Arg Ser Ile Asn Leu Gln Gln Pro Arg Met Ala Thr Glu Arg
            35                  40                  45

Gly Asn Leu Val Phe Leu Thr Gly Ser Ala Gln Asn Ile Glu Phe Arg
    50                  55                  60

Thr Gly Ser Leu Gly Lys Ile Lys Leu Asn Asp Glu Asp Leu Ser Glu
65                  70                  75                  80

Cys Leu His Gln Ile Gln Lys Asn Lys Glu Asp Ile Ile Glu Leu Lys
                85                  90                  95

Gly Ser Ala Ile Gly Leu Pro Gln Asn Ile Ser Ser Gln Ile Tyr Gln
                100                 105                 110

Leu Asn Ser Lys Leu Val Asp Leu Glu Arg Lys Phe Gln Gly Leu Gln
            115                 120                 125

Gln Thr Val Asp Lys Lys Val Cys Ser Ser Asn Pro Cys Gln Asn Gly
    130                 135                 140

Gly Thr Cys Leu Asn Leu His Asp Ser Phe Phe Cys Ile Cys Pro Pro
145                 150                 155                 160

Gln Trp Lys Gly Pro Leu Cys Ser Ala Asp Val Asn Glu Cys Glu Ile
                165                 170                 175

Tyr Ser Gly Thr Pro Leu Ser Cys Gln Asn Gly Gly Thr Cys Val Asn
                180                 185                 190

Thr Met Gly Ser Tyr Ser Cys His Cys Pro Pro Glu Thr Tyr Gly Pro
            195                 200                 205

Gln Cys Ala Ser Lys Tyr Asp Asp Cys Glu Gly Gly Ser Val Ala Arg
    210                 215                 220

Cys Val His Gly Ile Cys Glu Asp Leu Met Arg Glu Gln Ala Gly Glu
225                 230                 235                 240

Pro Lys Tyr Ser Cys Val Cys Asp Ala Gly Trp Met Phe Ser Pro Asn
                245                 250                 255

Ser Pro Ala Cys Thr Leu Asp Arg Asp Glu Cys Ser Phe Gln Pro Gly
                260                 265                 270

Pro Cys Ser Thr Leu Val Gln Cys Phe Asn Thr Gln Gly Ser Phe Tyr
            275                 280                 285

Cys Gly Ala Cys Pro Thr Gly Trp Gln Gly Asn Gly Tyr Ile Cys Glu
    290                 295                 300

Asp Ile Asn Glu Cys Glu Ile Asn Asn Gly Gly Cys Ser Val Ala Pro
305                 310                 315                 320
```

```
Pro Val Glu Cys Val Asn Thr Pro Gly Ser Ser His Cys Gln Ala Cys
                325                 330                 335

Pro Pro Gly Tyr Gln Gly Asp Gly Arg Val Cys Thr Leu Thr Asp Ile
            340                 345                 350

Cys Ser Val Ser Asn Gly Gly Cys His Pro Asp Ala Ser Cys Ser Ser
            355                 360                 365

Thr Leu Gly Ser Leu Pro Leu Cys Thr Cys Leu Pro Gly Tyr Thr Gly
        370                 375                 380

Asn Gly Tyr Gly Pro Asn Gly Cys Val Gln Leu Ser Asn Ile Cys Leu
385                 390                 395                 400

Ser His Pro Cys Leu Asn Gly Gln Cys Ile Asp Thr Val Ser Gly Tyr
                405                 410                 415

Phe Cys Lys Cys Asp Ser Gly Trp Thr Gly Val Asn Cys Thr Glu Asn
            420                 425                 430

Ile Asn Glu Cys Leu Ser Asn Pro Cys Leu Asn Gly Gly Thr Cys Val
        435                 440                 445

Asp Gly Val Asp Ser Phe Ser Cys Glu Cys Thr Arg Leu Trp Thr Gly
        450                 455                 460

Ala Leu Cys Gln Val Pro Gln Gln Val Cys Gly Glu Ser Leu Ser Gly
465                 470                 475                 480

Ile Asn Gly Ser Phe Ser Tyr Arg Ser Pro Asp Val Gly Tyr Val His
                485                 490                 495

Asp Val Asn Cys Phe Trp Val Ile Lys Thr Glu Met Gly Lys Val Leu
            500                 505                 510

Arg Ile Thr Phe Thr Phe Phe Arg Leu Glu Ser Met Asp Asn Cys Pro
        515                 520                 525

His Glu Phe Leu Gln Val Tyr Asp Gly Asp Ser Ser Ser Ala Phe Gln
        530                 535                 540

Leu Gly Arg Phe Cys Gly Ser Ser Leu Pro His Glu Leu Leu Ser Ser
545                 550                 555                 560

Asp Asn Ala Leu Tyr Phe His Leu Tyr Ser Glu His Leu Arg Asn Gly
                565                 570                 575

Arg Gly Phe Thr Val Arg Trp Glu Thr Gln Pro Glu Cys Gly Gly
            580                 585                 590

Ile Leu Thr Gly Pro Tyr Gly Ser Ile Lys Ser Pro Gly Tyr Pro Gly
        595                 600                 605

Asn Tyr Pro Pro Gly Arg Asp Cys Val Trp Ile Val Thr Ser Pro
610                 615                 620

Asp Leu Leu Val Thr Phe Thr Phe Gly Thr Leu Ser Leu Glu His His
625                 630                 635                 640

Asp Asp Cys Asn Lys Asp Tyr Leu Glu Ile Arg Asp Gly Pro Leu Tyr
                645                 650                 655

Gln Asp Pro Leu Leu Gly Lys Phe Cys Thr Thr Phe Ser Val Pro Pro
            660                 665                 670

Leu Gln Thr Thr Gly Pro Phe Ala Arg Ile His Phe His Ser Asp Ser
        675                 680                 685

Gln Ile Ser Asp Gln Gly Phe His Ile Thr Tyr Leu Thr Ser Pro Ser
        690                 695                 700

Asp Leu Arg Cys Gly Gly Asn Tyr Thr Asp Pro Glu Gly Glu Leu Phe
705                 710                 715                 720

Leu Pro Glu Leu Ser Gly Pro Phe Thr His Thr Arg Gln Cys Val Tyr
                725                 730                 735
```

-continued

```
Met Met Lys Gln Pro Gln Gly Glu Gln Ile Gln Ile Asn Phe Thr His
            740                 745                 750

Val Glu Leu Gln Cys Gln Ser Asp Ser Ser Gln Asn Tyr Ile Glu Val
            755                 760                 765

Arg Asp Gly Glu Thr Leu Leu Gly Lys Val Cys Gly Asn Gly Thr Ile
            770                 775                 780

Ser His Ile Lys Ser Ile Thr Asn Ser Val Trp Ile Arg Phe Lys Ile
785                 790                 795                 800

Asp Ala Ser Val Glu Lys Ala Ser Phe Arg Ala Val Tyr Gln Val Ala
                    805                 810                 815

Cys Gly Asp Glu Leu Thr Gly Glu Gly Val Ile Arg Ser Pro Phe Phe
                    820                 825                 830

Pro Asn Val Tyr Pro Gly Glu Arg Thr Cys Arg Trp Thr Ile His Gln
                    835                 840                 845

Pro Gln Ser Gln Val Ile Leu Leu Asn Phe Thr Val Phe Glu Ile Gly
                    850                 855                 860

Ser Ser Ala His Cys Glu Thr Asp Tyr Val Glu Ile Gly Ser Ser Ser
865                 870                 875                 880

Ile Leu Gly Ser Pro Glu Asn Lys Lys Tyr Cys Gly Thr Asp Ile Pro
                    885                 890                 895

Ser Phe Ile Thr Ser Val Tyr Asn Phe Leu Tyr Val Thr Phe Val Lys
                    900                 905                 910

Ser Ser Ser Thr Glu Asn His Gly Phe Met Ala Lys Phe Ser Ala Glu
                    915                 920                 925

Asp Leu Ala Cys Gly Ile Leu Thr Glu Ser Thr Gly Thr Ile Gln
                    930                 935                 940

Ser Pro Gly His Pro Asn Val Tyr Pro His Gly Ile Asn Cys Thr Trp
945                 950                 955                 960

His Ile Leu Val Gln Pro Asn His Leu Ile His Leu Met Phe Glu Thr
                    965                 970                 975

Phe His Leu Glu Phe His Tyr Asn Cys Thr Asn Asp Tyr Leu Glu Val
                    980                 985                 990

Tyr Asp Thr Asp Ser Glu Thr Ser Leu Gly Arg Tyr Cys Gly Lys Ser
                    995                 1000                1005

Ile Pro Pro Ser Leu Thr Ser Gly Asn Ser Leu Met Leu Val
        1010                1015                1020

Phe Val Thr Asp Ser Asp Leu Ala Tyr Glu Gly Phe Leu Ile Asn
        1025                1030                1035

Tyr Glu Ala Ile Ser Ala Ala Thr Ala Cys Leu Gln Asp Tyr Thr
        1040                1045                1050

Asp Asp Leu Gly Thr Phe Thr Ser Pro Asn Phe Pro Asn Asn Tyr
        1055                1060                1065

Pro Asn Asn Trp Glu Cys Ile Tyr Arg Ile Thr Val Arg Thr Gly
        1070                1075                1080

Gln Leu Ile Ala Val His Phe Thr Asn Phe Ser Leu Glu Glu Ala
        1085                1090                1095

Ile Gly Asn Tyr Tyr Thr Asp Phe Leu Glu Ile Arg Asp Gly Gly
        1100                1105                1110

Tyr Glu Lys Ser Pro Leu Leu Gly Ile Phe Tyr Gly Ser Asn Leu
        1115                1120                1125

Pro Pro Thr Ile Ile Ser His Ser Asn Lys Leu Trp Leu Lys Phe
        1130                1135                1140

Lys Ser Asp Gln Ile Asp Thr Arg Ser Gly Phe Ser Ala Tyr Trp
```

-continued

```
            1145                1150                1155

Asp Gly Ser Ser Thr Gly Cys Gly Gly Asn Leu Thr Thr Ser Ser
    1160                1165                1170

Gly Thr Phe Ile Ser Pro Asn Tyr Pro Met Pro Tyr Tyr His Ser
    1175                1180                1185

Ser Glu Cys Tyr Trp Trp Leu Lys Ser Ser His Gly Ser Ala Phe
    1190                1195                1200

Glu Leu Glu Phe Lys Asp Phe His Leu Glu His His Pro Asn Cys
    1205                1210                1215

Thr Leu Asp Tyr Leu Ala Val Tyr Asp Gly Pro Ser Ser Asn Ser
    1220                1225                1230

His Leu Leu Thr Gln Leu Cys Gly Asp Glu Lys Pro Pro Leu Ile
    1235                1240                1245

Arg Ser Ser Gly Asp Ser Met Phe Ile Lys Leu Arg Thr Asp Glu
    1250                1255                1260

Gly Gln Gln Gly Arg Gly Phe Lys Ala Glu Tyr Arg Gln Thr Cys
    1265                1270                1275

Glu Asn Val Val Ile Val Asn Gln Thr Tyr Gly Ile Leu Glu Ser
    1280                1285                1290

Ile Gly Tyr Pro Asn Pro Tyr Ser Glu Asn Gln His Cys Asn Trp
    1295                1300                1305

Thr Ile Arg Ala Thr Thr Gly Asn Thr Val Asn Tyr Thr Phe Leu
    1310                1315                1320

Ala Phe Asp Leu Glu His His Ile Asn Cys Ser Thr Asp Tyr Leu
    1325                1330                1335

Glu Leu Tyr Asp Gly Pro Arg Gln Met Gly Arg Tyr Cys Gly Val
    1340                1345                1350

Asp Leu Pro Pro Pro Gly Ser Thr Thr Ser Ser Lys Leu Gln Val
    1355                1360                1365

Leu Leu Leu Thr Asp Gly Val Gly Arg Arg Glu Lys Gly Phe Gln
    1370                1375                1380

Met Gln Trp Phe Val Tyr Gly Cys Gly Gly Glu Leu Ser Gly Ala
    1385                1390                1395

Thr Gly Ser Phe Ser Ser Pro Gly Phe Pro Asn Arg Tyr Pro Pro
    1400                1405                1410

Asn Lys Glu Cys Ile Trp Tyr Ile Arg Thr Asp Pro Gly Ser Ser
    1415                1420                1425

Ile Gln Leu Thr Ile His Asp Phe Asp Val Glu Tyr His Ser Arg
    1430                1435                1440

Cys Asn Phe Asp Val Leu Glu Ile Tyr Gly Gly Pro Asp Phe His
    1445                1450                1455

Ser Pro Arg Ile Ala Gln Leu Cys Thr Gln Arg Ser Pro Glu Asn
    1460                1465                1470

Pro Met Gln Val Ser Ser Thr Gly Asn Glu Leu Ala Ile Arg Phe
    1475                1480                1485

Lys Thr Asp Leu Ser Ile Asn Gly Arg Gly Phe Asn Ala Ser Trp
    1490                1495                1500

Gln Ala Val Thr Gly Gly Cys Gly Gly Ile Phe Gln Ala Pro Ser
    1505                1510                1515

Gly Glu Ile His Ser Pro Asn Tyr Pro Ser Pro Tyr Arg Ser Asn
    1520                1525                1530

Thr Asp Cys Ser Trp Val Ile Arg Val Asp Arg Asn His Arg Val
    1535                1540                1545
```

-continued

Leu Leu Asn Phe Thr Asp Phe Asp Leu Glu Pro Gln Asp Ser Cys
1550                1555                1560

Ile Met Ala Tyr Asp Gly Leu Ser Ser Thr Met Ser Arg Leu Ala
1565                1570                1575

Arg Thr Cys Gly Arg Glu Gln Leu Ala Asn Pro Ile Val Ser Ser
1580                1585                1590

Gly Asn Ser Leu Phe Leu Arg Phe Gln Ser Gly Pro Ser Arg Gln
1595                1600                1605

Asn Arg Gly Phe Arg Ala Gln Phe Arg Gln Ala Cys Gly Gly His
1610                1615                1620

Ile Leu Thr Ser Ser Phe Asp Thr Val Ser Ser Pro Arg Phe Pro
1625                1630                1635

Ala Asn Tyr Pro Asn Asn Gln Asn Cys Ser Trp Ile Ile Gln Ala
1640                1645                1650

Gln Pro Pro Leu Asn His Ile Thr Leu Ser Phe Thr His Phe Glu
1655                1660                1665

Leu Glu Arg Ser Thr Thr Cys Ala Arg Asp Phe Val Glu Ile Leu
1670                1675                1680

Asp Gly Gly His Glu Asp Ala Pro Leu Arg Gly Arg Tyr Cys Gly
1685                1690                1695

Thr Asp Met Pro His Pro Ile Thr Ser Phe Ser Ser Ala Leu Thr
1700                1705                1710

Leu Arg Phe Val Ser Asp Ser Ser Ile Ser Ala Gly Gly Phe His
1715                1720                1725

Thr Thr Val Thr Ala Ser Val Ser Ala Cys Gly Gly Thr Phe Tyr
1730                1735                1740

Met Ala Glu Gly Ile Phe Asn Ser Pro Gly Tyr Pro Asp Ile Tyr
1745                1750                1755

Pro Pro Asn Val Glu Cys Val Trp Asn Ile Val Ser Ser Pro Gly
1760                1765                1770

Asn Arg Leu Gln Leu Ser Phe Ile Ser Phe Gln Leu Glu Asp Ser
1775                1780                1785

Gln Asp Cys Ser Arg Asp Phe Val Glu Ile Arg Glu Gly Asn Ala
1790                1795                1800

Thr Gly His Leu Val Gly Arg Tyr Cys Gly Asn Ser Phe Pro Leu
1805                1810                1815

Asn Tyr Ser Ser Ile Val Gly His Thr Leu Trp Val Arg Phe Ile
1820                1825                1830

Ser Asp Gly Ser Gly Ser Gly Thr Gly Phe Gln Ala Thr Phe Met
1835                1840                1845

Lys Ile Phe Gly Asn Asp Asn Ile Val Gly Thr His Gly Lys Val
1850                1855                1860

Ala Ser Pro Phe Trp Pro Glu Asn Tyr Pro His Asn Ser Asn Tyr
1865                1870                1875

Gln Trp Thr Val Asn Val Asn Ala Ser His Val Val His Gly Arg
1880                1885                1890

Ile Leu Glu Met Asp Ile Glu Glu Ile Gln Asn Cys Tyr Tyr Asp
1895                1900                1905

Lys Leu Arg Ile Tyr Asp Gly Pro Ser Ile His Ala Arg Leu Ile
1910                1915                1920

Gly Ala Tyr Cys Gly Thr Gln Thr Glu Ser Phe Ser Ser Thr Gly
1925                1930                1935

```
Asn Ser Leu Thr Phe His Phe Tyr Ser Asp Ser Ser Ile Ser Gly
1940                1945                1950

Lys Gly Phe Leu Leu Glu Trp Phe Ala Val Asp Ala Pro Asp Gly
1955                1960                1965

Val Leu Pro Thr Ile Ala Pro Gly Ala Cys Gly Gly Phe Leu Arg
1970                1975                1980

Thr Gly Asp Ala Pro Val Phe Leu Phe Ser Pro Gly Trp Pro Asp
1985                1990                1995

Ser Tyr Ser Asn Arg Val Asp Cys Thr Trp Leu Ile Gln Ala Pro
2000                2005                2010

Asp Ser Thr Val Glu Leu Asn Ile Leu Ser Leu Asp Ile Glu Ser
2015                2020                2025

His Arg Thr Cys Ala Tyr Asp Ser Leu Val Ile Arg Asp Gly Asp
2030                2035                2040

Asn Asn Leu Ala Gln Gln Leu Ala Val Leu Cys Gly Arg Glu Ile
2045                2050                2055

Pro Gly Pro Ile Arg Ser Thr Gly Glu Tyr Met Phe Ile Arg Phe
2060                2065                2070

Thr Ser Asp Ser Ser Val Thr Arg Ala Gly Phe Asn Ala Ser Phe
2075                2080                2085

His Lys Ser Cys Gly Gly Tyr Leu His Ala Asp Arg Gly Ile Ile
2090                2095                2100

Thr Ser Pro Lys Tyr Pro Glu Thr Tyr Pro Ser Asn Leu Asn Cys
2105                2110                2115

Ser Trp His Val Leu Val Gln Ser Gly Leu Thr Ile Ala Val His
2120                2125                2130

Phe Glu Gln Pro Phe Gln Ile Pro Asn Gly Asp Ser Ser Cys Asn
2135                2140                2145

Gln Gly Asp Tyr Leu Val Leu Arg Asn Gly Pro Asp Ile Cys Ser
2150                2155                2160

Pro Pro Leu Gly Pro Pro Gly Gly Asn Gly His Phe Cys Gly Ser
2165                2170                2175

His Ala Ser Ser Thr Leu Phe Thr Ser Asp Asn Gln Met Phe Val
2180                2185                2190

Gln Phe Ile Ser Asp His Ser Asn Glu Gly Gln Gly Phe Lys Ile
2195                2200                2205

Lys Tyr Glu Ala Lys Ser Leu Ala Cys Gly Gly Asn Val Tyr Ile
2210                2215                2220

His Asp Ala Asp Ser Ala Gly Tyr Val Thr Ser Pro Asn His Pro
2225                2230                2235

His Asn Tyr Pro Pro His Ala Asp Cys Ile Trp Ile Leu Ala Ala
2240                2245                2250

Pro Pro Glu Thr Arg Ile Gln Leu Gln Phe Glu Asp Arg Phe Asp
2255                2260                2265

Ile Glu Val Thr Pro Asn Cys Thr Ser Asn Tyr Leu Glu Leu Arg
2270                2275                2280

Asp Gly Val Asp Ser Asp Ala Pro Ile Leu Ser Lys Phe Cys Gly
2285                2290                2295

Thr Ser Leu Pro Ser Ser Gln Trp Ser Ser Gly Glu Val Met Tyr
2300                2305                2310

Leu Arg Phe Arg Ser Asp Asn Ser Pro Thr His Val Gly Phe Lys
2315                2320                2325

Ala Lys Tyr Ser Ile Ala Gln Cys Gly Gly Arg Val Pro Gly Gln
```

-continued

```
                    2330                2335                2340

Ser Gly Val Val Glu Ser Ile Gly His Pro Thr Leu Pro Tyr Arg
            2345                2350                2355

Asp Asn Leu Phe Cys Glu Trp His Leu Gln Gly Leu Ser Gly His
            2360                2365                2370

Tyr Leu Thr Ile Ser Phe Glu Asp Phe Asn Leu Gln Asn Ser Ser
            2375                2380                2385

Gly Cys Glu Lys Asp Phe Val Glu Ile Trp Asp Asn His Thr Ser
            2390                2395                2400

Gly Asn Ile Leu Gly Arg Tyr Cys Gly Asn Thr Ile Pro Asp Ser
            2405                2410                2415

Ile Asp Thr Ser Ser Asn Thr Ala Val Val Arg Phe Val Thr Asp
            2420                2425                2430

Gly Ser Val Thr Ala Ser Gly Phe Arg Leu Arg Phe Glu Ser Ser
            2435                2440                2445

Met Glu Glu Cys Gly Gly Asp Leu Gln Gly Ser Ile Gly Thr Phe
            2450                2455                2460

Thr Ser Pro Asn Tyr Pro Asn Pro Asn Pro His Gly Arg Ile Cys
            2465                2470                2475

Glu Trp Arg Ile Thr Ala Pro Glu Gly Arg Arg Ile Thr Leu Met
            2480                2485                2490

Phe Asn Asn Leu Arg Leu Ala Thr His Pro Ser Cys Asn Asn Glu
            2495                2500                2505

His Val Ile Val Phe Asn Gly Ile Arg Ser Asn Ser Pro Gln Leu
            2510                2515                2520

Glu Lys Leu Cys Ser Ser Val Asn Val Ser Asn Glu Ile Lys Ser
            2525                2530                2535

Ser Gly Asn Thr Met Lys Val Ile Phe Phe Thr Asp Gly Ser Arg
            2540                2545                2550

Pro Tyr Gly Gly Phe Thr Ala Ser Tyr Thr Ser Ser Glu Asp Ala
            2555                2560                2565

Val Cys Gly Gly Ser Leu Pro Asn Thr Pro Glu Gly Asn Phe Thr
            2570                2575                2580

Ser Pro Gly Tyr Asp Gly Val Arg Asn Tyr Ser Arg Asn Leu Asn
            2585                2590                2595

Cys Glu Trp Thr Leu Ser Asn Pro Asn Gln Gly Asn Ser Ser Ile
            2600                2605                2610

Ser Ile His Phe Glu Asp Phe Tyr Leu Glu Ser His Gln Asp Cys
            2615                2620                2625

Gln Phe Asp Val Leu Glu Arg Val Gly Asp Ala Asp Gly Pro
            2630                2635                2640

Leu Met Trp Arg Leu Cys Gly Pro Ser Lys Pro Thr Leu Pro Leu
            2645                2650                2655

Val Ile Pro Tyr Ser Gln Val Trp Ile His Phe Val Thr Asn Glu
            2660                2665                2670

Arg Val Glu His Ile Gly Phe His Ala Lys Tyr Ser Phe Thr Asp
            2675                2680                2685

Cys Gly Gly Ile Gln Ile Gly Asp Ser Gly Val Ile Thr Ser Pro
            2690                2695                2700

Asn Tyr Pro Asn Ala Tyr Asp Ser Leu Thr His Cys Ser Ser Leu
            2705                2710                2715

Leu Glu Ala Pro Gln Gly His Thr Ile Thr Leu Thr Phe Ser Asp
            2720                2725                2730
```

```
Phe Asp Ile Glu Pro His Thr Thr Cys Ala Trp Asp Ser Val Thr
2735                2740                2745

Val Arg Asn Gly Gly Ser Pro Glu Ser Pro Ile Ile Gly Gln Tyr
2750                2755                2760

Cys Gly Asn Ser Asn Pro Arg Thr Ile Gln Ser Gly Ser Asn Gln
2765                2770                2775

Leu Val Val Thr Phe Asn Ser Asp His Ser Leu Gln Gly Gly Gly
2780                2785                2790

Phe Tyr Ala Thr Trp Asn Thr Gln Thr Leu Gly Cys Gly Gly Ile
2795                2800                2805

Phe His Ser Asp Asn Gly Thr Ile Arg Ser Pro His Trp Pro Gln
2810                2815                2820

Asn Phe Pro Glu Asn Ser Arg Cys Ser Trp Thr Ala Ile Thr His
2825                2830                2835

Lys Ser Lys His Leu Glu Ile Ser Phe Asp Asn Phe Leu Ile
2840                2845                2850

Pro Ser Gly Asp Gly Gln Cys Gln Asn Ser Phe Val Lys Val Trp
2855                2860                2865

Ala Gly Thr Glu Glu Val Asp Lys Ala Leu Leu Ala Thr Gly Cys
2870                2875                2880

Gly Asn Val Ala Pro Gly Pro Val Ile Thr Pro Ser Asn Thr Phe
2885                2890                2895

Thr Ala Val Phe Gln Ser Gln Glu Ala Pro Ala Gln Gly Phe Ser
2900                2905                2910

Ala Ser Phe Val Ser Arg Cys Gly Ser Asn Phe Thr Gly Pro Ser
2915                2920                2925

Gly Tyr Ile Ile Ser Pro Asn Tyr Pro Lys Gln Tyr Asp Asn Asn
2930                2935                2940

Met Asn Cys Thr Tyr Val Ile Glu Ala Asn Pro Leu Ser Val Val
2945                2950                2955

Leu Leu Thr Phe Val Ser Phe His Leu Glu Ala Arg Ser Ala Val
2960                2965                2970

Thr Gly Ser Cys Val Asn Asp Gly Val His Ile Ile Arg Gly Tyr
2975                2980                2985

Ser Val Met Ser Thr Pro Phe Ala Thr Val Cys Gly Asp Glu Met
2990                2995                3000

Pro Ala Pro Leu Thr Ile Ala Gly Pro Val Leu Leu Asn Phe Tyr
3005                3010                3015

Ser Asn Glu Gln Ile Thr Asp Phe Gly Phe Lys Phe Ser Tyr Arg
3020                3025                3030

Ile Ile Ser Cys Gly Gly Val Phe Asn Phe Ser Ser Gly Ile Ile
3035                3040                3045

Thr Ser Pro Ala Tyr Ser Tyr Ala Asp Tyr Pro Asn Asp Met His
3050                3055                3060

Cys Leu Tyr Thr Ile Thr Val Ser Asp Asp Lys Val Ile Glu Leu
3065                3070                3075

Lys Phe Ser Asp Phe Asp Val Val Pro Ser Thr Ser Cys Ser His
3080                3085                3090

Asp Tyr Leu Ala Ile Tyr Asp Gly Ala Asn Thr Ser Asp Pro Leu
3095                3100                3105

Leu Gly Lys Phe Cys Gly Ser Lys Arg Pro Pro Asn Val Lys Ser
3110                3115                3120
```

-continued

```
Ser Asn Asn Ser Met Leu Leu Val Phe Lys Thr Asp Ser Phe Gln
3125                3130                3135

Thr Ala Lys Gly Trp Lys Met Ser Phe Arg Gln Thr Leu Gly Pro
3140                3145                3150

Gln Gln Gly Cys Gly Gly Tyr Leu Thr Gly Ser Asn Asn Thr Phe
3155                3160                3165

Ala Ser Pro Asp Ser Asp Ser Asn Gly Met Tyr Asp Lys Asn Leu
3170                3175                3180

Asn Cys Val Trp Ile Ile Ile Ala Pro Val Asn Lys Val Ile His
3185                3190                3195

Leu Thr Phe Asn Thr Phe Ala Leu Glu Ala Ala Ser Thr Arg Gln
3200                3205                3210

Arg Cys Leu Tyr Asp Tyr Val Lys Leu Tyr Asp Gly Asp Ser Glu
3215                3220                3225

Asn Ala Asn Leu Ala Gly Thr Phe Cys Gly Ser Thr Val Pro Ala
3230                3235                3240

Pro Phe Ile Ser Ser Gly Asn Phe Leu Thr Val Gln Phe Ile Ser
3245                3250                3255

Asp Leu Thr Leu Glu Arg Glu Gly Phe Asn Ala Thr Tyr Thr Ile
3260                3265                3270

Met Asp Met Pro Cys Gly Gly Thr Tyr Asn Ala Thr Trp Thr Pro
3275                3280                3285

Gln Asn Ile Ser Ser Pro Asn Ser Ser Asp Pro Asp Val Pro Phe
3290                3295                3300

Ser Ile Cys Thr Trp Val Ile Asp Ser Pro Pro His Gln Gln Val
3305                3310                3315

Lys Ile Thr Val Trp Ala Leu Gln Leu Thr Ser Gln Asp Cys Thr
3320                3325                3330

Gln Asn Tyr Leu Gln Leu Gln Asp Ser Pro Gln Gly His Gly Asn
3335                3340                3345

Ser Arg Phe Gln Phe Cys Gly Arg Asn Ala Ser Ala Val Pro Val
3350                3355                3360

Phe Tyr Ser Ser Met Ser Thr Ala Met Val Ile Phe Lys Ser Gly
3365                3370                3375

Val Val Asn Arg Asn Ser Arg Met Ser Phe Thr Tyr Gln Ile Ala
3380                3385                3390

Asp Cys Asn Arg Asp Tyr His Lys Ala Phe Gly Asn Leu Arg Ser
3395                3400                3405

Pro Gly Trp Pro Asp Asn Tyr Asp Asn Asp Lys Asp Cys Thr Val
3410                3415                3420

Thr Leu Thr Ala Pro Gln Asn His Thr Ile Ser Leu Phe Phe His
3425                3430                3435

Ser Leu Gly Ile Glu Asn Ser Val Glu Cys Arg Asn Asp Phe Leu
3440                3445                3450

Glu Val Arg Asn Gly Ser Asn Ser Asn Ser Pro Leu Leu Gly Lys
3455                3460                3465

Tyr Cys Gly Thr Leu Leu Pro Asn Pro Val Phe Ser Gln Asn Asn
3470                3475                3480

Glu Leu Tyr Leu Arg Phe Lys Ser Asp Ser Val Thr Ser Asp Arg
3485                3490                3495

Gly Tyr Glu Ile Ile Trp Thr Ser Ser Pro Ser Gly Cys Gly Gly
3500                3505                3510

Thr Leu Tyr Gly Asp Arg Gly Ser Phe Thr Ser Pro Gly Tyr Pro
```

```
          3515                3520                3525

Gly Thr Tyr Pro Asn Asn Thr Tyr Cys Glu Trp Val Leu Val Ala
    3530                3535                3540

Pro Ala Gly Arg Leu Val Thr Ile Asn Phe Tyr Phe Ile Ser Ile
    3545                3550                3555

Asp Asp Pro Gly Asp Cys Val Gln Asn Tyr Leu Thr Leu Tyr Asp
    3560                3565                3570

Gly Pro Asn Ala Ser Ser Pro Ser Ser Gly Pro Tyr Cys Gly Gly
    3575                3580                3585

Asp Thr Ser Ile Ala Pro Phe Val Ala Ser Ser Asn Gln Val Phe
    3590                3595                3600

Ile Lys Phe His Ala Asp Tyr Ala Arg Arg Pro Ser Ala Phe Arg
    3605                3610                3615

Leu Thr Trp Asp Ser
    3620

<210> SEQ ID NO 239
<211> LENGTH: 463
<212> TYPE: PRT
<213> ORGANISM: Homo sapiens

<400> SEQUENCE: 239

Met His Ser Ala Ser Ser Met Leu Gly Ala Val Lys Met Glu Gly His
1               5                   10                  15

Glu Pro Ser Asp Trp Ser Ser Tyr Tyr Ala Glu Pro Glu Gly Tyr Ser
                20                  25                  30

Ser Val Ser Asn Met Asn Ala Gly Leu Gly Met Asn Gly Met Asn Thr
            35                  40                  45

Tyr Met Ser Met Ser Ala Ala Met Gly Ser Gly Ser Gly Asn Met
    50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Gly Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
    210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255
```

```
Arg Gln Lys Arg Phe Lys Cys Glu Lys Gln Leu Ala Leu Lys Glu Ala
                260                 265                 270

Ala Gly Ala Ala Gly Ser Gly Lys Lys Ala Ala Gly Ala Gln Ala
            275                 280                 285

Ser Gln Ala Gln Leu Gly Glu Ala Ala Gly Pro Ala Ser Glu Thr Pro
        290                 295                 300

Ala Gly Thr Glu Ser Pro His Ser Ser Ala Ser Pro Cys Gln Glu His
305                 310                 315                 320

Lys Arg Gly Gly Leu Gly Glu Leu Lys Gly Thr Pro Ala Ala Ala Leu
                325                 330                 335

Ser Pro Pro Glu Pro Ala Pro Ser Pro Gly Gln Gln Gln Gln Ala Ala
                340                 345                 350

Ala His Leu Leu Gly Pro Pro His His Pro Gly Leu Pro Pro Glu Ala
            355                 360                 365

His Leu Lys Pro Glu His His Tyr Ala Phe Asn His Pro Phe Ser Ile
        370                 375                 380

Asn Asn Leu Met Ser Ser Glu Gln Gln His His Ser His His His
385                 390                 395                 400

His Gln Pro His Lys Met Asp Leu Lys Ala Tyr Glu Gln Val Met His
                405                 410                 415

Tyr Pro Gly Tyr Gly Ser Pro Met Pro Gly Ser Leu Ala Met Gly Pro
                420                 425                 430

Val Thr Asn Lys Thr Gly Leu Asp Ala Ser Pro Leu Ala Ala Asp Thr
            435                 440                 445

Ser Tyr Tyr Gln Gly Val Tyr Ser Arg Pro Ile Met Asn Ser Ser
        450                 455                 460

<210> SEQ ID NO 240
<211> LENGTH: 428
<212> TYPE: PRT
<213> ORGANISM: Mus musculus

<400> SEQUENCE: 240

Met Glu Arg Arg Arg Ile Thr Ser Ala Arg Ser Tyr Ala Ser Glu
1               5                   10                  15

Thr Val Val Arg Gly Leu Gly Pro Ser Arg Gln Leu Gly Thr Met Pro
                20                  25                  30

Arg Phe Ser Leu Ser Arg Met Thr Pro Pro Leu Pro Ala Arg Val Asp
            35                  40                  45

Phe Ser Leu Ala Gly Ala Leu Asn Ala Gly Phe Lys Glu Thr Arg Ala
        50                  55                  60

Ser Glu Arg Ala Glu Met Met Glu Leu Asn Asp Arg Phe Ala Ser Tyr
65                  70                  75                  80

Ile Glu Lys Val Arg Phe Leu Glu Gln Gln Asn Lys Ala Leu Ala Ala
                85                  90                  95

Glu Leu Asn Gln Leu Arg Ala Lys Glu Pro Thr Lys Leu Ala Asp Val
            100                 105                 110

Tyr Gln Ala Glu Leu Arg Glu Leu Arg Leu Arg Leu Asp Gln Leu Thr
        115                 120                 125

Ala Asn Ser Ala Arg Leu Glu Val Glu Arg Asp Asn Phe Ala Gln Asp
    130                 135                 140

Leu Gly Thr Leu Arg Gln Lys Leu Gln Asp Glu Thr Asn Leu Arg Leu
145                 150                 155                 160

Glu Ala Glu Asn Asn Leu Ala Ala Tyr Arg Gln Glu Ala Asp Glu Ala
                165                 170                 175
```

-continued

Thr Leu Ala Arg Val Asp Leu Glu Arg Lys Val Glu Ser Leu Glu Glu
            180                 185                 190

Glu Ile Gln Phe Leu Arg Lys Ile Tyr Glu Glu Val Arg Glu Leu
        195                 200                 205

Arg Glu Gln Leu Ala Gln Gln Val His Val Glu Met Asp Val Ala
    210                 215                 220

Lys Pro Asp Leu Thr Ala Ala Leu Arg Glu Ile Arg Thr Gln Tyr Glu
225                 230                 235                 240

Ala Val Ala Thr Ser Asn Met Gln Glu Thr Glu Glu Trp Tyr Arg Ser
                245                 250                 255

Lys Phe Ala Asp Leu Thr Asp Ala Ala Ser Arg Asn Ala Glu Leu Leu
                260                 265                 270

Arg Gln Ala Lys His Glu Ala Asn Asp Tyr Arg Arg Gln Leu Gln Ala
            275                 280                 285

Leu Thr Cys Asp Leu Glu Ser Leu Arg Gly Thr Asn Glu Ser Leu Glu
        290                 295                 300

Arg Gln Met Arg Glu Gln Glu Glu Arg His Ala Arg Glu Ser Ala Ser
305                 310                 315                 320

Tyr Gln Glu Ala Leu Ala Arg Leu Glu Glu Glu Gly Gln Ser Leu Lys
                325                 330                 335

Glu Glu Met Ala Arg His Leu Gln Glu Tyr Gln Asp Leu Leu Asn Val
                340                 345                 350

Lys Leu Ala Leu Asp Ile Glu Ile Ala Thr Tyr Arg Lys Leu Leu Glu
            355                 360                 365

Gly Glu Glu Asn Arg Ile Thr Ile Pro Val Gln Thr Phe Ser Asn Leu
        370                 375                 380

Gln Ile Arg Gly Gly Lys Ser Thr Lys Glu Gly Glu Gly Gln Lys Val
385                 390                 395                 400

Thr Arg Pro Leu Lys Arg Leu Thr Ile Gln Val Val Pro Ile Gln Ala
                405                 410                 415

His Gln Ile Glu Asn Gly Ala Leu Pro Ala Leu Pro
            420                 425

<210> SEQ ID NO 241
<211> LENGTH: 4655
<212> TYPE: PRT
<213> ORGANISM: Homo sapiens

<400> SEQUENCE: 241

Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
        35                  40                  45

Gly Thr Lys Asp Cys Ser Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Asn Ser Trp Val Cys Asp Gln Asp Gln Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp

-continued

```
            115                 120                 125
His Val Arg Asp Cys Pro Asp Gly Ala Asp Glu Asn Asp Cys Gln Tyr
        130                 135                 140
Pro Thr Cys Glu Gln Leu Thr Cys Asp Asn Gly Ala Cys Tyr Asn Thr
145                 150                 155                 160
Ser Gln Lys Cys Asp Trp Lys Val Asp Cys Arg Asp Ser Ser Asp Glu
                165                 170                 175
Ile Asn Cys Thr Glu Ile Cys Leu His Asn Glu Phe Ser Cys Gly Asn
                180                 185                 190
Gly Glu Cys Ile Pro Arg Ala Tyr Val Cys Asp His Asp Asn Asp Cys
            195                 200                 205
Gln Asp Gly Ser Asp Glu His Ala Cys Asn Tyr Pro Thr Cys Gly Gly
        210                 215                 220
Tyr Gln Phe Thr Cys Pro Ser Gly Arg Cys Ile Tyr Gln Asn Trp Val
225                 230                 235                 240
Cys Asp Gly Glu Asp Asp Cys Lys Asp Asn Gly Asp Glu Asp Gly Cys
                245                 250                 255
Glu Ser Gly Pro His Asp Val His Lys Cys Ser Pro Arg Glu Trp Ser
                260                 265                 270
Cys Pro Glu Ser Gly Arg Cys Ile Ser Ile Tyr Lys Val Cys Asp Gly
            275                 280                 285
Ile Leu Asp Cys Pro Gly Arg Glu Asp Glu Asn Asn Thr Ser Thr Gly
        290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
                325                 330                 335
Ile Ile Asn His Asn Asp Ser Arg Thr Cys Val Glu Phe Asp Asp Cys
            340                 345                 350
Gln Ile Trp Gly Ile Cys Asp Gln Lys Cys Glu Ser Arg Pro Gly Arg
        355                 360                 365
His Leu Cys His Cys Glu Glu Gly Tyr Ile Leu Glu Arg Gly Gln Tyr
        370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
                405                 410                 415
Leu Val Glu Ser Gln Asn Arg Gly Val Ala Val Gly Val Ala Phe His
                420                 425                 430
Tyr His Leu Gln Arg Val Phe Trp Thr Asp Thr Val Gln Asn Lys Val
            435                 440                 445
Phe Ser Val Asp Ile Asn Gly Leu Asn Ile Gln Glu Val Leu Asn Val
        450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
                485                 490                 495
Asp Gly Ser Tyr Arg Val Thr Leu Ile Thr Glu Asn Leu Gly His Pro
                500                 505                 510
Arg Gly Ile Ala Val Asp Pro Thr Val Gly Tyr Leu Phe Phe Ser Asp
            515                 520                 525
Trp Glu Ser Leu Ser Gly Glu Pro Lys Leu Glu Arg Ala Phe Met Asp
        530                 535                 540
```

```
Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
            565                 570                 575

Arg Phe Asp Tyr Ile Glu Thr Val Thr Tyr Asp Gly Ile Gln Arg Lys
                580                 585                 590

Thr Val Val His Gly Gly Ser Leu Ile Pro His Pro Phe Gly Val Ser
            595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
            645                 650                 655

Pro Tyr Ala Thr Asn Pro Cys Lys Asp Asn Asn Gly Gly Cys Glu Gln
                660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Val Gly Ile Asp Phe Asp Ala Gln Asp
            740                 745                 750

Ser Thr Ile Phe Phe Ser Asp Met Ser Lys His Met Ile Phe Lys Gln
            755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
            885                 890                 895

Ser Thr Phe Asp Gly Leu Asp Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
            930                 935                 940

Gly Glu Met Thr Val Ile Arg Ser Gly Ile Ala Tyr Ile Leu His Leu
945                 950                 955                 960
```

-continued

Lys Ser Tyr Asp Val Asn Ile Gln Thr Gly Ser Asn Ala Cys Asn Gln
            965                 970                 975

Pro Thr His Pro Asn Gly Asp Cys Ser His Phe Cys Phe Pro Val Pro
        980                 985                 990

Asn Phe Gln Arg Val Cys Gly Cys Pro Tyr Gly Met Arg Leu Ala Ser
        995                 1000                1005

Asn His Leu Thr Cys Glu Gly Asp Pro Thr Asn Glu Pro Pro Thr
    1010                1015                1020

Glu Gln Cys Gly Leu Phe Ser Phe Pro Cys Lys Asn Gly Arg Cys
    1025                1030                1035

Val Pro Asn Tyr Tyr Leu Cys Asp Gly Val Asp Asp Cys His Asp
    1040                1045                1050

Asn Ser Asp Glu Gln Leu Cys Gly Thr Leu Asn Asn Thr Cys Ser
    1055                1060                1065

Ser Ser Ala Phe Thr Cys Gly His Gly Glu Cys Ile Pro Ala His
    1070                1075                1080

Trp Arg Cys Asp Lys Arg Asn Asp Cys Val Asp Gly Ser Asp Glu
    1085                1090                1095

His Asn Cys Pro Thr His Ala Pro Ala Ser Cys Leu Asp Thr Gln
    1100                1105                1110

Tyr Thr Cys Asp Asn His Gln Cys Ile Ser Lys Asn Trp Val Cys
    1115                1120                1125

Asp Thr Asp Asn Asp Cys Gly Asp Gly Ser Asp Glu Lys Asn Cys
    1130                1135                1140

Asn Ser Thr Glu Thr Cys Gln Pro Ser Gln Phe Asn Cys Pro Asn
    1145                1150                1155

His Arg Cys Ile Asp Leu Ser Phe Val Cys Asp Gly Asp Lys Asp
    1160                1165                1170

Cys Val Asp Gly Ser Asp Glu Val Gly Cys Val Leu Asn Cys Thr
    1175                1180                1185

Ala Ser Gln Phe Lys Cys Ala Ser Gly Asp Lys Cys Ile Gly Val
    1190                1195                1200

Thr Asn Arg Cys Asp Gly Val Phe Asp Cys Ser Asp Asn Ser Asp
    1205                1210                1215

Glu Ala Gly Cys Pro Thr Arg Pro Pro Gly Met Cys His Ser Asp
    1220                1225                1230

Glu Phe Gln Cys Gln Glu Asp Gly Ile Cys Ile Pro Asn Phe Trp
    1235                1240                1245

Glu Cys Asp Gly His Pro Asp Cys Leu Tyr Gly Ser Asp Glu His
    1250                1255                1260

Asn Ala Cys Val Pro Lys Thr Cys Pro Ser Ser Tyr Phe His Cys
    1265                1270                1275

Asp Asn Gly Asn Cys Ile His Arg Ala Trp Leu Cys Asp Arg Asp
    1280                1285                1290

Asn Asp Cys Gly Asp Met Ser Asp Glu Lys Asp Cys Pro Thr Gln
    1295                1300                1305

Pro Phe Arg Cys Pro Ser Trp Gln Trp Gln Cys Leu Gly His Asn
    1310                1315                1320

Ile Cys Val Asn Leu Ser Val Val Cys Asp Gly Ile Phe Asp Cys
    1325                1330                1335

Pro Asn Gly Thr Asp Glu Ser Pro Leu Cys Asn Gly Asn Ser Cys
    1340                1345                1350

Ser Asp Phe Asn Gly Gly Cys Thr His Glu Cys Val Gln Glu Pro

```
            1355                1360                1365

Phe Gly Ala Lys Cys Leu Cys Pro Leu Gly Phe Leu Leu Ala Asn
            1370                1375                1380

Asp Ser Lys Thr Cys Glu Asp Ile Asp Glu Cys Asp Ile Leu Gly
            1385                1390                1395

Ser Cys Ser Gln His Cys Tyr Asn Met Arg Gly Ser Phe Arg Cys
            1400                1405                1410

Ser Cys Asp Thr Gly Tyr Met Leu Glu Ser Asp Gly Arg Thr Cys
            1415                1420                1425

Lys Val Thr Ala Ser Glu Ser Leu Leu Leu Val Ala Ser Gln
            1430                1435                1440

Asn Lys Ile Ile Ala Asp Ser Val Thr Ser Gln Val His Asn Ile
            1445                1450                1455

Tyr Ser Leu Val Glu Asn Gly Ser Tyr Ile Val Ala Val Asp Phe
            1460                1465                1470

Asp Ser Ile Ser Gly Arg Ile Phe Trp Ser Asp Ala Thr Gln Gly
            1475                1480                1485

Lys Thr Trp Ser Ala Phe Gln Asn Gly Thr Asp Arg Arg Val Val
            1490                1495                1500

Phe Asp Ser Ser Ile Ile Leu Thr Glu Thr Ile Ala Ile Asp Trp
            1505                1510                1515

Val Gly Arg Asn Leu Tyr Trp Thr Asp Tyr Ala Leu Glu Thr Ile
            1520                1525                1530

Glu Val Ser Lys Ile Asp Gly Ser His Arg Thr Val Leu Ile Ser
            1535                1540                1545

Lys Asn Leu Thr Asn Pro Arg Gly Leu Ala Leu Asp Pro Arg Met
            1550                1555                1560

Asn Glu His Leu Leu Phe Trp Ser Asp Trp Gly His His Pro Arg
            1565                1570                1575

Ile Glu Arg Ala Ser Met Asp Gly Ser Met Arg Thr Val Ile Val
            1580                1585                1590

Gln Asp Lys Ile Phe Trp Pro Cys Gly Leu Thr Ile Asp Tyr Pro
            1595                1600                1605

Asn Arg Leu Leu Tyr Phe Met Asp Ser Tyr Leu Asp Tyr Met Asp
            1610                1615                1620

Phe Cys Asp Tyr Asn Gly His His Arg Arg Gln Val Ile Ala Ser
            1625                1630                1635

Asp Leu Ile Ile Arg His Pro Tyr Ala Leu Thr Leu Phe Glu Asp
            1640                1645                1650

Ser Val Tyr Trp Thr Asp Arg Ala Thr Arg Arg Val Met Arg Ala
            1655                1660                1665

Asn Lys Trp His Gly Gly Asn Gln Ser Val Val Met Tyr Asn Ile
            1670                1675                1680

Gln Trp Pro Leu Gly Ile Val Ala Val His Pro Ser Lys Gln Pro
            1685                1690                1695

Asn Ser Val Asn Pro Cys Ala Phe Ser Arg Cys Ser His Leu Cys
            1700                1705                1710

Leu Leu Ser Ser Gln Gly Pro His Phe Tyr Ser Cys Val Cys Pro
            1715                1720                1725

Ser Gly Trp Ser Leu Ser Pro Asp Leu Leu Asn Cys Leu Arg Asp
            1730                1735                1740

Asp Gln Pro Phe Leu Ile Thr Val Arg Gln His Ile Ile Phe Gly
            1745                1750                1755
```

-continued

```
Ile Ser Leu Asn Pro Glu Val Lys Ser Asn Asp Ala Met Val Pro
    1760            1765            1770

Ile Ala Gly Ile Gln Asn Gly Leu Asp Val Glu Phe Asp Asp Ala
    1775            1780            1785

Glu Gln Tyr Ile Tyr Trp Val Glu Asn Pro Gly Glu Ile His Arg
    1790            1795            1800

Val Lys Thr Asp Gly Thr Asn Arg Thr Val Phe Ala Ser Ile Ser
    1805            1810            1815

Met Val Gly Pro Ser Met Asn Leu Ala Leu Asp Trp Ile Ser Arg
    1820            1825            1830

Asn Leu Tyr Ser Thr Asn Pro Arg Thr Gln Ser Ile Glu Val Leu
    1835            1840            1845

Thr Leu His Gly Asp Ile Arg Tyr Arg Lys Thr Leu Ile Ala Asn
    1850            1855            1860

Asp Gly Thr Ala Leu Gly Val Gly Phe Pro Ile Gly Ile Thr Val
    1865            1870            1875

Asp Pro Ala Arg Gly Lys Leu Tyr Trp Ser Asp Gln Gly Thr Asp
    1880            1885            1890

Ser Gly Val Pro Ala Lys Ile Ala Ser Ala Asn Met Asp Gly Thr
    1895            1900            1905

Ser Val Lys Thr Leu Phe Thr Gly Asn Leu Glu His Leu Glu Cys
    1910            1915            1920

Val Thr Leu Asp Ile Glu Glu Gln Lys Leu Tyr Trp Ala Val Thr
    1925            1930            1935

Gly Arg Gly Val Ile Glu Arg Gly Asn Val Asp Gly Thr Asp Arg
    1940            1945            1950

Met Ile Leu Val His Gln Leu Ser His Pro Trp Gly Ile Ala Val
    1955            1960            1965

His Asp Ser Phe Leu Tyr Tyr Thr Asp Glu Gln Tyr Glu Val Ile
    1970            1975            1980

Glu Arg Val Asp Lys Ala Thr Gly Ala Asn Lys Ile Val Leu Arg
    1985            1990            1995

Asp Asn Val Pro Asn Leu Arg Gly Leu Gln Val Tyr His Arg Arg
    2000            2005            2010

Asn Ala Ala Glu Ser Ser Asn Gly Cys Ser Asn Asn Met Asn Ala
    2015            2020            2025

Cys Gln Gln Ile Cys Leu Pro Val Pro Gly Gly Leu Phe Ser Cys
    2030            2035            2040

Ala Cys Ala Thr Gly Phe Lys Leu Asn Pro Asp Asn Arg Ser Cys
    2045            2050            2055

Ser Pro Tyr Asn Ser Phe Ile Val Val Ser Met Leu Ser Ala Ile
    2060            2065            2070

Arg Gly Phe Ser Leu Glu Leu Ser Asp His Ser Glu Thr Met Val
    2075            2080            2085

Pro Val Ala Gly Gln Gly Arg Asn Ala Leu His Val Asp Val Asp
    2090            2095            2100

Val Ser Ser Gly Phe Ile Tyr Trp Cys Asp Phe Ser Ser Ser Val
    2105            2110            2115

Ala Ser Asp Asn Ala Ile Arg Arg Ile Lys Pro Asp Gly Ser Ser
    2120            2125            2130

Leu Met Asn Ile Val Thr His Gly Ile Gly Glu Asn Gly Val Arg
    2135            2140            2145
```

```
Gly Ile Ala Val Asp Trp Val Ala Gly Asn Leu Tyr Phe Thr Asn
            2150                2155                2160

Ala Phe Val Ser Glu Thr Leu Ile Glu Val Leu Arg Ile Asn Thr
    2165                2170                2175

Thr Tyr Arg Arg Val Leu Leu Lys Val Thr Val Asp Met Pro Arg
    2180                2185                2190

His Ile Val Val Asp Pro Lys Asn Arg Tyr Leu Phe Trp Ala Asp
    2195                2200                2205

Tyr Gly Gln Arg Pro Lys Ile Glu Arg Ser Phe Leu Asp Cys Thr
    2210                2215                2220

Asn Arg Thr Val Leu Val Ser Glu Gly Ile Val Thr Pro Arg Gly
    2225                2230                2235

Leu Ala Val Asp Arg Ser Asp Gly Tyr Val Tyr Trp Val Asp Asp
    2240                2245                2250

Ser Leu Asp Ile Ile Ala Arg Ile Arg Ile Asn Gly Glu Asn Ser
    2255                2260                2265

Glu Val Ile Arg Tyr Gly Ser Arg Tyr Pro Thr Pro Tyr Gly Ile
    2270                2275                2280

Thr Val Phe Glu Asn Ser Ile Ile Trp Val Asp Arg Asn Leu Lys
    2285                2290                2295

Lys Ile Phe Gln Ala Ser Lys Glu Pro Glu Asn Thr Glu Pro Pro
    2300                2305                2310

Thr Val Ile Arg Asp Asn Ile Asn Trp Leu Arg Asp Val Thr Ile
    2315                2320                2325

Phe Asp Lys Gln Val Gln Pro Arg Ser Pro Ala Glu Val Asn Asn
    2330                2335                2340

Asn Pro Cys Leu Glu Asn Asn Gly Gly Cys Ser His Leu Cys Phe
    2345                2350                2355

Ala Leu Pro Gly Leu His Thr Pro Lys Cys Asp Cys Ala Phe Gly
    2360                2365                2370

Thr Leu Gln Ser Asp Gly Lys Asn Cys Ala Ile Ser Thr Glu Asn
    2375                2380                2385

Phe Leu Ile Phe Ala Leu Ser Asn Ser Leu Arg Ser Leu His Leu
    2390                2395                2400

Asp Pro Glu Asn His Ser Pro Pro Phe Gln Thr Ile Asn Val Glu
    2405                2410                2415

Arg Thr Val Met Ser Leu Asp Tyr Asp Ser Val Ser Asp Arg Ile
    2420                2425                2430

Tyr Phe Thr Gln Asn Leu Ala Ser Gly Val Gly Gln Ile Ser Tyr
    2435                2440                2445

Ala Thr Leu Ser Ser Gly Ile His Thr Pro Thr Val Ile Ala Ser
    2450                2455                2460

Gly Ile Gly Thr Ala Asp Gly Ile Ala Phe Asp Trp Ile Thr Arg
    2465                2470                2475

Arg Ile Tyr Tyr Ser Asp Tyr Leu Asn Gln Met Ile Asn Ser Met
    2480                2485                2490

Ala Glu Asp Gly Ser Asn Arg Thr Val Ile Ala Arg Val Pro Lys
    2495                2500                2505

Pro Arg Ala Ile Val Leu Asp Pro Cys Gln Gly Tyr Leu Tyr Trp
    2510                2515                2520

Ala Asp Trp Asp Thr His Ala Lys Ile Glu Arg Ala Thr Leu Gly
    2525                2530                2535

Gly Asn Phe Arg Val Pro Ile Val Asn Ser Ser Leu Val Met Pro
```

-continued

```
                    2540                2545                2550
Ser Gly Leu Thr Leu Asp Tyr Glu Glu Asp Leu Leu Tyr Trp Val
    2555                2560                2565
Asp Ala Ser Leu Gln Arg Ile Glu Arg Ser Thr Leu Thr Gly Val
    2570                2575                2580
Asp Arg Glu Val Ile Val Asn Ala Ala Val His Ala Phe Gly Leu
    2585                2590                2595
Thr Leu Tyr Gly Gln Tyr Ile Tyr Trp Thr Asp Leu Tyr Thr Gln
    2600                2605                2610
Arg Ile Tyr Arg Ala Asn Lys Tyr Asp Gly Ser Gly Gln Ile Ala
    2615                2620                2625
Met Thr Thr Asn Leu Leu Ser Gln Pro Arg Gly Ile Asn Thr Val
    2630                2635                2640
Val Lys Asn Gln Lys Gln Cys Asn Asn Pro Cys Glu Gln Phe
    2645                2650                2655
Asn Gly Gly Cys Ser His Ile Cys Ala Pro Gly Pro Asn Gly Ala
    2660                2665                2670
Glu Cys Gln Cys Pro His Glu Gly Asn Trp Tyr Leu Ala Asn Asn
    2675                2680                2685
Arg Lys His Cys Ile Val Asp Asn Gly Glu Arg Cys Gly Ala Ser
    2690                2695                2700
Ser Phe Thr Cys Ser Asn Gly Arg Cys Ile Ser Glu Glu Trp Lys
    2705                2710                2715
Cys Asp Asn Asp Asn Asp Cys Gly Asp Gly Ser Asp Glu Met Glu
    2720                2725                2730
Ser Val Cys Ala Leu His Thr Cys Ser Pro Thr Ala Phe Thr Cys
    2735                2740                2745
Ala Asn Gly Arg Cys Val Gln Tyr Ser Tyr Arg Cys Asp Tyr Tyr
    2750                2755                2760
Asn Asp Cys Gly Asp Gly Ser Asp Glu Ala Gly Cys Leu Phe Arg
    2765                2770                2775
Asp Cys Asn Ala Thr Thr Glu Phe Met Cys Asn Asn Arg Arg Cys
    2780                2785                2790
Ile Pro Arg Glu Phe Ile Cys Asn Gly Val Asp Asn Cys His Asp
    2795                2800                2805
Asn Asn Thr Ser Asp Glu Lys Asn Cys Pro Asp Arg Thr Cys Gln
    2810                2815                2820
Ser Gly Tyr Thr Lys Cys His Asn Ser Asn Ile Cys Ile Pro Arg
    2825                2830                2835
Val Tyr Leu Cys Asp Gly Asp Asn Asp Cys Gly Asp Asn Ser Asp
    2840                2845                2850
Glu Asn Pro Thr Tyr Cys Thr Thr His Thr Cys Ser Ser Ser Glu
    2855                2860                2865
Phe Gln Cys Ala Ser Gly Arg Cys Ile Pro Gln His Trp Tyr Cys
    2870                2875                2880
Asp Gln Glu Thr Asp Cys Phe Asp Ala Ser Asp Glu Pro Ala Ser
    2885                2890                2895
Cys Gly His Ser Glu Arg Thr Cys Leu Ala Asp Glu Phe Lys Cys
    2900                2905                2910
Asp Gly Gly Arg Cys Ile Pro Ser Glu Trp Ile Cys Asp Gly Asp
    2915                2920                2925
Asn Asp Cys Gly Asp Met Ser Asp Glu Asp Lys Arg His Gln Cys
    2930                2935                2940
```

```
Gln Asn Gln Asn Cys Ser Asp Ser Glu Phe Leu Cys Val Asn Asp
2945                2950                2955

Arg Pro Pro Asp Arg Arg Cys Ile Pro Gln Ser Trp Val Cys Asp
2960                2965                2970

Gly Asp Val Asp Cys Thr Asp Gly Tyr Asp Glu Asn Gln Asn Cys
2975                2980                2985

Thr Arg Arg Thr Cys Ser Glu Asn Glu Phe Thr Cys Gly Tyr Gly
2990                2995                3000

Leu Cys Ile Pro Lys Ile Phe Arg Cys Asp Arg His Asn Asp Cys
3005                3010                3015

Gly Asp Tyr Ser Asp Glu Arg Gly Cys Leu Tyr Gln Thr Cys Gln
3020                3025                3030

Gln Asn Gln Phe Thr Cys Gln Asn Gly Arg Cys Ile Ser Lys Thr
3035                3040                3045

Phe Val Cys Asp Glu Asp Asn Asp Cys Gly Asp Gly Ser Asp Glu
3050                3055                3060

Leu Met His Leu Cys His Thr Pro Glu Pro Thr Cys Pro Pro His
3065                3070                3075

Glu Phe Lys Cys Asp Asn Gly Arg Cys Ile Glu Met Met Lys Leu
3080                3085                3090

Cys Asn His Leu Asp Asp Cys Leu Asp Asn Ser Asp Glu Lys Gly
3095                3100                3105

Cys Gly Ile Asn Glu Cys His Asp Pro Ser Ile Ser Gly Cys Asp
3110                3115                3120

His Asn Cys Thr Asp Thr Leu Thr Ser Phe Tyr Cys Ser Cys Arg
3125                3130                3135

Pro Gly Tyr Lys Leu Met Ser Asp Lys Arg Thr Cys Val Asp Ile
3140                3145                3150

Asp Glu Cys Thr Glu Met Pro Phe Val Cys Ser Gln Lys Cys Glu
3155                3160                3165

Asn Val Ile Gly Ser Tyr Ile Cys Lys Cys Ala Pro Gly Tyr Leu
3170                3175                3180

Arg Glu Pro Asp Gly Lys Thr Cys Arg Gln Asn Ser Asn Ile Glu
3185                3190                3195

Pro Tyr Leu Ile Phe Ser Asn Arg Tyr Tyr Leu Arg Asn Leu Thr
3200                3205                3210

Ile Asp Gly Tyr Phe Tyr Ser Leu Ile Leu Glu Gly Leu Asp Asn
3215                3220                3225

Val Val Ala Leu Asp Phe Asp Arg Val Glu Lys Arg Leu Tyr Trp
3230                3235                3240

Ile Asp Thr Gln Arg Gln Val Ile Glu Arg Met Phe Leu Asn Lys
3245                3250                3255

Thr Asn Lys Glu Thr Ile Ile Asn His Arg Leu Pro Ala Ala Glu
3260                3265                3270

Ser Leu Ala Val Asp Trp Val Ser Arg Lys Leu Tyr Trp Leu Asp
3275                3280                3285

Ala Arg Leu Asp Gly Leu Phe Val Ser Asp Leu Asn Gly Gly His
3290                3295                3300

Arg Arg Met Leu Ala Gln His Cys Val Asp Ala Asn Asn Thr Phe
3305                3310                3315

Cys Phe Asp Asn Pro Arg Gly Leu Ala Leu His Pro Gln Tyr Gly
3320                3325                3330
```

-continued

| | | | | | | | | | | | |
|---|---|---|---|---|---|---|---|---|---|---|---|
|Tyr|Leu 3335|Tyr|Trp|Ala|Asp 3340|Trp|Gly|His|Arg|Ala 3345|Tyr|Ile|Gly|Arg|
|Val|Gly 3350|Met|Asp|Gly|Thr 3355|Asn|Lys|Ser|Val|Ile 3360|Ser|Thr|Lys|
|Leu|Glu 3365|Trp|Pro|Asn|Gly 3370|Ile|Thr|Ile|Asp|Tyr 3375|Thr|Asn|Asp|Leu|
|Leu|Tyr 3380|Trp|Ala|Asp|Ala 3385|His|Leu|Gly|Tyr|Ile 3390|Glu|Tyr|Ser|Asp|
|Leu|Glu 3395|Gly|His|His|Arg 3400|His|Thr|Val|Tyr|Asp 3405|Gly|Ala|Leu|Pro|
|His|Pro 3410|Phe|Ala|Ile|Thr 3415|Ile|Phe|Glu|Asp|Thr 3420|Ile|Tyr|Trp|Thr|
|Asp|Trp 3425|Asn|Thr|Arg|Thr 3430|Val|Glu|Lys|Gly|Asn 3435|Lys|Tyr|Asp|Gly|
|Ser|Asn 3440|Arg|Gln|Thr|Leu 3445|Val|Asn|Thr|Thr|His 3450|Arg|Pro|Phe|Asp|
|Ile|His 3455|Val|Tyr|His|Pro 3460|Tyr|Arg|Gln|Pro|Ile 3465|Val|Ser|Asn|Pro|
|Cys|Gly 3470|Thr|Asn|Asn|Gly 3475|Gly|Cys|Ser|His|Leu 3480|Cys|Leu|Ile|Lys|
|Pro|Gly 3485|Gly|Lys|Gly|Phe 3490|Thr|Cys|Glu|Cys|Pro 3495|Asp|Asp|Phe|Arg|
|Thr|Leu 3500|Gln|Leu|Ser|Gly 3505|Ser|Thr|Tyr|Cys|Met 3510|Pro|Met|Cys|Ser|
|Ser|Thr 3515|Gln|Phe|Leu|Cys 3520|Ala|Asn|Asn|Glu|Lys 3525|Cys|Ile|Pro|Ile|
|Trp|Trp 3530|Lys|Cys|Asp|Gly 3535|Gln|Lys|Asp|Cys|Ser 3540|Asp|Gly|Ser|Asp|
|Glu|Leu 3545|Ala|Leu|Cys|Pro 3550|Gln|Arg|Phe|Cys|Arg 3555|Leu|Gly|Gln|Phe|
|Gln|Cys 3560|Ser|Asp|Gly|Asn 3565|Cys|Thr|Ser|Pro|Gln 3570|Thr|Leu|Cys|Asn|
|Ala|His 3575|Gln|Asn|Cys|Pro 3580|Asp|Gly|Ser|Asp|Glu 3585|Asp|Arg|Leu|Leu|
|Cys|Glu 3590|Asn|His|His|Cys 3595|Asp|Ser|Asn|Glu|Trp 3600|Gln|Cys|Ala|Asn|
|Lys|Arg 3605|Cys|Ile|Pro|Glu 3610|Ser|Trp|Gln|Cys|Asp 3615|Thr|Phe|Asn|Asp|
|Cys|Glu 3620|Asp|Asn|Ser|Asp 3625|Glu|Asp|Ser|Ser|His 3630|Cys|Ala|Ser|Arg|
|Thr|Cys 3635|Arg|Pro|Gly|Gln 3640|Phe|Arg|Cys|Ala|Asn 3645|Gly|Arg|Cys|Ile|
|Pro|Gln 3650|Ala|Trp|Lys|Cys 3655|Asp|Val|Asp|Asn|Asp 3660|Cys|Gly|Asp|His|
|Ser|Asp 3665|Glu|Pro|Ile|Glu 3670|Glu|Cys|Met|Ser|Ser 3675|Ala|His|Leu|Cys|
|Asp|Asn 3680|Phe|Thr|Glu|Phe 3685|Ser|Cys|Lys|Thr|Asn 3690|Tyr|Arg|Cys|Ile|
|Pro|Lys 3695|Trp|Ala|Val|Cys 3700|Asn|Gly|Val|Asp|Asp 3705|Cys|Arg|Asp|Asn|
|Ser|Asp 3710|Glu|Gln|Gly|Cys 3715|Glu|Glu|Arg|Thr|Cys 3720|His|Pro|Val|Gly|
|Asp|Phe|Arg|Cys|Lys|Asn|His|His|Cys|Ile|Pro|Leu|Arg|Trp|Gln|

```
          3725                3730                3735
Cys Asp Gly Gln Asn Asp Cys Gly Asp Asn Ser Asp Glu Glu Asn
    3740                3745                3750

Cys Ala Pro Arg Glu Cys Thr Glu Ser Glu Phe Arg Cys Val Asn
    3755                3760                3765

Gln Gln Cys Ile Pro Ser Arg Trp Ile Cys Asp His Tyr Asn Asp
    3770                3775                3780

Cys Gly Asp Asn Ser Asp Glu Arg Asp Cys Glu Met Arg Thr Cys
    3785                3790                3795

His Pro Glu Tyr Phe Gln Cys Thr Ser Gly His Cys Val His Ser
    3800                3805                3810

Glu Leu Lys Cys Asp Gly Ser Ala Asp Cys Leu Asp Ala Ser Asp
    3815                3820                3825

Glu Ala Asp Cys Pro Thr Arg Phe Pro Asp Gly Ala Tyr Cys Gln
    3830                3835                3840

Ala Thr Met Phe Glu Cys Lys Asn His Val Cys Ile Pro Pro Tyr
    3845                3850                3855

Trp Lys Cys Asp Gly Asp Asp Cys Gly Asp Gly Ser Asp Glu
    3860                3865                3870

Glu Leu His Leu Cys Leu Asp Val Pro Cys Asn Ser Pro Asn Arg
    3875                3880                3885

Phe Arg Cys Asp Asn Asn Arg Cys Ile Tyr Ser His Glu Val Cys
    3890                3895                3900

Asn Gly Val Asp Asp Cys Gly Asp Gly Thr Asp Glu Thr Glu Glu
    3905                3910                3915

His Cys Arg Lys Pro Thr Pro Lys Pro Cys Thr Glu Tyr Glu Tyr
    3920                3925                3930

Lys Cys Gly Asn Gly His Cys Ile Pro His Asp Asn Val Cys Asp
    3935                3940                3945

Asp Ala Asp Asp Cys Gly Asp Trp Ser Asp Glu Leu Gly Cys Asn
    3950                3955                3960

Lys Gly Lys Glu Arg Thr Cys Ala Glu Asn Ile Cys Glu Gln Asn
    3965                3970                3975

Cys Thr Gln Leu Asn Glu Gly Gly Phe Ile Cys Ser Cys Thr Ala
    3980                3985                3990

Gly Phe Glu Thr Asn Val Phe Asp Arg Thr Ser Cys Leu Asp Ile
    3995                4000                4005

Asn Glu Cys Glu Gln Phe Gly Thr Cys Pro Gln His Cys Arg Asn
    4010                4015                4020

Thr Lys Gly Ser Tyr Glu Cys Val Cys Ala Asp Gly Phe Thr Ser
    4025                4030                4035

Met Ser Asp Arg Pro Gly Lys Arg Cys Ala Ala Glu Gly Ser Ser
    4040                4045                4050

Pro Leu Leu Leu Leu Pro Asp Asn Val Arg Ile Arg Lys Tyr Asn
    4055                4060                4065

Leu Ser Ser Glu Arg Phe Ser Glu Tyr Leu Gln Asp Glu Glu Tyr
    4070                4075                4080

Ile Gln Ala Val Asp Tyr Asp Trp Asp Pro Lys Asp Ile Gly Leu
    4085                4090                4095

Ser Val Val Tyr Tyr Thr Val Arg Gly Glu Gly Ser Arg Phe Gly
    4100                4105                4110

Ala Ile Lys Arg Ala Tyr Ile Pro Asn Phe Glu Ser Gly Arg Asn
    4115                4120                4125
```

```
Asn Leu Val Gln Glu Val Asp Leu Lys Leu Lys Tyr Val Met Gln
        4130                4135                4140

Pro Asp Gly Ile Ala Val Asp Trp Val Gly Arg His Ile Tyr Trp
        4145                4150                4155

Ser Asp Val Lys Asn Lys Arg Ile Glu Val Ala Lys Leu Asp Gly
        4160                4165                4170

Arg Tyr Arg Lys Trp Leu Ile Ser Thr Asp Leu Asp Gln Pro Ala
        4175                4180                4185

Ala Ile Ala Val Asn Pro Lys Leu Gly Leu Met Phe Trp Thr Asp
        4190                4195                4200

Trp Gly Lys Glu Pro Lys Ile Glu Ser Ala Trp Met Asn Gly Glu
        4205                4210                4215

Asp Arg Asn Ile Leu Val Phe Glu Asp Leu Gly Trp Pro Thr Gly
        4220                4225                4230

Leu Ser Ile Asp Tyr Leu Asn Asn Asp Arg Ile Tyr Trp Ser Asp
        4235                4240                4245

Phe Lys Glu Asp Val Ile Glu Thr Ile Lys Tyr Asp Gly Thr Asp
        4250                4255                4260

Arg Arg Val Ile Ala Lys Glu Ala Met Asn Pro Tyr Ser Leu Asp
        4265                4270                4275

Ile Phe Glu Asp Gln Leu Tyr Trp Ile Ser Lys Glu Lys Gly Glu
        4280                4285                4290

Val Trp Lys Gln Asn Lys Phe Gly Gln Gly Lys Lys Glu Lys Thr
        4295                4300                4305

Leu Val Val Asn Pro Trp Leu Thr Gln Val Arg Ile Phe His Gln
        4310                4315                4320

Leu Arg Tyr Asn Lys Ser Val Pro Asn Leu Cys Lys Gln Ile Cys
        4325                4330                4335

Ser His Leu Cys Leu Leu Arg Pro Gly Gly Tyr Ser Cys Ala Cys
        4340                4345                4350

Pro Gln Gly Ser Ser Phe Ile Glu Gly Ser Thr Thr Glu Cys Asp
        4355                4360                4365

Ala Ala Ile Glu Leu Pro Ile Asn Leu Pro Pro Pro Cys Arg Cys
        4370                4375                4380

Met His Gly Gly Asn Cys Tyr Phe Asp Glu Thr Asp Leu Pro Lys
        4385                4390                4395

Cys Lys Cys Pro Ser Gly Tyr Thr Gly Lys Tyr Cys Glu Met Ala
        4400                4405                4410

Phe Ser Lys Gly Ile Ser Pro Gly Thr Thr Ala Val Ala Val Leu
        4415                4420                4425

Leu Thr Ile Leu Leu Ile Val Val Ile Gly Ala Leu Ala Ile Ala
        4430                4435                4440

Gly Phe Phe His Tyr Arg Arg Thr Gly Ser Leu Leu Pro Ala Leu
        4445                4450                4455

Pro Lys Leu Pro Ser Leu Ser Ser Leu Val Lys Pro Ser Glu Asn
        4460                4465                4470

Gly Asn Gly Val Thr Phe Arg Ser Gly Ala Asp Leu Asn Met Asp
        4475                4480                4485

Ile Gly Val Ser Gly Phe Gly Pro Glu Thr Ala Ile Asp Arg Ser
        4490                4495                4500

Met Ala Met Ser Glu Asp Phe Val Met Glu Met Gly Lys Gln Pro
        4505                4510                4515
```

```
Ile Ile Phe Glu Asn Pro Met Tyr Ser Ala Arg Asp Ser Ala Val
    4520                4525                4530

Lys Val Val Gln Pro Ile Gln Val Thr Val Ser Glu Asn Val Asp
    4535                4540                4545

Asn Lys Asn Tyr Gly Ser Pro Ile Asn Pro Ser Glu Ile Val Pro
    4550                4555                4560

Glu Thr Asn Pro Thr Ser Pro Ala Ala Asp Gly Thr Gln Val Thr
    4565                4570                4575

Lys Trp Asn Leu Phe Lys Arg Lys Ser Lys Gln Thr Thr Asn Phe
    4580                4585                4590

Glu Asn Pro Ile Tyr Ala Gln Met Glu Asn Glu Gln Lys Glu Ser
    4595                4600                4605

Val Ala Ala Thr Pro Pro Pro Ser Pro Ser Leu Pro Ala Lys Pro
    4610                4615                4620

Lys Pro Pro Ser Arg Arg Asp Pro Thr Pro Thr Tyr Ser Ala Thr
    4625                4630                4635

Glu Asp Thr Phe Lys Asp Thr Ala Asn Leu Val Lys Glu Asp Ser
    4640                4645                4650

Glu Val
    4655

<210> SEQ ID NO 242
<211> LENGTH: 498
<212> TYPE: PRT
<213> ORGANISM: Mus musculus

<400> SEQUENCE: 242

Met Ala Asp Glu Arg Lys Asp Glu Gly Lys Ala Pro His Trp Thr Ser
1               5                   10                  15

Ala Ser Leu Thr Glu Ala Ala His Pro His Ser Pro Glu Met Lys
                20                  25                  30

Asp Gln Gly Gly Ala Gly Glu Gly Leu Ser Arg Asn Ala Asn Gly Phe
            35                  40                  45

Pro Tyr Arg Glu Glu Glu Gly Ala Phe Gly Glu His Arg Ser Gln
    50                  55                  60

Gly Thr Tyr Ser Asp Thr Lys Glu Asn Gly Ile Asn Gly Glu Leu Thr
65                  70                  75                  80

Ser Ala Asp Arg Glu Thr Ala Glu Val Ser Ala Arg Ile Val Gln
                85                  90                  95

Val Val Thr Ala Glu Ala Val Ala Val Leu Lys Gly Glu Gln Glu Lys
                100                 105                 110

Glu Ala Gln His Lys Asp Gln Pro Ala Ala Leu Pro Leu Ala Ala Glu
            115                 120                 125

Glu Thr Ala Asn Leu Pro Pro Ser Pro Pro Pro Ser Pro Ala Ser Glu
        130                 135                 140

Gln Thr Ala Thr Val Glu Glu Ala Ala Ser Gly Asp Leu Ala Gln Ala
145                 150                 155                 160

Pro Gly Ala Phe Lys Gln Ala Lys Asp Lys Val Thr Asp Gly Ile Ser
                165                 170                 175

Lys Ser Pro Glu Lys Arg Ser Leu Pro Arg Pro Ser Ser Ile Leu
                180                 185                 190

Pro Pro Arg Arg Gly Val Ser Gly Asp Arg Glu Glu Asn Ser Phe Ser
            195                 200                 205

Leu Asn Ser Ser Ile Ser Ser Ala Arg Arg Thr Thr Arg Ser Glu Pro
        210                 215                 220
```

```
Ile Arg Arg Ala Gly Lys Ser Gly Thr Ser Thr Pro Thr Thr Pro Gly
225                 230                 235                 240

Ser Thr Ala Ile Thr Pro Gly Thr Pro Pro Ser Tyr Ser Ser Arg Thr
            245                 250                 255

Pro Gly Thr Pro Gly Thr Pro Ser Tyr Pro Arg Thr Pro Gly Thr Pro
        260                 265                 270

Lys Ser Gly Ile Leu Val Pro Ser Glu Lys Val Ala Ile Ile Arg
        275                 280                 285

Thr Pro Pro Lys Ser Pro Ala Thr Pro Lys Gln Leu Arg Leu Ile Asn
290                 295                 300

Gln Pro Leu Pro Asp Leu Lys Asn Val Lys Ser Lys Ile Gly Ser Thr
305                 310                 315                 320

Asp Asn Ile Lys Tyr Gln Pro Lys Gly Gly Gln Val Arg Ile Leu Asn
                325                 330                 335

Lys Lys Ile Asp Phe Ser Lys Val Gln Ser Arg Cys Gly Ser Lys Asp
                340                 345                 350

Asn Ile Lys His Ser Ala Gly Gly Asn Val Gln Ile Val Thr Lys
            355                 360                 365

Lys Ile Asp Leu Ser His Val Thr Ser Lys Cys Gly Ser Leu Lys Asn
        370                 375                 380

Ile Arg His Arg Pro Gly Gly Gly Arg Val Lys Ile Glu Ser Val Lys
385                 390                 395                 400

Leu Asp Phe Lys Glu Lys Ala Gln Ala Lys Val Gly Ser Leu Asp Asn
                405                 410                 415

Ala His His Val Pro Gly Gly Gly Asn Val Lys Ile Asp Ser Gln Lys
            420                 425                 430

Leu Asn Phe Arg Glu His Ala Lys Ala Arg Val Asp His Gly Ala Glu
        435                 440                 445

Ile Ile Thr Gln Ser Pro Ser Arg Ser Ser Val Ala Ser Pro Arg Arg
450                 455                 460

Leu Ser Asn Val Ser Ser Ser Gly Ser Ile Asn Leu Leu Glu Ser Pro
465                 470                 475                 480

Gln Leu Ala Thr Leu Ala Glu Asp Val Thr Ala Ala Leu Ala Lys Gln
                485                 490                 495

Gly Leu

<210> SEQ ID NO 243
<211> LENGTH: 195
<212> TYPE: PRT
<213> ORGANISM: Mus musculus

<400> SEQUENCE: 243

Met Gly Asn His Ser Gly Lys Arg Glu Leu Ser Ala Glu Lys Ala Ser
1               5                   10                  15

Lys Asp Gly Glu Ile His Arg Gly Glu Ala Gly Lys Lys Arg Ser Val
            20                  25                  30

Gly Lys Leu Ser Gln Thr Ala Ser Glu Asp Ser Asp Val Phe Gly Glu
        35                  40                  45

Ala Asp Ala Ile Gln Asn Asn Gly Thr Ser Ala Glu Asp Thr Ala Val
    50                  55                  60

Thr Asp Ser Lys His Thr Ala Asp Pro Lys Asn Asn Trp Gln Gly Ala
65                  70                  75                  80

His Pro Ala Asp Pro Gly Asn Arg Pro His Leu Ile Arg Leu Phe Ser
                85                  90                  95
```

```
Arg Asp Ala Pro Gly Arg Glu Asp Asn Thr Phe Lys Asp Arg Pro Ser
                100                 105                 110

Glu Ser Asp Glu Leu Gln Thr Ile Gln Glu Asp Pro Thr Ala Ala Ser
        115                 120                 125

Gly Gly Leu Asp Val Met Ala Ser Gln Lys Arg Pro Ser Gln Arg Ser
130                 135                 140

Lys Tyr Leu Ala Thr Ala Ser Thr Met Asp His Ala Arg His Gly Phe
145                 150                 155                 160

Leu Pro Arg His Arg Asp Thr Gly Ile Leu Asp Ser Ile Gly Arg Phe
                165                 170                 175

Phe Ser Gly Asp Arg Gly Ala Pro Lys Arg Gly Ser Gly Lys Val Ser
                180                 185                 190

Ser Glu Pro
        195

<210> SEQ ID NO 244
<211> LENGTH: 303
<212> TYPE: PRT
<213> ORGANISM: Homo sapiens

<400> SEQUENCE: 244

Met Ala Pro Ala Ala Asp Met Thr Ser Leu Pro Leu Gly Val Lys Val
1               5                   10                  15

Glu Asp Ser Ala Phe Gly Lys Pro Ala Gly Gly Ala Gly Gln Ala
                20                  25                  30

Pro Ser Ala Ala Ala Thr Ala Ala Met Gly Ala Asp Glu Glu
        35                  40                  45

Gly Ala Lys Pro Lys Val Ser Pro Ser Leu Leu Pro Phe Ser Val Glu
    50                  55                  60

Ala Leu Met Ala Asp His Arg Lys Pro Gly Ala Lys Glu Ser Ala Leu
65                  70                  75                  80

Ala Pro Ser Glu Gly Val Gln Ala Gly Gly Ser Ala Gln Pro Leu
                85                  90                  95

Gly Val Pro Pro Gly Ser Leu Gly Ala Pro Asp Ala Pro Ser Ser Pro
                100                 105                 110

Arg Pro Leu Gly His Phe Ser Val Gly Gly Leu Leu Lys Leu Pro Glu
        115                 120                 125

Asp Ala Leu Val Lys Ala Glu Ser Pro Glu Lys Pro Glu Arg Thr Pro
    130                 135                 140

Trp Met Gln Ser Pro Arg Phe Ser Pro Pro Ala Arg Arg Leu Ser
145                 150                 155                 160

Pro Pro Ala Cys Thr Leu Arg Lys His Lys Thr Asn Arg Lys Pro Arg
                165                 170                 175

Thr Pro Phe Thr Thr Ala Gln Leu Leu Ala Leu Glu Arg Lys Phe Arg
                180                 185                 190

Gln Lys Gln Tyr Leu Ser Ile Ala Glu Arg Ala Glu Phe Ser Ser Ser
        195                 200                 205

Leu Ser Leu Thr Glu Thr Gln Val Lys Ile Trp Phe Gln Asn Arg Arg
    210                 215                 220

Ala Lys Ala Lys Arg Leu Gln Glu Ala Glu Leu Glu Lys Leu Lys Met
225                 230                 235                 240

Ala Ala Lys Pro Met Leu Pro Pro Ala Ala Phe Gly Leu Ser Phe Pro
                245                 250                 255

Leu Gly Gly Pro Ala Ala Val Ala Ala Ala Ala Gly Ala Ser Leu Tyr
```

```
                    260                 265                 270
Gly Ala Ser Gly Pro Phe Gln Arg Ala Ala Leu Pro Val Ala Pro Val
                275                 280                 285

Gly Leu Tyr Thr Ala His Val Gly Tyr Ser Met Tyr His Leu Thr
        290                 295                 300

<210> SEQ ID NO 245
<211> LENGTH: 313
<212> TYPE: PRT
<213> ORGANISM: Mus musculus

<400> SEQUENCE: 245

Met Ala Gln Pro Tyr Pro Pro Ala Gln Tyr Pro Pro Pro Gln Asn
1               5                   10                  15

Gly Ile Pro Ala Glu Tyr Ala Pro Pro Pro His Pro Thr Gln Asp
                20                  25                  30

Tyr Ser Gly Gln Thr Pro Val Pro Pro Glu His Gly Met Thr Leu Tyr
            35                  40                  45

Thr Pro Ala Gln Thr His Pro Glu Gln Pro Gly Thr Glu Ala Ser Thr
50                  55                  60

Gln Pro Ile Ala Gly Thr Gln Thr Val Pro Gln Ala Asp Glu Ala Ala
65                  70                  75                  80

Gln Thr Asp Asn Gln Gln Leu His Pro Ser Asp Pro Thr Glu Lys Gln
                85                  90                  95

Gln Pro Lys Arg Leu His Val Ser Asn Ile Pro Phe Arg Phe Arg Asp
                100                 105                 110

Pro Asp Leu Arg Gln Met Phe Gly Gln Phe Gly Lys Ile Leu Asp Val
                115                 120                 125

Glu Ile Ile Phe Asn Glu Arg Gly Ser Lys Gly Phe Gly Phe Val Thr
                130                 135                 140

Phe Glu Thr Ser Ser Asp Ala Asp Arg Ala Arg Glu Lys Leu Asn Gly
145                 150                 155                 160

Thr Ile Val Glu Gly Arg Lys Ile Glu Val Asn Asn Ala Thr Ala Arg
                165                 170                 175

Val Met Thr Asn Lys Lys Pro Gly Asn Pro Tyr Ala Asn Gly Trp Lys
                180                 185                 190

Leu Asn Pro Val Val Gly Thr Val Tyr Gly Pro Glu Phe Tyr Ala Val
                195                 200                 205

Thr Ser Phe Pro Tyr Pro Thr Thr Gly Thr Ala Val Ala Tyr Arg Gly
                210                 215                 220

Ala His Leu Arg Gly Arg Gly Arg Ala Val Tyr Asn Thr Phe Arg Ala
225                 230                 235                 240

Ala Pro Pro Pro Pro Ile Pro Thr Tyr Gly Ala Val Val Tyr Gln
                245                 250                 255

Asp Gly Phe Tyr Gly Ala Glu Ile Tyr Gly Gly Tyr Ala Ala Tyr Arg
                260                 265                 270

Tyr Ala Gln Pro Ala Ala Ala Thr Ala Ala Tyr Ser Asp Ser Tyr
                275                 280                 285

Gly Arg Val Tyr Ala Ala Ala Asp Pro Tyr His His Thr Ile Gly Pro
                290                 295                 300

Thr Ala Thr Tyr Ser Ile Gly Thr Met
305                 310

<210> SEQ ID NO 246
<211> LENGTH: 357
```

<212> TYPE: PRT
<213> ORGANISM: Mus musculus

<400> SEQUENCE: 246

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Asp Glu
    50                  55                  60

Asp Leu Glu Glu Glu Glu Glu Glu Glu Glu Glu Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

Phe Asp Ser His Ser His His Glu Arg Val Met Ser Ala Gln Leu Asn
            340                 345                 350

Ala Ile Phe His Asp
        355
```

<210> SEQ ID NO 247
<211> LENGTH: 1090
<212> TYPE: PRT
<213> ORGANISM: Mus musculus

<400> SEQUENCE: 247

```
Met Met Ser Phe Gly Ser Ala Asp Ala Leu Leu Gly Ala Pro Phe Ala
1               5                   10                  15

Pro Leu His Gly Gly Gly Ser Leu His Tyr Ser Leu Ser Arg Lys Ala
            20                  25                  30

Gly Pro Gly Gly Thr Arg Ser Ala Ala Gly Ser Ser Ser Gly Phe His
        35                  40                  45

Ser Trp Ala Arg Thr Ser Ser Ser Val Ser Ala Ser Pro Ser Arg
    50                  55                  60

Phe Arg Gly Ala Ala Ser Ser Thr Asp Ser Leu Asp Thr Leu Ser Asn
65                  70                  75                  80

Gly Pro Glu Gly Cys Val Val Ala Ala Val Ala Arg Ser Glu Lys
                85                  90                  95

Glu Gln Leu Gln Ala Leu Asn Asp Arg Phe Ala Gly Tyr Ile Asp Lys
            100                 105                 110

Val Arg Gln Leu Glu Ala His Asn Arg Ser Leu Glu Gly Glu Ala Ala
        115                 120                 125

Ala Leu Arg Gln Gln Gln Ala Gly Arg Ala Ala Met Gly Glu Leu Tyr
    130                 135                 140

Glu Arg Glu Val Arg Glu Met Arg Gly Ala Val Leu Arg Leu Gly Ala
145                 150                 155                 160

Ala Arg Gly Gln Leu Arg Leu Glu Gln Glu His Leu Leu Glu Asp Ile
                165                 170                 175

Ala His Val Arg Gln Arg Leu Asp Glu Glu Ala Arg Gln Arg Glu Glu
            180                 185                 190

Ala Glu Ala Ala Arg Ala Leu Ala Arg Phe Ala Gln Glu Ala Glu
    195                 200                 205

Ala Ala Arg Val Glu Leu Gln Lys Lys Ala Gln Ala Leu Gln Glu Glu
210                 215                 220

Cys Gly Tyr Leu Arg Arg His His Gln Glu Val Gly Glu Leu Leu
225                 230                 235                 240

Gly Gln Ile Gln Gly Cys Gly Ala Ala Gln Ala Gln Ala Gln Ala Glu
                245                 250                 255

Ala Arg Asp Ala Leu Lys Cys Asp Val Thr Ser Ala Leu Arg Glu Ile
            260                 265                 270

Arg Ala Gln Leu Glu Gly His Ala Val Gln Ser Thr Leu Gln Ser Glu
        275                 280                 285

Glu Trp Phe Arg Val Arg Leu Asp Arg Leu Ser Glu Ala Ala Lys Val
    290                 295                 300

Asn Thr Asp Ala Met Arg Ser Ala Gln Glu Glu Ile Thr Glu Tyr Arg
305                 310                 315                 320

Arg Gln Leu Gln Ala Arg Thr Thr Glu Leu Glu Ala Leu Lys Ser Thr
                325                 330                 335

Lys Glu Ser Leu Glu Arg Gln Arg Ser Glu Leu Glu Asp Arg His Gln
            340                 345                 350

Ala Asp Ile Ala Ser Tyr Gln Asp Ala Ile Gln Gln Leu Asp Ser Glu
        355                 360                 365

Leu Arg Asn Thr Lys Trp Glu Met Ala Ala Gln Leu Arg Glu Tyr Gln
    370                 375                 380

Asp Leu Leu Asn Val Lys Met Ala Leu Asp Ile Glu Ile Ala Ala Tyr
385                 390                 395                 400

Arg Lys Leu Leu Glu Gly Glu Glu Cys Arg Ile Gly Phe Gly Pro Ser
```

```
                405                 410                 415
Pro Phe Ser Leu Thr Glu Gly Leu Pro Lys Ile Pro Ser Ile Ser Thr
            420                 425                 430

His Ile Lys Val Lys Ser Glu Glu Met Ile Lys Val Glu Lys Ser
            435                 440                 445

Glu Lys Glu Thr Val Ile Val Glu Gly Gln Thr Glu Ile Arg Val
        450                 455                 460

Thr Glu Gly Val Thr Glu Glu Asp Lys Glu Ala Gln Gly Gln Glu
465                 470                 475                 480

Gly Glu Glu Ala Glu Glu Gly Glu Glu Lys Glu Glu Glu Glu Gly Ala
                485                 490                 495

Ala Ala Thr Ser Pro Pro Ala Glu Glu Ala Ala Ser Pro Glu Lys Glu
            500                 505                 510

Thr Lys Ser Arg Val Lys Glu Glu Ala Lys Ser Pro Gly Glu Ala Lys
            515                 520                 525

Ser Pro Gly Glu Ala Lys Ser Pro Ala Glu Ala Lys Ser Pro Gly Glu
            530                 535                 540

Ala Lys Ser Pro Gly Glu Ala Lys Ser Pro Gly Glu Ala Lys Ser Pro
545                 550                 555                 560

Ala Glu Pro Lys Ser Pro Ala Glu Pro Lys Ser Pro Ala Glu Ala Lys
                565                 570                 575

Ser Pro Ala Glu Pro Lys Ser Pro Ala Thr Val Lys Ser Pro Gly Glu
            580                 585                 590

Ala Lys Ser Pro Ser Glu Ala Lys Ser Pro Ala Glu Ala Lys Ser Pro
            595                 600                 605

Ala Glu Ala Lys Ser Pro Ala Glu Ala Lys Ser Pro Ala Glu Ala Lys
            610                 615                 620

Ser Pro Ala Glu Ala Lys Ser Pro Ala Glu Ala Lys Ser Pro Ala Thr
625                 630                 635                 640

Val Lys Ser Pro Gly Glu Ala Lys Ser Pro Ser Glu Ala Lys Ser Pro
                645                 650                 655

Ala Glu Ala Lys Ser Pro Ala Glu Ala Lys Ser Pro Ala Glu Ala Lys
            660                 665                 670

Ser Pro Ala Glu Val Lys Ser Pro Gly Glu Ala Lys Ser Pro Ala Glu
            675                 680                 685

Pro Lys Ser Pro Ala Glu Ala Lys Ser Pro Ala Glu Val Lys Ser Pro
            690                 695                 700

Ala Glu Ala Lys Ser Pro Ala Glu Val Lys Ser Pro Gly Glu Ala Lys
705                 710                 715                 720

Ser Pro Ala Ala Val Lys Ser Pro Ala Glu Ala Lys Ser Pro Ala Ala
                725                 730                 735

Val Lys Ser Pro Gly Glu Ala Lys Ser Pro Gly Glu Ala Lys Ser Pro
            740                 745                 750

Ala Glu Ala Lys Ser Pro Ala Glu Ala Lys Ser Pro Ile Glu Val Lys
            755                 760                 765

Ser Pro Glu Lys Ala Lys Thr Pro Val Lys Glu Gly Ala Lys Ser Pro
770                 775                 780

Ala Glu Ala Lys Ser Pro Glu Lys Ala Lys Ser Pro Val Lys Glu Asp
785                 790                 795                 800

Ile Lys Pro Pro Ala Glu Ala Lys Ser Pro Glu Lys Ala Lys Ser Pro
                805                 810                 815

Val Lys Glu Gly Ala Lys Pro Pro Glu Lys Ala Lys Pro Leu Asp Val
            820                 825                 830
```

```
Lys Ser Pro Glu Ala Gln Thr Pro Val Gln Glu Ala Lys His Pro
        835                 840                 845

Thr Asp Ile Arg Pro Pro Glu Gln Val Lys Ser Pro Ala Lys Glu Lys
    850                 855                 860

Ala Lys Ser Pro Glu Lys Glu Ala Lys Thr Ser Glu Lys Val Ala
865                 870                 875                 880

Pro Lys Lys Glu Glu Val Lys Ser Pro Val Lys Glu Val Lys Ala
            885                 890                 895

Lys Glu Pro Pro Lys Lys Val Glu Glu Lys Thr Leu Pro Thr Pro
        900                 905                 910

Lys Thr Glu Ala Lys Glu Ser Lys Lys Asp Glu Ala Pro Lys Glu Ala
            915                 920                 925

Pro Lys Pro Lys Val Glu Glu Lys Lys Glu Thr Pro Thr Glu Lys Pro
        930                 935                 940

Lys Asp Ser Thr Ala Glu Ala Lys Lys Glu Glu Ala Gly Glu Lys Lys
945                 950                 955                 960

Lys Ala Val Ala Ser Glu Glu Thr Pro Ala Lys Leu Gly Val Lys
                965                 970                 975

Glu Glu Ala Lys Pro Lys Glu Lys Thr Glu Thr Thr Lys Thr Glu Ala
            980                 985                 990

Glu Asp Thr Lys Ala Lys Glu Pro Ser Lys Pro Thr Glu Thr Glu Lys
        995                 1000                1005

Pro Lys Lys Glu Glu Met Pro Ala Ala Pro Lys Lys Asp Thr
    1010                1015                1020

Lys Glu Glu Lys Thr Thr Glu Ser Arg Lys Pro Glu Glu Lys Pro
    1025                1030                1035

Lys Met Glu Ala Lys Val Lys Glu Asp Asp Lys Ser Leu Ser Lys
    1040                1045                1050

Glu Pro Ser Lys Pro Lys Thr Glu Lys Ala Glu Lys Ser Ser Ser
    1055                1060                1065

Thr Asp Gln Lys Glu Ser Gln Pro Pro Glu Lys Thr Thr Glu Asp
    1070                1075                1080

Lys Ala Thr Lys Gly Glu Lys
    1085                1090

<210> SEQ ID NO 248
<211> LENGTH: 543
<212> TYPE: PRT
<213> ORGANISM: Mus musculus

<400> SEQUENCE: 248

Met Ser Ser Phe Gly Tyr Asp Pro Tyr Phe Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
```

-continued

```
                100                 105                 110
Gln Gln Asn Lys Val Leu Glu Ala Glu Leu Leu Val Leu Arg Gln Lys
            115                 120                 125

His Ser Glu Pro Ser Arg Phe Arg Ala Leu Tyr Gln Glu Ile Arg
        130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
                180                 185                 190

Met Glu Ala Arg Lys Gly Ala Asp Glu Ala Ala Leu Ala Arg Ala Glu
            195                 200                 205

Leu Glu Lys Arg Ile Asp Ser Leu Met Asp Glu Ile Ala Phe Leu Lys
        210                 215                 220

Lys Val His Glu Glu Ile Ala Glu Leu Gln Ala Gln Ile Gln Tyr
225                 230                 235                 240

Ala Gln Ile Ser Val Glu Met Asp Val Ser Lys Pro Asp Leu Ser
                245                 250                 255

Ala Ala Leu Lys Asp Ile Arg Ala Gln Tyr Glu Lys Leu Ala Ala Lys
                260                 265                 270

Asn Met Gln Asn Ala Glu Glu Trp Phe Lys Ser Arg Phe Thr Val Leu
            275                 280                 285

Thr Glu Ser Ala Ala Lys Asn Thr Asp Ala Val Arg Ala Ala Lys Asp
        290                 295                 300

Glu Val Ser Glu Ser Arg Arg Leu Leu Lys Ala Lys Thr Leu Glu Ile
305                 310                 315                 320

Glu Ala Cys Arg Gly Met Asn Glu Ala Leu Glu Lys Gln Leu Gln Glu
                325                 330                 335

Leu Glu Asp Lys Gln Asn Ala Asp Ile Ser Ala Met Gln Asp Thr Ile
                340                 345                 350

Asn Lys Leu Glu Asn Glu Leu Arg Ser Thr Lys Ser Glu Met Ala Arg
            355                 360                 365

Tyr Leu Lys Glu Tyr Gln Asp Leu Leu Asn Val Lys Met Ala Leu Asp
        370                 375                 380

Ile Glu Ile Ala Ala Tyr Arg Lys Leu Leu Glu Gly Glu Glu Thr Arg
385                 390                 395                 400

Leu Ser Phe Thr Ser Val Gly Ser Ile Thr Ser Gly Tyr Ser Gln Ser
                405                 410                 415

Ser Gln Val Phe Gly Arg Ser Ala Tyr Ser Gly Leu Gln Ser Ser Ser
                420                 425                 430

Tyr Leu Met Ser Ala Arg Ser Phe Pro Ala Tyr Tyr Thr Ser His Val
            435                 440                 445

Gln Glu Glu Gln Thr Glu Val Glu Glu Thr Ile Glu Ala Thr Lys Ala
        450                 455                 460

Glu Glu Ala Lys Asp Glu Pro Pro Ser Glu Gly Ala Glu Glu Glu
465                 470                 475                 480

Glu Lys Glu Lys Glu Glu Gly Glu Glu Glu Gly Ala Glu Glu Glu
                485                 490                 495

Glu Ala Ala Lys Asp Glu Ser Glu Asp Thr Lys Glu Glu Glu Glu Gly
                500                 505                 510

Gly Glu Gly Glu Glu Glu Asp Thr Lys Glu Ser Glu Glu Glu Glu Lys
            515                 520                 525
```

-continued

Lys Glu Glu Ser Ala Gly Glu Glu Gln Val Ala Lys Lys Asp
530                 535                 540

<210> SEQ ID NO 249
<211> LENGTH: 848
<212> TYPE: PRT
<213> ORGANISM: Mus musculus

<400> SEQUENCE: 249

Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
            20                  25                  30

Ser Gly Phe Arg Ser Gln Ser Trp Ser Arg Gly Ser Pro Ser Thr Val
        35                  40                  45

Ser Ser Ser Tyr Lys Arg Ser Ala Leu Ala Pro Arg Leu Ala Tyr Ser
    50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Gly Asp Tyr Lys Leu Ser Arg
                85                  90                  95

Ser Asn Glu Lys Glu Gln Leu Gln Gly Leu Asn Asp Arg Phe Ala Gly
            100                 105                 110

Tyr Ile Glu Lys Val His Tyr Leu Glu Gln Gln Asn Lys Glu Ile Glu
        115                 120                 125

Ala Glu Ile Gln Ala Leu Arg Gln Lys Gln Ala Ser His Ala Gln Leu
    130                 135                 140

Gly Asp Ala Tyr Asp Gln Glu Ile Arg Glu Leu Arg Ala Thr Leu Glu
145                 150                 155                 160

Met Val Asn His Glu Lys Ala Gln Val Gln Leu Asp Ser Asp His Leu
                165                 170                 175

Glu Glu Asp Ile His Arg Leu Lys Glu Arg Phe Glu Glu Glu Ala Arg
            180                 185                 190

Leu Arg Asp Asp Thr Glu Ala Ala Ile Arg Ala Leu Arg Lys Asp Ile
        195                 200                 205

Glu Glu Ser Ser Met Val Lys Val Glu Leu Asp Lys Lys Val Gln Ser
    210                 215                 220

Leu Gln Asp Glu Val Ala Phe Leu Arg Ser Asn His Glu Glu Glu Val
225                 230                 235                 240

Ala Asp Leu Leu Ala Gln Ile Gln Ala Ser His Ile Thr Val Glu Arg
                245                 250                 255

Lys Asp Tyr Leu Lys Thr Asp Ile Ser Thr Ala Leu Lys Glu Ile Arg
            260                 265                 270

Ser Gln Leu Glu Cys His Ser Asp Gln Asn Met His Gln Ala Glu Glu
        275                 280                 285

Trp Phe Lys Cys Arg Tyr Ala Lys Leu Thr Glu Ala Ala Glu Gln Asn
    290                 295                 300

Lys Glu Ala Ile Arg Ser Ala Lys Glu Glu Ile Ala Glu Tyr Arg Arg
305                 310                 315                 320

Gln Leu Gln Ser Lys Ser Ile Glu Leu Glu Ser Val Arg Gly Thr Lys
                325                 330                 335

Glu Ser Leu Glu Arg Gln Leu Ser Asp Ile Glu Glu Arg His Asn His
            340                 345                 350

Asp Leu Ser Ser Tyr Gln Asp Thr Ile Gln Gln Leu Glu Asn Glu Leu

-continued

```
            355                 360                 365
Arg Gly Thr Lys Trp Glu Met Ala Arg His Leu Arg Glu Tyr Gln Asp
    370                 375                 380

Leu Leu Asn Val Lys Met Ala Leu Asp Ile Glu Ile Ala Ala Tyr Arg
385                 390                 395                 400

Lys Leu Leu Glu Gly Glu Glu Thr Arg Phe Ser Thr Phe Ser Gly Ser
                405                 410                 415

Ile Thr Gly Pro Leu Tyr Thr His Arg Gln Pro Ser Val Thr Ile Ser
            420                 425                 430

Ser Lys Ile Gln Lys Thr Lys Val Glu Ala Pro Lys Leu Lys Val Gln
        435                 440                 445

His Lys Phe Val Glu Glu Ile Ile Glu Glu Thr Lys Val Glu Asp Glu
    450                 455                 460

Lys Ser Glu Met Glu Glu Thr Leu Thr Ala Ile Ala Glu Glu Leu Ala
465                 470                 475                 480

Ala Ser Ala Lys Glu Glu Lys Glu Ala Glu Glu Lys Glu Glu
                485                 490                 495

Pro Glu Ala Glu Lys Ser Pro Val Lys Ser Pro Glu Ala Lys Glu Glu
            500                 505                 510

Glu Glu Glu Gly Glu Lys Glu Glu Glu Glu Gly Gln Glu Glu
        515                 520                 525

Glu Glu Glu Asp Glu Gly Val Lys Ser Asp Gln Ala Glu Glu Gly Gly
    530                 535                 540

Ser Glu Lys Glu Gly Ser Ser Glu Lys Asp Glu Gly Glu Gln Glu Glu
545                 550                 555                 560

Glu Glu Gly Glu Thr Glu Ala Glu Gly Glu Gly Glu Ala Glu Ala
                565                 570                 575

Lys Glu Glu Lys Lys Ile Glu Gly Lys Val Glu Val Ala Val Lys
            580                 585                 590

Glu Glu Ile Lys Val Glu Lys Pro Glu Lys Ala Lys Ser Pro Met Pro
        595                 600                 605

Lys Ser Pro Val Glu Glu Val Lys Pro Lys Pro Glu Ala Lys Ala Gly
    610                 615                 620

Lys Gly Glu His Lys Glu Glu Glu Lys Val Glu Glu Lys Lys Glu
625                 630                 635                 640

Val Thr Lys Glu Ser Pro Lys Glu Glu Lys Val Glu Lys Lys Glu Glu
                645                 650                 655

Lys Pro Lys Asp Val Ala Asp Lys Lys Ala Glu Ser Pro Val Lys
            660                 665                 670

Glu Lys Ala Val Glu Glu Val Ile Thr Ile Ser Lys Ser Val Lys Val
        675                 680                 685

Ser Leu Glu Lys Asp Thr Lys Glu Glu Lys Leu Gln Pro Gln Glu Lys
    690                 695                 700

Val Lys Glu Lys Ala Glu Glu Gly Gly Ser Glu Glu Gly Ser
705                 710                 715                 720

Asp Arg Ser Pro Gln Glu Ser Lys Lys Glu Asp Ile Ala Ile Asn Gly
                725                 730                 735

Glu Val Glu Gly Lys Glu Glu Glu Gln Glu Thr Gln Glu Lys Gly
            740                 745                 750

Ser Gly Arg Glu Glu Glu Lys Gly Val Val Thr Asn Gly Leu Asp Val
        755                 760                 765

Ser Pro Ala Glu Glu Lys Lys Gly Glu Asp Ser Ser Asp Asp Lys Val
    770                 775                 780
```

```
Val Val Thr Lys Lys Val Glu Lys Ile Thr Ser Glu Gly Gly Asp Gly
785                 790                 795                 800

Ala Thr Lys Tyr Ile Thr Lys Ser Val Thr Val Gln Lys Val Glu
            805                 810                 815

Glu His Glu Glu Thr Phe Glu Leu Lys Leu Val Ser Thr Lys Lys Val
            820                 825                 830

Glu Lys Val Thr Ser His Ala Ile Val Lys Glu Val Thr Gln Gly Asp
        835                 840                 845

<210> SEQ ID NO 250
<211> LENGTH: 2327
<212> TYPE: PRT
<213> ORGANISM: Mus musculus

<400> SEQUENCE: 250

Met Leu Leu Gly Pro Gly His Pro Leu Ser Ala Pro Ala Leu Ala Leu
1               5                   10                  15

Ala Leu Thr Leu Ala Leu Leu Val Arg Ser Thr Ala Pro Ala Ser Phe
            20                  25                  30

Phe Gly Glu Asn His Leu Glu Val Pro Val Pro Ser Ala Leu Thr Arg
            35                  40                  45

Val Asp Leu Leu Gln Phe Ser Thr Ser Gln Pro Glu Ala Leu Leu
50                  55                  60

Leu Leu Ala Ala Gly Gln Asp Asp His Leu Leu Gln Leu His Ser
65                  70                  75                  80

Gly Cys Leu Gln Val Arg Leu Ala Leu Gly Gln Lys Glu Leu Lys Leu
            85                  90                  95

Gln Thr Pro Ala Asp Thr Val Leu Ser Asp Ser Ala Pro His Thr Val
            100                 105                 110

Val Leu Thr Val Ser Asp Ser Trp Ala Val Leu Ser Val Asp Gly Val
            115                 120                 125

Leu Asn Thr Ser Ala Pro Ile Pro Arg Ala Ser His Leu Lys Ala Thr
130                 135                 140

Tyr Gly Leu Phe Val Gly Ser Ser Gly Ser Leu Asp Leu Pro Tyr Leu
145                 150                 155                 160

Lys Gly Ile Ser Arg Pro Leu Arg Gly Cys Leu His Ser Ala Ile Leu
            165                 170                 175

Asn Gly Arg Asn Leu Leu Arg Pro Leu Thr Ser Asp Val His Glu Gly
            180                 185                 190

Cys Ala Glu Glu Phe Ser Ala Gly Asp Glu Val Gly Leu Gly Phe Ser
            195                 200                 205

Gly Pro His Ser Leu Ala Ala Phe Pro Ala Trp Ser Thr Arg Glu Glu
210                 215                 220

Gly Thr Leu Glu Phe Thr Leu Thr Thr Arg Ser Gln Gln Ala Pro Leu
225                 230                 235                 240

Ala Phe Gln Ala Gly Asp Lys Arg Gly Asn Phe Ile Tyr Val Asp Ile
            245                 250                 255

Phe Glu Gly His Leu Arg Ala Val Val Glu Lys Gly Gln Gly Thr Met
            260                 265                 270

Leu Leu Arg Asn Ser Val Pro Val Ala Asp Gly Gln Pro His Glu Val
            275                 280                 285

Ser Val His Ile Asp Val His Arg Leu Glu Ile Ser Val Asp Gln Tyr
290                 295                 300

Pro Thr Arg Thr Phe Asn Arg Gly Val Leu Ser Tyr Leu Glu Pro Arg
```

```
            305                 310                 315                 320
       Gly Ser Leu Leu Leu Gly Gly Leu Asp Thr Glu Ala Ser Arg His Leu
                       325                 330                 335

Gln Glu His Arg Leu Gly Leu Ala Pro Gly Ala Ala Asn Ile Ser Leu
                       340                 345                 350

Val Gly Cys Ile Glu Asp Phe Ser Val Asn Gly Arg Gln Gly Leu
                       355                 360                 365

Arg Asp Ala Trp Leu Thr Arg Asp Met Ser Ala Gly Cys Arg Pro Glu
                       370                 375                 380

Glu Asp Glu Tyr Glu Glu Val Tyr Gly Pro Tyr Glu Thr Phe Ser
       385                 390                 395                 400

Thr Leu Ala Pro Glu Ala Trp Pro Ala Met Glu Leu Pro Glu Pro Cys
                       405                 410                 415

Ile Pro Glu Pro Gly Leu Pro Ala Val Phe Ala Asn Phe Thr Gln Leu
                       420                 425                 430

Leu Thr Ile Ser Pro Leu Val Val Ala Glu Gly Gly Thr Ala Trp Leu
                       435                 440                 445

Glu Trp Arg His Val Gln Pro Thr Leu Asp Leu Thr Glu Ala Glu Leu
                       450                 455                 460

Arg Lys Ser Gln Val Leu Phe Ser Val Ser Gln Ser Ala Arg His Gly
       465                 470                 475                 480

Asp Leu Glu Leu Asp Ile Leu Gly Ala Gln Thr Arg Lys Met Phe Thr
                       485                 490                 495

Leu Leu Asp Val Val Asn Arg Lys Ala Arg Phe Val His Asp Gly Ser
                       500                 505                 510

Glu Asp Thr Ser Asp Gln Leu Met Leu Glu Val Ser Val Thr Ala Arg
                       515                 520                 525

Ala Pro Val Pro Ser Cys Leu Arg Gly Gln Ile Tyr Ile Leu Pro
                       530                 535                 540

Ile Gln Val Asn Pro Val Asn Asp Pro Pro Arg Ile Ile Phe Pro His
       545                 550                 555                 560

Gly Ser Leu Met Val Ile Leu Glu His Thr Gln Lys Pro Leu Gly Pro
                       565                 570                 575

Glu Ile Phe Gln Ala Tyr Asp Pro Asp Ser Ala Cys Glu Gly Leu Thr
                       580                 585                 590

Phe Gln Leu Leu Gly Val Ser Ser Gly Val Pro Val Glu His Arg Asp
                       595                 600                 605

Gln Pro Gly Glu Pro Ala Thr Glu Phe Ser Cys Arg Glu Leu Glu Val
                       610                 615                 620

Gly Asp Ile Val Tyr Val His Arg Gly Gly Pro Ala Gln Asp Leu Thr
       625                 630                 635                 640

Phe Arg Val Ser Asp Gly Met Gln Ala Ser Ala Pro Ala Thr Leu Lys
                       645                 650                 655

Val Val Ala Val Arg Pro Ala Ile Gln Ile Leu His Asn Thr Gly Leu
                       660                 665                 670

His Leu Ala Gln Gly Ser Ala Ala Ile Leu Pro Ala Asn Leu Ser
                       675                 680                 685

Val Glu Thr Asn Ala Val Gly Gln Asp Val Ser Val Leu Phe Arg Val
                       690                 695                 700

Thr Gly Thr Leu Gln Phe Gly Glu Leu Gln Lys Gln Gly Ala Gly Gly
       705                 710                 715                 720

Val Glu Gly Thr Glu Trp Trp Asp Thr Leu Ala Phe His Gln Arg Asp
                       725                 730                 735
```

-continued

```
Val Glu Gln Gly Arg Val Arg Tyr Leu Ser Thr Asp Pro Gln His His
                740                 745                 750

Thr Gln Asp Thr Val Glu Asp Leu Ile Leu Glu Val Gln Val Gly Gln
            755                 760                 765

Glu Thr Leu Ser Asn Leu Ser Phe Pro Val Thr Ile Gln Arg Ala Thr
    770                 775                 780

Val Trp Met Leu Arg Leu Glu Pro Leu His Thr Gln Asn Pro His Gln
785                 790                 795                 800

Glu Thr Leu Thr Pro Ala His Leu Glu Ala Ser Leu Glu Glu Glu Glu
                805                 810                 815

Glu Glu Gly Ser Pro Gln Pro His Thr Phe His Tyr Glu Leu Val Gln
            820                 825                 830

Ala Pro Arg Arg Gly Asn Leu Leu Leu Gln Gly Thr Arg Leu Ser Asp
        835                 840                 845

Gly Glu Ser Phe Ser Gln Ser Asp Leu Gln Ala Gly Arg Val Thr Tyr
    850                 855                 860

Arg Ala Thr Met Arg Thr Ser Glu Ala Ala Asp Ser Phe Arg Phe
865                 870                 875                 880

Arg Val Thr Ser Pro Pro His Phe Ser Pro Leu Tyr Thr Phe Pro Ile
                885                 890                 895

His Ile Gly Gly Asp Pro Asn Ala Pro Val Leu Thr Asn Val Leu Leu
            900                 905                 910

Met Val Pro Glu Gly Gly Glu Gly Val Leu Ser Ala Asp His Leu Phe
        915                 920                 925

Val Lys Ser Leu Asn Ser Ala Ser Tyr Leu Tyr Glu Val Met Glu Gln
    930                 935                 940

Pro His His Gly Lys Leu Ala Trp Arg Asp Pro Lys Gly Lys Ser Thr
945                 950                 955                 960

Pro Val Thr Ser Phe Thr Asn Glu Asp Leu Leu His Gly Arg Leu Val
                965                 970                 975

Tyr Gln His Asp Asp Ser Glu Thr Ile Glu Asp Asp Ile Pro Phe Val
            980                 985                 990

Ala Thr Arg Gln Gly Glu Gly Ser  Gly Asp Met Ala Trp  Glu Glu Val
        995                 1000                 1005

Arg Gly Val Phe Arg Val Ala  Ile Gln Pro Val Asn  Asp His Ala
    1010                1015                1020

Pro Val  Gln Thr Ile Ser Arg  Val Phe His Val Ala  Arg Gly Gly
    1025                1030                1035

Gln Arg  Leu Leu Thr Thr Asp  Asp Val Ala Phe Ser  Asp Ala Asp
    1040                1045                1050

Ser Gly  Phe Ser Asp Ala Gln  Leu Val Leu Thr Arg  Lys Asp Leu
    1055                1060                1065

Leu Phe  Gly Ser Ile Val Ala  Met Glu Glu Pro Thr  Arg Pro Ile
    1070                1075                1080

Tyr Arg  Phe Thr Gln Glu Asp  Leu Arg Lys Lys Gln  Val Leu Phe
    1085                1090                1095

Val His  Ser Gly Ala Asp His  Gly Trp Leu Gln Leu  Gln Val Ser
    1100                1105                1110

Asp Gly  Gln His Gln Ala Thr  Ala Met Leu Glu Val  Gln Ala Ser
    1115                1120                1125

Glu Pro  Tyr Leu His Val Ala  Asn Ser Ser Ser Leu  Val Val Pro
    1130                1135                1140
```

```
Gln Gly Gly Gln Gly Thr Ile Asp Thr Ala Val Leu Gln Leu Asp
    1145                1150                1155
Thr Asn Leu Asp Ile Arg Ser Gly Asn Glu Val His Tyr His Val
    1160                1165                1170
Thr Ala Gly Pro Gln Trp Gly Gln Leu Leu Arg Asp Gly Gln Ser
    1175                1180                1185
Val Thr Ser Phe Ser Gln Arg Asp Leu Leu Asp Gly Ala Ile Leu
    1190                1195                1200
Tyr Ser His Asn Gly Ser Leu Ser Pro Gln Asp Thr Leu Ala Phe
    1205                1210                1215
Ser Val Ala Ala Gly Pro Val His Thr Asn Thr Phe Leu Gln Val
    1220                1225                1230
Thr Ile Ala Leu Glu Gly Pro Leu Ala Pro Leu Gln Leu Val Gln
    1235                1240                1245
His Lys Lys Ile Tyr Val Phe Gln Gly Glu Ala Ala Glu Ile Arg
    1250                1255                1260
Arg Asp Gln Leu Glu Val Val Gln Glu Ala Val Leu Pro Ala Asp
    1265                1270                1275
Ile Met Phe Ser Leu Arg Ser Pro Pro Asn Ala Gly Tyr Leu Val
    1280                1285                1290
Met Val Ser His Gly Ala Ser Ala Glu Glu Pro Pro Ser Leu Asp
    1295                1300                1305
Pro Val Gln Ser Phe Ser Gln Glu Ala Val Asn Ser Gly Arg Val
    1310                1315                1320
Leu Tyr Leu His Ser Arg Pro Gly Ala Trp Ser Asp Ser Phe Ser
    1325                1330                1335
Leu Asp Val Ala Ser Gly Leu Gly Asp Pro Leu Glu Gly Ile Ser
    1340                1345                1350
Val Glu Leu Glu Val Leu Pro Thr Val Ile Pro Leu Asp Val Gln
    1355                1360                1365
Asn Phe Ser Val Pro Glu Gly Gly Thr Arg Thr Leu Ala Pro Pro
    1370                1375                1380
Leu Val Gln Ile Thr Gly Pro Tyr Phe Pro Thr Leu Pro Gly Leu
    1385                1390                1395
Val Leu Gln Val Leu Glu Pro Pro Gln His Gly Ala Leu Gln Lys
    1400                1405                1410
Glu Asp His Ser Gln Asp Gly Ser Leu Ser Thr Phe Ser Trp Arg
    1415                1420                1425
Glu Val Glu Glu Gln Leu Ile Arg Tyr Val His Asp Gly Ser Glu
    1430                1435                1440
Thr Gln Thr Asp Ala Phe Val Leu Leu Ala Asn Ala Ser Glu Met
    1445                1450                1455
Asp Arg Gln Ser Gln Pro Val Ala Phe Thr Ile Thr Ile Leu Pro
    1460                1465                1470
Val Asn Asp Gln Pro Pro Val Leu Thr Thr Asn Thr Gly Leu Gln
    1475                1480                1485
Ile Trp Glu Gly Ala Ile Val Pro Ile Pro Pro Glu Ala Leu Arg
    1490                1495                1500
Gly Thr Asp Asn Asp Ser Gly Pro Glu Asp Leu Val Tyr Thr Ile
    1505                1510                1515
Glu Gln Pro Ser Asn Gly Arg Ile Ala Leu Arg Val Ala Pro Asp
    1520                1525                1530
Thr Glu Val His Arg Phe Thr Gln Ala Gln Leu Asp Ser Gly Leu
```

-continued

```
            1535                1540                1545

Val Leu Phe Ser His Arg Gly Ala Leu Glu Gly Gly Phe His Phe
    1550                1555                1560

Asp Leu Ser Asp Gly Ala His Thr Ser Pro Gly His Phe Phe Arg
    1565                1570                1575

Val Val Ala Gln Lys Gln Ala Leu Leu Ser Leu Glu Gly Thr Arg
    1580                1585                1590

Lys Leu Thr Val Cys Pro Glu Ser Val Gln Pro Leu Ser Ser Gln
    1595                1600                1605

Ser Leu Ser Ala Ser Ser Ser Thr Gly Ala Asp Pro Arg His Leu
    1610                1615                1620

Leu Tyr Arg Val Val Arg Gly Pro Gln Leu Gly Arg Leu Leu His
    1625                1630                1635

Ala Gln Gln Gly Ser Ala Glu Glu Val Leu Val Asn Phe Thr Gln
    1640                1645                1650

Ala Glu Val Asn Ala Gly Asn Ile Leu Tyr Glu His Glu Met Ser
    1655                1660                1665

Ser Glu Pro Phe Trp Glu Ala His Asp Thr Ile Gly Leu Leu Leu
    1670                1675                1680

Ser Ser Pro Pro Ala Arg Asp Leu Ala Ala Thr Leu Ala Val Met
    1685                1690                1695

Val Ser Phe Asp Ala Ala Cys Pro Gln Arg Pro Ser Arg Leu Trp
    1700                1705                1710

Lys Asn Lys Gly Leu Trp Val Pro Glu Gly Gln Arg Ala Lys Ile
    1715                1720                1725

Thr Val Ala Ala Leu Asp Ala Ala Asn Leu Leu Ala Ser Val Pro
    1730                1735                1740

Ala Ser Gln Arg Ser Arg His Asp Val Leu Phe Gln Val Thr Gln
    1745                1750                1755

Phe Pro Thr Arg Gly Gln Leu Leu Val Ser Glu Glu Pro Leu His
    1760                1765                1770

Ala Arg Arg Pro Tyr Phe Leu Gln Ser Glu Leu Ala Ala Gly Gln
    1775                1780                1785

Leu Val Tyr Ala His Gly Gly Gly Gly Thr Gln Gln Asp Gly Phe
    1790                1795                1800

Arg Phe Arg Ala His Leu Gln Gly Pro Thr Gly Thr Ser Val Ala
    1805                1810                1815

Gly Pro Gln Thr Ser Glu Ala Phe Val Ile Thr Val Arg Asp Val
    1820                1825                1830

Asn Glu Arg Pro Pro Gln Pro Gln Ala Ser Ile Pro Leu Arg Val
    1835                1840                1845

Thr Arg Gly Ser Arg Ala Pro Val Ser Arg Ala Gln Leu Ser Val
    1850                1855                1860

Val Asp Pro Asp Ser Ala Pro Gly Glu Ile Glu Tyr Glu Val Gln
    1865                1870                1875

Arg Ala Pro His Asn Gly Phe Leu Ser Leu Ala Gly Asp Asn Thr
    1880                1885                1890

Gly Pro Val Thr His Phe Thr Gln Ala Asp Val Asp Ala Gly Arg
    1895                1900                1905

Leu Ala Phe Val Ala Asn Gly Ser Ser Val Ala Gly Val Phe Gln
    1910                1915                1920

Leu Ser Met Ser Asp Gly Ala Ser Pro Pro Ile Pro Met Ser Leu
    1925                1930                1935
```

-continued

Ala Val Asp Val Leu Pro Ser Thr Ile Glu Val Gln Leu Arg Ala
    1940            1945                1950

Pro Leu Glu Val Pro Gln Ala Leu Gly Arg Thr Ser Leu Ser Arg
    1955            1960                1965

Gln Gln Leu Gln Val Ile Ser Asp Arg Glu Glu Pro Asp Val Ala
    1970            1975                1980

Tyr Arg Leu Thr Gln Gly Pro Leu Tyr Gly Gln Leu Leu Val Gly
    1985            1990                1995

Gly Gln Pro Ala Ser Ala Phe Ser Gln Leu Gln Val Asp Gln Gly
    2000            2005                2010

Asp Val Val Phe Val Phe Thr Asn Phe Ser Ser Ser Gln Asp His
    2015            2020                2025

Phe Lys Val Val Ala Leu Ala Arg Gly Val Asn Ala Ser Ala Thr
    2030            2035                2040

Val Asn Val Thr Val Gln Ala Leu Leu His Val Trp Ala Gly Gly
    2045            2050                2055

Pro Trp Pro Gln Gly Thr Thr Leu Arg Leu Asp Pro Thr Val Leu
    2060            2065                2070

Asp Ala Ser Glu Leu Ala Asn Arg Thr Gly Ser Met Pro His Phe
    2075            2080                2085

Arg Leu Leu Ala Gly Pro Arg Tyr Gly Arg Val Val Arg Val Ser
    2090            2095                2100

Gln Gly Arg Thr Glu Ser Arg Ser Asn Gln Leu Val Glu His Phe
    2105            2110                2115

Thr Gln Arg Asp Leu Glu Glu Gly Gln Leu Gly Leu Glu Val Gly
    2120            2125                2130

Lys Pro Glu Gly Arg Ser Thr Gly Pro Ala Gly Asp Arg Leu Thr
    2135            2140                2145

Leu Glu Leu Trp Ala Lys Gly Val Pro Pro Ala Val Ala Leu Leu
    2150            2155                2160

Asp Phe Ala Thr Glu Pro Tyr His Ala Ala Lys Ser Tyr Ser Val
    2165            2170                2175

Ala Leu Leu Ser Val Pro Glu Ala Val Arg Thr Glu Thr Glu Lys
    2180            2185                2190

Pro Gly Arg Ser Val Pro Thr Gly Gln Pro Gly Gln Ala Ala Ser
    2195            2200                2205

Ser Pro Val Pro Thr Ala Ala Lys Gly Gly Phe Leu Gly Phe Leu
    2210            2215                2220

Glu Ala Asn Met Phe Ser Ile Ile Pro Val Cys Leu Ile Leu
    2225            2230                2235

Leu Leu Leu Ala Leu Ile Leu Pro Leu Leu Phe Tyr Leu Arg Lys
    2240            2245                2250

Arg Asn Lys Thr Gly Lys His Asp Val Gln Val Leu Thr Ala Lys
    2255            2260                2265

Pro Arg Asn Gly Leu Ala Gly Asp Thr Glu Thr Phe Arg Lys Val
    2270            2275                2280

Glu Pro Gly Gln Ala Ile Pro Leu Ile Thr Val Pro Gly Gln Gly
    2285            2290                2295

Pro Pro Pro Gly Gly Gln Pro Asp Pro Glu Leu Leu Gln Phe Cys
    2300            2305                2310

Arg Thr Pro Asn Pro Ala Leu Arg Asn Gly Gln Tyr Trp Val
    2315            2320                2325

-continued

```
<210> SEQ ID NO 251
<211> LENGTH: 1241
<212> TYPE: PRT
<213> ORGANISM: Homo sapiens

<400> SEQUENCE: 251
```

| | | | | | | | | | | | | | | | |
|---|---|---|---|---|---|---|---|---|---|---|---|---|---|---|---|
| Met | Ala | Leu | Gly | Thr | Thr | Leu | Arg | Ala | Ser | Leu | Leu | Leu | Leu | Gly | Leu |
| 1 | | | | 5 | | | | | 10 | | | | | 15 | |
| Leu | Thr | Glu | Gly | Leu | Ala | Gln | Leu | Ala | Ile | Pro | Ala | Ser | Val | Pro | Arg |
| | | | 20 | | | | | 25 | | | | | 30 | | |
| Gly | Phe | Trp | Ala | Leu | Pro | Glu | Asn | Leu | Thr | Val | Val | Glu | Gly | Ala | Ser |
| | | 35 | | | | | 40 | | | | | 45 | | | |
| Val | Glu | Leu | Arg | Cys | Gly | Val | Ser | Thr | Pro | Gly | Ser | Ala | Val | Gln | Trp |
| | 50 | | | | | 55 | | | | | 60 | | | | |
| Ala | Lys | Asp | Gly | Leu | Leu | Leu | Gly | Pro | Asp | Pro | Arg | Ile | Pro | Gly | Phe |
| 65 | | | | | 70 | | | | | 75 | | | | | 80 |
| Pro | Arg | Tyr | Arg | Leu | Glu | Gly | Asp | Pro | Ala | Arg | Gly | Glu | Phe | His | Leu |
| | | | | 85 | | | | | 90 | | | | | 95 | |
| His | Ile | Glu | Ala | Cys | Asp | Leu | Ser | Asp | Asp | Ala | Glu | Tyr | Glu | Cys | Gln |
| | | | | 100 | | | | | 105 | | | | | 110 | |
| Val | Gly | Arg | Ser | Glu | Met | Gly | Pro | Glu | Leu | Val | Ser | Pro | Arg | Val | Ile |
| | | | 115 | | | | | 120 | | | | | 125 | | |
| Leu | Ser | Ile | Leu | Val | Pro | Pro | Lys | Leu | Leu | Leu | Thr | Pro | Glu | Ala |
| | 130 | | | | | 135 | | | | | 140 | | | | |
| Gly | Thr | Met | Val | Thr | Trp | Val | Ala | Gly | Gln | Glu | Tyr | Val | Val | Asn | Cys |
| 145 | | | | | 150 | | | | | 155 | | | | | 160 |
| Val | Ser | Gly | Asp | Ala | Lys | Pro | Ala | Pro | Asp | Ile | Thr | Ile | Leu | Leu | Ser |
| | | | | 165 | | | | | 170 | | | | | 175 | |
| Gly | Gln | Thr | Ile | Ser | Asp | Ile | Ser | Ala | Asn | Val | Asn | Glu | Gly | Ser | Gln |
| | | | | 180 | | | | | 185 | | | | | 190 | |
| Gln | Lys | Leu | Phe | Thr | Val | Glu | Ala | Thr | Ala | Arg | Val | Thr | Pro | Arg | Ser |
| | | | 195 | | | | | 200 | | | | | 205 | | |
| Ser | Asp | Asn | Arg | Gln | Leu | Leu | Val | Cys | Glu | Ala | Ser | Ser | Pro | Ala | Leu |
| | 210 | | | | | 215 | | | | | 220 | | | | |
| Glu | Ala | Pro | Ile | Lys | Ala | Ser | Phe | Thr | Val | Asn | Val | Leu | Phe | Pro | Pro |
| 225 | | | | | 230 | | | | | 235 | | | | | 240 |
| Gly | Pro | Pro | Val | Ile | Glu | Trp | Pro | Gly | Leu | Asp | Glu | Gly | His | Val | Arg |
| | | | | 245 | | | | | 250 | | | | | 255 | |
| Ala | Gly | Gln | Ser | Leu | Glu | Leu | Pro | Cys | Val | Ala | Arg | Gly | Gly | Asn | Pro |
| | | | | 260 | | | | | 265 | | | | | 270 | |
| Leu | Ala | Thr | Leu | Gln | Trp | Leu | Lys | Asn | Gly | Gln | Pro | Val | Ser | Thr | Ala |
| | | | 275 | | | | | 280 | | | | | 285 | | |
| Trp | Gly | Thr | Glu | His | Thr | Gln | Ala | Val | Ala | Arg | Ser | Val | Leu | Val | Met |
| | 290 | | | | | 295 | | | | | 300 | | | | |
| Thr | Val | Arg | Pro | Glu | Asp | His | Gly | Ala | Gln | Leu | Ser | Cys | Glu | Ala | His |
| 305 | | | | | 310 | | | | | 315 | | | | | 320 |
| Asn | Ser | Val | Ser | Ala | Gly | Thr | Gln | Glu | His | Gly | Ile | Thr | Leu | Gln | Val |
| | | | | 325 | | | | | 330 | | | | | 335 | |
| Thr | Phe | Pro | Pro | Ser | Ala | Ile | Ile | Ile | Leu | Gly | Ser | Ala | Ser | Gln | Thr |
| | | | | 340 | | | | | 345 | | | | | 350 | |
| Glu | Asn | Lys | Asn | Val | Thr | Leu | Ser | Cys | Val | Ser | Lys | Ser | Ser | Arg | Pro |
| | | | 355 | | | | | 360 | | | | | 365 | | |
| Arg | Val | Leu | Leu | Arg | Trp | Trp | Leu | Gly | Trp | Arg | Gln | Leu | Leu | Pro | Met |
| | 370 | | | | | 375 | | | | | 380 | | | | |

```
Glu Glu Thr Val Met Asp Gly Leu His Gly Gly His Ile Ser Met Ser
385                 390                 395                 400

Asn Leu Thr Phe Leu Ala Arg Arg Glu Asp Asn Gly Leu Thr Leu Thr
            405                 410                 415

Cys Glu Ala Phe Ser Glu Ala Phe Thr Lys Glu Thr Phe Lys Lys Ser
        420                 425                 430

Leu Ile Leu Asn Val Lys Tyr Pro Ala Gln Lys Leu Trp Ile Glu Gly
    435                 440                 445

Pro Pro Glu Gly Gln Lys Leu Arg Ala Gly Thr Arg Val Arg Leu Val
450                 455                 460

Cys Leu Ala Ile Gly Gly Asn Pro Glu Pro Ser Leu Met Trp Tyr Lys
465                 470                 475                 480

Asp Ser Arg Thr Val Thr Glu Ser Arg Leu Pro Gln Glu Ser Arg Arg
            485                 490                 495

Val His Leu Gly Ser Val Glu Lys Ser Gly Ser Thr Phe Ser Arg Glu
        500                 505                 510

Leu Val Leu Val Thr Gly Pro Ser Asp Asn Gln Ala Lys Phe Thr Cys
    515                 520                 525

Lys Ala Gly Gln Leu Ser Ala Ser Thr Gln Leu Ala Val Gln Phe Pro
530                 535                 540

Pro Thr Asn Val Thr Ile Leu Ala Asn Ala Ser Ala Leu Arg Pro Gly
545                 550                 555                 560

Asp Ala Leu Asn Leu Thr Cys Val Ser Val Ser Ser Asn Pro Pro Val
            565                 570                 575

Asn Leu Ser Trp Asp Lys Glu Gly Glu Arg Leu Glu Gly Val Ala Ala
        580                 585                 590

Pro Pro Arg Arg Ala Pro Phe Lys Gly Ser Ala Ala Arg Ser Val
    595                 600                 605

Leu Leu Gln Val Ser Ser Arg Asp His Gly Gln Arg Val Thr Cys Arg
610                 615                 620

Ala His Ser Ala Glu Leu Arg Glu Thr Val Ser Ser Phe Tyr Arg Leu
625                 630                 635                 640

Asn Val Leu Tyr Arg Pro Glu Phe Leu Gly Glu Gln Val Leu Val Val
            645                 650                 655

Thr Ala Val Glu Gln Gly Glu Ala Leu Leu Pro Val Ser Val Ser Ala
        660                 665                 670

Asn Pro Ala Pro Glu Ala Phe Asn Trp Thr Phe Arg Gly Tyr Arg Leu
    675                 680                 685

Ser Pro Ala Gly Gly Pro Arg His Arg Ile Leu Ser Ser Gly Ala Leu
    690                 695                 700

His Leu Trp Asn Val Thr Arg Ala Asp Asp Gly Leu Tyr Gln Leu His
705                 710                 715                 720

Cys Gln Asn Ser Glu Gly Thr Ala Glu Ala Arg Leu Arg Leu Asp Val
            725                 730                 735

His Tyr Ala Pro Thr Ile Arg Ala Leu Gln Asp Pro Thr Glu Val Asn
        740                 745                 750

Val Gly Gly Ser Val Asp Ile Val Cys Thr Val Asp Ala Asn Pro Ile
    755                 760                 765

Leu Pro Gly Met Phe Asn Trp Glu Arg Leu Gly Glu Asp Glu Glu Asp
    770                 775                 780

Gln Ser Leu Asp Asp Met Glu Lys Ile Ser Arg Gly Pro Thr Gly Arg
785                 790                 795                 800
```

```
Leu Arg Ile His His Ala Lys Leu Ala Gln Ala Gly Ala Tyr Gln Cys
            805                 810                 815

Ile Val Asp Asn Gly Val Ala Pro Pro Ala Arg Arg Leu Leu Arg Leu
        820                 825                 830

Val Val Arg Phe Ala Pro Gln Val Glu His Pro Thr Pro Leu Thr Lys
        835                 840                 845

Val Ala Ala Ala Gly Asp Ser Thr Ser Ser Ala Thr Leu His Cys Arg
850                 855                 860

Ala Arg Gly Val Pro Asn Ile Val Phe Thr Trp Thr Lys Asn Gly Val
865                 870                 875                 880

Pro Leu Asp Leu Gln Asp Pro Arg Tyr Thr Glu His Thr Tyr His Gln
                885                 890                 895

Gly Gly Val His Ser Ser Leu Leu Thr Ile Ala Asn Val Ser Ala Ala
                900                 905                 910

Gln Asp Tyr Ala Leu Phe Thr Cys Thr Ala Thr Asn Ala Leu Gly Ser
            915                 920                 925

Asp Gln Thr Asn Ile Gln Leu Val Ser Ile Ser Arg Pro Asp Pro Pro
930                 935                 940

Ser Gly Leu Lys Val Val Ser Leu Thr Pro His Ser Val Gly Leu Glu
945                 950                 955                 960

Trp Lys Pro Gly Phe Asp Gly Gly Leu Pro Gln Arg Phe Cys Ile Arg
                965                 970                 975

Tyr Glu Ala Leu Gly Thr Pro Gly Phe His Tyr Val Asp Val Val Pro
            980                 985                 990

Pro Gln Ala Thr Thr Phe Thr Leu Thr Gly Leu Gln Pro Ser Thr Arg
        995                 1000                1005

Tyr Arg Val Trp Leu Leu Ala Ser Asn Ala Leu Gly Asp Ser Gly
    1010                1015                1020

Leu Ala Asp Lys Gly Thr Gln Leu Pro Ile Thr Thr Pro Gly Leu
    1025                1030                1035

His Gln Pro Ser Gly Glu Pro Glu Asp Gln Leu Pro Thr Glu Pro
    1040                1045                1050

Pro Ser Gly Pro Ser Gly Leu Pro Leu Leu Pro Val Leu Phe Ala
    1055                1060                1065

Leu Gly Gly Leu Leu Leu Leu Ser Asn Ala Ser Cys Val Gly Gly
    1070                1075                1080

Val Leu Trp Gln Arg Arg Leu Arg Arg Leu Ala Glu Gly Ile Ser
    1085                1090                1095

Glu Lys Thr Glu Ala Gly Ser Glu Glu Asp Arg Val Arg Asn Glu
    1100                1105                1110

Tyr Glu Glu Ser Gln Trp Thr Gly Glu Arg Asp Thr Gln Ser Ser
    1115                1120                1125

Thr Val Ser Thr Thr Glu Ala Glu Pro Tyr Tyr Arg Ser Leu Arg
    1130                1135                1140

Asp Phe Ser Pro Gln Leu Pro Pro Thr Gln Glu Glu Val Ser Tyr
    1145                1150                1155

Ser Arg Gly Phe Thr Gly Glu Asp Glu Asp Met Ala Phe Pro Gly
    1160                1165                1170

His Leu Tyr Asp Glu Val Glu Arg Thr Tyr Pro Pro Ser Gly Ala
    1175                1180                1185

Trp Gly Pro Leu Tyr Asp Glu Val Gln Met Gly Pro Trp Asp Leu
    1190                1195                1200

His Trp Pro Glu Asp Thr Tyr Gln Asp Pro Arg Gly Ile Tyr Asp
```

```
                    1205                1210                1215
Gln Val Ala Gly Asp Leu Asp Thr Leu Glu Pro Asp Ser Leu Pro
        1220                1225                1230

Phe Glu Leu Arg Gly His Leu Val
        1235                1240

<210> SEQ ID NO 252
<211> LENGTH: 297
<212> TYPE: PRT
<213> ORGANISM: Homo sapiens

<400> SEQUENCE: 252

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
                20                  25                  30

Gly Pro Trp Ala Ser Cys Pro Ala Ala Thr Pro Arg Lys Gln Arg Arg
            35                  40                  45

Glu Arg Thr Thr Phe Thr Arg Ala Gln Leu Asp Val Leu Glu Ala Leu
        50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                85                  90                  95

Arg Arg Ala Lys Cys Arg Gln Gln Gln Gln Gln Gln Asn Gly Gly
            100                 105                 110

Gln Asn Lys Val Arg Pro Ala Lys Lys Lys Thr Ser Pro Ala Arg Glu
        115                 120                 125

Val Ser Ser Glu Ser Gly Thr Ser Gly Gln Phe Thr Pro Pro Ser Ser
    130                 135                 140

Thr Ser Val Pro Thr Ile Ala Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Leu Pro Gly Pro Gly
    210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
    290                 295

<210> SEQ ID NO 253
<211> LENGTH: 120
<212> TYPE: PRT
<213> ORGANISM: Homo sapiens
```

-continued

<400> SEQUENCE: 253

Met Pro Gly Ala Glu Asp Val Val Thr Pro Gly Thr Ser Glu Asp
1               5                   10                  15

Arg Tyr Lys Ser Gly Leu Thr Thr Leu Val Ala Thr Ser Val Asn Ser
                20                  25                  30

Val Thr Gly Ile Arg Ile Glu Asp Leu Pro Thr Ser Glu Ser Thr Val
            35                  40                  45

His Ala Gln Glu Gln Ser Pro Ser Ala Thr Ala Ser Asn Val Ala Thr
    50                  55                  60

Ser His Ser Thr Glu Lys Val Asp Gly Asp Thr Gln Thr Thr Val Glu
65                  70                  75                  80

Lys Asp Gly Leu Ser Thr Val Thr Leu Val Gly Ile Ile Val Gly Val
                85                  90                  95

Leu Leu Ala Ile Gly Phe Ile Gly Ala Ile Ile Val Val Val Met Arg
            100                 105                 110

Lys Met Ser Gly Arg Tyr Ser Pro
                115                 120

<210> SEQ ID NO 254
<211> LENGTH: 283
<212> TYPE: PRT
<213> ORGANISM: Homo sapiens

<400> SEQUENCE: 254

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
                20                  25                  30

Pro Ala Cys Leu Tyr Met Gly Arg Gln Pro Pro Pro Pro Pro Pro His
            35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

```
Pro Pro Pro Pro Gly Ala Val Pro Ala Ala Pro Val Ala Ala
            245             250             255

Arg Glu Gly Arg Leu Pro Pro Gly Leu Ser Ala Ser Pro Gln Pro Ser
        260                 265                 270

Ser Val Ala Pro Arg Arg Pro Gln Glu Pro Arg
        275                 280

<210> SEQ ID NO 255
<211> LENGTH: 4302
<212> TYPE: PRT
<213> ORGANISM: Homo sapiens

<400> SEQUENCE: 255

Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Pro Gly Ala Ala Cys Arg
        35                  40                  45

Val Asn Cys Ser Gly Arg Gly Leu Arg Thr Leu Gly Pro Ala Leu Arg
50                  55                  60

Ile Pro Ala Asp Ala Thr Ala Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335
```

```
Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
            355                 360                 365

Ser Asp Glu Ser Leu Asp Leu Ser Ile Gln Asn Arg Gly Gly Ser Gly
        370                 375                 380

Leu Glu Ala Ala Tyr Ser Ile Val Ala Leu Gly Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
            435                 440                 445

Ser Pro Ala Val Gln Arg Phe Leu Val Ser Arg Val Thr Arg Ser Leu
        450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
        515                 520                 525

Val Cys Glu Leu Gln Pro Gly Pro Val Gln Asp Ala Glu Asn Leu
        530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
            580                 585                 590

Glu Phe Gly Thr Gln Glu Leu Arg Arg Pro Ala Gln Leu Arg Leu Gln
            595                 600                 605

Val Tyr Arg Leu Leu Ser Thr Ala Gly Thr Pro Glu Asn Gly Ser Glu
        610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
            660                 665                 670

Pro Gly Leu Pro Gly Ala Pro Tyr Ala Leu Trp Arg Glu Phe Leu Phe
        675                 680                 685

Ser Val Pro Ala Gly Pro Ala Gln Tyr Ser Val Thr Leu His Gly
        690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
                725                 730                 735

Gly Pro Gln Ala Pro Tyr Leu Ser Ala Asn Ala Ser Ser Trp Leu Pro
            740                 745                 750
```

His Leu Pro Ala Gln Leu Glu Gly Thr Trp Ala Cys Pro Ala Cys Ala
    755                 760                 765

Leu Arg Leu Leu Ala Ala Thr Glu Gln Leu Thr Val Leu Leu Gly Leu
    770                 775                 780

Arg Pro Asn Pro Gly Leu Arg Leu Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
            820                 825                 830

Asp Gly Arg Leu Tyr Val Pro Thr Asn Gly Ser Ala Leu Val Leu Gln
        835                 840                 845

Val Asp Ser Gly Ala Asn Ala Thr Ala Thr Ala Arg Trp Pro Gly Gly
    850                 855                 860

Ser Val Ser Ala Arg Phe Glu Asn Val Cys Pro Ala Leu Val Ala Thr
865                 870                 875                 880

Phe Val Pro Gly Cys Pro Trp Glu Thr Asn Asp Thr Leu Phe Ser Val
                885                 890                 895

Val Ala Leu Pro Trp Leu Ser Glu Gly Glu His Val Val Asp Val Val
            900                 905                 910

Val Glu Asn Ser Ala Ser Arg Ala Asn Leu Ser Leu Arg Val Thr Ala
        915                 920                 925

Glu Glu Pro Ile Cys Gly Leu Arg Ala Thr Pro Ser Pro Glu Ala Arg
    930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
            980                 985                 990

Lys Leu Ser Leu Thr Ala Ser Asn  His Val Ser Asn Val  Thr Val Asn
        995                  1000                  1005

Tyr Asn  Val Thr Val Glu Arg  Met Asn Arg Met Gln  Gly Leu Gln
   1010                  1015                  1020

Val Ser  Thr Val Pro Ala Val  Leu Ser Pro Asn Ala  Thr Leu Ala
    1025                 1030                 1035

Leu Thr  Ala Gly Val Leu Val  Asp Ser Ala Val Glu  Val Ala Phe
    1040                 1045                 1050

Leu Trp  Thr Phe Gly Asp Gly  Glu Gln Ala Leu His  Gln Phe Gln
    1055                 1060                 1065

Pro Pro  Tyr Asn Glu Ser Phe  Pro Val Pro Asp Pro  Ser Val Ala
    1070                 1075                 1080

Gln Val  Leu Val Glu His Asn  Val Met His Thr Tyr  Ala Ala Pro
    1085                 1090                 1095

Gly Glu  Tyr Leu Leu Thr Val  Leu Ala Ser Asn Ala  Phe Glu Asn
    1100                 1105                 1110

Leu Thr  Gln Gln Val Pro Val  Ser Val Arg Ala Ser  Leu Pro Ser
    1115                 1120                 1125

Val Ala  Val Gly Val Ser Asp  Gly Val Leu Val Ala  Gly Arg Pro
    1130                 1135                 1140

Val Thr  Phe Tyr Pro His Pro  Leu Pro Ser Pro Gly  Gly Val Leu
    1145                 1150                 1155

Tyr Thr  Trp Asp Phe Gly Asp  Gly Ser Pro Val Leu  Thr Gln Ser

-continued

```
            1160              1165              1170

Gln Pro Ala Ala Asn His Thr Tyr Ala Ser Arg Gly Thr Tyr His
    1175              1180              1185

Val Arg Leu Glu Val Asn Asn Thr Val Ser Gly Ala Ala Ala Gln
    1190              1195              1200

Ala Asp Val Arg Val Phe Glu Glu Leu Arg Gly Leu Ser Val Asp
    1205              1210              1215

Met Ser Leu Ala Val Glu Gln Gly Ala Pro Val Val Ser Ala
    1220              1225              1230

Ala Val Gln Thr Gly Asp Asn Ile Thr Trp Thr Phe Asp Met Gly
    1235              1240              1245

Asp Gly Thr Val Leu Ser Gly Pro Glu Ala Thr Val Glu His Val
    1250              1255              1260

Tyr Leu Arg Ala Gln Asn Cys Thr Val Thr Val Gly Ala Ala Ser
    1265              1270              1275

Pro Ala Gly His Leu Ala Arg Ser Leu His Val Leu Val Phe Val
    1280              1285              1290

Leu Glu Val Leu Arg Val Glu Pro Ala Ala Cys Ile Pro Thr Gln
    1295              1300              1305

Pro Asp Ala Arg Leu Thr Ala Tyr Val Thr Gly Asn Pro Ala His
    1310              1315              1320

Tyr Leu Phe Asp Trp Thr Phe Gly Asp Gly Ser Ser Asn Thr Thr
    1325              1330              1335

Val Arg Gly Cys Pro Thr Val Thr His Asn Phe Thr Arg Ser Gly
    1340              1345              1350

Thr Phe Pro Leu Ala Leu Val Leu Ser Ser Arg Val Asn Arg Ala
    1355              1360              1365

His Tyr Phe Thr Ser Ile Cys Val Glu Pro Glu Val Gly Asn Val
    1370              1375              1380

Thr Leu Gln Pro Glu Arg Gln Phe Val Gln Leu Gly Asp Glu Ala
    1385              1390              1395

Trp Leu Val Ala Cys Ala Trp Pro Pro Phe Pro Tyr Arg Tyr Thr
    1400              1405              1410

Trp Asp Phe Gly Thr Glu Glu Ala Ala Pro Thr Arg Ala Arg Gly
    1415              1420              1425

Pro Glu Val Thr Phe Ile Tyr Arg Asp Pro Gly Ser Tyr Leu Val
    1430              1435              1440

Thr Val Thr Ala Ser Asn Asn Ile Ser Ala Ala Asn Asp Ser Ala
    1445              1450              1455

Leu Val Glu Val Gln Glu Pro Val Leu Val Thr Ser Ile Lys Val
    1460              1465              1470

Asn Gly Ser Leu Gly Leu Glu Leu Gln Gln Pro Tyr Leu Phe Ser
    1475              1480              1485

Ala Val Gly Arg Gly Arg Pro Ala Ser Tyr Leu Trp Asp Leu Gly
    1490              1495              1500

Asp Gly Gly Trp Leu Glu Gly Pro Glu Val Thr His Ala Tyr Asn
    1505              1510              1515

Ser Thr Gly Asp Phe Thr Val Arg Val Ala Gly Trp Asn Glu Val
    1520              1525              1530

Ser Arg Ser Glu Ala Trp Leu Asn Val Thr Val Lys Arg Arg Val
    1535              1540              1545

Arg Gly Leu Val Val Asn Ala Ser Arg Thr Val Val Pro Leu Asn
    1550              1555              1560
```

-continued

```
Gly Ser Val Ser Phe Ser Thr Ser Leu Glu Ala Gly Ser Asp Val
1565                1570                1575

Arg Tyr Ser Trp Val Leu Cys Asp Arg Cys Thr Pro Ile Pro Gly
1580                1585                1590

Gly Pro Thr Ile Ser Tyr Thr Phe Arg Ser Val Gly Thr Phe Asn
1595                1600                1605

Ile Ile Val Thr Ala Glu Asn Glu Val Gly Ser Ala Gln Asp Ser
1610                1615                1620

Ile Phe Val Tyr Val Leu Gln Leu Ile Glu Gly Leu Gln Val Val
1625                1630                1635

Gly Gly Gly Arg Tyr Phe Pro Thr Asn His Thr Val Gln Leu Gln
1640                1645                1650

Ala Val Val Arg Asp Gly Thr Asn Val Ser Tyr Ser Trp Thr Ala
1655                1660                1665

Trp Arg Asp Arg Gly Pro Ala Leu Ala Gly Ser Gly Lys Gly Phe
1670                1675                1680

Ser Leu Thr Val Leu Glu Ala Gly Thr Tyr His Val Gln Leu Arg
1685                1690                1695

Ala Thr Asn Met Leu Gly Ser Ala Trp Ala Asp Cys Thr Met Asp
1700                1705                1710

Phe Val Glu Pro Val Gly Trp Leu Met Val Ala Ala Ser Pro Asn
1715                1720                1725

Pro Ala Ala Val Asn Thr Ser Val Thr Leu Ser Ala Glu Leu Ala
1730                1735                1740

Gly Gly Ser Gly Val Val Tyr Thr Trp Ser Leu Glu Glu Gly Leu
1745                1750                1755

Ser Trp Glu Thr Ser Glu Pro Phe Thr Thr His Ser Phe Pro Thr
1760                1765                1770

Pro Gly Leu His Leu Val Thr Met Thr Ala Gly Asn Pro Leu Gly
1775                1780                1785

Ser Ala Asn Ala Thr Val Glu Val Asp Val Gln Val Pro Val Ser
1790                1795                1800

Gly Leu Ser Ile Arg Ala Ser Glu Pro Gly Gly Ser Phe Val Ala
1805                1810                1815

Ala Gly Ser Ser Val Pro Phe Trp Gly Gln Leu Ala Thr Gly Thr
1820                1825                1830

Asn Val Ser Trp Cys Trp Ala Val Pro Gly Gly Ser Ser Lys Arg
1835                1840                1845

Gly Pro His Val Thr Met Val Phe Pro Asp Ala Gly Thr Phe Ser
1850                1855                1860

Ile Arg Leu Asn Ala Ser Asn Ala Val Ser Trp Val Ser Ala Thr
1865                1870                1875

Tyr Asn Leu Thr Ala Glu Glu Pro Ile Val Gly Leu Val Leu Trp
1880                1885                1890

Ala Ser Ser Lys Val Val Ala Pro Gly Gln Leu Val His Phe Gln
1895                1900                1905

Ile Leu Leu Ala Ala Gly Ser Ala Val Thr Phe Arg Leu Gln Val
1910                1915                1920

Gly Gly Ala Asn Pro Glu Val Leu Pro Gly Pro Arg Phe Ser His
1925                1930                1935

Ser Phe Pro Arg Val Gly Asp His Val Val Ser Val Arg Gly Lys
1940                1945                1950
```

```
Asn His Val Ser Trp Ala Gln Ala Gln Val Arg Ile Val Val Leu
1955                1960                1965

Glu Ala Val Ser Gly Leu Gln Val Pro Asn Cys Cys Glu Pro Gly
1970                1975                1980

Ile Ala Thr Gly Thr Glu Arg Asn Phe Thr Ala Arg Val Gln Arg
1985                1990                1995

Gly Ser Arg Val Ala Tyr Ala Trp Tyr Phe Ser Leu Gln Lys Val
2000                2005                2010

Gln Gly Asp Ser Leu Val Ile Leu Ser Gly Arg Asp Val Thr Tyr
2015                2020                2025

Thr Pro Val Ala Ala Gly Leu Leu Glu Ile Gln Val Arg Ala Phe
2030                2035                2040

Asn Ala Leu Gly Ser Glu Asn Arg Thr Leu Val Leu Glu Val Gln
2045                2050                2055

Asp Ala Val Gln Tyr Val Ala Leu Gln Ser Gly Pro Cys Phe Thr
2060                2065                2070

Asn Arg Ser Ala Gln Phe Glu Ala Ala Thr Ser Pro Ser Pro Arg
2075                2080                2085

Arg Val Ala Tyr His Trp Asp Phe Gly Asp Gly Ser Pro Gly Gln
2090                2095                2100

Asp Thr Asp Glu Pro Arg Ala Glu His Ser Tyr Leu Arg Pro Gly
2105                2110                2115

Asp Tyr Arg Val Gln Val Asn Ala Ser Asn Leu Val Ser Phe Phe
2120                2125                2130

Val Ala Gln Ala Thr Val Thr Val Gln Val Leu Ala Cys Arg Glu
2135                2140                2145

Pro Glu Val Asp Val Val Leu Pro Leu Gln Val Leu Met Arg Arg
2150                2155                2160

Ser Gln Arg Asn Tyr Leu Glu Ala His Val Asp Leu Arg Asp Cys
2165                2170                2175

Val Thr Tyr Gln Thr Glu Tyr Arg Trp Glu Val Tyr Arg Thr Ala
2180                2185                2190

Ser Cys Gln Arg Pro Gly Arg Pro Ala Arg Val Ala Leu Pro Gly
2195                2200                2205

Val Asp Val Ser Arg Pro Arg Leu Val Leu Pro Arg Leu Ala Leu
2210                2215                2220

Pro Val Gly His Tyr Cys Phe Val Phe Val Val Ser Phe Gly Asp
2225                2230                2235

Thr Pro Leu Thr Gln Ser Ile Gln Ala Asn Val Thr Val Ala Pro
2240                2245                2250

Glu Arg Leu Val Pro Ile Ile Glu Gly Gly Ser Tyr Arg Val Trp
2255                2260                2265

Ser Asp Thr Arg Asp Leu Val Leu Asp Gly Ser Glu Ser Tyr Asp
2270                2275                2280

Pro Asn Leu Glu Asp Gly Asp Gln Thr Pro Leu Ser Phe His Trp
2285                2290                2295

Ala Cys Val Ala Ser Thr Gln Arg Glu Ala Gly Gly Cys Ala Leu
2300                2305                2310

Asn Phe Gly Pro Arg Gly Ser Ser Thr Val Thr Ile Pro Arg Glu
2315                2320                2325

Arg Leu Ala Ala Gly Val Glu Tyr Thr Phe Ser Leu Thr Val Trp
2330                2335                2340

Lys Ala Gly Arg Lys Glu Glu Ala Thr Asn Gln Thr Val Leu Ile
```

-continued

```
                2345                2350                2355

Arg Ser Gly Arg Val Pro Ile Val Ser Leu Glu Cys Val Ser Cys
    2360                2365                2370

Lys Ala Gln Ala Val Tyr Glu Val Ser Arg Ser Ser Tyr Val Tyr
    2375                2380                2385

Leu Glu Gly Arg Cys Leu Asn Cys Ser Ser Gly Ser Lys Arg Gly
    2390                2395                2400

Arg Trp Ala Ala Arg Thr Phe Ser Asn Lys Thr Leu Val Leu Asp
    2405                2410                2415

Glu Thr Thr Thr Ser Thr Gly Ser Ala Gly Met Arg Leu Val Leu
    2420                2425                2430

Arg Arg Gly Val Leu Arg Asp Gly Glu Gly Tyr Thr Phe Thr Leu
    2435                2440                2445

Thr Val Leu Gly Arg Ser Gly Glu Glu Glu Gly Cys Ala Ser Ile
    2450                2455                2460

Arg Leu Ser Pro Asn Arg Pro Pro Leu Gly Gly Ser Cys Arg Leu
    2465                2470                2475

Phe Pro Leu Gly Ala Val His Ala Leu Thr Thr Lys Val His Phe
    2480                2485                2490

Glu Cys Thr Gly Trp His Asp Ala Glu Asp Ala Gly Ala Pro Leu
    2495                2500                2505

Val Tyr Ala Leu Leu Leu Arg Arg Cys Arg Gln Gly His Cys Glu
    2510                2515                2520

Glu Phe Cys Val Tyr Lys Gly Ser Leu Ser Ser Tyr Gly Ala Val
    2525                2530                2535

Leu Pro Pro Gly Phe Arg Pro His Phe Glu Val Gly Leu Ala Val
    2540                2545                2550

Val Val Gln Asp Gln Leu Gly Ala Ala Val Val Ala Leu Asn Arg
    2555                2560                2565

Ser Leu Ala Ile Thr Leu Pro Glu Pro Asn Gly Ser Ala Thr Gly
    2570                2575                2580

Leu Thr Val Trp Leu His Gly Leu Thr Ala Ser Val Leu Pro Gly
    2585                2590                2595

Leu Leu Arg Gln Ala Asp Pro Gln His Val Ile Glu Tyr Ser Leu
    2600                2605                2610

Ala Leu Val Thr Val Leu Asn Glu Tyr Glu Arg Ala Leu Asp Val
    2615                2620                2625

Ala Ala Glu Pro Lys His Glu Arg Gln His Arg Ala Gln Ile Arg
    2630                2635                2640

Lys Asn Ile Thr Glu Thr Leu Val Ser Leu Arg Val His Thr Val
    2645                2650                2655

Asp Asp Ile Gln Gln Ile Ala Ala Ala Leu Ala Gln Cys Met Gly
    2660                2665                2670

Pro Ser Arg Glu Leu Val Cys Arg Ser Cys Leu Lys Gln Thr Leu
    2675                2680                2685

His Lys Leu Glu Ala Met Met Leu Ile Leu Gln Ala Glu Thr Thr
    2690                2695                2700

Ala Gly Thr Val Thr Pro Thr Ala Ile Gly Asp Ser Ile Leu Asn
    2705                2710                2715

Ile Thr Gly Asp Leu Ile His Leu Ala Ser Ser Asp Val Arg Ala
    2720                2725                2730

Pro Gln Pro Ser Glu Leu Gly Ala Glu Ser Pro Ser Arg Met Val
    2735                2740                2745
```

-continued

```
Ala Ser Gln Ala Tyr Asn Leu Thr Ser Ala Leu Met Arg Ile Leu
    2750            2755            2760

Met Arg Ser Arg Val Leu Asn Glu Glu Pro Leu Thr Leu Ala Gly
    2765            2770            2775

Glu Glu Ile Val Ala Gln Gly Lys Arg Ser Asp Pro Arg Ser Leu
    2780            2785            2790

Leu Cys Tyr Gly Gly Ala Pro Gly Pro Gly Cys His Phe Ser Ile
    2795            2800            2805

Pro Glu Ala Phe Ser Gly Ala Leu Ala Asn Leu Ser Asp Val Val
    2810            2815            2820

Gln Leu Ile Phe Leu Val Asp Ser Asn Pro Phe Pro Phe Gly Tyr
    2825            2830            2835

Ile Ser Asn Tyr Thr Val Ser Thr Lys Val Ala Ser Met Ala Phe
    2840            2845            2850

Gln Thr Gln Ala Gly Ala Gln Ile Pro Ile Glu Arg Leu Ala Ser
    2855            2860            2865

Glu Arg Ala Ile Thr Val Lys Val Pro Asn Asn Ser Asp Trp Ala
    2870            2875            2880

Ala Arg Gly His Arg Ser Ser Ala Asn Ser Ala Asn Ser Val Val
    2885            2890            2895

Val Gln Pro Gln Ala Ser Val Gly Ala Val Val Thr Leu Asp Ser
    2900            2905            2910

Ser Asn Pro Ala Ala Gly Leu His Leu Gln Leu Asn Tyr Thr Leu
    2915            2920            2925

Leu Asp Gly His Tyr Leu Ser Glu Glu Pro Glu Pro Tyr Leu Ala
    2930            2935            2940

Val Tyr Leu His Ser Glu Pro Arg Pro Asn Glu His Asn Cys Ser
    2945            2950            2955

Ala Ser Arg Arg Ile Arg Pro Glu Ser Leu Gln Gly Ala Asp His
    2960            2965            2970

Arg Pro Tyr Thr Phe Phe Ile Ser Pro Gly Ser Arg Asp Pro Ala
    2975            2980            2985

Gly Ser Tyr His Leu Asn Leu Ser Ser His Phe Arg Trp Ser Ala
    2990            2995            3000

Leu Gln Val Ser Val Gly Leu Tyr Thr Ser Leu Cys Gln Tyr Phe
    3005            3010            3015

Ser Glu Glu Asp Met Val Trp Arg Thr Glu Gly Leu Leu Pro Leu
    3020            3025            3030

Glu Glu Thr Ser Pro Arg Gln Ala Val Cys Leu Thr Arg His Leu
    3035            3040            3045

Thr Ala Phe Gly Ala Ser Leu Phe Val Pro Pro Ser His Val Arg
    3050            3055            3060

Phe Val Phe Pro Glu Pro Thr Ala Asp Val Asn Tyr Ile Val Met
    3065            3070            3075

Leu Thr Cys Ala Val Cys Leu Val Thr Tyr Met Val Met Ala Ala
    3080            3085            3090

Ile Leu His Lys Leu Asp Gln Leu Asp Ala Ser Arg Gly Arg Ala
    3095            3100            3105

Ile Pro Phe Cys Gly Gln Arg Gly Arg Phe Lys Tyr Glu Ile Leu
    3110            3115            3120

Val Lys Thr Gly Trp Gly Arg Gly Ser Gly Thr Thr Ala His Val
    3125            3130            3135
```

-continued

```
Gly Ile Met Leu Tyr Gly Val Asp Ser Arg Ser Gly His Arg His
    3140                3145                3150

Leu Asp Gly Asp Arg Ala Phe His Arg Asn Ser Leu Asp Ile Phe
    3155                3160                3165

Arg Ile Ala Thr Pro His Ser Leu Gly Ser Val Trp Lys Ile Arg
    3170                3175                3180

Val Trp His Asp Asn Lys Gly Leu Ser Pro Ala Trp Phe Leu Gln
    3185                3190                3195

His Val Ile Val Arg Asp Leu Gln Thr Ala Arg Ser Ala Phe Phe
    3200                3205                3210

Leu Val Asn Asp Trp Leu Ser Val Glu Thr Glu Ala Asn Gly Gly
    3215                3220                3225

Leu Val Glu Lys Glu Val Leu Ala Ala Ser Asp Ala Ala Leu Leu
    3230                3235                3240

Arg Phe Arg Arg Leu Leu Val Ala Glu Leu Gln Arg Gly Phe Phe
    3245                3250                3255

Asp Lys His Ile Trp Leu Ser Ile Trp Asp Arg Pro Pro Arg Ser
    3260                3265                3270

Arg Phe Thr Arg Ile Gln Arg Ala Thr Cys Cys Val Leu Leu Ile
    3275                3280                3285

Cys Leu Phe Leu Gly Ala Asn Ala Val Trp Tyr Gly Ala Val Gly
    3290                3295                3300

Asp Ser Ala Tyr Ser Thr Gly His Val Ser Arg Leu Ser Pro Leu
    3305                3310                3315

Ser Val Asp Thr Val Ala Val Gly Leu Val Ser Ser Val Val Val
    3320                3325                3330

Tyr Pro Val Tyr Leu Ala Ile Leu Phe Leu Phe Arg Met Ser Arg
    3335                3340                3345

Ser Lys Val Ala Gly Ser Pro Ser Pro Thr Pro Ala Gly Gln Gln
    3350                3355                3360

Val Leu Asp Ile Asp Ser Cys Leu Asp Ser Ser Val Leu Asp Ser
    3365                3370                3375

Ser Phe Leu Thr Phe Ser Gly Leu His Ala Glu Ala Phe Val Gly
    3380                3385                3390

Gln Met Lys Ser Asp Leu Phe Leu Asp Asp Ser Lys Ser Leu Val
    3395                3400                3405

Cys Trp Pro Ser Gly Glu Gly Thr Leu Ser Trp Pro Asp Leu Leu
    3410                3415                3420

Ser Asp Pro Ser Ile Val Gly Ser Asn Leu Arg Gln Leu Ala Arg
    3425                3430                3435

Gly Gln Ala Gly His Gly Leu Gly Pro Glu Glu Asp Gly Phe Ser
    3440                3445                3450

Leu Ala Ser Pro Tyr Ser Pro Ala Lys Ser Phe Ser Ala Ser Asp
    3455                3460                3465

Glu Asp Leu Ile Gln Gln Val Leu Ala Glu Gly Val Ser Ser Pro
    3470                3475                3480

Ala Pro Thr Gln Asp Thr His Met Glu Thr Asp Leu Leu Ser Ser
    3485                3490                3495

Leu Ser Ser Thr Pro Gly Glu Lys Thr Glu Thr Leu Ala Leu Gln
    3500                3505                3510

Arg Leu Gly Glu Leu Gly Pro Pro Ser Pro Gly Leu Asn Trp Glu
    3515                3520                3525

Gln Pro Gln Ala Ala Arg Leu Ser Arg Thr Gly Leu Val Glu Gly
```

-continued

|      |      |      |      |      | 3530 |      |      |      | 3535 |      |      |      | 3540 |      |

Leu Arg Lys Arg Leu Leu Pro Ala Trp Cys Ala Ser Leu Ala His
3545                3550                3555

Gly Leu Ser Leu Leu Leu Val Ala Val Ala Val Ser Gly
3560                3565                3570

Trp Val Gly Ala Ser Phe Pro Pro Gly Val Ser Val Ala Trp Leu
3575                3580                3585

Leu Ser Ser Ser Ala Ser Phe Leu Ala Ser Phe Leu Gly Trp Glu
3590                3595                3600

Pro Leu Lys Val Leu Leu Glu Ala Leu Tyr Phe Ser Leu Val Ala
3605                3610                3615

Lys Arg Leu His Pro Asp Glu Asp Thr Leu Val Glu Ser Pro
3620                3625                3630

Ala Val Thr Pro Val Ser Ala Arg Val Pro Arg Val Arg Pro Pro
3635                3640                3645

His Gly Phe Ala Leu Phe Leu Ala Lys Glu Glu Ala Arg Lys Val
3650                3655                3660

Lys Arg Leu His Gly Met Leu Arg Ser Leu Leu Val Tyr Met Leu
3665                3670                3675

Phe Leu Leu Val Thr Leu Leu Ala Ser Tyr Gly Asp Ala Ser Cys
3680                3685                3690

His Gly His Ala Tyr Arg Leu Gln Ser Ala Ile Lys Gln Glu Leu
3695                3700                3705

His Ser Arg Ala Phe Leu Ala Ile Thr Arg Ser Glu Glu Leu Trp
3710                3715                3720

Pro Trp Met Ala His Val Leu Leu Pro Tyr Val His Gly Asn Gln
3725                3730                3735

Ser Ser Pro Glu Leu Gly Pro Pro Arg Leu Arg Gln Val Arg Leu
3740                3745                3750

Gln Glu Ala Leu Tyr Pro Asp Pro Pro Gly Pro Arg Val His Thr
3755                3760                3765

Cys Ser Ala Ala Gly Gly Phe Ser Thr Ser Asp Tyr Asp Val Gly
3770                3775                3780

Trp Glu Ser Pro His Asn Gly Ser Gly Thr Trp Ala Tyr Ser Ala
3785                3790                3795

Pro Asp Leu Leu Gly Ala Trp Ser Trp Gly Ser Cys Ala Val Tyr
3800                3805                3810

Asp Ser Gly Gly Tyr Val Gln Glu Leu Gly Leu Ser Leu Glu Glu
3815                3820                3825

Ser Arg Asp Arg Leu Arg Phe Leu Gln Leu His Asn Trp Leu Asp
3830                3835                3840

Asn Arg Ser Arg Ala Val Phe Leu Glu Leu Thr Arg Tyr Ser Pro
3845                3850                3855

Ala Val Gly Leu His Ala Ala Val Thr Leu Arg Leu Glu Phe Pro
3860                3865                3870

Ala Ala Gly Arg Ala Leu Ala Leu Ser Val Arg Pro Phe Ala
3875                3880                3885

Leu Arg Arg Leu Ser Ala Gly Leu Ser Leu Pro Leu Leu Thr Ser
3890                3895                3900

Val Cys Leu Leu Leu Phe Ala Val His Phe Ala Val Ala Glu Ala
3905                3910                3915

Arg Thr Trp His Arg Glu Gly Arg Trp Arg Val Leu Arg Leu Gly
3920                3925                3930

Ala Trp Ala Arg Trp Leu Leu Val Ala Leu Thr Ala Ala Thr Ala
3935                3940                3945

Leu Val Arg Leu Ala Gln Leu Gly Ala Ala Asp Arg Gln Trp Thr
3950                3955                3960

Arg Phe Val Arg Gly Arg Pro Arg Arg Phe Thr Ser Phe Asp Gln
3965                3970                3975

Val Ala Gln Leu Ser Ser Ala Ala Arg Gly Leu Ala Ala Ser Leu
3980                3985                3990

Leu Phe Leu Leu Leu Val Lys Ala Ala Gln Gln Leu Arg Phe Val
3995                4000                4005

Arg Gln Trp Ser Val Phe Gly Lys Thr Leu Cys Arg Ala Leu Pro
4010                4015                4020

Glu Leu Leu Gly Val Thr Leu Gly Leu Val Val Leu Gly Val Ala
4025                4030                4035

Tyr Ala Gln Leu Ala Ile Leu Leu Val Ser Ser Cys Val Asp Ser
4040                4045                4050

Leu Trp Ser Val Ala Gln Ala Leu Leu Val Leu Cys Pro Gly Thr
4055                4060                4065

Gly Leu Ser Thr Leu Cys Pro Ala Glu Ser Trp His Leu Ser Pro
4070                4075                4080

Leu Leu Cys Val Gly Leu Trp Ala Leu Arg Leu Trp Gly Ala Leu
4085                4090                4095

Arg Leu Gly Ala Val Ile Leu Arg Trp Arg Tyr His Ala Leu Arg
4100                4105                4110

Gly Glu Leu Tyr Arg Pro Ala Trp Glu Pro Gln Asp Tyr Glu Met
4115                4120                4125

Val Glu Leu Phe Leu Arg Arg Leu Arg Leu Trp Met Gly Leu Ser
4130                4135                4140

Lys Val Lys Glu Phe Arg His Lys Val Arg Phe Glu Gly Met Glu
4145                4150                4155

Pro Leu Pro Ser Arg Ser Ser Arg Gly Ser Lys Val Ser Pro Asp
4160                4165                4170

Val Pro Pro Pro Ser Ala Gly Ser Asp Ala Ser His Pro Ser Thr
4175                4180                4185

Ser Ser Ser Gln Leu Asp Gly Leu Ser Val Ser Leu Gly Arg Leu
4190                4195                4200

Gly Thr Arg Cys Glu Pro Glu Pro Ser Arg Leu Gln Ala Val Phe
4205                4210                4215

Glu Ala Leu Leu Thr Gln Phe Asp Arg Leu Asn Gln Ala Thr Glu
4220                4225                4230

Asp Val Tyr Gln Leu Glu Gln Gln Leu His Ser Leu Gln Gly Arg
4235                4240                4245

Arg Ser Ser Arg Ala Pro Ala Gly Ser Ser Arg Gly Pro Ser Pro
4250                4255                4260

Gly Leu Arg Pro Ala Leu Pro Ser Arg Leu Ala Arg Ala Ser Arg
4265                4270                4275

Gly Val Asp Leu Ala Thr Gly Pro Ser Arg Thr Pro Leu Arg Ala
4280                4285                4290

Lys Asn Lys Val His Pro Ser Ser Thr
4295                4300

<210> SEQ ID NO 256
<211> LENGTH: 968

<212> TYPE: PRT
<213> ORGANISM: Homo sapiens

<400> SEQUENCE: 256

```
Met Val Asn Ser Ser Arg Val Gln Pro Gln Gln Pro Gly Asp Ala Lys
1               5                   10                  15

Arg Pro Pro Ala Pro Arg Ala Pro Asp Pro Gly Arg Leu Met Ala Gly
            20                  25                  30

Cys Ala Ala Val Gly Ala Ser Leu Ala Ala Pro Gly Gly Leu Cys Glu
            35                  40                  45

Gln Arg Gly Leu Glu Ile Glu Met Gln Arg Ile Arg Gln Ala Ala Ala
        50                  55                  60

Arg Asp Pro Pro Ala Gly Ala Ala Ser Pro Ser Pro Pro Leu Ser
65                  70                  75                  80

Ser Cys Ser Arg Gln Ala Trp Ser Arg Asp Asn Pro Gly Phe Glu Ala
                85                  90                  95

Glu Glu Glu Glu Glu Glu Val Glu Gly Glu Glu Gly Gly Met Val Val
            100                 105                 110

Glu Met Asp Val Glu Trp Arg Pro Gly Ser Arg Arg Ser Ala Ala Ser
        115                 120                 125

Ser Ala Val Ser Ser Val Gly Ala Arg Ser Arg Gly Leu Gly Gly Tyr
    130                 135                 140

His Gly Ala Gly His Pro Ser Gly Arg Arg Arg Arg Glu Asp Gln
145                 150                 155                 160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
                180                 185                 190

Leu Val Arg Gly Leu Arg Gly Leu Trp Gly Thr Arg Leu Met Glu Glu
            195                 200                 205

Ser Ser Thr Asn Arg Glu Lys Tyr Leu Lys Ser Val Leu Arg Glu Leu
        210                 215                 220

Val Thr Tyr Leu Leu Phe Leu Ile Val Leu Cys Ile Leu Thr Tyr Gly
225                 230                 235                 240

Met Met Ser Ser Asn Val Tyr Tyr Tyr Thr Arg Met Met Ser Gln Leu
                245                 250                 255

Phe Leu Asp Thr Pro Val Ser Lys Thr Glu Lys Thr Asn Phe Lys Thr
                260                 265                 270

Leu Ser Ser Met Glu Asp Phe Trp Lys Phe Thr Glu Gly Ser Leu Leu
            275                 280                 285

Asp Gly Leu Tyr Trp Lys Met Gln Pro Ser Asn Gln Thr Glu Ala Asp
        290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
                325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
        355                 360                 365

Thr Ser Glu Lys Asp Leu Asn Gly Ser Ser His Trp Gly Ile Ile Ala
    370                 375                 380

Thr Tyr Ser Gly Ala Gly Tyr Tyr Leu Asp Leu Ser Arg Thr Arg Glu
385                 390                 395                 400
```

```
Glu Thr Ala Ala Gln Val Ala Ser Leu Lys Lys Asn Val Trp Leu Asp
            405                 410                 415

Arg Gly Thr Arg Ala Thr Phe Ile Asp Phe Ser Val Tyr Asn Ala Asn
            420                 425                 430

Ile Asn Leu Phe Cys Val Val Arg Leu Leu Val Glu Phe Pro Ala Thr
            435                 440                 445

Gly Gly Val Ile Pro Ser Trp Gln Phe Gln Pro Leu Lys Leu Ile Arg
            450                 455                 460

Tyr Val Thr Thr Phe Asp Phe Phe Leu Ala Ala Cys Glu Ile Ile Phe
465                 470                 475                 480

Cys Phe Phe Ile Phe Tyr Tyr Val Val Glu Glu Ile Leu Glu Ile Arg
                485                 490                 495

Ile His Lys Leu His Tyr Phe Arg Ser Phe Trp Asn Cys Leu Asp Val
            500                 505                 510

Val Ile Val Val Leu Ser Val Val Ala Ile Gly Ile Asn Ile Tyr Arg
            515                 520                 525

Thr Ser Asn Val Glu Val Leu Leu Gln Phe Leu Glu Asp Gln Asn Thr
            530                 535                 540

Phe Pro Asn Phe Glu His Leu Ala Tyr Trp Gln Ile Gln Phe Asn Asn
545                 550                 555                 560

Ile Ala Ala Val Thr Val Phe Phe Val Trp Ile Lys Leu Phe Lys Phe
                565                 570                 575

Ile Asn Phe Asn Arg Thr Met Ser Gln Leu Ser Thr Thr Met Ser Arg
            580                 585                 590

Cys Ala Lys Asp Leu Phe Gly Phe Ala Ile Met Phe Phe Ile Ile Phe
            595                 600                 605

Leu Ala Tyr Ala Gln Leu Ala Tyr Leu Val Phe Gly Thr Gln Val Asp
            610                 615                 620

Asp Phe Ser Thr Phe Gln Glu Cys Ile Phe Thr Gln Phe Arg Ile Ile
625                 630                 635                 640

Leu Gly Asp Ile Asn Phe Ala Glu Ile Glu Glu Ala Asn Arg Val Leu
                645                 650                 655

Gly Pro Ile Tyr Phe Thr Thr Phe Val Phe Phe Met Phe Phe Ile Leu
            660                 665                 670

Leu Asn Met Phe Leu Ala Ile Ile Asn Asp Thr Tyr Ser Glu Val Lys
            675                 680                 685

Ser Asp Leu Ala Gln Gln Lys Ala Glu Met Glu Leu Ser Asp Leu Ile
            690                 695                 700

Arg Lys Gly Tyr His Lys Ala Leu Val Lys Leu Lys Leu Lys Lys Asn
705                 710                 715                 720

Thr Val Asp Asp Ile Ser Glu Ser Leu Arg Gln Gly Gly Gly Lys Leu
                725                 730                 735

Asn Phe Asp Glu Leu Arg Gln Asp Leu Lys Gly Lys Gly His Thr Asp
            740                 745                 750

Ala Glu Ile Glu Ala Ile Phe Thr Lys Tyr Asp Gln Asp Gly Asp Gln
            755                 760                 765

Glu Leu Thr Glu His Glu His Gln Gln Met Arg Asp Asp Leu Glu Lys
            770                 775                 780

Glu Arg Glu Asp Leu Asp Leu Asp His Ser Ser Leu Pro Arg Pro Met
785                 790                 795                 800

Ser Ser Arg Ser Phe Pro Arg Ser Leu Asp Asp Ser Glu Glu Asp Asp
                805                 810                 815
```

-continued

```
Asp Glu Asp Ser Gly His Ser Ser Arg Arg Gly Ser Ile Ser Ser
            820                 825                 830

Gly Val Ser Tyr Glu Glu Phe Gln Val Leu Val Arg Arg Val Asp Arg
835                 840                 845

Met Glu His Ser Ile Gly Ser Ile Val Ser Lys Ile Asp Ala Val Ile
850                 855                 860

Val Lys Leu Glu Ile Met Glu Arg Ala Lys Leu Lys Arg Arg Glu Val
865                 870                 875                 880

Leu Gly Arg Leu Leu Asp Gly Val Ala Glu Asp Glu Arg Leu Gly Arg
                885                 890                 895

Asp Ser Glu Ile His Arg Glu Gln Met Glu Arg Leu Val Arg Glu Glu
                900                 905                 910

Leu Glu Arg Trp Glu Ser Asp Ala Ala Ser Gln Ile Ser His Gly
            915                 920                 925

Leu Gly Thr Pro Val Gly Leu Asn Gly Gln Pro Arg Pro Arg Ser Ser
            930                 935                 940

Arg Pro Ser Ser Ser Gln Ser Thr Glu Gly Met Glu Gly Ala Gly Gly
945                 950                 955                 960

Asn Gly Ser Ser Asn Val His Val
                965

<210> SEQ ID NO 257
<211> LENGTH: 94
<212> TYPE: PRT
<213> ORGANISM: Mus musculus

<400> SEQUENCE: 257

Met Gly Ser Glu Leu Glu Ser Ala Met Glu Thr Leu Ile Asn Val Phe
1               5                   10                  15

His Ala His Ser Gly Lys Glu Gly Asp Lys Tyr Lys Leu Ser Lys Lys
                20                  25                  30

Glu Leu Lys Asp Leu Leu Gln Thr Glu Leu Ser Gly Phe Leu Asp Val
            35                  40                  45

Gln Lys Asp Ala Asp Ala Val Asp Lys Val Met Lys Glu Leu Asp Glu
        50                  55                  60

Asn Gly Asp Gly Glu Val Asp Phe Lys Glu Tyr Val Val Leu Val Ala
65                  70                  75                  80

Ala Leu Thr Val Ala Cys Asn Asn Phe Phe Trp Glu Thr Ser
                85                  90

<210> SEQ ID NO 258
<211> LENGTH: 92
<212> TYPE: PRT
<213> ORGANISM: Mus musculus

<400> SEQUENCE: 258

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
                20                  25                  30

Leu Lys Glu Leu Ile Asn Asn Glu Leu Ser His Phe Leu Glu Glu Ile
            35                  40                  45

Lys Glu Gln Glu Val Val Asp Lys Val Met Glu Thr Leu Asp Glu Asp
        50                  55                  60

Gly Asp Gly Glu Cys Asp Phe Gln Glu Phe Met Ala Phe Val Ala Met
65                  70                  75                  80
```

Val Thr Thr Ala Cys His Glu Phe Phe Glu His Glu
              85                  90

<210> SEQ ID NO 259
<211> LENGTH: 669
<212> TYPE: PRT
<213> ORGANISM: Homo sapiens

<400> SEQUENCE: 259

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
    290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

```
Leu Arg Pro Gly Val Glu Thr Ser Ile Ser Met Arg Lys Glu Thr Leu
        370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
                420                 425                 430

Tyr Ile Phe Tyr Pro Arg Pro Gln Asn Val Glu Tyr Cys Asp Tyr Arg
            435                 440                 445

Lys His Ser Ser Trp Gly Tyr Cys Tyr Tyr Lys Leu Gln Val Asp Phe
        450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
        515                 520                 525

Lys Glu Leu Asn Tyr Lys Thr Asn Ser Glu Ser Pro Ser Val Thr Met
530                 535                 540

Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                565                 570                 575

Leu Val Ile Met Phe Leu Met Leu Leu Arg Arg Phe Arg Ser Arg Tyr
            580                 585                 590

Trp Ser Pro Gly Arg Gly Gly Arg Gly Ala Gln Glu Val Ala Ser Thr
        595                 600                 605

Leu Ala Ser Ser Pro Pro Ser His Phe Cys Pro His Pro Met Ser Leu
610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
                645                 650                 655

Ala Gly Ala Ser Ser Ser Thr Cys Pro Leu Gly Gly Pro
            660                 665

<210> SEQ ID NO 260
<211> LENGTH: 664
<212> TYPE: PRT
<213> ORGANISM: Homo sapiens

<400> SEQUENCE: 260

Met Asp Ser Ser Thr Trp Ser Pro Lys Thr Thr Ala Val Thr Arg Pro
1               5                   10                  15

Val Glu Thr His Glu Leu Ile Arg Asn Ala Ala Asp Ile Ser Ile Ile
                20                  25                  30

Val Ile Tyr Phe Val Val Met Ala Val Gly Leu Trp Ala Met Phe
            35                  40                  45

Ser Thr Asn Arg Gly Thr Val Gly Gly Phe Phe Leu Ala Gly Arg Ser
        50                  55                  60

Met Val Trp Trp Pro Ile Gly Ala Ser Leu Phe Ala Ser Asn Ile Gly
```

```
                65                  70                  75                  80
Ser Gly His Phe Val Gly Leu Ala Gly Thr Gly Ala Ala Ser Gly Ile
                        85                  90                  95

Ala Ile Gly Gly Phe Glu Trp Asn Ala Leu Val Leu Val Val Val Leu
                100                 105                 110

Gly Trp Leu Phe Val Pro Ile Tyr Ile Lys Ala Gly Val Val Thr Met
                115                 120                 125

Pro Glu Tyr Leu Arg Lys Arg Phe Gly Gly Gln Arg Ile Gln Val Tyr
        130                 135                 140

Leu Ser Leu Leu Ser Leu Leu Tyr Ile Phe Thr Lys Ile Ser Ala
145                 150                 155                 160

Asp Ile Phe Ser Gly Ala Ile Phe Ile Asn Leu Ala Leu Gly Leu Asn
                        165                 170                 175

Leu Tyr Leu Ala Ile Phe Leu Leu Ala Ile Thr Ala Leu Tyr Thr
                180                 185                 190

Ile Thr Gly Gly Leu Ala Ala Val Ile Tyr Thr Asp Thr Leu Gln Thr
                195                 200                 205

Val Ile Met Leu Val Gly Ser Leu Ile Leu Thr Gly Phe Ala Phe His
    210                 215                 220

Glu Val Gly Gly Tyr Asp Ala Phe Met Glu Lys Tyr Met Lys Ala Ile
225                 230                 235                 240

Pro Thr Ile Val Ser Asp Gly Asn Thr Thr Phe Gln Glu Lys Cys Tyr
                        245                 250                 255

Thr Pro Arg Ala Asp Ser Phe His Ile Phe Arg Asp Pro Leu Thr Gly
                260                 265                 270

Asp Leu Pro Trp Pro Gly Phe Ile Phe Gly Met Ser Ile Leu Thr Leu
            275                 280                 285

Trp Tyr Trp Cys Thr Asp Gln Val Ile Val Gln Arg Cys Leu Ser Ala
        290                 295                 300

Lys Asn Met Ser His Val Lys Gly Gly Cys Ile Leu Cys Gly Tyr Leu
305                 310                 315                 320

Lys Leu Met Pro Met Phe Ile Met Val Met Pro Gly Met Ile Ser Arg
                325                 330                 335

Ile Leu Tyr Thr Glu Lys Ile Ala Cys Val Val Pro Ser Glu Cys Glu
                340                 345                 350

Lys Tyr Cys Gly Thr Lys Val Gly Cys Thr Asn Ile Ala Tyr Pro Thr
        355                 360                 365

Leu Val Val Glu Leu Met Pro Asn Gly Leu Arg Gly Leu Met Leu Ser
    370                 375                 380

Val Met Leu Ala Ser Leu Met Ser Ser Leu Thr Ser Ile Phe Asn Ser
385                 390                 395                 400

Ala Ser Thr Leu Phe Thr Met Asp Ile Tyr Ala Lys Val Arg Lys Arg
                        405                 410                 415

Ala Ser Glu Lys Glu Leu Met Ile Ala Gly Arg Leu Phe Ile Leu Val
                420                 425                 430

Leu Ile Gly Ile Ser Ile Ala Trp Val Pro Ile Val Gln Ser Ala Gln
            435                 440                 445

Ser Gly Gln Leu Phe Asp Tyr Ile Gln Ser Ile Thr Ser Tyr Leu Gly
        450                 455                 460

Pro Pro Ile Ala Ala Val Phe Leu Leu Ala Ile Phe Trp Lys Arg Val
465                 470                 475                 480

Asn Glu Pro Gly Ala Phe Trp Gly Leu Ile Leu Gly Leu Leu Ile Gly
                        485                 490                 495
```

```
Ile Ser Arg Met Ile Thr Glu Phe Ala Tyr Gly Thr Gly Ser Cys Met
            500                 505                 510

Glu Pro Ser Asn Cys Pro Thr Ile Ile Cys Gly Val His Tyr Leu Tyr
            515                 520                 525

Phe Ala Ile Ile Leu Phe Ala Ile Ser Phe Ile Thr Ile Val Val Ile
            530                 535                 540

Ser Leu Leu Thr Lys Pro Ile Pro Asp Val His Leu Tyr Arg Leu Cys
545                 550                 555                 560

Trp Ser Leu Arg Asn Ser Lys Glu Glu Arg Ile Asp Leu Asp Ala Glu
            565                 570                 575

Glu Glu Asn Ile Gln Glu Gly Pro Lys Glu Thr Ile Glu Ile Glu Thr
            580                 585                 590

Gln Val Pro Glu Lys Lys Lys Gly Ile Phe Arg Arg Ala Tyr Asp Leu
            595                 600                 605

Phe Cys Gly Leu Glu Gln His Gly Ala Pro Lys Met Thr Glu Glu Glu
            610                 615                 620

Glu Lys Ala Met Lys Met Lys Met Thr Asp Thr Ser Glu Lys Pro Leu
625                 630                 635                 640

Trp Arg Thr Val Leu Asn Val Asn Gly Ile Ile Leu Val Thr Val Ala
            645                 650                 655

Val Phe Cys His Ala Tyr Phe Ala
            660

<210> SEQ ID NO 261
<211> LENGTH: 414
<212> TYPE: PRT
<213> ORGANISM: Homo sapiens

<400> SEQUENCE: 261

Met Ser Ser Pro Asp Ala Gly Tyr Ala Ser Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
            35                  40                  45

Pro Ala Asn Ser Gly Ala Pro Ala Gly Ala Ala Gly Arg Ala Lys Gly
            50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
            85                  90                  95

Glu Leu Ser Lys Met Leu Gly Lys Ser Trp Lys Ala Leu Thr Leu Ala
            100                 105                 110

Glu Lys Arg Pro Phe Val Glu Glu Ala Glu Arg Leu Arg Val Gln His
            115                 120                 125

Met Gln Asp His Pro Asn Tyr Lys Tyr Arg Pro Arg Arg Arg Lys Gln
            130                 135                 140

Val Lys Arg Leu Lys Arg Val Glu Gly Gly Phe Leu His Gly Leu Ala
145                 150                 155                 160

Glu Pro Gln Ala Ala Ala Leu Gly Pro Glu Gly Arg Val Ala Met
            165                 170                 175

Asp Gly Leu Gly Leu Gln Phe Pro Glu Gln Gly Phe Pro Ala Gly Pro
            180                 185                 190

Pro Leu Leu Pro Pro His Met Gly Gly His Tyr Arg Asp Cys Gln Ser
```

```
              195                 200                 205
Leu Gly Ala Pro Pro Leu Asp Gly Tyr Pro Leu Pro Thr Pro Asp Thr
210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
                275                 280                 285

Pro Pro Ser Ala Leu His Val Tyr Tyr Gly Ala Met Gly Ser Pro Gly
        290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
            340                 345                 350

Glu Leu Leu Gly Glu Val Asp Arg Thr Glu Phe Glu Gln Tyr Leu His
                355                 360                 365

Phe Val Cys Lys Pro Glu Met Gly Leu Pro Tyr Gln Gly His Asp Ser
370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410

<210> SEQ ID NO 262
<211> LENGTH: 555
<212> TYPE: PRT
<213> ORGANISM: Homo sapiens

<400> SEQUENCE: 262

Met Asn Phe Glu Thr Ser Arg Cys Ala Thr Leu Gln Tyr Cys Pro Asp
1               5                   10                  15

Pro Tyr Ile Gln Arg Phe Val Glu Thr Pro Ala His Phe Ser Trp Lys
                20                  25                  30

Glu Ser Tyr Tyr Arg Ser Thr Met Ser Gln Ser Thr Gln Thr Asn Glu
            35                  40                  45

Phe Leu Ser Pro Glu Val Phe Gln His Ile Trp Asp Phe Leu Glu Gln
        50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
                100                 105                 110

Asn Leu Gly Leu Leu Asn Ser Met Asp Gln Gln Ile Gln Asn Gly Ser
            115                 120                 125

Ser Ser Thr Ser Pro Tyr Asn Thr Asp His Ala Gln Asn Ser Val Thr
        130                 135                 140

Ala Pro Ser Pro Tyr Ala Gln Pro Ser Ser Thr Phe Asp Ala Leu Ser
145                 150                 155                 160
```

```
Pro Ser Pro Ala Ile Pro Ser Asn Thr Asp Tyr Pro Gly Pro His Ser
            165                 170                 175

Phe Asp Val Ser Phe Gln Gln Ser Ser Thr Ala Lys Ser Ala Thr Trp
        180                 185                 190

Thr Tyr Ser Thr Glu Leu Lys Lys Leu Tyr Cys Gln Ile Ala Lys Thr
            195                 200                 205

Cys Pro Ile Gln Ile Lys Val Met Thr Pro Pro Gln Gly Ala Val
210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser His Cys Thr Pro Pro Pro Tyr Pro
    530                 535                 540

Thr Asp Cys Ser Ile Val Arg Ile Trp Gln Val
545                 550                 555

<210> SEQ ID NO 263
<211> LENGTH: 450
<212> TYPE: PRT
```

<213> ORGANISM: Mus musculus

<400> SEQUENCE: 263

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Ser Gly Asn Tyr Val Gly Asp Ser Asp Leu Gln Leu Glu Arg Ile Ser
        35                  40                  45

Val Tyr Tyr Asn Glu Ala Ser Ser His Lys Tyr Val Pro Arg Ala Ile
50                  55                  60

Leu Val Asp Leu Glu Pro Gly Thr Met Asp Ser Val Arg Ser Gly Ala
65                  70                  75                  80

Phe Gly His Leu Phe Arg Pro Asp Asn Phe Ile Phe Gly Gln Ser Gly
            85                  90                  95

Ala Gly Asn Asn Trp Ala Lys Gly His Tyr Thr Glu Gly Ala Glu Leu
        100                 105                 110

Val Asp Ser Val Leu Asp Val Val Arg Lys Glu Cys Glu Asn Cys Asp
    115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Ala Thr Pro Thr Tyr Gly Asp
210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ser Ser Thr Phe Ile
        355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

```
Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Ser Glu Ala Gln Gly
        435                 440                 445

Pro Lys
    450

<210> SEQ ID NO 264
<211> LENGTH: 640
<212> TYPE: PRT
<213> ORGANISM: Homo sapiens

<400> SEQUENCE: 264

Met Gly Gln Pro Ser Leu Thr Trp Met Leu Met Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
        115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
        195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
        275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320
```

```
Phe Asn Ile Thr Asp Ile Ser Leu Leu Glu His Arg Leu Glu Cys Gly
                325                 330                 335

Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
            355                 360                 365

Phe Asn Asp Arg Asp Asn Arg Asp Trp Val Ser Val Thr Pro Ala
        370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
            405                 410                 415

Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Ala Leu Asn Ile
            435                 440                 445

Arg Val Gly Gly Thr Gly Met Phe Thr Val Arg Met Ala Leu Phe Gln
            450                 455                 460

Thr Pro Ser Tyr Thr Gln Pro Tyr Gln Gly Ser Ser Val Thr Leu Ser
465                 470                 475                 480

Thr Glu Ala Phe Leu Tyr Val Gly Thr Met Leu Asp Gly Gly Asp Leu
                485                 490                 495

Ser Arg Phe Ala Leu Leu Met Thr Asn Cys Tyr Ala Thr Pro Ser Ser
            500                 505                 510

Asn Ala Thr Asp Pro Leu Lys Tyr Phe Ile Ile Gln Asp Arg Cys Pro
            515                 520                 525

His Thr Arg Asp Ser Thr Ile Gln Val Val Glu Asn Gly Glu Ser Ser
            530                 535                 540

Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
                565                 570                 575

Lys Cys Lys Pro Thr Cys Ser Gly Thr Arg Phe Arg Ser Gly Ser Val
            580                 585                 590

Ile Asp Gln Ser Arg Val Leu Asn Leu Gly Pro Ile Thr Arg Lys Gly
            595                 600                 605

Val Gln Ala Thr Val Ser Arg Ala Phe Ser Ser Leu Gly Leu Leu Lys
            610                 615                 620

Val Trp Leu Pro Leu Leu Leu Ser Ala Thr Leu Thr Leu Thr Phe Gln
625                 630                 635                 640

<210> SEQ ID NO 265
<211> LENGTH: 447
<212> TYPE: PRT
<213> ORGANISM: Mus musculus

<400> SEQUENCE: 265

Met Leu Leu Asp Ala Gly Pro Gln Tyr Pro Ala Ile Gly Val Thr Thr
1               5                   10                  15

Phe Gly Ala Ser Arg His His Ser Ala Gly Asp Val Ala Glu Arg Asp
            20                  25                  30

Val Gly Leu Gly Ile Asn Pro Phe Ala Asp Gly Met Gly Ala Phe Lys
        35                  40                  45

Leu Asn Pro Ser Ser His Glu Leu Ala Ser Ala Gly Gln Thr Ala Phe
```

-continued

```
                50                  55                  60
        Thr Ser Gln Ala Pro Gly Tyr Ala Ala Ala Ala Leu Gly His His
        65                  70                  75                  80

His His Pro Gly His Val Gly Ser Tyr Ser Ala Ala Phe Asn Ser
                        85                  90                  95

Thr Arg Asp Phe Leu Phe Arg Asn Arg Gly Phe Gly Asp Ala Ala Ala
                        100                 105                 110

Ala Ala Ser Ala Gln His Ser Leu Phe Ala Ala Ser Ala Gly Gly Phe
                        115                 120                 125

Gly Gly Pro His Gly His Thr Asp Ala Ala Gly His Leu Leu Phe Ser
        130                 135                 140

Gly Leu His Glu Gln Ala Ala Gly His Ala Ser Pro Asn Val Val Asn
        145                 150                 155                 160

Gly Gln Met Arg Leu Gly Phe Ser Gly Asp Met Tyr Pro Arg Pro Glu
                        165                 170                 175

Gln Tyr Gly Gln Val Thr Ser Pro Arg Ser Glu His Tyr Ala Ala Pro
                        180                 185                 190

Gln Leu His Gly Tyr Gly Pro Met Asn Val Asn Met Ala Ala His His
                        195                 200                 205

Gly Ala Gly Ala Phe Phe Arg Tyr Met Arg Gln Pro Ile Lys Gln Glu
        210                 215                 220

Leu Ile Cys Lys Trp Ile Glu Pro Glu Gln Leu Ala Asn Pro Lys Lys
        225                 230                 235                 240

Ser Cys Asn Lys Thr Phe Ser Thr Met His Glu Leu Val Thr His Val
                        245                 250                 255

Thr Val Glu His Val Gly Gly Pro Glu Gln Ser Asn His Ile Cys Phe
                        260                 265                 270

Trp Glu Glu Cys Pro Arg Glu Gly Lys Pro Phe Lys Ala Lys Tyr Lys
                        275                 280                 285

Leu Val Asn His Ile Arg Val His Thr Gly Glu Lys Pro Phe Pro Cys
        290                 295                 300

Pro Phe Pro Gly Cys Gly Lys Val Phe Ala Arg Ser Glu Asn Leu Lys
        305                 310                 315                 320

Ile His Lys Arg Thr His Thr Gly Glu Lys Pro Phe Lys Cys Glu Phe
                        325                 330                 335

Glu Gly Cys Asp Arg Arg Phe Ala Asn Ser Ser Asp Arg Lys Lys His
                        340                 345                 350

Met His Val His Thr Ser Asp Lys Pro Tyr Leu Cys Lys Met Cys Asp
                        355                 360                 365

Lys Ser Tyr Thr His Pro Ser Ser Leu Arg Lys His Met Lys Val His
        370                 375                 380

Glu Ser Ser Ser Gln Gly Ser Gln Pro Ser Pro Ala Ala Ser Ser Gly
        385                 390                 395                 400

Tyr Glu Ser Ser Thr Pro Pro Thr Ile Val Ser Pro Thr Thr Asp Asn
                        405                 410                 415

Pro Thr Thr Ser Ser Met Ser Pro Ser Ser Ala Val His His Thr
                        420                 425                 430

Ala Gly His Ser Ala Leu Ser Ser Asn Phe Asn Glu Trp Tyr Val
                        435                 440                 445
```

REPROGRAMMING CELLS BY THREE-DIMENSIONAL CULTIVATION

BACKGROUND OF THE INVENTION

Stem cells are characterized in their capability of proliferation while maintaining potency and differentiation capacity into specialized cell types. Such characteristics are also called stemness, which endows stem cells with great promise for scientific research and therapeutic applications. Considerable interests have been focused on cell stemness, especially how to reprogram somatic cells to acquire stemness. Previous work of Yamanaka et al. demonstrated that pluripotent stem cells can be generated from somatic cells via forced overexpression of key transcription factors, creating a new method for stemness manipulation (Takahashi and Yamanaka, 2006). Since then, great efforts have been devoted to designing safer and more efficient methods for induced pluripotent stem cells (iPS), such as the utilization of proteins (Kim et al., 2009; Zhou et al., 2009), RNAs (Warren et al.), microRNAs (Anokye-Danso et al.) or defined chemicals(Shi et al., 2008; Zhu et al.). Although these methods have proven effective in manipulating stemness of the cells, the efficiency and the risk control are still yet to be improved. Therefore, there exist great needs in finding alternative methods to reprogram cells.

BRIEF SUMMARY OF THE INVENTION

One aspect of the present disclosure relates to methods of reprogramming cells comprising culturing the cells under a condition that allows formation of a three-dimensional (3D) cell aggregate, wherein the cells are induced into reprogramming.

In certain embodiments, the cells are cultured on a low-adherent substrate to allow formation of a three-dimensional cell aggregate. In certain embodiments, the low-adherent substrate comprises a hydrogel layer that is hydrophilic and neutrally charged. In certain embodiments, the low-adherent substrate comprises a hydrophobic surface.

In certain embodiments, the cells are cultured in suspension in a drop of culture medium hanging onto a supporting material to allow formation of a three-dimensional cell aggregate.

In certain embodiments, the three-dimensional cell aggregate is a multicellular and multilayer cell aggregate. In certain embodiments, the three-dimensional cell aggregate has a sphere-like shape.

In certain embodiments, the cells are reprogrammed to up-regulate one or more stem cell markers. In certain embodiments, the cells are reprogrammed to up-regulate one or more transdifferentiation markers.

In certain embodiments, the methods further comprising introducing an inducing agent into the culture. In certain embodiments, the inducing agent is a protein capable of inducing reprogramming of a cell. In certain embodiments, the inducing agent is a nucleic acid encoding for a protein that is capable of inducing reprogramming of a cell. In certain embodiments, the inducing agent is a chemical compound capable of inducing reprogramming of a cell.

Another aspect of the present disclosure relates to reprogrammed cells obtained using any of the methods provided in the present disclosure.

Another aspect of the present disclosure relates to reprogrammed three-dimensional cell aggregates obtained using any of the methods provided in the present disclosure.

Another aspect of the present disclosure relates to kits for reprogramming cells, comprising a low-adherent substrate, and optionally a culture medium.

BRIEF DESCRIPTION OF THE DRAWINGS

FIG. 1. 3D sphere formation of RT4 cells leads to expression of stem cell markers:

Figure 5:
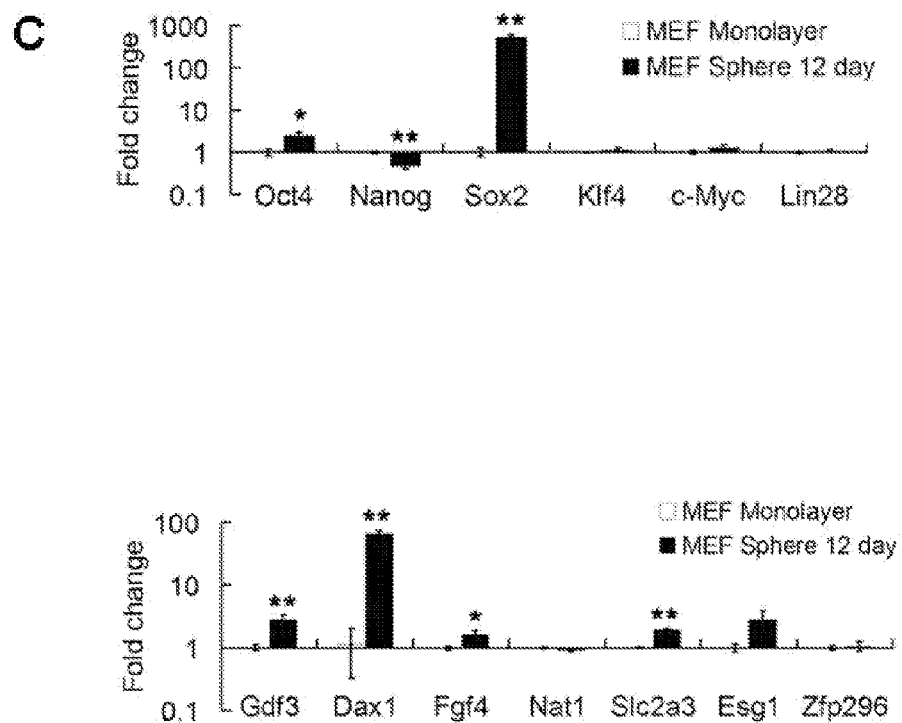

A. Phase-contrast images of RT4 cells in monolayer (left) and sphere culture (right). Scale bars=200 μm.

B. Quantitative PCR (Q-PCR) analysis results for the stem cell marker genes of RT4 cells in monolayer and sphere culture.

C. Western blotting results for NANOG and SOX2 expression of RT4 cells in monolayer and 7-day-sphere culture. Teratoma cell line PA-1 was used as a positive control.

FIG. 2. 3D sphere formation of RT4 cells generates cells with characteristics of cancer stem cell.

A. Quantitative analysis results of migrated cells in monolayer (left) and 7-day-sphere culture (right).

B Q-PCR analysis results for genes related with epithelial mesenchymal transition (EMT) of RT4 cells in monolayer and 7-day-sphere culture.

C. Table summarizing results of nude mice tumor formation assay of RT4 cells. Monolayer indicates trypsinized RT4 cells in monolayer culture; Sphere indicates trypsinized RT4 sphere cells.

FIG. 3. Human embryonic kidney (HEK293) cells cultured in 3D spheres partly acquired embryonic stem cell phenotype.

A. Phase-contrast images of HEK293 cells in monolayer (left) and sphere culture (right). Scale bars=200 μm.

B. Q-PCR analysis results for the stem cell marker genes of HEK293 cells in monolayer and sphere culture.

C. Western blotting results for NANOG and SOX2 expression of HEK293 cells in monolayer and 10-day-sphere culture.

D. Luciferase assay indicating OCT4, NANOG and SOX2/OCT4 transcriptional activities in monolayer HEK293 and sphere HEK293 cells (n=3). Vector indicates control luciferase reporter. (M) indicates monolayer HEK293 cells and (S) indicates 10-day-sphere HEK293 cells.

E. Bisulfite genomic sequencing of the transcriptional regulatory regions of OCT4, NANOG and SOX2 of HEK293 cells in monolayer (panels on top row) and 10-day-sphere culture (panels on bottom row). The starting site is designated as +1. Open circles indicate unmethylated cytosine guanine dinucleotides (CpGs), while closed circles indicate methylated CpGs.

F. Q-PCR analysis results for embryonic stem (ES) cell marker genes of HEK293 cells in monolayer and sphere culture.

G. Q-PCR analysis results for marker genes of endoderm, mesoderm and ectoderm of HEK293 cells in monolayer and 10-day-sphere culture.

H. Alkaline phosphatase (AP) staining results for HEK293 cells in monolayer (left) and 10-day-sphere culture (right).

I. Table summarizing the results of nude mice tumor formation assay of HEK293 cells. "A" indicates trypsinized HEK293 cells in monolayer culture; "B" indicates trypsinized HEK293 cell spheres; "C" indicates non-trypsinized HEK293 spheres.

FIG. 4. Q-PCR analysis results of genes expressed in metanephric mesenchyme and the fully differentiated renal unit.

A. Sketch map of renal unit.

B-F. Q-PCR analysis results for genes expressed in metanephric mesenchyme (B), glomeruli (podocyte) (C), proximal tubule (D), Henle's loop (E), distal tubule and collecting duct (F) of HEK293 cells in monolayer, 5-day-sphere culture and 10-day-sphere culture.

FIG. 5. 3D sphere formation of mouse embryonic fibroblasts (MEF) cells leads to partial embryonic stem cell phenotype.

A. Phase-contrast images of MEF cells in monolayer (left) and sphere culture (right). Scale bars=200 μm.

B. Q-PCR analysis results for the stem cell marker genes of MEF cells in monolayer and 7-day-sphere culture.

C. Q-PCR analysis results for the stem cell marker genes of MEF cells in monolayer and 12-day-sphere culture.

D. Western blotting analysis results for Sox2 expression of MEF cells in monolayer and 7-day-sphere culture.

E. Alkaline phosphatase staining results for MEF cells in monolayer (left) and 7-day-sphere culture (right).

Figure 6:
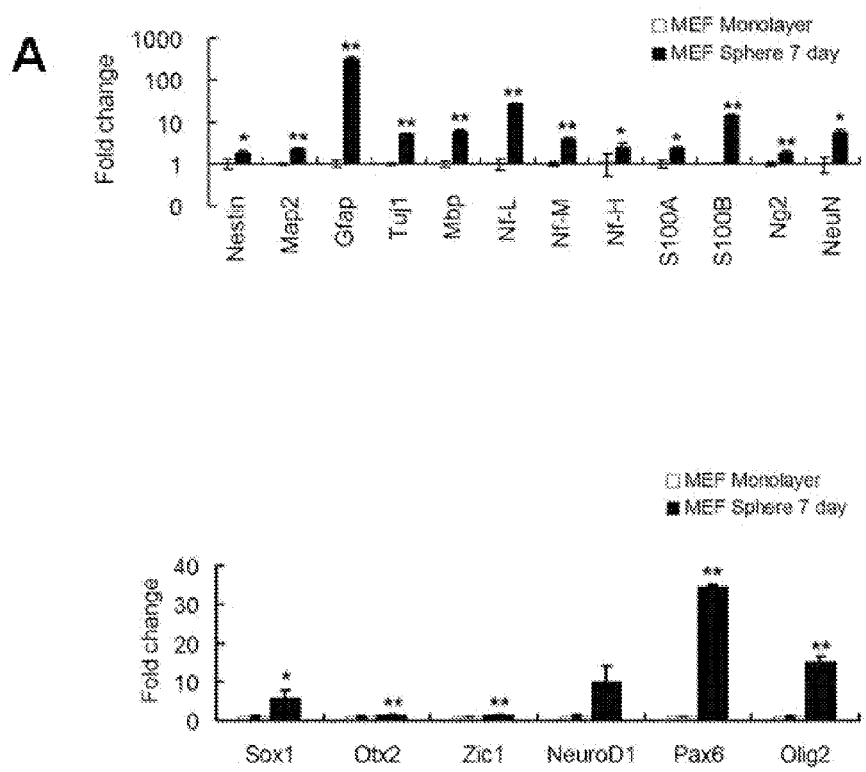

FIG. 6. 3D sphere formation of MEF cells leads to phenotypes of neuro spheres.

A. Q-PCR analysis results for the marker genes of MEF cells in monolayer and 7-day-sphere culture.

B. Q-PCR analysis results for the marker genes of MEF cells in monolayer and 12-day-sphere culture.

C. Western blotting for Tuj1 and Gfap expression of MEF cells in monolayer and sphere culture. Mouse neurosphere was used as a positive control.

D-H. Percentage of cells positive for Tuj1 (D), Neurofilament (E), S100 (F), Gfap (G) and GABA (H) in monolayer MEFs and in 7-day-sphere derived adherent MEFs.

I. Q-PCR analysis results of the marker genes of MEFs after neurogenic differentiation by butylated hydroxyanisole (BHA).

Figure 7:
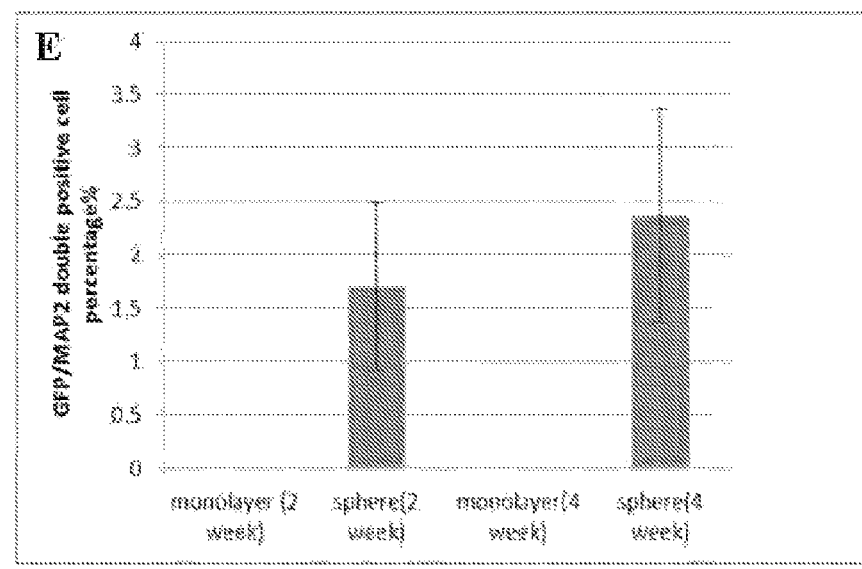

FIG. 7. Percentage of transplanted MEFs in vivo positive for both GFP and neural markers.

A-E. Percentage of transplanted MEFs in vivo positive for both GFP and neural markers including Tuj1 (A), GFAP (B), S100 (C), NeuN (D), or MAP2 (E).

FIG. 8. 3D sphere formation of mouse tail-tip fibroblasts (TTF) cells leads to emergence of neural cells.

A. Phase-contrast images of TTFs in monolayer (left) and sphere culture (right). Scale bars=200 μm.

B. Western blotting analysis results for Sox2 expression of TTFs in monolayer and 7-day-sphere culture.

C. Q-PCR analysis results for the marker genes of TTFs in monolayer and 7-day-sphere culture.

D-E. Percentage of cells positive for Tuj1 (D) and S100 (E) of Monolayer TTFs and 7-day-spheres derived adherent TTFs.

FIG. 9. 3D sphere formation of MCF-7 cells leads to up-regulation of stem cell markers.

A. Phase-contrast images of MCF-7 cells in monolayer (left) and sphere culture (right).

B. Q-PCR analysis results for the marker genes of MCF-7 cells in monolayer and sphere culture.

FIG. 10. 3D sphere formation of rat osteoblast cells leads to up-regulation of some stem cell markers.

A. Phase-contrast images of rat osteoblast cells in monolayer (left) and sphere culture (right).

B. Q-PCR analysis results for the marker genes of rat osteoblast cells in monolayer and sphere culture.

FIG. 11. 3D sphere formation of rat neuronal stem cells leads to up-regulation of stem cell markers.

A. Phase-contrast images of rat neuronal stem cells in monolayer (left) and sphere culture (right).

B. Q-PCR analysis results for the marker genes of rat neuronal stem cells in monolayer and sphere culture.

FIG. 12A-J. Exemplary protein sequences of some stem cell markers.

FIG. 13A-R. Exemplary protein sequences of some trans-differentiation markers.

DETAILED DESCRIPTION OF THE INVENTION

The present disclosure provide methods for reprogramming cells under a condition that allows formation of a three-dimensional cell aggregate and induces the cells into reprogramming. The present disclosure also provides cells that are reprogrammed using the methods of the present disclosure. The present disclosure further provides compositions and kits for reprogramming cells using the methods of the present disclosure.

One aspect of the present disclosure relates to a method of reprogramming cells comprising culturing the cells under a condition that allows formation of a three-dimensional cell aggregate, wherein the cells are induced into reprogramming.

As used herein, the term "reprogram" or "reprogramming" refers to a process in which a differentiated cell is induced to generate one or more characteristics of a stem cell.

A differentiated cell is a cell that is committed to become or has become a specialized cell and shows one or more biological or functional characteristics of such specialized cell. A differentiated cell may be partially differentiated wherein the cell has not completed the process of becoming the specialized cell and does not contain all the characteristics of the specialized cell. A partially differentiated cell may also include a specialized cell that is in the process of reverting into a non-specialized cell and has lost some of the characteristics of the specialized cell. A differentiated cell may be terminally differentiated wherein the cell has completed the process of becoming the specialized cell and contain all the characteristics of the specialized cell. The term "differentiated cell" as used herein includes partially differentiated cells and/or terminally differentiated cells.

A stem cell is a cell that has the potential of differentiating into various specialized cell types. A stem cell may be pluripotent, i.e. capable of differentiating into most types of specialized cells, such as embryonic stem cells. A stem cell may be multipotent, i.e. capable of differentiating into certain types of specialized cells, such as bone marrow stem cells or hematopoietic stem cells. A stem cell may be unipotent, i.e. capable of differentiating into a specific type of specialized cell. A stem cell may be totipotent, i.e. a fertilized egg. The term "stem cell" as used herein includes any and all types of stem cells with the above mentioned various levels of potency.

The methods of the present disclosure may be used to reprogram any cells that can be induced to exhibit one or more biological and/or functional characteristics of stem cells under a culturing condition that allows formation of a three-dimensional cell aggregate. In certain embodiments, the cells of the present disclosure to be reprogrammed are adherent cells. Adherent cells are cells that require attachment to a solid substrate for growth in vitro (see, John M. Davis, Animal Cell Culture: Essential Methods., published by John Wiley & Sons in 2011, Section 4.2; Jennie P. Mather, et al., Introduction to Cell and Tissue Culture:

Theory and Technique, published by Springer, 1998, p. 64-65). The adherent cells do not grow or live, or grow or live poorly in suspension cultures. Adherent cells are usually derived from solid tissues and organs. Examples of adherent cells include, without limitation, endothelial cells, smooth-muscle cells, epithelial cells and fibroblasts.

In certain embodiments, adherent cells has a less than 15% survival rate in suspension cultures. In certain embodiments, adherent cells has a less than 10% survival rate in suspension cultures. In certain embodiments, adherent cells has a less than 5% survival rate in suspension cultures. In certain embodiments, adherent cells has a less than 1% survival rate in suspension cultures. The cell survival rate is calculated as the percentage of the number of living cells out of the total number of cells in a cell culture. The cell viability may be measured by known methods such as propidium iodide staining.

In certain embodiments, the cells of the present disclosure to be reprogrammed by the methods of the present disclosure are somatic cells. Examples of somatic cells include, without limitation, fibroblast cells (e.g. mouse embryonic fibroblasts (MEFs), mouse tail-tip fibroblasts (TTFs) cells, and human fibroblast-like synoviocytes (HFLs)), urinary bladder cells (e.g., human urinary bladder papilloma (RT4) cells), baby hamster kidney (BHK21) cells, ovarian cells (e.g., Chinese hamster ovary (CHO-K1) cells), cervical cells (e.g. HeLa cells), muscle cells, embryonic cells (e.g. human embryonic kidney (HEK) 293 cells, NIH3T3 cells), lung cells (e.g. human fetal lung fibroblast (MRC-5) cells, MRC-9 cells), liver cells (e.g. Hep G2 cells), epithelial cells (e.g. WPE-stem cells), endothelium cells (e.g. HUV-EC-C cells), brain cells (e.g. T98G cells), bone cells (e.g. KHOS-240S cells). In certain embodiments, the somatic cells are non-cancer cells.

In certain embodiments, the somatic cells are cancer cells such as breast cancer cells (e.g. MCF-7 cells, MDA-MB-231 cells, MDA-MB-435 cells or SK-BR-3 cells), colon cancer cells (e.g. DLD-1 cells, HCT-15 cells, T84 cells, HCT-8 cells), renal cancer cells (e.g. A-498 cells, 769-P cells, G401 cells), lung cancer cells (e.g. NCI-H2126 cells, DMS 79 cells, A549 cells), liver cancer cells (e.g., Hep G2 cells), cervical cancer cells (e.g. HeLa cells), glioma cells (e.g. M059K cells, LN-18 cells), neuronal cells (e.g., Rat pheochromocytoma (PC12) cells, Human neuoblastoma (SH-SY5Y) cells), prostate cancer cells (e.g., DU145 cells, LNCaP cells), and osteosarcoma cells (e.g. KHOS/NP cells).

In certain embodiments, the cells that are partially differentiated are induced into reprogramming by the methods of the present disclosure. In certain embodiments, stem cells are induced into reprogramming by the methods of the present disclosure.

In certain embodiments, the present disclosure provides a method of reprogramming cells including culturing the cells in vitro under a condition that allows formation of a three-dimensional cell aggregate, wherein the cells are induced into reprogramming. In certain embodiments, the culturing condition is a low-adherent condition. A low-adherent condition means a culturing environment in which the cells do not attach to a solid substrate or the cell attachment to the solid substrate is reduced or inhibited. In certain embodiment, in a low-adherent condition, cell attachment to a substrate is reduced by at least 30%, 40%, 50%, 60%, 70%, 80% or 90% when compared to a regular adherent condition. Regular adherent conditions may be provided by commercially available cell culture vessels, for example, Corning cell culture dishes (e.g. Cat. No. 430589 Corning® Not Treated Cell Culture Dish (New York, US) or Cat. No. 3353002 Falcon™ Cell Culture Dish (New York, US) or Cat. No. 715001 NEST Cell Culture Dish (Wuxi, China)).

In certain embodiments, the low-adherent condition is provided by a low-adherent substrate that reduces or inhibits cell attachment on its surface (see, John M. Davis, supra). In certain embodiments, the low-adherent substrates include cell culture vessels (e.g., a dish, plate, round-bottom tubes or flask) that are coated with a material that reduces or inhibits cell adhesion. In certain embodiments, such material contains a hydrogel layer that is hydrophilic and neutrally charged. A "hydrogel" as used herein, refers to a semisolid composition constituting a certain amount of water, and in which polymers or mixtures thereof are dissolved or dispersed. In certain embodiments, the hydrogel is made of polystyrene. In certain embodiments, the polystyrene is selected from the group consisting of polystyrene-block-poly(N-isopropylacrylamide)-block-poly styrene, poly(styrene-co-maleic anhydride) (SMA), poly(styrene-divinyl benzene) (P(ST-DVB)), poly(styrene sulfonic acid) (PSSA), poly(glycidyl methacrylate-co-α-methyl styrene), polyaniline-poly(styrene sulfonate) (Pan-PSS), poly(styrene-block-(methoxy diethylene glycol acrylate)-block-styrene) and poly(sodium 4-styrene sulfonate).

In certain embodiments, the hydrogel is made of agar, agarose. In certain embodiments, the low-adherent substrate is coated with agarose in a concentration ranging from 0.2 to 5.0%. In certain embodiments, the low-adherent substrate is coated with agar in a concentration ranging from 1-5%.

In certain embodiments, the hydrogel is made of poly(2-hydrozy-ethyl methacralate. In certain embodiments, the low-adherent substrate is coated with poly(2-hydrozy-ethyl methacralate in a concentration ranging from 40-50%.

In certain embodiments, the low-adherent substrate is coated with a hydrogel mixed with a culture medium (e.g., Dulbecco's Modified Eagle Medium (DMEM) or McCoy's 5A Medium).

In certain embodiments, the material that reduces or inhibits cell adhesion can modulate the functions of extracellular proteins of a target cell and thus reduces attachment of the cell to the substrate. Examples of inhibitors of the extracellular proteins include, without limitation, proteoglycans (see, e.g. Yamagata, M. et al., Journal of Biological Chemistry, 264 (14): 8012-8018, 1989), heparin combined with hydrocortisone or cycloheximide, L-azetidine-2-carboxylic acid, trypsin and Ethylenediaminetetraacetic acid (EDTA), Dispase, dextran, polyethylene oxide, synthetic peptides such as glycine-arginine-glycine-asparate-serine-proline, glycine-arginine-glycine-asparate-serine (see, e.g. Whalen, G. F. et al., Ann. Surg., 210 (6): 758-764, 1989).

In certain embodiments, a material that reduces or inhibits cell adhesion is coated on the surface of the low-adherent substrate as a layer or film or membrane. In certain embodiments, a material that reduces or inhibits cell adhesion is embedded in the substrate.

In certain embodiments, the low-adherent substrate comprises a hydrophobic surface. In certain embodiments, a hydrophobic surface is formed with polymer and copolymer films having hydrophobic components. In certain embodiments, the hydrophobic surface is formed with poly(methyl methacrylate) (PMMA), poly(ethyleneoxide)-poly(methylmethacrylate) (PEO-PMMA), polydimethylsiloxane (PDMS), perfluoropolyether (PFPE), polyvinylidene fluoride (PVDF), polytetrafluoroethylene (PTFE), polystyrene (PS).

Any suitable culture medium may be used in a method of the present disclosure. Examples of commonly used culture medium include, without limitation, DMEM (Gibco®), RPMI 1640 (Gibco®), McCoy's 5A (Hyclone, Thermo Scientific), and DMEM/Nutrient Mixture F-12 (DMEM/F12, Gibco®).

In another aspect, the cells are cultured in suspension in a drop of culture medium hanging onto a supporting material such as the bottom of a petri dish and the wall of a rolling bottle. In certain embodiments, the drop of the culture medium has a volume of no more than 1 ml, 2 ml, 3 ml, 4 ml or 5 ml. In certain embodiments, the drop of culture medium hangs upside down on the bottom of a culturing container such as a petri dish.

In certain embodiments, the cells are cultured in a rotating, or shaking or static state.

In certain embodiments, the method of reprogramming cells comprises culturing the cells in the absence of any supporting substrate or structure suspending, floating or otherwise disposed within the culture medium.

The term "three-dimensional cell aggregate" as used herein refers to cells growing into a three-dimensional (3D) shape as opposed to a cell monolayer. A three-dimensional cell aggregate can be grown on two-dimensional, three-dimensional or multi-dimensional substrates. In certain embodiments, the three-dimensional cell aggregate of the present disclosure is a multicellular and multilayer cell aggregate. In certain embodiments, the three-dimensional cell aggregate of the present disclosure is in a sphere-like shape. In certain embodiments, the sphere-like shaped cell aggregate of the present disclosure can maintain a stable morphology for several weeks. In certain embodiments, the three-dimensional cell aggregate has a diameter of at least 10 μm, 15 μm or 20 μm.

In certain embodiments, the cells are reprogrammed to up-regulate one or more stem cell markers. The stem cell markers are genes and proteins that are characteristic of stem cells. Examples of stem cell markers for use with the methods described herein include, without limitation, Oct4, Nanog, Sox2, Klf4, c-Myc, Lin28, Rex1, Tdgf1, Leftb, Ebaf, Grb7, Podx1, Nodal, Fgf4, Nestin, Gdf3, Dax1, Nat1, Esg1, Slc2a3, Sox1, Olig2 and Pax6. The NCBI (National Center for Biotechnology Information) reference numbers of these stem cell markers (both nucleotide and protein) are shown in Table 1 below. The exemplary protein sequences are also shown in FIG. 12 A-J.

In certain embodiments, the stem cell markers can be embryonic stem cells markers such as Oct4, Nanog, Sox2, Rex1, Gdf3, Dax1, Nat1, Esg1, Slc2a3, Tdgf1, Leftb, Ebaf, Grb7, Podx1, and Fgf4.

In certain embodiments, the stem cell markers can be renal stem cell markers such as Pax2, Wt1, Integrin Alpha 8, Sall1, Lim1, Ncam1, Six2, Frizzled 2, Frizzled 7, Acvr2b and Ntrk2.

In certain embodiments, the stem cell markers can be neural stem cell markers such as Sox2 (Episkopou, 2005; Reynolds and Weiss, 1992).

Reprogramming of a cell by a method of the present disclosure may be identified by the presence or absence of a stem cell marker or by the increase or decrease of a stem cell marker in the gene level or protein level. In certain embodiments, the cells that express no stem cell markers are induced into reprogramming by the methods of the present disclosure to express one or more stem cell markers. In certain embodiments, the cells that express one or more stem cell markers are induced into reprogramming by the methods of the present disclosure to express additional one or more stem cell markers. In certain embodiments, the reprogrammed cells of the present disclosure express at least two, three, four or five stem cell markers at the gene level and/or protein level.

In certain embodiments, the reprogrammed cells of the present disclosure express in an increased level of gene and/or protein of at least one, two, three, four, five or six stem cell markers selected from the group consisting of Oct4, Nanog, Sox2, Klf4, c-Myc, and Lin 28. In certain embodiments, the reprogrammed cells of the present disclosure express in an increased level of gene and/or protein of at least one, two, three, four or five stem cell markers selected from the group consisting of Oct4, Nanog, Sox2, Klf4, and c-Myc.

In certain embodiments, reprogramming of cells using the methods described herein cause cells to up-regulate stem cell markers Oct4, Sox2, c-Myc and Klf4 at the gene level while up-regulating stem cell markers Nanog and Sox2 at the protein level.

In another aspect, the methods of the present disclosure can also transdifferentiate a cell, in which a partially or terminally differentiated cell is transformed into a different

TABLE 1

| Marker Name | NCBI Reference No. (Nucleotide) | NCBI Reference No. (Protein) | Marker Name | NCBI Reference No. | NCBI Reference No. (Protein) |
|---|---|---|---|---|---|
| Acvr2b | NM_001106 | NP_001097.2 | Ncam1 | NM_000615.6 | NP_000606.3 |
| c-Myc | NM_002467 | NP_002458.2 | Nestin | NM_006617 | NP_006608.1 |
| Dax1 | NM_007430 | NP_031456.1 | Nodal | NM_018055 | NP_060525.3 |
| Ebaf | NM_001172425 | NP_001165896.1 | Ntrk2 | NM_001007097 | NP_001007098.1 |
| Esg1 | NM_001025290 | NP_001020461.1 | Oct4 | NM_001173531 | NP_001167002.1 |
| Fgf4 | NM_002007 | NP_001998.1 | Olig2 | NM_016967 | NP_058663.2 |
| Frizzled 2 | NM_001466 | NP_001457.1 | Pax2 | NM_000278 | NP_000269.2 |
| Frizzled 7 | NM_003507 | NP_003498.1 | Pax6 | NM_001244198 | NP_001231127.1 |
| Gdf3 | NM_008108 | NP_032134.2 | Podxl | NM_001018111 | NP_001018121.1 |
| Grb7 | NM_001030002 | NP_001025173.1 | Rex1 | NM_020695 | NP_065746.3 |
| Integrin Alpha 8 | NM_003638 | NP_003629.1 | Slc2a3 | NM_011401 | NP_035531.3 |
| Klf4 | NM_004235 | NP_004226.3 | Sall1 | NM_001127892 | NP_001121364.1 |
| Leftb | NM_020997 | NP_066277.1 | Six2 | NM_016932 | NP_058628.3 |
| Lim1 | NM_005568 | NP_005559.2 | Sox1 | NM_009233 | NP_033259.2 |
| Lin28 | NM_024674 | NP_078950.1 | Sox2 | NM_003106.3 | NP_003097.1 |
| Nanog | NM_024865 | NP_079141.2 | Tdgf1 | NM_001174136 | NP_001167607.1 |
| Nat1 | NM_008673 | NP_032699.1 | Wt1 | NM_000378 | NP_000369.3 | type of differentiated cell, or an induced stem cell is transformed into a specialized cell that is different from the type of specialized cell before inducement.

In certain embodiments, the transdifferentiated cells are characterized by one or more transdifferentiation markers. The term "transdifferentiation marker" as used herein refers to characteristic gene and/or protein that can be used to identify transdifferentiation of a cell.

Examples of transdifferentiation markers may include, for example, endoderm markers such as Foxa2, Afp, Sox17 and Pdx-1, mesoderm markers such as Branchyury and Msx1, ectoderm markers such as Nestin, Otx2 and Tp63, renal glomeruli markers such as Nphs1, Actn4, Cd2ap, Cdh3, Pdpn and Podx1, renal proximal tubule markers such as Aqp1, Clcn5, Cubn, Lrp2 and Slc5a1, renal Henle's loop markers such as Umod and Pkd2, and renal distal tubule and collecting duct markers such as Scnn1a and Pkd1, neuron markers such as Map2, NeuN, Tuj1, NF-L, NF-M and NF-H, astrocyte markers such as Gfap, S100A and S100B, and oligodendrocyte markers such as Mbp and Ng2, and neuro-specific transcription factors such as Pax6, Sox1, Otx2, Zic1, NeuroD1 and Olig2. The NCBI reference numbers of the above mentioned transdifferentiation markers are shown in the Table 2 below. The exemplary protein sequences are shown in FIG. 13 A-R.

such proteins include, without limitation, Oct4, Sox2, c-Myc, Klf4, Nanog, and Lin28. The proteins can be recombinantly expressed in a suitable host cell and purified using methods known in the art (e.g. affinity chromatography). The proteins can be delivered to the cells using methods known in the art. For example, proteins can be delivered to cytosol by reversible permeabilization mediated by streptolysin O, which forms a pore in plasma membrane and allows protein delivery (see, e.g. Walev, I. et al, PNAS, 98(6): 3185-3190, 2001; Cho, H. J. et al., Blood, 116: 386-395, 2010). For another example, the proteins can be fused to a transduction domain such as HIV tat and polyarginine, which can mediate the transmembrane delivery of the proteins to the cytosol (see, e.g. Zhou, H. et al., Cell stem cell, 4: 381-384, 2009).

In certain embodiments, the inducing agent is a polynucleotide encoding for a protein that is capable of inducing reprogramming of a cell. Examples of such polynucleotides include, without limitation, polynucleotides encoding for Oct4, Sox2, c-Myc, Klf4, Nanog, and Lin28. When introduced to the cells to be reprogrammed, the polynucleotides can be expressed to produce gene products that can stimulate the reprogramming. The polynucleotides can be an expression cassette containing the encoding sequence and promoter, or an expression vector, which can be readily con-

TABLE 2

| Marker Name | NCBI Ref. No. (Nucleotide) | NCBI Ref. No. (Protein) | Marker Name | NCBI Ref. No. (Nucleotide) | NCBI Ref. No. (Protein) |
| --- | --- | --- | --- | --- | --- |
| Actn4 | NM_004924 | NP_004915.2 | Ng2 | NM_139001 | NP_620570.2 |
| Afp | NM_001134 | NP_001125.1 | Nphs1 | NM_004646 | NP_004637.1 |
| Aqp1 | NM_001185060 | NP_001171989.1 | Olig2 | NM_016967 | NP_058663.2 |
| Branchyury | NM_003181 | NP_003172.1 | Otx2 | NM_021728 | NP_068374.1 |
| Cd2ap | NM 012120 | NP_036252.1 | Pax6 | NM_001244198 | NP_001231127.1 |
| Cdh3 | NM_001793 | NP_001784.2 | Pdpn | NM_001006624 | NP_001006625.1 |
| Clcn5 | NM_000084 | NP 000075.1 | Pdx-1 | NM_000209 | NP 000200.1 |
| Cubn | NM_001081 | NP 001072.2 | Pkd1 | NM_000296 | NP_000287.3 |
| Foxa2 | NM_021784 | NP_068556.2 | Pkd2 | NM_000297 | NP_000288.1 |
| Gfap | NM_001131020 | NP_001124492.1 | Podxl | NM_001018111 | NP_001018121.1 |
| Lrp2 | NM_004525 | NP_004516.2 | S100A | NM_011309 | NP_035439.1 |
| Map2 | NM_001039934 | NP_001035023.1 | S100B | NM_009115 | NP_033141.1 |
| Mbp | NM_001025245 | NP_001020416.1 | Scnn1a | NM_001038 | NP_001029.1 |
| Msx1 | NM_002448 | NP_002439.2 | Slc5a1 | NM_000343 | NP_000334.1 |
| Nestin | NM_006617 | NP 006608.1 | Sox1 | NM_009233 | NP_033259.2 |
| NeuN | NM_001024931 | NP_001020102.2 | Sox17 | NM_022454 | NP_071899.1 |
| NeuroD1 | NM_010894 | NP_035024.1 | Tp63 | NM_001114978 | NP_001108450.1 |
| NF-H | NM_010904 | NP_035034.2 | Tuj1 | NM_023279 | NP_075768.1 |
| NF-L | NM 010910 | NP 035040.1 | Umod | NM_001008389 | NP 001008390.1 |
| NF-M | NM 008691 | NP_032717.2 | Zic1 | NM_009573 | NP_033599.2 |

In certain embodiments, cells reprogrammed using the methods of the present disclosure show both stem cell markers and transdifferentiation markers. For example, the methods of the present disclosure can induce an embryonic cell HEK293 to up-regulate certain stem cell markers (e.g., Six2, Frizzled2, Frizzled7, Acvr2b and Ntrk2) as well as certain transdifferentiation markers (e.g., Nphs1, Actn4, Cd2ap, Cdh3, Aqp1, Clcn5, Cubn, Umod Pkd2, Scnn1a, Pkd1), which indicates that the HEK293 cells have been transdifferentiated into mature renal cells.

In another aspect, the methods of the present disclosure further include introducing into the cell culture an inducing agent that is capable of inducing a differentiated cell to transform into a stem cell. An inducing agent can be any chemical or biochemical substance including, without limitation, a small molecule compound, a nucleotide, a peptide, or any combination thereof.

In certain embodiments, the inducing agent is a protein capable of inducing reprogramming of a cell. Examples of structed using molecular cloning techniques (e.g. cDNA preparation followed by insertion into a plasmid vector) and can be introduced into cells by transfection methods (e.g. using lipofectamine reagent or calcium phosphate).

In certain embodiments, the inducing agent is a chemical compound capable of inducing reprogramming of a cell. Examples of such chemical compounds include, without limitation, BIX-01294 and BayK8644 (see, e.g. Shi et al, cell stem cell, 3: 568-574, 2008), valproic acid, and 5' azacytidine.

In another aspect, the present disclosure provides a reprogrammed cell obtained using the methods of the present disclosure. In certain embodiments, such reprogrammed cells show up-regulation in at least one, two, three, four, five or six stem cell markers. In certain embodiments, such reprogrammed cells show up-regulation in the gene and/or protein level of at least one, two, three, four, five or six stem cell markers selected from the group consisting of Oct4, Nanog, Sox2, Klf4, c-Myc and Lin28. In certain embodiments, such reprogrammed cells show up-regulation in at least one, two, three, four, five or six stem cell markers, and up-regulation in at least one, two, three, four, five or six transdifferentiation markers.

In another aspect, the present disclosure provides reprogrammed three-dimensional cell aggregates obtained using the methods of the present disclosure. In certain embodiments, the reprogrammed cell aggregates have sphere like shape. In certain embodiments, the reprogrammed cell aggregates have a diameter of at least 10 µm, 15 µm or 20 µm.

In another aspect, the present disclosure provides a kit for reprogramming cells, containing a low-adherent substrate and a culture medium. In certain embodiments, the kit further contains an instruction manual. In certain embodiments, the low-adherent substrate contains agarose or poly (2-hydrozy-ethyl methacrylate).

The reprogramming methods and the reprogrammed cells or cell aggregates of the present disclosure are useful for generating desired cells or tissues in vitro or in vivo. Such cells or tissues can be used for wound healing, neural re-generation, tissue re-generation, drug screening and the like.

All publications and patents cited in this specification are herein incorporated by reference to their entirety.

EXAMPLES

The invention will be more readily understood with reference to the following examples, which are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1. Cell Culture

RT4 and Human Embryonic Kidney (HEK) 293 cells were cultured in McCOY'5A (HYCLONE) and DMEM (HYCLONE), respectively.

The mouse embryonic fibroblasts (MEF) cells were derived from E13.5 day ICR mouse embryos. For hippocampus transplantation experiment, green fluorescent protein (GFP) transgenic mouse was used. Briefly, after removing of head, limbs, visceral tissues and vertebral column, the remaining parts of the isolated embryos were cut into pieces followed by trypsinization. Cells were collected from the supernatant of the trypsinized tissues by centrifugation and then resuspended in fresh medium. The P0 MEF cells were allowed to grow to confluence before being passaged. The P2 MEF cells were use for further 2D and 3D culture.

Mouse tail tip fibroblast (TTF) cells were isolated from 24 h ICR mouse. Briefly, the front ¼-⅕ part of tail was cut into pieces which were then plated on to cell culture dishes and cultured for 2-3 days. The cells started to migrate out from the pieces at about 72 hours. After another 2-3 days culture, the cells migrating out were passaged. The P3 TTF cells were used for further 2D and 3D culture.

For 3D culture, low-adherent culture dish was prepared by coating cell culture dish with soft gel, which was made by mixing 1% melted agarose gel with an equal amount of 2×DMEM medium. $3 \times 10^6$ RT4 or HEK293 cells were transferred to a 60 mm low-adherent dish. $6 \times 10^6$ MEF cells or TTF cells were transferred to 60 mm low-adherent dish.

For 2D culture, regular cell culture dish was used, without coating the dish with any soft gel.

Example 2. Reprogramming of RT4 Cells

Human urinary bladder papilloma cell line RT4 cells were cultured by monolayer adherent culture (2D) and sphere culture (3D), respectively. We used complete growth medium with 10% fetal bovine serum instead of serum-free medium supplemented with growth factors.

2.a. Cell Morphology of RT4 Cells

As shown in FIG. 1A (left), human urinary bladder papilloma cell line RT4 cells were cultured by monolayer adherent culture on regular attachment dish and demonstrated epithelial morphology. In contrast, in FIG. 1A (right), RT4 cells cultured on low attachment dish were detached from the plate and formed floating 3D spheres which maintained for several weeks.

2.b. The Stem Cell Characteristics of RT4 Spheres

Expression levels of the stem cell markers were determined using quantitative PCR (Q-PCR). Briefly, total RNA was isolated from the cells with Trizol LS reagent (Invitrogen), and then mixed with reverse transcriptase reaction mix (SuperScript III First-Strand Synthesis System, Invitrogen) and oligo-dT primers (Invitrogen). Q-PCR was performed using Power SYBR Green RT-PCR Kit (Applied Biosystems). GADPH was used as the control to normalize the cDNA inputs. The results were shown as fold change of the expression level of a testing marker in the testing cell culture relative to that in the 2D culture. Data were shown as mean±standard derivation, N=3. Student's T test was used to determine if the results for the 3D cultured cells are statistically different from the 2D cultured cells. Differences having statistical significance were marked with one asterisk (*, P<0.05) or two asterisks (**, P<0.01) in the Figures. All Q-PCR studies in the Examples and Figures were performed using the similar methods, unless otherwise specified.

Quantitative PCR analysis results of the genes expression showed that OCT4, NANOG, SOX2, KLF4 and c-MYC were up-regulated in sphere culture group compared to monolayer culture group (FIG. 1B, the primers used in the Q-PCR analysis are listed in Table 3 below). The protein levels of NANOG and SOX2 were significantly up-regulated in RT4 spheres as demonstrated by western blotting (FIG. 1C), using primary antibodies against NANOG (1:5000 diluted, abcam) and SOX2 (1:200 diluted, invitrogen), respectively, and secondary antibodies conjugated with horseradish peroxidase (HRP).

2.c. The Cancer Stem Cell Characteristics of RT4 Cells

The percentage of stem cells was detected by "Side Population" (SP) discrimination assay, a flow cytometry method for detection of stem cell percentage using dye efflux properties of stem cells. Briefly, cells were trypsinized and incubated with 5 ug/ml Hoechst 33342 (Sigma) at 37° C. for 90 min, either alone or with 50 ug/ml verapamil (Sigma). The cells were spun down and subject to flow cytometry cell sorting (FACS) analysis with a FACSVantage SE (BD Biosciences) after excluding the dead cells. The percentage of SP cells in sphere culture group was 0.83±0.32%, compared to 0.37±0.12% in monolayer culture group.

The metastasis ability of RT4 cell was detected by transwell assay, and the migrated cells was stained with crystal violet. Briefly, cells cultured by 2D or 3D method were serum-starved for 24 h before being trypsinized and resuspended in serum-free media. The cell suspensions were plated on the top chamber of a 24-well transwell containing 8 um pores (Corning), and the bottom chamber was filled with medium supplemented with 10% FBS. After 24 h, cells migrated in response to FBS to the bottom chamber were stained with 0.1% crystal violet, and the stained cells were counted under microscope. Quantitative analysis of the migrated RT4 cells indicated sphere culture promoted cell metastasis ability (FIG. 2A). 4 stochastic fields were counted for each experimental group, and the results are shown as mean±standard deviation.

Gene expression associated with epithelial mesenchymal transition (EMT) was examined by Q-PCR. The results demonstrated FOXC2, SNAIL and ZEB2 were up-regulated in RT4 spheres compared to the monolayer (FIG. 2B, the primers used in the Q-PCR analysis are listed in Table 3 below).

We performed in vivo nude mice tumor formation assay. Cells were injected subcutaneously into the back flanks of 4-5 week old nude mice (8 BALB/c-nu). As shown in FIG. 2C, $1 \times 10^6$ monolayer RT4 cells formed tumors in 11 out of 14 mice, while $1 \times 10^6$ sphere derived RT4 cells formed tumors in 14 out of 14 mice. Furthermore, $1 \times 10^4$ monolayer RT4 cells failed to form any tumors, while $1 \times 10^4$ sphere derived cells formed tumors in 4 out of 14 mice (FIG. 2C). The data indicated that 3D sphere cultures of RT4 tumor cells promoted cancer stem cell properties.

Example 3. Reprogramming of HEK293 Cells 3.a. Cell Morphology of HEK 293 Cells

HEK293 is a non-cancerous cell line originally derived from human embryonic kidney cells. HEK293 cells adhered to the cell culture dish showed monolayer epithelial morphology (FIG. 3A left), while cultured on the low-adherent plate HEK293 formed floating 3D spheres (FIG. 3A right).

3.b. The Stem Cell Characteristics of HEK 293 Cells

Expression of some stem cell markers was determined by Q-PCR and Western blotting using both the 2D cultured and the 3D cultured HEK293 cells. Q-PCR analyses of the known iPS inducing factors showed that OCT4, NANOG, SOX2, KLF4 and LIN28 were all up-regulated in sphere culture at 5 and 10 days compared to monolayer cultures (FIG. 3B, the primers used in the Q-PCR analysis are listed in Table 3 below). Western blotting analyses also showed that the protein levels of NANOG and SOX2 in sphere culture group were higher compared to the monolayer group (FIG. 3C). Primary antibody and secondary antibody were the same as these in Example 2.

The 2D cultured and the 3D cultured HEK293 cells were also compared for transcriptive activities of the stem cell markers, using reporter gene assay and bisulfite genomic sequencing.

For reporter gene assay, HEK293 cells from 2D or 3D cultures were transfected with luciferase reporter constructs of the binding sequences of OCT4, NANOG or SOX2/OCT4 (i.e., Oct4-Luc vector (constructed by inserting 6W enhancer into PGL3 vector with tk promoter), Nanog-Luc vector (constructed by ligating Nanog binding site P5N to the SalI site of p37tk-luciferase vector, see also in: Pan, G. et al, Journal of Biological Chemistry, 280:1401-1407 (2005)), and Sox2/Oct4-Luc vector (constructed by cloning a sequence containing six copies of Oct4/Sox2 binding oligonucleotides to the upstream of the FGF-4 promoter in PGL3 vector). Luciferase assay was carried out according to the standard protocol (Promega). We found that OCT4, NANOG and SOX2/OCT4 proteins in 3D cultured cells had higher transcription activities (FIG. 3D).

For bisulfite genomic sequencing, bisulfite treatment was performed using Epi-Tect Bisulfite kit (Qiagen), and the transcription regulatory regions of OCT4, NANOG and SOX2 were amplified by PCR (Hotstar HiFidelity DNA polymerase) with respective primers shown in Table 3 below. The PCR products were subcloned into pMD18-T vector and 20 clones of each sample were picked out randomly and sequenced. Bisulfite genomic sequencing analyses evaluated the methylation status of cytosine guanine dinucleotides (CpG) in the transcriptional regulatory regions of OCT4, NANOG and SOX2, and the results revealed that the methylation status in HEK293 spheres were lower than those in monolayer HEK293 cells (FIG. 3E).

The 2D cultured and the 3D cultured HEK293 cells were further tested to see if they demonstrate any characteristics of undifferentiated ES cells. Q-PCR analyses of mRNA expression of several undifferentiated ES cell marker genes showed that REX1, TDGF1, LEFTB, EBAF, GRB7, PODX1 and FGF4 were up-regulated in HEK293 3D cells (FIG. 3F, the primers used in the Q-PCR analysis are listed in Table 3 below). Q-PCR analyses of the differentiation ability of HEK293 spheres into endoderm, mesoderm and ectoderm indicated that the endoderm markers (FOXA2, AFP, SOX17 and PDX-1), mesoderm markers (BRANCHYURY and MSX1) and ectoderm markers (NESTIN, OTX2 and TP63) were all up-regulated in spheres (FIG. 3G, the primers used in the Q-PCR analysis are listed in Table 3 below). Alkaline phosphatase expression was detected by alkaline phosphatase (AP) staining. As shown in FIG. 3H, AP staining was positive in HEK293 sphere cells but negative in monolayer cells.

The tumorigenicity of HEK293 spheres were examined by in vivo nude mice tumor formation assay. $3 \times 10^6$ HEK293 monolayer cells and $3 \times 10^6$ HEK293 cells in sphere culture were injected subcutaneously into the back flanks of 4-5 week old nude mice, respectively. As shown in FIG. 3I, we found HEK293 monolayer cells failed to form any tumors, while HEK293 spheres formed tumors in 3 out of 7 mice in the subcutaneous tissue and trypsinized sphere cells formed tumors in 1 out of 7 mice. No definite structures of endoderm, mesoderm and ectoderm were detected, indicating certain disparity may exist between these tumors and teratomas formed by ESCs. These results demonstrated that HEK293 cells cultured as 3D spheres could partly generate embryonic stem cell phenotypes.

Example 4. Transdifferentiation of HEK 293 Cells

In this example, HEK293 cells were tested for the reprogramming activities towards renal stem cell phenotype, and also the transdifferentiation reprogramming activities towards distinct types of terminally differentiated cells in kidney.

Kidney progenitor cells reside in the metanephric mesenchyme, which further differentiate into nephrons, which are composed of glomeruli (podocyte), proximal tubule, Henle's loop, distal tubule and collecting duct (FIG. 4A).

The 2D cultured and the 3D cultured HEK293 cells were tested for expression of metanephric mesenchyme specific genes and renal progenitor cell markers. Q-PCR analyses of the metanephric mesenchyme specific gene expression indicated that PAX2, WT1, INTEGRIN alpha 8, SALL1, LIM1 and NCAM1 were up-regulated in HEK293 spheres. The renal progenitor cell markers SIX2, FRIZZLED 2, FRIZZLED 7, ACVR2b and NTRK2 were also up-regulated in HEK293 spheres (FIG. 4B, the primers used in the Q-PCR analysis are listed in Table 3 below). These results demonstrated that sphere formation of HEK293 could promote renal stem cell phenotype.

The 2D cultured and the 3D cultured HEK293 cells were further tested for nephron differentiation markers. The Q-PCR examination of differentiated markers of glomeruli, proximal tubule, Henle's loop, distal tubule and collecting duct showed that Glomeruli markers (NPHS1, ACTN4, CD2AP, CDH3, PDPN and PODX1), proximal tubule markers (AQP1, CLCN5, CUBN, LRP2 and SLC5A1), Henle's loop markers (UMOD and PKD2) and distal tubule and collecting duct markers (SCNN1a and PKD1) of HEK293 spheres were all up-regulated significantly in 3D cells when they were cultured for 5 and 10 days (FIG. 4C-F, the primers used in the Q-PCR analysis are listed in Table 3 below). The data suggested that the sphere culture could promote kidney tissue specific dedifferentiation that accompanied with redifferentiation into mature renal units.

Example 5. Reprogramming of MEF Cells

To further evaluate the effect of sphere culture on primary cell, MEFs were cultured into spheres. MEFs showed typical morphology with branched cytoplasm surrounding an elliptical nucleus when they were adhered to cell culture plates, while cultured on low-adherent plates they formed 3D spheres (FIG. 5A). The expression of iPS inducing factors and several undifferentiated ES cell marker genes were examined by Q-PCR. The expression of Sox2, Gdf3, Dax1 and Slc2a3 was higher in MEFs spheres than monolayer MEFs after cultured for 7 and 12 days (FIG. 5B, the primers used in the Q-PCR analysis are listed in Table 3 below). While Oct4, Nanog and Klf4 were not up-regulated in MEFs spheres (FIGS. 5B and 5C), high level of Sox2 protein in MEFs spheres was confirmed by western blotting, which was comparable to that in teratoma cell line PA-1. In contrast, no expression of Sox2 was detected in monolayer MEFs by Western Blotting (FIG. 5D). AP staining was performed to determine the expression of alkaline phosphatase. As illustrated in FIG. 5E, positive AP staining was found in MEFs spheres but not in monolayer MEFs. These data revealed that sphere culture of MEFs could promote the expression of some embryonic stem cell genes.

Example 6. Transdifferentiation of MEF and TTF Cells into Neuron Cells

Considering the high expression of Sox2 in MEFs spheres, we tested whether MEF spheres acquired neurosphere properties. As illustrated in FIG. 6A-B, Nestin was up-regulated in MEFs spheres cultured for 7 and 12 days. We also analyzed the expression of genes associated with differentiated neurons, astrocytes and oligodendrocytes in MEF spheres. The neuron markers (Map2, NeuN, Tuj1, NF-L, NF-M and NF-H), astrocyte markers (Gfap, S100A and S100B) and oligodendrocyte markers (Mbp and Ng2) were all up-regulated in MEFs spheres (FIG. 6A-B, data were shown as mean±standard derivation, N=4). Several neuro-specific transcription factors (Pax6, Sox1, Otx2, Zic1, NeuroD1 and Olig2) were also higher expressed in MEFs spheres (FIG. 6A-B). Tuj1 and Gfap proteins were detected in MEFs spheres cultured for 1, 3, 5 and 7 days and increased over time, but not expressed in monolayer MEFs (FIG. 6C).

When MEF spheres were re-adhered to cell culture dish, cells in the spheres migrated back onto the dish to form a monolayer. We name these back-migrated cells as sphere derived adherent cells. Immunocytochemistry staining was performed, and immunofluorescence pictures were taken for both monolayer cells and sphere cultured cells. For each cell culture, four representative pictures were taken, and percentage of cells that were positive for a particular marker was calculated for each picture by dividing the number of the positive cells by the total number of the cells in the picture. The results showed that some cells in sphere derived adherent cells were positive for Tuj1 (FIG. 6D), Neurofilament (FIG. 6E), S-100 (FIG. 6F) and Gfap (FIG. 6G), but monolayer MEFs were negative (FIG. 6D-G). In addition, we found some cells in MEFs sphere derived cells labelled with antibodies against GABA, the major inhibitory neurotransmitter of neurons in brain (FIG. 6H). The data demonstrated that 3D sphere culture could reprogram MEFs to acquire neurosphere properties. The immunocytochemistry staining was performed using primary antibodies included anti-Tuj1 (1:500 diluted, Millipore), anti-GFAP (1:500 diluted, Millipore), anti-Neurofilament (1:1000 diluted, Abcam), anti-S100 (1:100 diluted, Sigma), anti-GABA (1:3000 diluted, Sigma), and secondary antibodies including Dylight 488-conjugated AffiniPure Donkey Anti-Mouse IgG (1:400 diluted, Jackson ImmunoResearch) and Alexa Fluor 488 donkey anti-rabbit IgG (1:1000 diluted, Invitrogen).

Next we tested whether MEF spheres could acquire neural cell phenotypes in neural induction medium. Several methods were attempted including RA, SHH, N2 (data not shown) and BHA, only BHA was effective. After 10 days induction, monolayer MEFs showed no obvious morphology change, while cells derived from MEFs spheres exhibited long neural process-like morphology with extensive branching. Q-PCR results illustrated most neural markers of monolayer MEFs with BHA induction remained unchanged or down-regulated compared to control. In contrast, in MEF sphere group, most neural markers were further up-regulated including Sox2, Nestin, Map2, Gfap, Tuj1, Nf-L, S100B, Ng2, NeuN, NeuroD1 and Pax6 after BHA induction (FIG. 6I, the primers used in the Q-PCR analysis are listed in Table 3 below). These data demonstrated BHA could promote the conversion of sphere MEFs to neural cells.

Hippocampus is a special structure in brain where neurogenesis occurs throughout adulthood. To further evaluate the neurosphere characteristics of MEFs spheres in vivo, GFP-labeled monolayer MEFs and sphere MEFs were transplanted into the hippocampus of rats, and the survival and differentiation capabilities were analyzed at 2 and 4 weeks. Compared to 2 weeks, the number of GFP positive cells at 4 weeks decreased dramatically in monolayer group while the number of sphere MEFs showed no apparent decrease, suggesting sphere MEFs possess higher viability. As shown in FIG. 7A-E, GFP positive sphere MEFs were detected by antibodies against Tuj1, GFAP, S100, NeuN and MAP2 at 2 weeks and 4 weeks after transplantation, while GFP positive cells in monolayer MEFs failed to express these neural markers (data were shown as mean±standard derivation, N=4). These results indicated sphere MEFs can generate viable neural cells in vivo. Moreover, the presence of NeuN and MAP2 positive cells in sphere MEFs suggested mature neurons could be generated after implantation.

Monolayer TTFs showed typical fibroblast morphology while TTFs cultured on low-adherent plates formed floating 3D spheres (FIG. 8A). Although some embryonic stem cell specific genes (Nanog, Gdf3, Dax1, Nat1 and Esg1) were not up-regulated in TTFs spheres, the mRNA and protein expression of sox2 in TTFs spheres were up-regulated significantly by western blotting and Q-PCR analyses compared to monolayer TTFs (FIGS. 8B and 8C). Q-PCR analysis also demonstrated that the neuron marker Nf-L, astrocyte marker Gfap and S100B, oligodendrocyte marker Ng2 and several neuro-specific transcription factors Pax6, Sox1 and Zic1 were higher expressed in TTFs spheres than monolayer TTFs (FIG. 8C). Immunocytochemistry staining was performed and percentages of cells stained positive were calculated using a similar method as provided above. The results indicated that some cells in TTFs sphere derived monolayer cells were positive for neuron marker Tuj1 and astrocyte marker S100 which are negative in monolayer TTFs (FIG. 8D-E, data were shown as mean±standard derivation, N=4.). These data suggested that 3D sphere of mouse postnatal fibroblasts could promote reprogramming and also demonstrate neurosphere properties.

Example 7. Reprogramming of MCF-7 Cells

Human breast cancer cell line, MCF-7 cell line, was cultured in DMEM-High glucose medium (HYCLONE).

For 3D culture, low-adherent culture dish was prepared by coating cell culture dish with soft gel, which was made by mixing 1% melting agarose gel with an equal amount of 2×DMEM medium. $3 \times 10^6$ MCF-7 cells were transferred to a 60 mm low-adherent dish.

After a few days, the MCF-7 cells cultured in the 3D culture grew into spheres (see FIG. 9A right), while the MCF-7 cells cultured in conventional 2D cell culture dishes formed a monolayer (see FIG. 9A left).

The expression of several stem cell marker genes was examined by Q-PCR for both the MCF-7 monolayer formed in the 2D culture and the MCF-7 spheres formed in the 3D culture. As shown in FIG. 9B, all of the tested stem cell markers were up-regulated in the MCF-7 spheres, including, Oct4, Nanog, Sox2, c-Myc, Klf4, Lin 28, Rex1, Fgf4, Esg1, Tdgf1, Leftb, Ebaf, Grb7, Podx1 and Nestin. These data revealed that sphere culture of MCF-7 cells promoted the expression of some stem cell marker genes, including some embryonic stem cell marker genes.

Example 8. Reprogramming of Rat Osteoblast Cells

Rat osteoblast cells were cultured in DMEM-High glucose medium (HYCLONE). Rat osteoblast cells were obtained by primary isolation from 1-day old rat cranium.

For 3D culture, low-adherent culture dish was prepared by coating cell culture dish with soft gel, which was made by mixing 1% melting agarose gel with an equal amount of 2×DMEM medium. $3 \times 10^6$ rat osteoblast cells were transferred to a 60 mm low-adherent dish.

After a few days, the rat osteoblast cells cultured in the 3D culture grew into spheres (see FIG. 10A right), while the rat osteoblast cells cultured in conventional 2D cell culture dishes formed a monolayer (see FIG. 10A left).

The expression of several stem cell marker genes was examined by Q-PCR for both the monolayer formed in the 2D culture and the spheres formed in the 3D culture. As shown in FIG. 10B, some of the tested stem cell markers were up-regulated in the rat osteoblast cells spheres, including Oct4, Nanog, Sox2, Lin 28, Fgf4, Nodal and Gal. Some of the marker genes, such as c-Myc, Klf4 and Rex1, were down-regulated. These data revealed that sphere culture induced the rat osteoblast cells to a reprogramming process, which resulted in up-regulation of some stem cell marker genes, including some embryonic stem cell marker genes.

Example 9. Reprogramming of Rat Neuronal Stem Cells

Rat neuronal stem cells were cultured in DMEM/F12 (HYCLONE). Rat neuronal stem cells were obtained by primary isolation from 1-day old rat brain.

For 3D culture, low-adherent culture dish was prepared by coating cell culture dish with soft gel, which was made by mixing 1% melting agarose gel with an equal amount of 2×DMEM medium. $3 \times 10^6$ rat neuronal stem cells were transferred to a 60 mm low-adherent dish.

After a few days, the rat neuronal stem cells cultured in the 3D culture grew into spheres (see FIG. 11A right), while the rat neuronal stem cells cultured in conventional 2D cell culture dishes formed a monolayer (see FIG. 11A left).

The expression of several stem cell marker genes was examined by Q-PCR for both the monolayer formed in the 2D culture and the spheres formed in the 3D culture. As shown in FIG. 11B, some of the tested stem cell markers were up-regulated in the rat neuronal stem cells spheres, including Nanog, Klf4, Fgf4 and Nodal. Some of the marker genes, such as Sox2, c-Myc, Lin28, and Gal were down-regulated. These data revealed that sphere culture induced the rat neuronal stem cells to a reprogramming process, which resulted in up-regulation of some stem cell marker genes.

TABLE 3

Primer Sequences

| Primer Name | Sequence | Note |
| --- | --- | --- |
| (METHY)OCT4-F | GTTAGAGGTTAAGGTTAGTGGGTG (SEQ ID NO: 1) | Methylation analysis of OCT3/4 |
| (METHY)OCT4-R | AAACCTTAAAAACTTAACCAAATCC (SEQ ID NO: 2) | |
| (METHY)NANOG-F | GAGTTAAAGAGTTTTGTTTTTAAAAATTAT (SEQ ID NO: 3) | Methylation analysis of NANOG |
| (METHY)NANOG-R | TCCCAAATCTAATAATTTATCATATCTTTC (SEQ ID NO: 4) | |

TABLE 3-continued

Primer Sequences

| Primer Name | Sequence | Note |
|---|---|---|
| (METHY)SOX2-F | TTGTTTTAGGAAAGGTAAAGAAAGGT (SEQ ID NO: 5) | Methylation analysis of SOX2 |
| (METHY)SOX2-R | AATTCCAACTTCTCCAAAATTATAACA (SEQ ID NO: 6) | |
| (HQ)OCT4A-F | CCCCTGGTGCCGTGAAG (SEQ ID NO: 7) | Q-PCR for human OCT3/4 |
| (HQ)OCT4A-R | GCAAATTGCTCGAGTTCTTTCTG (SEQ ID NO: 8) | |
| (HQ)GAPDH-F | ATGGAAATCCCATCACCATCTT (SEQ ID NO: 9) | Q-PCR for human GAPDH |
| (HQ)GAPDH-R | CGCCCCACTTGATTTTGG (SEQ ID NO: 10) | |
| (HQ)NANOG-F | CCAAAGGCAAACAACCCACTT (SEQ ID NO: 11) | Q-PCR for human NANOG |
| (HQ)NANOG-R | CGGGACCTTGTCTTCCTTTTT (SEQ ID NO: 12) | |
| (HQ)SOX2-F | CCCCTTTATTTTCCGTAGTTGTATTT (SEQ ID NO: 13) | Q-PCR for human SOX2 |
| (HQ)SOX2-R | GATTCTCGGCAGACTGATTCAA (SEQ ID NO: 14) | |
| (HQ)KLF4-F | CATCTTGTGAGTGGATAATCAGGAA (SEQ ID NO: 15) | Q-PCR for human KLF4 |
| (HQ)KLF4-R | GACCCCATCTGTTCTTTGATTTTT (SEQ ID NO: 16) | |
| (HQ)C-MYC-F | CACTTTGCACTGGAACTTACAACA (SEQ ID NO: 17) | Q-PCR for human C-MYC |
| (HQ)C-MYC-R | CCCGCGTCGGGAGAGT (SEQ ID NO: 18) | |
| (HQ)LIN28-F | AGCCCAAGAAGTGCCACTTCT (SEQ ID NO: 19) | Q-PCR for human LIN28 |
| (HQ)LIN28-R | GGGCCTTCAGCGGACAT (SEQ ID NO: 20) | |
| (HQ)FOXC2-F | CACGCCGCCTCTCTATCG (SEQ ID NO: 21) | Q-PCR for human FOXC2 |
| (HQ)FOXC2-R | CGTCAGTATTTCGTGCAGTCGTA (SEQ ID NO: 22) | |
| (HQ)ZEB1-F | TGTGAATGGGCGACCAAGA (SEQ ID NO: 23) | Q-PCR for human ZEB1 |
| (HQ)ZEB1-R | GTGGGACTGCCTGGTGATG (SEQ ID NO: 24) | |
| (HQ)TWIST1-F | GCGCTGCGGAAGATCATC (SEQ ID NO: 25) | Q-PCR for human TWIST1 |
| (HQ)TWIST1-R | GGTCTGAATCTTGCTCAGCTTGT (SEQ ID NO: 26) | |
| (HQ)TWIST2-F | GCCCAGTGGAGCATGCA (SEQ ID NO: 27) | Q-PCR for human TWIST2 |
| (HQ)TWIST2-R | GGTGGGACACCGAGATGGT (SEQ ID NO: 28) | |
| (HQ)SNAIL-F | GTTTCCCGGGCAATTTAACA (SEQ ID NO: 29) | Q-PCR for human SNAIL |
| (HQ)SNAIL-R | CCCGACAAGTGACAGCCATT (SEQ ID NO: 30) | |
| (HQ)ZEB2-F | GCCGAGTCCATGCGAACT (SEQ ID NO: 31) | Q-PCR for human ZEB2 |
| (HQ)ZEB2-R | CCATGATCGGCTGCTTCAT (SEQ ID NO: 32) | |
| (HQ)REX1-F | TCCAAGACTACCACCACCATCAT (SEQ ID NO: 33) | Q-PCR for human REX1 |
| (HQ)REX1-R | TTCTTTAAACTCTGTAAGGATGGACTGT (SEQ ID NO: 34) | |

TABLE 3-continued

Primer Sequences

| Primer Name | Sequence | Note |
|---|---|---|
| (HQ)ESG1-F | GGCTGTTGAACGTGCCAAA (SEQ ID NO: 35) | Q-PCR for human ESG1 |
| (HQ)ESG1-R | TGCCCGATGATGGCATTC (SEQ ID NO: 36) | |
| (HQ)DPPA2-F | CCTGGGTGCCT ACCACTCA (SEQ ID NO: 37) | Q-PCR for human DPPA2 |
| (HQ)DPPA2-R | AAATGCAGGCAGGTAACAAGAAG (SEQ ID NO: 38) | |
| (HQ)TDGF1-F | ACGATGTGCGCAAAGAGAACT (SEQ ID NO: 39) | Q-PCR for human TDGF1 |
| (HQ)TDGF1-R | TGGGCAGCCAGGTGTCA (SEQ ID NO: 40) | |
| (HQ)LEFTB-F | GAGCTGGCGATGACTGAACTG (SEQ ID NO: 41) | Q-PCR for human LEFTB |
| (HQ)LEFTB-R | GCAAATTCAGGGCTCACTAGAGA (SEQ ID NO: 42) | |
| (HQ)NODAL-F | ACTGGACGTTTGCTTTTGACTTC (SEQ ID NO: 43) | Q-PCR for human NODAL |
| (HQ)NODAL-R | CAGCCCATGCCAGATCCT (SEQ ID NO: 44) | |
| (HQ)EBAF-F | CATTTTCAGCTGGGAGTTTCTGT (SEQ ID NO: 45) | Q-PCR for human EBAF |
| (HQ)EBAF-R | GGGTATTATTGTTCCAGACTCAGTGA (SEQ ID NO: 46) | |
| (HQ)GRB7-F | TCTACGGGATGCCCACTGA (SEQ ID NO: 47) | Q-PCR for human GRB7 |
| (HQ)GRB7-R | GGCCATTTCGAAGCTTGTTG (SEQ ID NO: 48) | |
| (HQ)PODXL-F | CTTTTATGGGCTCGGCAGTTA (SEQ ID NO: 49) | Q-PCR for human PODXL |
| (HQ)PODXL-R | TCACCATGCCCACTGCTTAG (SEQ ID NO: 50) | |
| (HQ)FGF4-F | AGTACCCCGGCATGTTCATC (SEQ ID NO: 51) | Q-PCR for human FGF4 |
| (HQ)FGF4-R | CGGTTCCCCTTCTTGGTCTT (SEQ ID NO: 52) | |
| (HQ)FOXD3-F | CCTCGCGCACACCTAAGC (SEQ ID NO: 53) | Q-PCR for human FOXD3 |
| (HQ)FOXD3-R | GGTTTTACCTGTATGGAAAGCTATCC (SEQ ID NO: 54) | |
| (HQ)FOXA2-F | CTGAAGCCGGAACACCACTAC (SEQ ID NO: 55) | Q-PCR for human FOXA2 |
| (HQ)FOXA2-R | CGAGGACATGAGGTTGTTGATG (SEQ ID NO: 56) | |
| (HQ)AFP-F | CCAACAGGAGGCCATGCTT (SEQ ID NO: 57) | Q-PCR for human AFP |
| (HQ)AFP-R | GAGAATGCAGGAGGGACATATGT (SEQ ID NO: 58) | |
| (HQ)SOX17-F | TGGCGCAGCAGAATCCA (SEQ ID NO: 59) | Q-PCR for human SOX17 |
| (HQ)SOX17-R | CGACTTGCCCAGCATCTTG (SEQ ID NO: 60) | |
| (HQ)GATA4-F | CGTCAGCCAGTCTCCACAGA (SEQ ID NO: 61) | Q-PCR for human GATA4 |
| (HQ)GATA4-R | CAAGACCAGGCTGTTCCAAGA (SEQ ID NO: 62) | |
| (HQ)PDX-1-F | TGCCTTTCCCATGGATGAA (SEQ ID NO: 63) | Q-PCR for human PDX-1 |

TABLE 3-continued

Primer Sequences

| Primer Name | Sequence | Note |
|---|---|---|
| (HQ)PDX-1-R | TGCCCACTGGCCTTTCC (SEQ ID NO: 64) | |
| (HQ) BRACHYURY-F | GCTGTGGCTGCGCTTCA (SEQ ID NO: 65) | Q-PCR for human BRACHYURY |
| (HQ) BRACHYURY-R | TCCTCCTGCCGTTCTTGGT (SEQ ID NO: 66) | |
| (HQ)MSX1-F | CTCGCTCAGCCTCACTGAGA (SEQ ID NO: 67) | Q-PCR for human MSX-1 |
| (HQ)MSX1-R | GGCGGCCATCTTCAGCTT (SEQ ID NO: 68) | |
| (HQ)MAP2-F | TCAATCAATTTGCCGATGTCTT (SEQ ID NO: 69) | Q-PCR for human MAP2 |
| (HQ)MAP2-R | CCCCGACCAAAGTTAAATCCA (SEQ ID NO: 70) | |
| (HQ)PAX6-F | CAGACACAGCCCTCACAAACAC (SEQ ID NO: 71) | Q-PCR for human PAX6 |
| (HQ)PAX6-R | TGGTGAAGCTGGGCATAGG (SEQ ID NO: 72) | |
| (HQ)NESTIN-F | AGCCCTGACCACTCCAGTTTAG (SEQ ID NO: 73) | Q-PCR for human NESTIN |
| (HQ)NESTIN-R | CCCTCTATGGCTGTTTCTTTCTCT (SEQ ID NO: 74) | |
| (HQ)OTX2-F | TCGGGCGCAGCTAGATGT (SEQ ID NO: 75) | Q-PCR for human OTX2 |
| (HQ)OTX2-R | TGTCTGGGTACCGGGTCTTG (SEQ ID NO: 76) | |
| (HQ)TP63-F | TTTCCCACCCCGAGATGA (SEQ ID NO: 77) | Q-PCR for human TP63 |
| (HQ)TP63-R | TGCGGCGAGCATCCAT (SEQ ID NO: 78) | |
| (HQ)SIX2-F | TTCCGCGAGCTCTACAAGATC (SEQ ID NO: 79) | Q-PCR for human SIX2 |
| (HQ)SIX2-R | CAGCTTGGCGTGGTTGTG (SEQ ID NO: 80) | |
| (HQ)NCAM1-F | CGATTCATAGTCCTGTCCAACAAC (SEQ ID NO: 81) | Q-PCR for human NCAM1 |
| (HQ)NCAM1-R | AGCGATAAGTGCCCTCATCTG (SEQ ID NO: 82) | |
| (HQ) FRIZZLED2-F | AGGAGGACGCAGGCCTAGAG (SEQ ID NO: 83) | Q-PCR for human FRIZZZLED2 |
| (HQ) FRIZZLED2-R | GCGAGCACTGCACCTTCAC (SEQ ID NO: 84) | |
| (HQ) FRIZZLED7-F | CCATGATCGTCGGCATCAC (SEQ ID NO: 85) | Q-PCR for human FRIZZZLED7 |
| (HQ) FRIZZLED7-R | GCCACGACTGCAGGGTCTT (SEQ ID NO: 86) | |
| (HQ)ACVR2B-F | CAGCATATTGCTCTACTGTATCACAAAC (SEQ ID NO: 87) | Q-PCR for human ACVR2B |
| (HQ)ACVR2B-R | AGCATGGCGCTGGTTCTG (SEQ ID NO: 88) | |
| (HQ)NTRK2-F | GGTCTTCGTCGATTAATACCTTGTG (SEQ ID NO: 89) | Q-PCR for human NTRK2 |
| (HQ)NTRK2-R | CTGCTCTACCTATCAGGGAAACG (SEQ ID NO: 90) | |
| (HQ)LIM1-F | CCGATCAGCCTCGTTTCCT (SEQ ID NO: 91) | Q-PCR for human LIM1 |
| (HQ)LIM1-R | GCCGTGCAAGCCAAAACT (SEQ ID NO: 92) | |
| (HQ)SALL1-F | GGTGGCATCCCTCCAATTC (SEQ ID NO: 93) | Q-PCR for human SALL1 |

TABLE 3-continued

Primer Sequences

| Primer Name | Sequence | Note |
|---|---|---|
| (HQ)SALL1-R | GCCCACTAACAGGTGAGCTGTT (SEQ ID NO: 94) | |
| (HQ)INTEGRIN ALPHA 8-F | AGCCAGCAAAACTCCCAGAA (SEQ ID NO: 95) | Q-PCR for human INTEGRIN alpha 8 |
| (HQ)INTEGRIN ALPHA 8-R | ACATTCGGAGTTGCCCAA ATA (SEQ ID NO: 96) | |
| (HQ)WT1-F | CCACACAACGCCCATCCT (SEQ ID NO: 97) | Q-PCR for human WT1 |
| (HQ)WT1-R | GAAGACACCGTGCGTGTGTATT (SEQ ID NO: 98) | |
| (HQ)PAX2-F | CGTCTCTTCCATCAACAGAATCAT (SEQ ID NO: 99) | Q-PCR for human PAX2 |
| (HQ)PAX2-R | GGCGTTGGGTGGAAAGG (SEQ ID NO: 100) | |
| (HQ)NPHS1-F | CGGATTCACCATGCCAAACT (SEQ ID NO: 101) | Q-PCR for human NPHS1 |
| (HQ)NPHS1-R | GGCGCCACCCCATTGT (SEQ ID NO: 102) | |
| (HQ)ACTN4-F | CGGGCTCAAGCTCATGCT (SEQ ID NO: 103) | Q-PCR for human ACTN4 |
| (HQ)ACTN4-R | CGCTCCGGCTTAGGTAACC (SEQ ID NO: 104) | |
| (HQ)CD2AP-F | TTTTGGCTGGGCCTACTTCA (SEQ ID NO: 105) | Q-PCR for human CD2AP |
| (HQ)CD2AP-R | TGATCCAGATGCAGTTTCACTCA (SEQ ID NO: 106) | |
| (HQ)CDH3-F | AGTGGAGGACCCCATGAACA (SEQ ID NO: 107) | Q-PCR for human CDH3 |
| (HQ)CDH3-R | TTGGGCTTGTGGTCATTCTG (SEQ ID NO: 108) | |
| (HQ)PDPN-F | GGCCGCGGTGCTTTTTA (SEQ ID NO: 109) | Q-PCR for human PDPN |
| (HQ)PDPN-R | GGGCCGAGCAGCAAGAT (SEQ ID NO: 110) | |
| (HQ)PODXL-F | AGCTCCCTGCCAAGGATGT (SEQ ID NO: 111) | Q-PCR for human PODXL |
| (HQ)PODXL-R | CCTCCTTTAGTTCATCCCATTTGT (SEQ ID NO: 112) | |
| (HQ)AQP1-F | AACCCTGCTCGGTCCTTTG (SEQ ID NO: 113) | Q-PCR for human AQP1 |
| (HQ)AQP1-R | CCAGTGGTTGCTGAAGTTGTGT (SEQ ID NO: 114) | |
| (HQ)CLCN5-F | CCCTTCACTGTGACTGACCTTACA (SEQ ID NO: 115) | Q-PCR for human CLCN5 |
| (HQ)CLCN5-R | CAGTCCCAGCTTTCGGAAAA (SEQ ID NO: 116) | |
| (HQ)CUBN-F | CACTGCCCACCTGAGACGTA (SEQ ID NO: 117) | Q-PCR for human CUBN |
| (HQ)CUBN-R | ACCCCCTTCACAGTCGTCATAT (SEQ ID NO: 118) | |
| (HQ)LRP2-F | TGAAACTCTGCAACCACCTAGATG (SEQ ID NO: 119) | Q-PCR for human LRP2 |
| (HQ)LRP2-R | AGGACGACAGGAACAATAGAAACTG (SEQ ID NO: 120) | |
| (HQ)SLC5A1-F | GCCAAGGTCCGCAAGAGA (SEQ ID NO: 121) | Q-PCR for human SLC5A1 |
| (HQ)SLC5A1-R | AAACAACCTTCCGGCAATCA (SEQ ID NO: 122) | |
| (HQ)UMOD-F | GTCCCATCACACGGAAAGGT (SEQ ID NO: 123) | Q-PCR for human UMOD |

TABLE 3-continued

Primer Sequences

| Primer Name | Sequence | Note |
|---|---|---|
| (HQ)UMOD-R | GCCCCAAGCTGCTAAAAGC (SEQ ID NO: 124) | |
| (HQ)SLC12A1-F | AACCGACCCAGCCTGCTT (SEQ ID NO: 125) | Q-PCR for human SLC12AL |
| (HQ)SLC12A1-R | GGGTGACTGCCACATTCTTTG (SEQ ID NO: 126) | |
| (HQ)PKD2-F | TCTGAGGAGGATGACGATGAAGA (SEQ ID NO: 127) | Q-PCR for human PKD2 |
| (HQ)PKD2-R | CTAGAAATGCTTCCCCTCCTTCT (SEQ ID NO: 128) | |
| (HQ)KCNJ1-F | TCCCCATTGACAATTTACCATGT (SEQ ID NO: 129) | Q-PCR for human KCNJ1 |
| (HQ)KCNJ1-R | TCCGCTGCCATGTGGAA (SEQ ID NO: 130) | |
| (HQ)SCNN1A-F | CTCCAGGTTGACTTCTCCTCAGA (SEQ ID NO: 131) | Q-PCR for human SCNN1A |
| (HQ)SCNN1A-R | CATGGCTTCCGGCACTTG (SEQ ID NO: 132) | |
| (HQ)SLC24A1-F | GCCATTGCGGTGGATGAG (SEQ ID NO: 133) | Q-PCR for human SLC24A1 |
| (HQ)SLC24A1-R | TCAGCAAGGACGGGAGCTT (SEQ ID NO: 134) | |
| (HQ)PKD1-F | GCTTGGCATCCCCTTGCT (SEQ ID NO: 135) | Q-PCR for human PKD1 |
| (HQ)PKD1-R | ACGGTGCCTGAGCTGTTGTC (SEQ ID NO: 136) | |
| (HQ)AQP-2-F | GACTGTGGAGCTCTTCCTGACA (SEQ ID NO: 137) | Q-PCR for human AQP-2 |
| (HQ)AQP-2-R | TCGGTGGAGGCGAAGATG (SEQ ID NO: 138) | |
| (mQ)Gapdh-F | CATGGCCTTCCGTGTTCCTA (SEQ ID NO: 139) | Q-PCR for mouse Gapdh |
| (mQ)Gapdh-R | GCGGCACGTCAGATCCA (SEQ ID NO: 140) | |
| (mQ)Oct4-F | CGACCGCCCCAATGC (SEQ ID NO: 141) | Q-PCR for mouse Oct3/4 |
| (mQ)Oct4-R | TGGGACTCCTCGGGAGTTG (SEQ ID NO: 142) | |
| (mQ)Nanog-F | AGGCCTGGACCGCTCAGT (SEQ ID NO: 143) | Q-PCR for mouse Nanog |
| (mQ)Nanog-R | AGTTATGGAGCGGAGCAGCAT (SEQ ID NO: 144) | |
| (mQ)Klf4-F | AGGCACACCTGCGAACTCA (SEQ ID NO: 145) | Q-PCR for mouse Klf4 |
| (mQ)Klf4-R | CAGCCGTCCCAGTCACAGT (SEQ ID NO: 146) | |
| (mQ)Sox2-F | CTGGACTGCGAACTGGAGAAG (SEQ ID NO: 147) | Q-PCR for mouse Sox2 |
| (mQ)Sox2-R | TTTGCACCCCTCCCAATTC (SEQ ID NO: 148) | |
| (mQ)Gdf3-F | AAGGTCAGCTCCAGTTCAACCT (SEQ ID NO: 149) | Q-PCR for mouse Gdf3 |
| (mQ)Gdf3-R | AGTCGGTTGCTGCTCCAATC (SEQ ID NO: 150) | |
| (mQ)Dax1-F | CCAAGATCACCTGCACTTCGA (SEQ ID NO: 151) | Q-PCR for mouse Dax1 |
| (mQ)Dax1-R | TTTCCTGCGTCGTGTTGGT (SEQ ID NO: 152) | |
| (mQ)Fgf4-F | GAGCAACCTCCCGAATTAACTTT (SEQ ID NO: 153) | Q-PCR for mouse Fgf4 |

TABLE 3-continued

Primer Sequences

| Primer Name | Sequence | Note |
|---|---|---|
| (mQ)Fgf4-R | TGCCAATGAGATTTTCCAGTCTT (SEQ ID NO: 154) | |
| (mQ)Slc2a3-F | CAGGCGCACTCTGGAAAAG (SEQ ID NO: 155) | Q-PCR for mouse Slc2a3 |
| (mQ)Slc2a3-R | TTGACCGGCTGCATGCT (SEQ ID NO: 156) | |
| (mQ)Esg1-F | GCCGTGCGTGGTGGAT (SEQ ID NO: 157) | Q-PCR for mouse Esg1 |
| (mQ)Esg1-R | TGCCAAGGAACCAGACTTCAG (SEQ ID NO: 158) | |
| (mQ)Zfp296-F | CCGCGTAGATCCCGATACC (SEQ ID NO: 159) | Q-PCR for mouse Zfp296 |
| (mQ)Zfp296-R | CCGGCTTTACATCCATGACA (SEQ ID NO: 160) | |
| (mQ)Nestin-F | TCTTCCCCCTTGCCTAATACC (SEQ ID NO: 161) | Q-PCR for mouse Nestin |
| (mQ)Nestin-R | TTAGGATAGGGAGCCTCAGACATAG (SEQ ID NO: 162) | |
| (mQ)Gfap-F | CCTGAGAGAGATTCGCACTCAA (SEQ ID NO: 163) | Q-PCR for mouse Gfap |
| (mQ)Gfap-R | CTCCTCTGTCTCTTGCATGTTACTG (SEQ ID NO: 164) | |
| (mQ)Tuj1-F | TCACGCAGCAGATGTTCGAT (SEQ ID NO: 165) | Q-PCR for mouse Tuj1 |
| (mQ)Tuj1-R | GTGGCGCGGGTCACA (SEQ ID NO: 166) | |
| (mQ)Mbp-F | ACAGAGACACGGGCATCCTT (SEQ ID NO: 167) | Q-PCR for mouse Mbp |
| (mQ)Mbp-R | CACCCCTGTCACCGCTAAAG (SEQ ID NO: 168) | |
| (mQ)Map2-F | TCCTCCAAAGTCCCCAGCTA (SEQ ID NO: 169) | Q-PCR for mouse Map2 |
| (mQ)Map2-R | CCGGCAGTGGTTGGTTAATAA (SEQ ID NO: 170) | |
| (mQ)Ng2-F | AACCCTATCTTCACGTAGCCAATAGTT (SEQ ID NO: 171) | Q-PCR for mouse Ng2 |
| (mQ)Ng2-R | GACCAGCGGTTACATGGTAGTG (SEQ ID NO: 172) | |
| (mQ)S100A-F | CTCCTCACCCCACCTGTACCT (SEQ ID NO: 173) | Q-PCR for mouse S100A |
| (mQ)S100A-R | CCTTGGTGCACGTCGAGACT (SEQ ID NO: 174) | |
| (mQ)S100B-F | GGATGTCCGAGCTGGAGAAG (SEQ ID NO: 175) | Q-PCR for mouse S100B |
| (mQ)S100B-R | CCCGGAGTACTGGTGGAAGA (SEQ ID NO: 176) | |
| (mQ)Nf-L-F | CATGCAGAACGCCGAAGA (SEQ ID NO: 177) | Q-PCR for mouse Nf-L |
| (mQ)Nf-L-R | CGGCGCTCTCGGTTAGC (SEQ ID NO: 178) | |
| (mQ)Nf-M-F | GGCTCCAGACATTGTATTTTCCTT (SEQ ID NO: 179) | Q-PCR for mouse Nf-M |
| (mQ)Nf-M-R | GGCACCCTGAGCTTGCAT (SEQ ID NO: 180) | |
| (mQ)Nf-H-F | GACTCCCAAAAATTCCCTCCAT (SEQ ID NO: 181) | Q-PCR for mouse Nf-H |
| (mQ)Nf-H-R | ACCTTTATCATCTCTTCGCTTTTGA (SEQ ID NO: 182) | |
| (mQ)NeuN-F | AGCAGCCTACAGTGACAGTTATGG (SEQ ID NO: 183) | Q-PCR for mouse NeuN |

TABLE 3-continued

Primer Sequences

| Primer Name | Sequence | Note |
|---|---|---|
| (mQ)NeuN-R | GGCCGATGGTGTGATGGTA (SEQ ID NO: 184) | |
| (mQ)Sox1-F | AAAACCCCAAGATGCACAACTC (SEQ ID NO: 185) | Q-PCR for mouse Sox1 |
| (mQ)Sox1-R | CCTCGGACATGACCTTCCA (SEQ ID NO: 186) | |
| (mQ)Pax6-F | ACCTGTCTCCTCCTTCACATCAG (SEQ ID NO: 187) | Q-PCR for mouse Pax6 |
| (mQ)Pax6-R | TTGGTGAGGGCGGTGTCT (SEQ ID NO: 188) | |
| (mQ)Otx2-F | GGGCATGGACTGTGGATCTT (SEQ ID NO: 189) | Q-PCR for mouse Otx2 |
| (mQ)Otx2-R | CCCCTGGTCCAGGAAGCT (SEQ ID NO: 190) | |
| (mQ)Zic1-F | AAGGTTTTCGCGCGTTCA (SEQ ID NO: 191) | Q-PCR for mouse Zic1 |
| (mQ)Zic1-R | TCTCCCCTGTGTGTGTCCTTT (SEQ ID NO: 192) | |
| (mQ)Olig2-F | CTGGCGCGAAACTACATCCT (SEQ ID NO: 193) | Q-PCR for mouse Olig2 |
| (mQ)Olig2-R | GCTCACCAGTCGCTTCATCTC (SEQ ID NO: 194) | |
| (mQ)NeuroD1-F | CCCAAAAAGAAAAAGATGACCAA (SEQ ID NO: 195) | Q-PCR for mouse NeuroD1 |
| (mQ)NeuroD1-R | GGCCTTCATGCGCCTTAA (SEQ ID NO: 196) | |

REFERENCES

Anokye-Danso, F., Trivedi, C. M., Juhr, D., Gupta, M., Cui, Z., Tian, Y., Zhang, Y., Yang, W., Gruber, P. J., Epstein, J. A., et al. Highly efficient miRNA-mediated reprogramming of mouse and human somatic cells to pluripotency. Cell Stem Cell 8, 376-388.

Birgersdotter, A., Sandberg, R., and Ernberg, I. (2005). Gene expression perturbation in vitro—a growing case for three-dimensional (3D) culture systems. Semin Cancer Biol 15, 405-412.

Cukierman, E., Pankov, R., Stevens, D. R., and Yamada, K. M. (2001). Taking cell-matrix adhesions to the third dimension. Science 294, 1708-1712.

Eiraku, M., Takata, N., Ishibashi, H., Kawada, M., Sakakura, E., Okuda, S., Sekiguchi, K., Adachi, T., and Sasai, Y. (2011). Self-organizing optic-cup morphogenesis in three-dimensional culture. Nature 472, 51-56.

Eiraku, M., Watanabe, K., Matsuo-Takasaki, M., Kawada, M., Yonemura, S., Matsumura, M., Wataya, T., Nishiyama, A., Muguruma, K., and Sasai, Y. (2008). Self-organized formation of polarized cortical tissues from ESCs and its active manipulation by extrinsic signals. Cell Stem Cell 3, 519-532.

Episkopou, V. (2005). SOX2 functions in adult neural stem cells. Trends Neurosci 28, 219-221.

Eshghi, S., and Schaffer, D. V. (2008). Engineering microenvironments to control stem cell fate and function.

Fischbach, C., Chen, R., Matsumoto, T., Schmelzle, T., Brugge, J. S., Polverini, P. J., and Mooney, D. J. (2007). Engineering tumors with 3D scaffolds. Nat Methods 4, 855-860.

Golebiewska, A., Brons, N. H., Bjerkvig, R., and Niclou, S. P. Critical appraisal of the side population assay in stem cell and cancer stem cell research. Cell Stem Cell 8, 136-147.

Griffith, L. G., and Swartz, M. A. (2006). Capturing complex 3D tissue physiology in vitro. Nat Rev Mol Cell Biol 7, 211-224.

Hendrix, M. J., Seftor, E. A., Seftor, R E., Kasemeier-Kulesa, J., Kulesa, P. M., and Postovit, L. M. (2007). Reprogramming metastatic tumour cells with embryonic microenvironments. Nat Rev Cancer 7, 246-255.

Huangfu, D., Maehr, R., Guo, W., Eijkelenboom, A., Snitow, M., Chen, A. E., and Melton, D. A. (2008). Induction of pluripotent stem cells by defined factors is greatly improved by small-molecule compounds. Nat Biotechnol 26, 795-797.

Ingber, D. (1991). Extracellular matrix and cell shape: potential control points for inhibition of angiogenesis. J Cell Biochem 47, 236-241.

Jensen, U. B., Lowell, S., and Watt, F. M. (1999). The spatial relationship between stem cells and their progeny in the basal layer of human epidermis: a new view based on whole-mount labelling and lineage analysis. Development 126, 2409-2418.

Jones, P. H., Harper, S., and Watt, F. M. (1995). Stem cell patterning and fate in human epidermis. Cell 80, 83-93.

Keung, A. J., Kumar, S., and Schaffer, D. V. (2010). Presentation counts: microenvironmental regulation of stem cells by biophysical and material cues. Annu Rev Cell Dev Biol 26, 533-556.

Kim, D., Kim, C. H., Moon, J. I., Chung, Y. G, Chang, M. Y., Han, B. S., Ko, S., Yang, E., Cha, K. Y., Lanza, R., et al. (2009). Generation of human induced pluripotent stem cells by direct delivery of reprogramming proteins. Cell Stem Cell 4, 472-476.

Kim, J., Efe, J. A., Zhu, S., Talantova, M., Yuan, X., Wang, S., Lipton, S. A., Zhang, K., and Ding, S. (2011). Direct reprogramming of mouse fibroblasts to neural progenitors. Proc Natl Acad Sci USA 108, 7838-7843.

Li, R., Liang, J., Ni, S., Zhou, T., Qing, X., Li, H., He, W., Chen, J., Li, F., Zhuang, Q., et al. A mesenchymal-to-epithelial transition initiates and is required for the nuclear reprogramming of mouse fibroblasts. Cell Stem Cell 7, 51-63.

Liu, J., Kuznetsova, L. A., Edwards, G. O., Xu, J., Ma, M., Purcell, W. M., Jackson, S. K., and Coakley, W. T. (2007). Functional three-dimensional HepG2 aggregate cultures generated from an ultrasound trap: comparison with HepG2 spheroids. J Cell Biochem 102, 1180-1189.

Liu, Y., Clem, B., Zuba-Surma, E. K., El-Naggar, S., Telang, S., Jenson, A. B., Wang, Y., Shao, H., Ratajczak, M. Z., Chesney, J., et al. (2009). Mouse fibroblasts lacking RB1 function form spheres and undergo reprogramming to a cancer stem cell phenotype. Cell Stem Cell 4, 336-347.

Manasek, F. J., Burnside, M. B., and Waterman, R. E. (1972). Myocardial cell shape change as a mechanism of embryonic heart looping. Dev Biol 29, 349-371.

Mani, S. A., Guo, W., Liao, M. J., Eaton, E. N., Ayyanan, A., Zhou, A. Y., Brooks, M., Reinhard, F., Zhang, C. C., Shipitsin, M., et al. (2008). The epithelial-mesenchymal transition generates cells with properties of stem cells. Cell 133, 704-715.

McBeath, R., Pirone, D. M., Nelson, C. M., Bhadriraju, K., and Chen, C. S. (2004). Cell shape, cytoskeletal tension, and RhoA regulate stem cell lineage commitment. Dev Cell 6, 483-495.

Nelson, C. M., and Bissell, M. J. (2006). Of extracellular matrix, scaffolds, and signaling: tissue architecture regulates development, homeostasis, and cancer. Annu Rev Cell Dev Biol 22, 287-309.

Osafune, K., Takasato, M., Kispert, A., Asashima, M., and Nishinakamura, R. (2006). Identification of multipotent progenitors in the embryonic mouse kidney by a novel colony-forming assay. Development 133, 151-161.

Pampaloni, F., Reynaud, E. G, and Stelzer, E. H. (2007). The third dimension bridges the gap between cell culture and live tissue. Nat Rev Mol Cell Biol 8, 839-845.

Shi, Y., Do, J. T., Desponts, C., Hahm, H. S., Scholer, H. R., and Ding, S. (2008). A combined chemical and genetic approach for the generation of induced pluripotent stem cells. Cell Stem Cell 2, 525-528.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Vazin, T., and Schaffer, D. V. (2010). Engineering strategies to emulate the stem cell niche. Trends Biotechnol 28, 117-124.

Warren, L., Manos, P D., Ahfeldt, T., Loh, Y. H., Li, H., Lau, F., Ebina, W., Mandal, P. K., Smith, Z. D., Meissner, A., et al. Highly efficient reprogramming to pluripotency and directed differentiation of human cells with synthetic modified mRNA. Cell Stem Cell 7, 618-630.

Yamada, K. M., and Cukierman, E. (2007). Modeling tissue morphogenesis and cancer in 3D. Cell 130, 601-610.

Yu, J., Vodyanik, M. A., Smuga-Otto, K., Antosiewicz-Bourget, J., Frane, J. L., Tian, S., Nie, J., Jonsdottir, G A., Ruotti, V., Stewart, R., et al. (2007). Induced pluripotent stem cell lines derived from human somatic cells. Science 318, 1917-1920.

Zhou, H., Wu, S., Joo, J. Y., Zhu, S., Han, D. W., Lin, T., Trauger, S., Bien, G, Yao, S., Zhu, Y., et al. (2009). Generation of induced pluripotent stem cells using recombinant proteins. Cell Stem Cell 4, 381-384.

Zhu, S., Li, W., Zhou, H., Wei, W., Ambasudhan, R., Lin, T., Kim, J., Zhang, K., and Ding, S. Reprogramming of human primary somatic cells by OCT4 and chemical compounds. Cell Stem Cell 7, 651-655.

The invention claimed is:

1. A method of reprogramming mammalian somatic cells comprising:
   culturing terminally differentiated mammalian somatic cells on a low-adherent substrate or in suspension in a drop of culture medium hanging onto a supporting material to allow formation of a three-dimensional cell aggregate, wherein the terminally differentiated mammalian somatic cells are induced into reprogramming by the formation of the three-dimensional cell aggregate.

2. The method of claim 1, wherein the low-adherent substrate comprises a material that reduces cell attachment.

3. The method of claim 2, wherein the material comprises a hydrogel layer that is hydrophilic and neutrally charged.

4. The method of claim 2, wherein the material is selected from the group consisting of agar, agarose and poly(2-hydrozy-ethyl methacrylate).

5. The method of claim 4, wherein the agarose is in a concentration ranging from 0.2 to 5.0%.

6. The method of claim 5, wherein the agarose is mixed with a culture medium.

7. The method of claim 2, wherein the material is coated as the surface of the low-adherent substrate.

8. The method of claim 2, wherein the material comprises polystyrene.

9. The method of claim 1, wherein the low-adherent substrate comprises a hydrophobic surface.

10. The method of claim 1, wherein the drop has a volume of no more than 1 ml.

11. The method of claim 1, wherein the drop of culture medium is hanging upside down on the bottom of a culturing container.

12. The method of claim 1, wherein the cells are cultured in a rotating, shaking or static state.

13. The method of claim 1, wherein the cells are cultured in the absence of any supporting substrate or structure disposed within the culture medium.

14. The method of claim 1, wherein the cells are selected from the group consisting of HEK293 cells, fibroblast cells, and cancer cells.

15. The method of claim 14, wherein the fibroblast cells are mouse embryonic fibroblasts cells or tail tip fibroblasts cells.

16. The method of claim 1, wherein the three-dimensional cell aggregate is a multicellular and multilayer cell aggregate.

17. The method of claim 16, wherein the three-dimensional cell aggregate has a sphere-like shape.

18. The method of claim 17, wherein the three-dimensional cell aggregate has a diameter of at least 10 μm.

19. The method of claim 1, wherein the cells are reprogrammed to up-regulate one or more stem cell markers.

20. The method of claim 19, wherein the stein cell marker is selected from the group consisting of Oct4, Nanog, Sox2, Klf4, c-Myc, Lin28, Rex1, Tdgf1, Leftb, Ebaf, Grb7, Podx1, Nodal, Fgf4, Nestin, Gdf3, Dax1, Slc2a3, Sox1, Olig2 and Pax6.

21. The method of claim 1, wherein the cells are reprogrammed to up-regulate one or more transdifferentiation markers.

22. The method of claim 1, wherein the terminally differentiated mammalian somatic cells are non-cancer cells.

23. A method of transdifferentiating cells comprising:
   culturing a first type of terminally differentiated cells under a condition that allows formation of a three-dimensional cell aggregate, wherein the first type of terminally differentiated cells are reprogrammed and transdifferentiated into a second type of differentiated cells by the formation of the three-dimensional cell aggregate.

24. The method of claim 23, wherein the first type of differentiated cells are non-genetically-modified cells.

25. The method of claim 23, wherein the first type of differentiated cells are fibroblast cells and the second type of differentiated cells are neural cells.

26. A method of reprogramming mammalian somatic cells comprising:
   (a) culturing the mammalian somatic cells on a low-adherent substrate or in suspension in a drop of culture medium hanging onto a supporting material to allow formation of a three-dimensional cell aggregate, wherein the mammalian somatic cells are induced into reprogramming by the formation of the three-dimensional cell aggregate; and
   (b) contacting reprogrammed cells obtained from step (a) with an inducing agent.

27. The method of claim 26, wherein the inducing agent is a protein capable of inducing reprogramming of a cell.

28. The method of claim 26, wherein the inducing agent is a nucleic acid encoding for a protein that is capable of inducing reprogramming of a cell.

29. The method of claim 26, wherein the inducing agent is a chemical compound capable of inducing reprogramming of a cell.

* * * * *